US011161855B2

United States Patent
Li et al.

(10) Patent No.: US 11,161,855 B2
(45) Date of Patent: *Nov. 2, 2021

(54) TRICYCLIC FUSED THIOPHENE DERIVATIVES AS JAK INHIBITORS

(71) Applicants: Incyte Corporation, Wilmington, DE (US); Incyte Holdings Corporation, Wilmington, DE (US)

(72) Inventors: Yun-Long Li, Chadds Ford, PA (US); Wenyu Zhu, Media, PA (US); Song Mei, Wilmington, DE (US); Joseph Glenn, Mount Royal, NJ (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/454,830

(22) Filed: Jun. 27, 2019

(65) Prior Publication Data

US 2020/0040002 A1 Feb. 6, 2020

Related U.S. Application Data

(63) Continuation of application No. 15/874,140, filed on Jan. 18, 2018, now Pat. No. 10,370,387, which is a continuation of application No. 14/873,078, filed on Oct. 1, 2015, now Pat. No. 9,908,895, which is a continuation of application No. 14/068,796, filed on Oct. 31, 2013, now Pat. No. 9,181,271.

(60) Provisional application No. 61/783,850, filed on Mar. 14, 2013, provisional application No. 61/721,308, filed on Nov. 1, 2012.

(51) Int. Cl.
 C07D 495/14 (2006.01)
 C07D 495/12 (2006.01)
 A61K 31/437 (2006.01)

(52) U.S. Cl.
 CPC .......... *C07D 495/14* (2013.01); *A61K 31/437* (2013.01); *C07D 495/12* (2013.01)

(58) Field of Classification Search
 CPC ... C07D 495/14; C07D 495/12; A61K 31/437
 USPC ........................................................ 546/83
 See application file for complete search history.

(56) References Cited

U.S. PATENT DOCUMENTS

| | | |
|---|---|---|
| 4,753,951 A | 6/1988 | Takada et al. |
| 5,521,184 A | 5/1996 | Zimmermann |
| 6,025,366 A | 2/2000 | Walsh et al. |
| 6,518,265 B1 | 2/2003 | Kato et al. |
| 7,335,667 B2 | 2/2008 | Rodgers et al. |
| 7,598,257 B2 | 10/2009 | Rodgers et al. |
| 7,683,171 B2 | 3/2010 | Pitts et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,445,488 B2 | 5/2013 | Rodger et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 9,181,271 B2 | 11/2015 | Li et al. |
| 9,221,845 B2 | 12/2015 | Liu et al. |
| 9,290,506 B2 | 3/2016 | Metcalf |
| 9,376,439 B2 | 6/2016 | Rodgers et al. |
| 9,498,467 B2 | 11/2016 | Leopold |
| 9,777,017 B2 | 10/2017 | Li et al. |
| 9,802,957 B2 | 10/2017 | Zhou et al. |
| 9,908,895 B2 | 3/2018 | Li et al. |

(Continued)

FOREIGN PATENT DOCUMENTS

| | | |
|---|---|---|
| AU | 2007338793 | 7/2008 |
| CN | 1323307 | 11/2001 |

(Continued)

OTHER PUBLICATIONS

26th Annual JPMorgan Healthcare Conference presentation dated Jan. 8, 2008, 28 pages.
Abe et al., "Effective Methods for Introducing Some Aryl and Heteroaryl Substituent onto 1-Azaazulene Nuclei", Heterocycles, 2005, 66: 229-240.
Abelson et al., "Alternate reference values for tear film break-up time in normal and dry eye populations, Lacrimal Gland, Tear Film, and Dry Eye Syndromes 3 Part B", Adv Exp Med Biol, 2002, 506: 1121-1125.
Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002, 506: 1079-86.
Abstract of Chilean patent application No. 3496-06 published in Official Gazette of the Republic of Chile (Jun. 1, 2007) and publication (2 pages).

(Continued)

*Primary Examiner* — Daniel R Carcanague
(74) *Attorney, Agent, or Firm* — Fish & Richardson P.C.

(57) ABSTRACT

The present invention provides tricyclic fused thiophene derivatives, as well as their compositions and methods of use, that modulate the activity of Janus kinase (JAK) and are useful in the treatment of diseases related to the activity of JAK including, for example, inflammatory disorders, autoimmune disorders, cancer, and other diseases.

54 Claims, No Drawings

(56) References Cited

U.S. PATENT DOCUMENTS

| | | |
|---|---|---|
| 10,053,465 B2 | 8/2018 | Li et al. |
| 10,064,866 B2 | 9/2018 | Scherle et al. |
| 10,077,277 B2 | 9/2018 | Li et al. |
| 10,370,387 B2 | 8/2019 | Li et al. |
| 10,450,325 B2 | 10/2019 | Zhou et al. |
| 2006/0106020 A1 | 5/2006 | Rodgers et al. |
| 2006/0178393 A1 | 8/2006 | Pitts |
| 2007/0149506 A1 | 6/2007 | Arvanitis et al. |
| 2008/0312259 A1 | 12/2008 | Rodgers et al. |
| 2009/0197869 A1 | 8/2009 | Arvanitis et al. |
| 2009/0215766 A1 | 8/2009 | Rodgers et al. |
| 2010/0022522 A1 | 1/2010 | Rodgers et al. |
| 2010/0113416 A1 | 5/2010 | Friedman et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0288107 A1 | 11/2011 | Parikh et al. |
| 2012/0014989 A1 | 1/2012 | Rodgers |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0264738 A1 | 10/2012 | Sugimoto et al. |
| 2012/0301464 A1 | 11/2012 | Friedman et al. |
| 2012/0329782 A1 | 12/2012 | Arvanitis et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0296299 A1 | 11/2013 | Rodgers et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2015/0065447 A1 | 3/2015 | Sandor |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0164900 A1 | 6/2015 | Rodgers et al. |
| 2015/0225411 A1 | 8/2015 | Yao et al. |
| 2015/0238492 A1 | 8/2015 | Rodgers et al. |
| 2015/0246046 A1 | 9/2015 | Vaddi et al. |
| 2015/0250790 A1 | 9/2015 | Parikh et al. |
| 2015/0342952 A1 | 12/2015 | Leopold |
| 2015/0344497 A1 | 12/2015 | Zhou et al. |
| 2016/0000795 A1 | 1/2016 | Scherle |
| 2016/0015695 A1 | 1/2016 | Li et al. |
| 2016/0024109 A1 | 1/2016 | Li |
| 2016/0067253 A1 | 3/2016 | Li et al. |
| 2016/0257687 A1 | 9/2016 | Metcalf |
| 2016/0272648 A1 | 9/2016 | Rodgers et al. |
| 2016/0289215 A1 | 10/2016 | Li et al. |
| 2016/0346286 A1 | 12/2016 | Rodgers et al. |
| 2016/0347734 A1 | 12/2016 | Liu et al. |
| 2018/0099978 A1 | 4/2018 | Zhou et al. |
| 2018/0148460 A1 | 5/2018 | Li et al. |
| 2019/0255053 A1* | 8/2019 | Montgomery ..... A61K 31/4155 |
| 2019/0328739 A1* | 10/2019 | Howell ................ A61K 31/519 |
| 2019/0331697 A1* | 10/2019 | Howell ................ A61K 31/573 |
| 2020/0063188 A1* | 2/2020 | Howell ................ G16H 50/30 |
| 2020/0129517 A1* | 4/2020 | Assad ................ A61K 31/437 |
| 2020/0348313 A1* | 11/2020 | Howell ................ A61P 17/00 |

FOREIGN PATENT DOCUMENTS

| | | |
|---|---|---|
| CN | 101516875 | 8/2009 |
| CN | 102131389 | 7/2011 |
| CN | 104918945 | 9/2015 |
| EP | 0223420 | 5/1987 |
| EP | 0587473 | 3/1994 |
| EP | 0727217 | 8/1996 |
| EP | 1104764 | 6/2001 |
| JP | H02124881 | 5/1990 |
| JP | H02225463 | 9/1990 |
| JP | H08104686 | 4/1996 |
| JP | 2000-119271 | 4/2000 |
| JP | 2003-002890 | 1/2003 |
| MX | 2015005428 | 7/2015 |
| TW | I646099 | 1/2019 |
| WO | WO 00/009495 | 2/2000 |
| WO | WO 00/053595 | 9/2000 |
| WO | WO 01/014402 | 3/2001 |
| WO | WO 01/064655 | 9/2001 |
| WO | WO 02/000196 | 1/2002 |
| WO | WO 02/016370 | 2/2002 |
| WO | WO 03/024967 | 3/2003 |
| WO | WO 03/037347 | 5/2003 |
| WO | WO 03/099771 | 12/2003 |
| WO | WO 04/005281 | 1/2004 |
| WO | WO 04/046120 | 6/2004 |
| WO | WO 04/056786 | 7/2004 |
| WO | WO 04/080980 | 9/2004 |
| WO | WO 05/028444 | 3/2005 |
| WO | WO 05/123719 | 12/2005 |
| WO | WO 06/056399 | 6/2006 |
| WO | WO 2007/044050 | 4/2007 |
| WO | WO 09/155156 | 12/2009 |
| WO | WO 11/003418 | 1/2011 |
| WO | WO 13/007765 | 1/2013 |
| WO | WO 13/007768 | 1/2013 |
| WO | WO 14/071031 | 5/2014 |
| WO | WO 12/121361 | 7/2014 |

OTHER PUBLICATIONS

Aho et al., Expression of human pim family genes is selectively up-regulated by cytokines promoting T helper type 1, but not T helper type 2, cell differentiation, Immunology, 2005, 116: 82-88.

Albach et al., "Diagnosis of keratoconjunctivitis sicca in rheumatoid arthritis. The value of various tests", Ophthalmologe, Apr. 1994; 91(2):229-34—in German (with English abstract/summary contained therein).

Anderson et al., "Biochemical characterization of GSK1070916, a potent and selective inhibitor of Aurora B and Aurora C kinases with an extremely long residence time", Biochem. J., 2009, 420(2): 259-265.

Bachmann et al., "The serine/threonine kinase Pim-1," The International Journal of Biochemistry and Cell Biology, 2005, 37: 726-730.

Banker et al., "Modern Pharmaceuticals" Third Edition, 1996, 596.

Barabino et al., "Tear film and ocular surface tests in animal models of dry eye; uses and limitations," Experimental Eye Research, 2004, 79: 613-621.

Barr et al., "Corneal scarring in the Collaborative Longitudinal Evaluation of Keratoconus (CLEK) Study: baseline prevalence and repeatability of detection", Cornea, 1999, 18(1):34-46.

Baudouin et al., "Flow cytometry in impression cytology specimens. A new method for evaluation of conjunctival Inflammation," Invest Ophthalmol Vis Sci, 1997, 38: 1458-1464.

Baytel et al., "The human Pim-2 proto-oncogene and its testicular expression," Biochimica et Biophysica Acta, 1998, 1442: 274-285.

(56) References Cited

OTHER PUBLICATIONS

Begley et al., "Use of the dry eye questionnaire to measure symptoms of ocular irritation in patients with aqueous tear deficient dry eye", Cornea, 2002, 21: 664-70.
Bell and Zalay, "Synthesis of Substituted 3-Amino [6, 5-b] triazinoindoles." Journal of Heterocyclic Chemistry, Oct. 1975, 12(5):1001-1004.
Berge et al., "Pharmaceutical salts", J. Pharma. Science, 1977, 66(1): 1-19.
Beyer, "Uber die Synthese von 2-Methylmercapto-1,3,4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).
Bhattacharya et al., "Polymorphism in Pharmaceutical Solids," Second Edition, 2009, 192:327-345.
Bhovi, et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, Jul.-Sep. 2004, 14: 15-18.
Bioreversible Carriers in Drug Design, ed. Edward B. Roche, American Pharmaceutical Association and Pergamon Press, 1987 **Too Voluminous to Provide.
Blume-Jensen et al, "Oncogenic kinase signaling", Nature, 2001, 411(6835):355-365.
Bock et al. "Managing drug resistance in cancer: lessons from HIV therapy." Nature, Jul. 2012, 12: 494-501.
Bolen, "Nonreceptor tyrosine protein kinases", Oncogene, 1993, 8(8):2025-31.
Bollrath et al., "gp130-Mediated Stat3 Activation in Enterocytes Regulates Cell Survival and Cell-Cycle Progression during Colitis-Associated Tumorigenesis," Cancer Cell, 2009, 15:91-102.
Borie et al., "Combined Use of the Jak3 Inhibitor CP-690, 550 with Mycophenolate Mofetil to Prevent Kidney Allograft Rejection in Nonhuman Primates", Transplantation, Dec. 2005, 80(12):1756-64.
Bosworth, "JAK1/JAK2 Inhibitor Ruxolitinib Is a Rising Start," Clinical Oncology, Apr. 2011, 06:04, 3 pages.
Boudny et al., "JAK/STAT signaling pathways and cancer," Neoplasm, 2002, 49:349-355.
Bourcier et al., "Expression of CD40 and CD40 ligand in the human conjunctival epithelium", Invest. Ophthalmol Vis Sci, 2000, 41:120-126.
Bowman et al. "STATs in oncogenesis", Oncogene, 2000, 19:2474-2488.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker APO2-7 by the Human Conjunctival Epithelium Positive correlation with class II HLA DR expression in inflammatory Ocular Surface Disorders", Exp Eye Res, 1998, 67:687-697.
Brignole et al., "Flow cytometric analysis of inflammatory markers in conjunctival epithelial cells of patients with dry eyes," Invest Ophthalmol Vis Sci, 2000, 41:1356-1363.
Brignole et al., "Flow cytometric analysis of inflammatory markers in KCS: 6-month treatment with topical cyclosporin A," Invest Ophthalmol Vis Sci, 2001, 42:90-95.
Brignole et al., "Flow cytometly in conjunctival impression cytology: a new tool for exploring ocular surface pathologies," Exp Eye Res, 2004, 78:473-481.
Bromberg et al., "Inflammation and Cancer: IL-6 and STAT3 Complete the Link," Cancer Cell, 2009, 15:79-80.
Bron et al., "Grading of corneal and conjunctival staining in the context of other dry eye tests", Cornea, 2003, 22(7):640-50.
Bron et al., "Methodologies to Diagnose and Monitor Dry Eye Disease: Report of the Diagnostic Methodology Subcommittee of the International Dry Eye Workshop (2007)", The Ocular Surface, Apr. 2007, 5(2): 108-152.

Burger et al., "Gp130 and ras mediated signaling in human plasma cell line IN/a-6: a cytokine-regulated tumor model for plasmacytoma", Hematol J., 2001, 2:42-53.
Burger et al., "Janus kinase inhibitor INCB20 has antiproliferative and apoptotic effects on human myeloma cells in vitro and in vivo", Mol. Cancer Ther., Jan. 2009, 8(1): 26-35.
Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, Jun. 2010, 35(6):457-465.
Candotti et al., "Structural and functional basis for JAK3-deficient severe combined immunodeficiency.", Blood, 1997, 90(10): 3996-4003.
Candotti et al., "Molecular aspects of primary immuno-deficiencies: lessons from cytokine and other signaling pathways.", J Clin Invest, May 2002, 109(10): 1261-9.
Carey and Sundberg, Advanced Organic Chemistry, Part B: Reactions and Synthesis, 4th ed., Kluwer Academic/Plenum Publishers:New York, 2001, 111-119.
Carey and Sundberg, Advanced Organic Chemistry, Part B: Reactions and Synthesis, Oxidations, 4th ed., Kluwer Academic/Plenum Publishers:New York, 2001, 747-757.
Cermak et al, "Is complete androgen insensitivity syndrome associated with alterations in the meibomian gland and ocular surface," Cornea, 2003, 22:516-521.
Cetkovic-Cvrlje et al., "Targeting JAK3 with JANEX-1 for prevention of autoimmune type 1 diabetes in NOD mice.", Clin Immunol, 2003, 106(3): 213-25.
Chalandon, "Targeting mutated protein tyrosine kinases and their signaling pathways in hematologic malignancies," Haematologica, 2005, 90(7):949-68.
Changelian et al., "Prevention of Organ Allograft Rejection by a Specific Janus Kinase 3 Inhibitor", Science, 2003, 302: 875-878.
Chauhan et al, "Autoimmunity in Dry Eye due to resistance of Th17 to Treg Suppression", J. Immunology, 2009, 182(3):1247-52.
Chemical encyclopedia publication "Soviet Encyclopedia," Moscow, 1988, 1:242-243.
Chen et al., "Stat3 Activation in Human Endometrial and Cervical Cancer", British Journal of Cancer, 2007, 96: 591-599.
Chew et al., "An instrument for quantifying meibomian lipid on the lid margin: the Meibometer", Curr Eye Res, 1993, 12:247-254.
Chew et al., "The casual level of meibomian lipids in humans", Current Eye Research, 1993, 12:255-259.
Chinese Office Action in Chinese Application No. 201380068740.2, dated Jun. 3, 2016, 17 pages (English Translation).
Chinese Office Action in Chinese Application No. 201580034662.3, dated Feb. 2, 2018, 17 pages (English Translation).
Cho et al, "Review of the tear break-up time and a closer look at the tear break-up time of Hong Kong Chinese", Optom Vis Sci, 1993, 70(1):30-8.
Choi Ha-Soon et al., "Design and synthesis of 7H-pyrrolo[2,3-d]pyrimidines as focal adhesion kinase inhibitors. Part 1", Bioorg. & Med. Chem. Lett., 2006, 16(8):2173-2176.
Chu-Moyer et al., "Preparation of the Four Regioisomeric 2-(Methylthio)oxazolopyridines: Useful Synthons for Elaboration to 2-(Amino substituted)oxazolopyridines", J. Org. Chem., 1995, 60(17): 5721-5725.
Cilloni et al., "Emerging drugs for chronic myeloid leukemia", Expert Opinion on Emerging Drugs, Jun. 2010, 15(2): 175-184.
Claridge et al., "Discovery of a novel and potent series of thieno[3,2-b]pyridine-based inhibitors of c-Met and VEGFR2 tyrosine kinases," Bioorganic & Medicinal Chemistry Letters, 2008, 2793-2798.
Clark et al., "Discovery and Development of Janus Kinase (JAK) inhibitors for Inflammatory Diseases," J Med Chem., 2014, A-P.
Coligan et al, Wiley Press; Methods in Molecular Biology: vol. 225, Inflammation Protocols., Winyard, P.G. and Willoughby, D.A., Humana Press (2003) **Too Voluminous to Provide.
Communication dated Jan. 22, 2009 for European Appln. No. 06839328.9 (5 pgs.).
Conklyn et al., "The JAK3 inhibitor CP-0690550 selectively reduces NK and CD8+ cell numbers in cynomolgus monkey blood following chronic oral dosing," Journal of Leukocyte Biology, Dec. 2004, 76: 1248-1255.

(56) References Cited

OTHER PUBLICATIONS

Costa Rican Office Action in CR Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (1988) **Too Voluminous to Provide.
Daniels et al., "Imatinib mesylate inhibits the profibrogenic activity of TGF-? and prevents bleomycinmediated lung fibrosis," J. Clin. Invest., Nov. 2004, 114(9):1308-1316.
Danjo et al., "Observation of precorneal tear film in patients with Sjogren's syndrome", Acta Ophthalmol Scand, 1995, 73:501-505.
De Paiva et al, "IL-17 disrupts corneal barrier following desiccating stress," Mucosal Immunol., 2009, 2(3):243-53.
De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 2000, 109(4): 823-8.
Deng Jun et al, "Rh-catalyzed asymmetric hydrogenation of gamma-phthalimido-substituted esters: an efficient enantioselective synthesis of beta-aryl-gamma-amino acids", Org. Lett., 2007, 9(23):4825-4827.
Deuse et al., "Novel Immunosuppression: R348, a JAK3- and Syk-Inhibitor Attenuates Acute Cardiac Allograft Rejection," Transplantation, 2008, 85(6): 885-892.
Doane, "An instrument for in vivo tear film interferometry", Optom Vis Sci, 1989, 66: 383-8.
Doleschall et al., "Thermal and Acid Catalysed Degradations of 3-alkylthio-6,7-dihydro[1.2.4]triazino[1,6-c]quinazolin-5-ium-1-olates," Tetrahedron, 1974, 30:3997-4012.
Dorwald, "Side Reactions in Organic Synthesis: A Guide to Successful Synthesis Design," Wiley-VCH, 2005, Chapter 1, 32 pages.
Dudley et al. "A VEGF/JAK2/STAT5 axis may partially mediate endothelial cell tolerance to hypoxia", Biochem. J., 2005, 390(Pt 2):427-36.
European Office Action in European Application No. 13789679.1 dated Jul. 19, 2017, 5 pages.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl et al., "Therapeutic applications of viscous and injectable poly(ortho esters)," Adv. Drug. Deliv. Rev., 2001, 53:45-73.
Eliason et al., "Staining of the conjunctiva and conjunctival tear film," Br J Ophthalmol, 1990, 74:519-22.
Expert Scientific Group on Phase One Clinical Trials Final Report, Nov. 30, 2006, pp. C1, C35-C38.
Saettone and Salminen, "Ocular inserts for topical delivery", Advanced Drug Delivery Reviews, 1995, 16:95-106.
Farrell et al., "A classification for dry eyes following comparison of tear thinning time with Schirmer tear test," Acta Ophthalmol (Copenh), 1992, 70(3):357-60.
Farrell et al., "A clinical procedure to predict the value of temporary occlusion therapy in keratoconjunctivitis sicca," Ophthal Physiol Opt, 2003, 23:1-8.
Farris, "Tear osmolarity—a new gold standard?" Adv Exp Med Biol, 1994, 350:495-503.
Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).

Flex et al., "Somatically acquired JAK1 mutations in adult acute lymphoblastic leukemia", J. Exp Med., 2008, 205:751-8.
Fonesca et al., "Interleukin-6 as a key player in systemic inflammation and joint destruction", Autoimmunity Reviews, 2009, 8:538-42.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Fridman et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman et al., "Preclinical evaluation of local JAK1 and JAK2 inhibition in cutaneous inflammation", Journal of Investigative Dermatology, Sep. 2011, 131(9): 1838-1844.
Fridman et al., "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman et al., "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman et al., "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Fujihara et al., "Evaluation of human conjunctival epithelium by a combination of brush cytology and flow cytometry: an approach to the quantitative technique", Diagn Cytopathol, 1997, 17:456-60.
Fujii et al., "Aberrant expression of serine/threonine kinase Pim-3 in hepatocellular carcinoma development and its role in the proliferation of human hepatoma cell lines" International Journal of Cancer, 2005, 114: 209-218.
Fukagawa et al., "Histological evaluation of brush cytology of rabbit conjunctiva", Nippon Ganka Gakkai Zasshi, 1993, 97:1173-8 (contains English abstract within the article).
Gaertner, "Cyclization of 1-Alkylamino-3-halo-2-alkanols to 1-Alkyl-3-azetidinols," J. Org. Chem., 1967, 32: 2972-76.
Gaestel et al., "Targeting innate immunity protein kinase signalling in inflammation," Nat Rev Drug Discov., Jun. 2009, 8(6):480-99.
Ghelardi et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother., 2004, 48:3396-3401.
Gilchrist et al., "5H-2-Pyridines from 2-Bromocyclopentene-1-carboxaldehyde," Tetrahedron, Jan. 1, 1995, 9119-9126.
Glasson et al., "Differences in clinical parameters and tear film of tolerant and intolerant contact lens wearers," Invest Ophthalmol Vis Sci, 2003, 44:5116-5124.
Glattfeld, "Improvements in the Preparation of DL-Threonic and DL-Erythronic Acids", J. Am. Chem. Soc., 1940, 62:974-977.
Gobbels et al., "Tear secretion in dry eyes as assessed by objective fluorophotometry.," Ger J Ophthalmol, 1992, 1:350-353.
Golding et al., "X-ray and scanning electron microscopic analysis of the structural composition of tear ferns", Cornea, Jan. 1994, 13(1):58-66.
Gomtsyan et al, "Design, synthesis, and structure-activity relationship of 6-alkynylpyrimidines as potent adenosine kinase inhibitors," J. Med. Chem., 2002, 45(17):3639-3648.
Gooseman et al., "The intramolecular b-fluorine . . . ammonium interaction in 4- and 8-membered rings", Chem. Commun, 2006, 30:3190-3192.

(56) References Cited

OTHER PUBLICATIONS

Gorre et al., "Clinical Resistance to STI-571 Cancer Therapy Caused by BCR-ABL Gene Mutation or Amplification." Science, 2001, 293:876-880.
Gotlieb, Alice, Presentation at the 2008 American Academy of Dermatology, 66th Annual Meeting, San Antonio, TX. Feb. 1, 2008, symposium-303 (12 pp.).
Goto et al., "Color mapping of tear lipid layer thickness distribution from the image analysis in DR-1 tear lipid layer interference images," ARVO abstract, 2004, 2 pages.
Goto et al., "Computer-synthesis of an interference color chart of human tear lipid layer by a colorimetric approach," Invest Ophthalmol Vis Sci, 2003, 44:4693-7.
Goto et al., "Differentiation of lipid tear deficiency dry eye by kinetic analysis of tear interference images,",Arch Ophthalmol, 2003, 121:173-80.
Goto et al., "Evaluation of the tear film stability after laser in situ keratomileusis using the tear film stability analysis system," Am J Ophthalmol, Jan. 2004, 137(1):116-20.
Goto et al., "Tear Film Stability Analysis System: Introducing a new application for videokeratography", Cornea, Nov. 2004, 23(8):S65-S70.
Goto et al., "Kinetic analysis of tear interference images in aqueous tear deficiency dry eye before and after punctal occlusion," Invest Ophthalmol Vis Sci, 2003, 44:1897-905.
Gottlieb, "Psoriasis: Emerging Therapeutic Strategies," Nat Rev Drug Disc., Jan. 2005, 4:19-34.
Grabbe et al., "Immunoregulatory mechanisms involved in elicitation of allergic—contact hypersensitivity," Immunol Today, Jan. 1998, 19(1):37-44 (only 1 page provide and marked "best available copy").
Green and Wuts, P.G.M.. Protective Groups in Organic Synthesis, 3rd. Ed., Wiley & Sons, Inc., New York (1999) **Too Voluminous to Provide.
Gregory et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Guillon, "Tear film photography and contact lens wear", J Br Contact Lens Assoc, 1982;5:84-7.
Gura, "Systems for Identifying New Drugs Are Often Faulty," Science, Nov. 1997, 278(5340): 1041-1042.
Guschin et al, "A major role for the protein tyrosine kinase JAK1 in the JAK/STAT signal transduction pathway in response to interleukin-6", Embo J 14:1421-1429 (1995).
Hamze' et al., "Synthesis of Various 3-Substituted 1,2,4-Oxadiazole-Containing Chiral ß3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Helal et al., "Stereoselective Synthesis of cis-1,3-Disubstituted Cyclobutyl Kinase Inhibitors," Organic Letters, (2004), 6(11), pp. 1853-1856.
Hickenbottom "Reactions of organic compounds," State Scientific-Technical Publishing Association, Chemical Literature Section, Moscow, 1939, pp. 360-362.
Higuchi et al., "Pro-drugs as Novel Delivery Systems," vol. 14 of the A.C.S. Symposium Series (1975)* too voluminous to provide.
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
International Search Report and Written Opinion in International Application No. PCT/US2013/067794, dated Dec. 17, 2013, 14 pages.
International Search Report and Written Opinion in International Application No. PCT/US2015/028224, dated Jul. 21, 2015, 9 pages.
Iranpoor, "A Rapid and Facile Conversion of Primary Amides and Aldoximes to Nitriles and Ketoximes to Amides with Triphenylphosphine and N-Chlorosuccinimide," G Syn., 2002, Commun 32:2535-41.
Ishizaki et al., "Pharmacological Properties of Y-27632, a Specific Inhibitor of Rho-Associated Kinases", Molecular Pharmacology, 2000, 57, 976-983.
Itagaki et al, "Expedient Synthesis of Potent Cannabinoid Receptor Agonist (-)-CP55,940", Organic Letters, 2005, 7(19): 4181-4183.
Japanese Office Action in Japanese Application No. 2015-540785, dated Oct. 3, 2017, 10 pages (English Translation).
James et al., "A unique clonal JAK2 mutation leading to constitutive signalling causes polycythaemia vera", Nature, 434 (7037):1144-8 (2005).
Janes et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee et al., "Overview: animal models of osteopenia and osteoporosis", J Musculoskel. Neuron, Interact., 1(3):193-207 (2001).
Jester et al., "In vivo biomicroscopy and photography of meibomian glands in a rabbit model of meibomian gland dysfunction", Invest Ophthalmol Vis Sci, 1982;22:660-7.
Johnson et al., "The effect of instilled fluorescein solution volume on the values and repeatability of TBUT measurements", Cornea, 2005;24:811-7.
Kaercher, "Ocular symptoms and signs in patients with ectodermal dysplasia syddromes", Graefe's Arch Clin Exp Ophthalmol, 2004;495-500.
Kamb, "What's wrong with our cancer models?," Nature Reviews, Feb. 2005, 161-165.
Kaushansky, "Lineage-Specific Hematopoietic Growth Factors," NEJM, 2006, 354:2034-45.
Kawamura et al., "Molecular cloning of L-JAK, a Janus family protein-tyrosine kinase expressed in natural killer cells and activated leukocytes," Proc Natl Acad Sci USA, 1994, 91(14): 6374-8.
Kharas et al., "ABL Oncogenes and Phosphoinositide 3-Kinase: Mechanism of Activation and Downstream Effectors," Cancer Res., Mar. 2005, 65(6):2047-2053.
Kim et al., "Zinc-Modified Cyanoborohydride as a Selective Reducing Agent," J. Org. Chem., 1985, 50: 1927-1932.
King-Smith et al., "Three interferometric methods for measuring the thickness of layers of the tear film," Optom Vis Sci, 1999, 76:19-32.
Kiss, "Recent developments on JAK2 inhibitors: A patent review", Expert Opinion on Therapeutic Patents, Apr. 2010, 20(4):471-495.
Kojima et al., "A new noninvasive tear stability analysis system for the assessment of thy eyes", Invest Ophthalmol Vis Sci, 2004, 45(5):1369-74.
Kola, "Can the pharmaceutical industry reduce attrition rates?" Nature Reviews Drug Discovery, 2004, 3:711-715.
Komuro et al., "Assessment of meibomian gland function by a newly developed laser meibometer", Adv Exp Med Biol, 2002, 506:517-520.
Korb et al., "The effect of two novel lubricant eye drops on tear film lipid layer thickness in subjects with dry eye symptoms", Optom Vis Sci, 2005, 82: 594-601.
Korb et al., "Increase in tear film lipid layer thickness following treatment of meibomian gland dysfunction", Adv Exp Med Biol, 1994, 350:293-8.
Korolev et al., "Pd-EDTA as an efficient catalyst for Suzuki-Miyaum reactions in water", Tet. Lett., 2005, 46: 5751-5754.
Kortylewski et al., "Regulation of the IL-23 and IL-12 balance by Stat3 signaling in the tumor microenvironment", Cancer Cell, 2009, 15:114-123.

(56) References Cited

OTHER PUBLICATIONS

Kontzias et al., "Jakinibs: a new class of kinase inhibitors in cancer and autoimmune disease," Curr. Opin. Pharm., 2012, 12: 464-470.
Kruh et al., "The complete coding sequence of arg defines the Abelson subfamily of cytoplasmic tyrosine kinases ", Proc. Natl. Acad. Sci., Aug. 1990, 87:5802-5806.
Kubinyi, "QSAR: Hansch Analysis and Related Approaches," Methods and Principles in Medicinal Chemistry, Manhold, R. ed. Weinheim, NY, 1993, 42 pages.
Kudelacz et al. "The JAK-3 inhibitor CP-690550 is a potent anti-inflammatory agent in a murine model of pulmonary eosinophilia", European Journal of Pharmacology, 2008, 582: 154-161.
Kumar, "Kinase drug discovery approaches in chronic myeloproliferative disorders", Oncogene, Jun. 2009, 28(24): 2305-23.
Kuo et al., "Pd-EDTA as an efficient catalyst for Suzuki-Miyaura reactions in water", Chem Commun, 2007, 301-3.
Kuppens et al., "Basal tear turnover and topical timolol in glaucoma patients and healthy controls by Fluorophotometry", Invest Ophthalmol Vis Sci, 1992, 33:3442-3448.
Lai et al., "Mechanistic Study on the Inactivation of General Acyl-CoA Dehydrogenase by a Metabolite of Hypoglycin A," J. Am. Chem. Soc., 1991, 113: 7388-7397.
Lam et al, "Tear Cytokine Profiles in Dysfunctional Tear Syndrome", Am J Ophthalmol 2009, 147(2):198-205.
Larock, "Comprehensive Organic Transformations", Wiley-VCH, 2nd Ed. (1999) pp. 1949-1950, 1958-1959, 1976, and 1983-1985.
Leaf, Clifton, Health Administrator vol. XVII, 2005, 1:172-183.
Lemp "Report of National Eye Institute/Industry Workshop on clinical trials in dry eyes," CLAO J, 1995, 21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (Jul. 5, 2010) (4 pages).
Levine et al., "Activating mutation in the tyrosine kinase JAK2 in polycythemia vera, essential thrombocythemia, and myeloid metaplasia with myelofibrosis", Cancer Cell, 2005, 7:387-397.
Levitzki, "Tyrosine kinases as targets for cancer therapy", Eur. J. Cancer, 2002, 38(suppl. 5):S11-S18.
Levy et al. "INCB018424 A Selective Janus Kinase 1/2 Inhibitor" Presentation at the 50th American Society of Hematology Annual Meeting (ASH), Dec. 8, 2008, 27 pages.
Li et al., "The synthesis and the antitumor activity of 5,7-disubstituted pyrazolo [1,5-a] pyrimidines," Chinese J Med Chem., Feb. 28, 2007, 17(1):18-22.
Li et al., "Pim-3, a proto-oncogene with serine/threonine kinase activity, is aberrantly expressed in human pancreatic cancer and phosphorylates Bad-mediated apoptosis in human pancreatic cell lines," Cancer Research, 2006, 66(13): 6741-7.
Lima and Barreiro, "Bioisosterism: a useful strategy for molecular modification and drug design," Curr Med Chem., 2005, 12(1):23-49.
Lin, "Constitutive Activation of JAK3/STAT3 in Colon Carcinoma Tumors and Cell Lines," Am J Pathol., 2005, 167(4):969-80.
Lin et al., "Enantioselective synthesis of Janus kinase inhibitor INCB018424 via an organocatalytic aza-Michael reaction," Organic Letters, 2009, 11(9): 1999-2002.
Ling et al., "Knockdown of STAT3 Expression by RNA Interference Inhibits the Induction of Breast Tumors in Immunocompetent Mice," Cancer Res, Apr. 2005 65:2532.
Liu et al., "Combined Inhibition of Janus Kinase 1/2 for the Treatment of JAK2V617F-Driven Neoplasms: Selective Effects on Mutant Cells and Improvements in Measures of Disease Severity," Clin Cancer Res, 2009, 15(22):6891-6900.
Lucet et al., "The structural basis of Janus kinas 2 inhibition by a potent and specific pan-Janus kinase inhibitor," Blood, 2006, 107(1):176-183.

Macchi et al., "Mutations of Jak-3 gene in patients with autosomal severe combined immune deficiency (SCID)", Nature, 1995, 377:65-8.
Madden et al., "Comparative study of two non-invasive tear film stability techniques," Curr Eye Res, 1994, 13(4):263-9.
Madhusudan et al., "Tyrosine kinase inhibitors in cancer therapy," Clin Biochem., 2004, 37(7):618-35.
Maffioli et al., "Mild and Reversible Dehydration of Primary Amides with PdCl2 in Aqueous Acetonitrile", Organic Letters, 2005, 7(23): 5237-39.
Main et al, "High throughput synthesis of diverse 2,5-disubstituted indoles using titanium carbenoids bearing boronate functionality", Tetrahedron, 2007, 64(5):901-914.
Mainstone et al., "Tear meniscus measurement in the diagnosis of dry eye", Curr Eye Res, 1996, 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Mandal, "Cancer Classification," 2014. Available from: <http://www.news-medical.net/health/Cancer-Classification.aspx, 6 pages.
Manjula et al., "Rapid Method of Converting Primary Amides to Nitriles and Nitriles to Primary Amides by ZnCl2 using Microwaves under Different Reaction Conditions", Syn. Commun, 2007, 37: 1545-50.
Manning et al., "The Protein Kinase Complement of the Human Genome," Science, 2002, 298(5600):1912-16 and 1933-34.
Mao et al., "Advances in research of tyrosine kinases inhibitor of vascular endothelial growth factor receptor," Chinese J New Drugs, Dec. 31, 2008, 17(7):544-550.
March, Jerry, Advanced Organic Chemistry: Reactions, Mechanisms, and Structure, 3rd ed., John Wiley & Sons:New York, pp. 845-855 (1985).
Marquardt et al., "Modification of tear film break-up time test for increased reliability" in Holly ed. The Preocular Tear Film in Health, Disease and Contact Lens Wear. Lubbock, Texas: Dry Eye Institute, 1986:57-63.
Maruyama et al., "Effect of environmental conditions on tear dynamics in soft contact lens wearers," Invest Ophthalmol Vis Sci, 2004, 45(8):2563-8.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996, 103:664-669.
Mathers et al., "Video imaging of the meibomian gland", Arch Ophthalmol, 1994, 112:448-9.
Mathers, "Evaporation from the ocular surface", Exp Eye Res, 2004, 78:389-394.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
McNamara et al., "Fluorometry in contact lens research: The next step," Optom Vis Sci, 1998, 75:316-322.

(56) References Cited

OTHER PUBLICATIONS

MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986, 64(4):441-4.
Mesa et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, Nov. 2011, 117(21): 4869-4877.
Mesa et al., "Emerging drugs for the therapy of primary and post essential thrombocythemia, post polycythemia vera myelofibrosis", Expert Opinion on Emerging Drugs England, 2009, 14(3): 471-479.
Methods in Molecular Biology: vol. 225, Inflammation Protocols., Winyard, P.G. and Willoughby,. D.A., Humana Press, 2003 **Too Voluminous to Provide.
Meydan et al., "Inhibition of acute lymphoblastic leukaemia by a Jak-2 inhibitor", Nature, Feb. 1996, 379(6566):645-8.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi et al., "Human Tyrosine Kinase 2 Deficiency Reveals Its Requisite Roles in Multiple Cytokine Signals Involved in Innate and Acquired Immunity", Immunity, 2006, 25:745-55.
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol., Sep. 2010, 85(3):192-9 Epub Jun. 2, 2010.
Mishima et al., "Determination of tear volume and tear flow", Invest Ophthalmol, 1966, 5:264-276.
Mishima, "Some physiological aspects of the precorneal tear film", Arch Ophthalmol, 1965, 73:233-241.
Mitsunobu, "The Use of Diethyl Azodicarboxylate and Triphenylphosphine in Synthesis and Transformation of Natural Products." Synthesis, 1981, (1): 1-28.
Miyata, et al., "Stereospecific nucleophilic addition reactions to olefins.", J. Org. Chem., 1991, 56:6556-6564.
Miyaura et al., "Palladium-Catalyzed Cross-Coupling Reactions of Organoboron Compounds," Chem. Rev., 1995, 95: 2457-2483.
Miyoshi et al., "Interleukin-8 concentrations in conjunctival epithelium brush cytology samples correlate with neutrophil, eosinophil infiltration, and corneal damage", Cornea, 2001, 20:743-7.
Moreland et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty et al., "The synthesis and SAR of 2-amino-pyrrolo[2,3-d]pyrimidines: A new class of Aurora-A kinase inhibitors", Bioorganic and Medicinal Chemistry Letters, 2006, 16(22), 5778-5783.
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan et al, "JAK mutations in high-risk childhood acute lymphoblastic leukemia", Proc Natl Acad Sci USA, 2009, 106:9414-8.
Naka, "The paradigm of IL-6: from basic science to medicine", Arthritis Res., 2002, 4 Suppl 3:S233-42.

Nakagawara, "Trk receptor tyrosine kinases. A bridge between cancer and neural development." Cancer Letters, 2001, 169:107-114.
Nally et al., "Ocular discomfort and tear film break-up time in dry eye patients: A correlation," Invest Ophthalmol Vis Sci, 2000, 41:4:1436 (Poster Presentation).
Naqvi et al., "A potential role of ruxolitinib in leukemia", Expert Opinion on Investigational Drugs, Aug. 2011, 20(8): 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Naus et al., "6-(Het)aryl-7-Deazapurine Ribonucleosides as Novel Potent Cytostatic Agents", J. Med. Chem., 2010, 53(1):460-470.
Neidle Cancer Drug Design and Discovery, (Elsevier/Academic Press, 2008) 427-431.
Nelson et al., "Tear film osmolality determination: an evaluation of potential errors in measurement," Curr Eye Res, 1986, 5(9):677-81.
Neubauer et al., "Jak2 Deficiency Defines an Essential Developmental Checkpoint in Definitive Hematopoiesis", Cell, 1998, 93(3): 397-409.
Nicholoff et al., "Recent Insights into the immunopathogenesis of psoriasis provide new therapeutic opportunities", J. Clin. Invest., 2004, 113: 1664-1675.
Nichols et al., "The lack of association between signs and symptoms in patients with dry eye disease", Cornea, 2004, 23(8):762-770.
Nichols et al., "The repeatability of clinical measurements of dry eye", Cornea, 2004, 23(3):272-85.
Nishio et al., "Tyrosine kinase-dependent modulation by interferon-α of the ATP-sensitive K+ current in rabbit ventricular myocytes", FEBS Letters, 1999, 445: 87-91.
Nitta et al., "Peptide-Titanium Complex as Catalyst for Asymmetric Addition of Hydrogen Cyanide to Aldehyde", J. Am. Chem. Soc., 1992, 114: 7969-75.
Norman, "Selective JAK1 inhibitor and selective Tyk2 inhibitor patents," *Expert Opinion*, Informa Healthcare. 2012, available at: <http://informahealthcare.com/dol/pdfplus/10.1517/13543776.2012.723693>.
Norn, "Quantitative tear ferning. Clinical investigations", Acta Ophthalmol (Copenh), 1994, 72(3):369-72.
Notice of Allowance and Fee(s) Due dated Sep. 21, 2007 in connection with U.S. Appl. No. 11/313,394 (6 pages).
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702 (9 pages).
Office Action (Non-final) dated Dec. 3, 2007 in connection with U.S. Appl. No. 11/524,641 (13 pages).
Office Action (Non-final) dated Feb. 25, 2009 for U.S. Appl. No. 12/137,892 (13 pgs.).
Office Action (Final) dated Feb. 7, 2008 for U.S. Appl. No. 11/115,702 (5 pages).
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394 (16 pages).
Office Action in U.S. Appl. No. 14/186,338, dated May 5, 2014, 18 pages.
Office Action received for European Application No. 06 839 328.9 (dated Jan. 22, 2009) (5 pages).
Office Action received for Japanese Application No. 2008-545733 dated Oct. 11, 2011 (5 pages).
Office Action received for New Zealand Application No. 569015 dated Feb. 24, 2010 (2 pages).
Office Action received for Singapore Application No. 2008-04386-1 (dated Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012 (3 pages).

(56) References Cited

OTHER PUBLICATIONS

Office Action, China, Patent Application No. 201080033308.6 dated Aug. 2, 2013, 10 pages.
Office Action, Eurasian Patent Office, prepared Feb. 5, 2010.
Office Action, European Patent Office, Application No. 06 839 328.9 dated Oct. 21, 2010.
Office Action, European Patent Office, dated Nov. 6, 2009 Application 06839328.9.
Office Action, Mexico, Patent Appl. No. MX/a/2008/007635 as received from foreign associate dated Jun. 15, 2010 (1 page).
Office Action, Mexico, Patent Appl. No. MX/a/2008/007635 as received from foreign associate dated Nov. 13, 2009 (4 pages).
Mexican Office Action in Mexican Application No. MX/a/2015/005428, dated Nov. 21, 2018, 3 pages.
Office Action/Examination Report received for Pakistan Application No. 211/2009 dated Jan. 18, 2010 (1 page).
Oguz et al., "The height and radius of the tear meniscus and methods for examining these parameters", Cornea, 2000, 19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008 1 page letter from Foreign Associate enclosing the translation (5 pages) of the Opposition.
Opposition, Ecuador Patent Office in Ecuador Application No. 2016-88985, mailed Dec. 10, 2018, 19 pages.
Ortmann et al., "Janus kinases and signal transducers and activators of transcription: their roles in cytokine signaling, development and immunoregulation," Arthritis Res, 2000, 2(1): 16-32.
Ostojic et al., "Ruxolitinib for the treatment of myelofibrosis," Drugs of Today, Nov. 2011, 47(11): 817-827.
Ousler et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer et al., "Multiple roles of ephrins in morphogenesis, neuronal networking, and brain function," Genes & Dev., 2003, 17:1429-1450.
Pardanani, "JAK2 inhibitor therapy in myeloproliferative disorders: rationale, preclinical studies and ongoing clinical trials JAK2 inhibitor therapy in MPD," Leukemia, Jan. 2008, 22: 23-30.
Parganas et al., "Jak2 is Essential for Signaling through a Variety of Cytokine Receptors," Cell, 1998, 93(3): 385-95.
Park et al., "Homogeneous Proximity Tyrosine Kinase Assays: Scintillation Proximity Assay versus Homogeneous Time-Resolved Fluorescence", Analytical Biochemistry, 1999, 269: 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani et al., "Bioisosterism: A Rational Approach in Drug Design", Chem. Rev., 1996, 96: 3147-3176.
Patrick, "An Introduction to medicinal chemistry" *Oxford University Press Inc.*, New York, 1995 (31 pages) (cited in Opposition from India dated Nov. 12, 2012.
Pearce et al., "Spatial location studies on the chemical composition of human tear ferns", Ophthalmic Physiol Opt, 2000, 20(4):306-13.
Pearce et al., "An improved fluorophotometric method for tear turnover assessment", Optom Vis Sci, 2001, 78(1):30-36.
Pensyl et al., "The repeatability of tear mucus ferning grading", Optom Vis Sci, 1998, 75(8):600-4.

Pernis et al., "JAK-STAT signaling in asthma" J Clin Invest, 2002, 109(10): 1279-83.
Peters et al., "Functional Significance of Tie2 Signaling in the Adult Vasculature", 2004, © The Endocrine Society (21 pages).
Pflugfelder et al., "Evaluation of subjective assessments and objective diagnostic tests for diagnosing tear-film disorders known to cause ocular irritation," Cornea, 1998, 17(1):38-56.
Pillonel "Evaluation of phenylaminopyrimidines as antifungal protein kinase inhibitors," Pest Management Science, Wiley & Sons, Jun. 2005, 61: 1069-1076.
Pirard et al., "Classification of Kinase Inhibitors Using BCUT Descriptors", J. Chem. Inf. Comput. Sci., 2000, 40: 1431-1440.
Pisella et al., "Flow cytometric analysis of conjunctival epithelium in ocular rosacea and keratoconjunctivitis sicca," Ophthalmology, 2000, 107:1841-1849.
Pisella et al., "Conjunctival proinflammatory and proapoptotic effects of latanoprost, preserved timolol and unpreserved timolol: an ex vivo and in vitro study." Invest Ophthalmol Vis Sci, 2004, 45:1360-1368.
Portnaya et. al., "Azomethine dyes. IV. Indoaniline dyes derived from heterocyclic N-substituted 1-hydroxy-2-naphthamide," Ts Vses Nauchn Issled Kinofotoinst, 1960, Issue 40, 106-8 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quesada et al, "One-pot conversion of activated alcohols into 1,1-dibromoalkenes and terminal alkynes using tandem oxidation processes with manganese dioxide", Tetrahedron, 2006, 62: 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, "Preformulation", Remington's Pharmaceutical Sciences, 17th ed., Mack Publishing Company, Easton, Pa., 1985, Chapter 76, 1409-1423.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action dated Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Roberts et al., "Trends in the Risks and Benefits to Patients With Cancer Participating in Phase 1 Clinical Trials," JAMA, 2004, 292(17):2130-2140.
Robin et al., "In vivo transillumination biomicroscopy and photography of meibomian gland dysfunction," Ophthalmology, 1985, 92:1423-6.
Rodig et al., "Disruption of the Jak1 gene demonstrates obligatory and nonredundant roles of the Jaks in cytokine-induced biologic responses." Cell, 1998, 93(3): 373-83.
Rolando et al., "Tear mucus crystallization in children with cystic fibrosis", Ophthalmologica, 1988, 197(4):202-6.

(56) References Cited

OTHER PUBLICATIONS

Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbock (Texas, USA), Dry Eye Institute, 1986, 203-210.
Rolando et al., "The effect of hyperosmolarity on tear mucus ferning", Fortschr Ophthalmol, 1986, 83:644-646.
Rolando et al., "The Ocular Surface and Tear Film and Their Dysfunction in Dry Eye Disease," Survey of Ophthalmology, Mar. 2001, 45(Supplement 2): S203-S210.
Rolando, "Tear mucus ferning test in normal and keratoconjunctivitis sicca eyes," Chibret Int J Ophthalmol, 1984, 2(4):32-41.
Roudebush et al., "Pharmacologic manipulation of a four day marine delayed type hyper sensitivity model", Agents Actions, 1993, 38(1-2):116-21.
Rousvoal et al. "Janus kinase 3 inhibition with CP-690,550 prevents allograft vasculopathy", Transpl Int., 2006, 19(12):1014-21.
Saemann et al., "Prevention of CD40-triggered dendritic cell maturation and induction of T-cell hyporeactivity by targeting of Janus kinase 3," Am J Transplant, 2003, 3(11): 1341-9.
Saettone et al., "Ocular inserts for topical delivery," Advanced Drug Delivery Reviews, 1995, 16: 95-106.
Samanta et al., "Janus kinase 2: a critical target in chronic myelogenous leukemia," Cancer Res., Jul. 2006, 66(13):6468-72.
Sawada et al, "Increased Lipophilicity and Subsequent Cell Partitioning Decrease Passive Transcellular Diffusion of Novel, Highly Lipophilic Antioxidants", The Journal of Pharmacology and Experimental Therapeutics, 1999, 288(3):1317-1326, p. 1321, compound 26.
Schindler et al., "Hormones and Signaling: Cytokines and STAT Signaling," Adv Pharmacol., 2000, 47:113-74.
Schrader et al., "Animal Models of Dry Eye," Developmental Ophthalmology, 2008, 41: 298-312.
Scott et al., "Jaks, STATs, Cytokines, and Sepsis." Clin Diagn Lab Immunol, 2002, 9(6): 1153-9.
Search Report in TW Application No. 100117866, dated Dec. 2014, 1 page.
Seefeld et al, "Discovery of 5-pyrrolopyridinyl-2-thiophenecarboxamides as potent AKT kinase," Bioorganic & Medicinal Chemistry Letters, 2009, 19(8):2244-2248.
Seela et al., "Synthesis of Pyrrolo[2,3-d]pyrimidine 2', 3'-Dideoxyribenucleosides Related to 2',3'-Dideoxyadenosine and 2',3'-Dideoxgtuanosine and Inhibitory Activity of 5'-Triphosphates on HIV-1 Reverse Transcriptase", Helvetica Chimica Acta, 1991, 74(3), 554-64.
Seki, "STAT3 and MAPK in human lung cancer tissues and suppression of oncogenic growth by JAB and dominant negative STAT3", Int J Oncol., 2004, 24(4):931-4.
Seto et al., "Enhanced Th2 cell-mediated allergic inflammation in Tyk2-deficient mice." J Immunol, 2003, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, Aug. 2002, 2:117-125.
Shi et al., "The pharmacokinetics, pharmacodynamics, and safety of orally dosed INCB018424 phosphate in healthy volunteers", Journal of Clinical Pharmacology, Dec. 2011, 51(12): 1644-1654.
Shimazaki et al., "Meibomian gland dysfunction in patients with Sjogren syndrome", Ophthalmology, 1998, 105(8):1485-8.
Smith et al, "Basic pathogenic mechanisms operating in experimental model acute anterior uveitis," Immunology and Cell Biology, 1998, 76: 497-512.
Smolen et al, "Effect of interleukin-6 receptor inhibition with tocilizumab in patients with rheumatoid arthritis (OPTION study): a double-blind, placebo-controlled, randomized trial", Lancet, 2008, 371:987.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodegeneration", J. Biol. Chem., 2004, 279(19):19936-47.
Staerk et. al., "JAK1 and Tyk2 activation by the homologous polycythemia vera JAK2 V617F mutation: cross-talk with IGF1 receptor", J Biol Chem., 2005, 280:41893-41899.
State Intellectual Property Office, PR China, Office Action, dated Sep. 3, 2010 Pat. Appl. No. 200680052750.7 (8 pages).
Stirewalt et al., "Predictors of relapse and overall survival in Philadelphia chromosome-positive acute lymphoblastic leukemia after transplantation", Biol Blood Marrow Transplant., Mar. 2003, 9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Sullivan et al., "4th International Conference on the Lacrimal Gland, Tear Film & Ocular Surface and Dry Eye Syndromes, Nov. 4, 2004" (2 pages).
Takahashi et al., "Solvent-Free Reaction Using Phosphonium Salts: Chlorination of Hydroxyheteroaromatics and dehydration of Primary Amides", Heterocycles, 2006, 68: 1973-1979.
Takano et al., "Inflammatory cells in brush cytology samples correlate with the severity of corneal lesions in atopic keratoconjunctivitis", Br J Ophthalmol, 2004, 88:1504-5.
Takemoto et al., "Proliferation of adult T cell leukemia/lymphoma cells is associated with the constitutive activation of JAK/STAT proteins." Proc Natl Acad Sci USA, 1997, 94(25): 13897-902.
Tan et al, "Racemization processes at a quaternary carbon center in the context of the asymmetric Michael reaction", Tetrahedron Lett., 2001, 42(30):5021-5023.
Tang et al., "Knowledge-based design of 7-azaindoles as selective B-Raf inhibitors", Bioorganic & Medicinal Chemistry Letters, 2008, 18(16):4610-4614.
Tasian et al., "Understanding the biology of CRLF2-overexpressing acute lymphoblastic leukemia", Critical Reviews in Oncogenesis, 2011, 16(1): 13-24.
Tefferi et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, "Primary myelofibrosis: 2012 update on diagnosis, risk stratification, and management," American Journal of Hematology, Dec. 2011, 86(12): 1017-1026.
Tefferi et al., "Serious adverse events during ruxolitinib treatment discontinuation in patients with myelofibrosis", Mayo Clinic Proceedings, Dec. 2011, 86(12): 1188-1191.
Thompson et al., "Photochemical Preparation of a Pyridone Containing Tetracycle: A Jak Protein Kinase Inhibitor", Bioorganic & Medicinal Chemistry Letters, 2002, 12: 1219-1223.
Tiffany et al., Meniscectomy using the Tearscope-plus (ARVO abstract). Invest Ophthalmol Vis Sci, 2001,42: s37 (1 page).
Tiffany, "Refractive index of meibomian and other lipids", Curr Eye Res, 1986, 5:887-9.
Ting et al., "The Synthesis of substituted bipiperidine amide compounds as CCR3 antagonists", Bioorg. Med. Chem. Lett., 2005, 15(5): 1375-1378.
Toyonaga, "Blockade of constitutively activated Janus kinase/signal transducer and activator of transcription-3 pathway inhibits growth of human pancreatic cancer", Cancer Lett., 2003, 201(1):107-16.
Tsubota et al., "Brush cytology for the evaluation of dry-eye", Nippon Ganka Gakkai Zasshi, 1990, 94:224-30 (English Abstract).
Tsubota et al., "Conjunctival brush cytology", Acta Cytol, 1990, 34(2):233-5.
Tsubota et al., "Detection by brush cytology of mast cells and eosinophils in allergic and vernal conjunctivitis," Cornea, 1991, 10(6):525-31.

(56) References Cited

OTHER PUBLICATIONS

Ueda et al., "1,2-Benzisoxazol-3-yl Diphenyl Phosphate: A New, Reactive Activating Agent for the Synthesis of Amides, Esters, and Peptides via Condensation", J. Org. Chem., 1985, 50:760-763.

Vaillant et al., "Turbidity of pulpy fruit juice: A key factor for predicting cross-flow microfiltration performance," J Membrane Sci., 2008, 325:404-412.

van Best et al., "Measurement of basal tear turnover using a standardized protocol", Graefe's Arch Clin Exp Ophthalmol, 1995, 233:1-7.

van Bijsterveld, "Diagnostic tests in the sicca syndrome", Arch Ophthalmol, 1969, 82:10-14.

Vannucchi et al., "The mTOR Inhibitor, RAD001, Inhibits the Growth of Cells From Patients with Myeloproliferative Neoplasms", Blood: ASH Annual Meeting Abstracts, $51^{st}$ Annual Meeting of the American Society of Hematology, 2009, 114(22), 2 pages.

Vannucchi et al., "Inhibitors of PI3K/Akt and/or mTOR Inhibit the Growth of Cells of Myeloproliferative Neoplasms and Synergize with JAK2 Inhibitor and Interferon", Blood, 2011, 118(21): 1638-1639, XP008150742ASH Annual Meeting Abstract 3835 American Society of Hematology.

Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, 114(22), 2 pages.

Vasilevsky et al., "Ethyl Vinyl Ether—an Agent for Protection of the Pyrazole NH-Fragment. A Convenient Method for the Preparation of N-Unsubstituted 6Alkynylpyrazoles", Heterocycles, 2003, 60(4):879-886.

Verma et al., "Jak family of kinases in cancer", Cancer and Metastasis Reviews, 2003, 22(4): 423-434, DOI: 10.1023/A:1023805715476.

Verstovsek, "Therapeutic Potential of JAK2 Inhibitors", Hematology Am Soc Hematol Educ Program, 2009:636-42.

Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).

Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).

Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).

Verstovsek, Srdan et al., "Characterization of JAKS V617F Allele Burden in Advanced Myelofibrosis (NT) Patients: No Change in V617F:WT JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).

Vitali et al. "The European Community Study Group on diagnostic criteria for Sjogren's syndrome. Sensitivity and specificity of tests for ocular and oral involvement in Sjogren's syndrome," Ann Rheum Dis, 1994, 53(10): 637-47.

Wagh et al., "Polymers used in ocular dosage form and drug delivery systems", Asian J. Pharm., Jan. 2008, 12-17.

WebMD. "Diabetes Health Center." Available at: < http://diabetes.webmd.com/guide/diabetestreatment_care >. 3 pages, retrieved from the Internet May 28, 2013.

Webster's New World Medical Dictionary, Sjogren's syndrome, 2003, Wiley Publishing, printed fro http://www.credoreference.com/entry/webstermed/sjogren_s_syndrome, 2 pages.

Weiss et al., "Evaluation of a Series of Naphthamides as Potent, Orally Active Vascular Endothelial Growth Factor Receptor-2 Tyrosine Kinase Inhibitors", J. Med Chem., 2008, 51:1668-1680.

Welch et al., "An approach to a more standardized method of evaluating tear film break-up time", Invest Ophthalmol Vis Sci, 2003, 2485/B324 (abstract only—2 pages).

White et al., "Human basic tear fluid osmolality. I. Importance of sample collection strategy", Acta Ophthalmol (Copenh), Aug. 1993, 71(4):524-9.

Williams and Ibrahim, "Carbodiimide Chemistry: Recent Advances", Chem. Rev., 1981, 81:589-636.

Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.

Wolf et al., "Burger's Medicinal Chemistry and Drug Discovery", 5th Ed. Part I, 1995, 975-977.

Wu et al., One-Pot Two-Step Microwave-Assisted Reaction in Construction 4,5-Disubstituted Pyrazolopyrimidines Organic Letters, 2003, 5(20): 3587-3590.

Wuts and Greene, Protective Groups in Organic Synthesis, 4th ed., John Wiley & Sons: New Jersey, 2007 **Too Voluminous to Provide.

Yamaoka et al., "Janus kinase (JAK) inhibitors in rheumatoid arthritis", Current Rheumatology Reviews, Nov. 2011, 7(4): 306-312.

Yang et al., "Constitutive NF-KB activation confers interleukin 6 (IL6) independence and resistance to dexamethasone and Janus kinase inhibitor INCB018424 in murine plasmacytoma cells", Journal of Biological Chemistry, Aug. 2011, 286(32):27988-27997.

Yao et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 2008, 58(11):3485-3497.

Yao, et al., "Glucocorticoid Excess in Mice Results in Early Activation of Osteoclastogenesis and Adipogenesis and Prolonged Suppression of Osteogenesis", Arthritis and Rheumatism, 2008, 58(6), 1674-1686.

Yokoi et al., "A newly developed video-meibography system featuring a newly designed probe", Jpn J Ophthalmol, 2007, 51: 53-6.

Yokoi et al., "Assessment of meibomian gland function in dry eye using meibometry", Arch Ophthalmol, 1999, 117:723-9.

Yokoi et al., "Correlation of tear lipid layer interference patterns with the diagnosis and severity of dry eye", Am J Ophthalmol, 1996, 122:818-24.

Yokoi et al., "Non-invasive methods of assessing the tear film", Exp Eye Res, 2004, 78:399-407.

Yu et al., "Constitutive activation of the Janus kinase-STAT pathway in T lymphoma overexpressing the Lck protein tyrosine kinase," J Immunol., 1997, 159(11):5206-10.

Zak et al., "Discovery and Optimization of C-2 Methyl Imidazopyrrolopyridines as Potent and Orally Bioavailable JAK1 Inhibitors with Selectivity over JAK2," Journal of Medicinal Chemistry, vol. 55, No. 13, 2012, pp. 6176-6193.

Zheng et al., "Discovery of INCB108201PF-4178903, a potent, selective, and orally bioavailable dual CCR2 and CCR5 antagonist", Bioorganic & Medicinal Chemistry Letters, 2011, 21: 1442-45.

Zoppellaro et al., "A Multifunctional High-Spin Biradical Pyrazolylbipyridine-bisnitronylnitroxide", Org. Lett., 2004, 6(26):4929-4932.

Zou et al., "Signaling Pathways Activated by Oncogenic Forms of Abl Tyrosine Kinase." Journal of Biological Chemistry, 1999, 274(26):18141-18144.

Colombian Office Action in Colombian Application No. NC2016/0004392, dated May 4, 2018 , 9 Pages.

Australian Office Action in Australian Application No. 2015253192, dated Oct. 12, 2018, 3 pages.

Japanese Office Action in Japanese Application No. 2016-565276, dated Nov. 27, 2018, 6 pages (English Translation).

(56) References Cited

OTHER PUBLICATIONS

Chinese office action in Chinese application No. 2015800346623, dated Nov. 14, 2018, 6 pages.
Japanese Office Action in Japanese Application No. 2016-565276, dated Jun. 25, 2019, 5 pages.
Taiwan Office Action in Taiwan Application No. 104113773, dated May 8, 2019, 7 pages.
Vietnamese Office Action in Vietnamese Application No. 1-2015-01897, dated Jun. 24, 2019, 4 pages.
Mexican Office Action in Mexican Application No. MX/a/2015/005428, dated Jun. 21, 2019, 3 pages.
Chinese Office Action in Chinese Application No. 201580034662.3, dated Jun. 19, 2019, 7 pages.
Brazilian Office Action in Brazilian Application No. BR112016025427-9, dated Oct. 16, 2020, 6 pages.
Korean Office Action in Korean Application No. 10-2015-7014467, dated Apr. 28, 2020, 12 pages.
Peruvian office action in Peruvian Application No. 2151, dated Sep. 4, 2020, 14 pages.

* cited by examiner

TRICYCLIC FUSED THIOPHENE DERIVATIVES AS JAK INHIBITORS

This application is a continuation of U.S. Ser. No. 15/874,140, filed Jan. 18, 2018, which is a continuation of U.S. Ser. No. 14/873,078, filed Oct. 1, 2015, which is a continuation of U.S. Ser. No. 14/068,796, filed Oct. 31, 2013, which claims the benefit of priority of U.S. Provisional Application No. 61/721,308, filed Nov. 1, 2012, and U.S. Provisional Application No. 61/783,850, filed Mar. 14, 2013, each of which is incorporated herein by reference in its entirety.

TECHNICAL FIELD

The present invention provides tricyclic fused thiophene derivatives, as well as their compositions and methods of use, that modulate the activity of Janus kinase (JAK) and are useful in the treatment of diseases related to the activity of JAK including, for example, inflammatory disorders, autoimmune disorders, cancer, and other diseases.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1−/− mice are runted at birth, fail to nurse, and die perinatally (Rodig, S. J., M. A. Meraz, et al. (1998) *Cell* 93(3): 373-83). Jak2−/− mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol.* 2000; 47:113-74).

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY

The present invention provides, inter alia, compounds of Formula I:

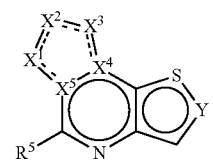

and pharmaceutically acceptable salts thereof; wherein Y, $X^1$, $X^2$, $X^3$, $X^4$, $X^5$, $R^5$, and $=\!=\!=$ are defined infra.

The present invention further provides compositions comprising a compound of Formula I, or a pharmaceutically acceptable salt thereof, and a pharmaceutically acceptable carrier.

The present invention further provides methods of modulating an activity of JAK1 comprising contacting JAK1 with a compound of Formula I, or a pharmaceutically acceptable salt thereof.

The present invention further provides methods of treating a disease or a disorder associated with abnormal kinase expression or activity in a patient by administering to a patient a therapeutically effective amount of a compound of Formula I, or a pharmaceutically acceptable salt thereof.

The present invention further provides methods of treating an autoimmune disease, a cancer, a myeloproliferative disorder, an inflammatory disease, a bone resorption disease, or organ transplant rejection in a patient in need thereof, comprising administering to said patient a therapeutically effective amount of a compound of Formula I, or a pharmaceutically acceptable salt thereof.

The present invention also provides compounds of Formula I, or pharmaceutically acceptable salts thereof, as described herein for use in treatment of autoimmune diseases, cancer, myeloproliferative disorders, inflammatory diseases, a bone resorption disease, or organ transplant rejection.

The present invention further provides compounds of Formula I as described herein, or pharmaceutically acceptable salts thereof, for use in modulating JAK1.

The present invention also provides uses of compounds of Formula I as described herein, or pharmaceutically acceptable salts thereof, for the preparation of medicaments for use in methods of modulating JAK1.

DETAILED DESCRIPTION

The present invention provides, inter alia, a compound of Formula I:

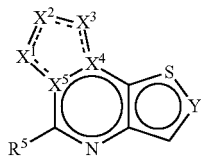

or a pharmaceutically acceptable salt thereof, wherein:
the

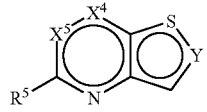

ring system is aromatic;
each ═ is independently selected from a single bond and a double bond;
Y is N or $CR^4$;
$X^1$ is selected from $CR^1$, $CR^4R^{1a}$, $C(=O)$, N, $NR^1$, O, and S;
$X^2$ is selected from $CR^2$, $C(=O)$, N, $NR^2$, and $C(=NR^{2a})$;
$X^3$ is selected from $CR^3$ and $NR^3$;
$X^4$ is selected from C and N; and $X^5$ is C; or
$X^4$ is C; and $X^5$ is selected from C and N;
provided that:
(i) the selections for each of $X^1$, $X^2$, $X^3$, $X^4$, $X^5$ and ═ maintain proper valency;
(ii) when $X^1$ is O or S, then $X^2$ is not $NR^2$ and $X^2$ ═ $X^3$ is not —C(=O)—$CR^3$—;

(iii) when $X^1$ is $NR^1$, then $X^2$ ═ $X^3$ is not —$NR^2$—$NR^3$—;
(iv) when $X^4$ is N, then $X^1$ ═ $X^2$ ═ $X^3$ is not =N—$NR^2$—$NR^3$—; and
(v) when $X^5$ is N, then $X^1$ ═ $X^2$ is not —$NR^1$—$NR^2$— and $X$ ═ $X^2$ ═ $X^3$ is not —$CR^1R^{1a}$—$NR^2$—$CR^3$═;

$R^1$ is selected from H, halo, CN, $NH_2$, $C_{1-3}$ alkyl, $C_{1-3}$ alkoxy, and $C_{1-3}$ haloalkyl;
$R^{1a}$ is selected from H, halo, CN, $NH_2$, $C_{1-3}$ alkyl, and $C_{1-3}$ haloalkyl;
$R^{2a}$ is selected from CN, OH, $OCH_3$, and $NO_2$;
$R^2$ is selected from H, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkyl-S—, CN, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^a$, $NR^cC(=O)NR^cR^d$, $C(=NR^e)R^b$, $C(=NR^e)NR^cR^d$, $NR^cC(=NR^e)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$; wherein said $C_{1-6}$ alkyl, $C_{2-6}$ alkenyl, $C_{2-6}$ alkynyl, $C_{1-6}$ alkoxy, and $C_{1-6}$ alkyl-S— are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

alternatively, $R^2$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $R^{21}$, $Cy^2$, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

provided that when $X^1$ ═ $X^2$ ═ $X^3$ is —N=$CR^2$—$NR^3$—, $X^4$ is C, and $X^5$ is C; and $Cy^4$ is unsubstituted or substituted 3-10 membered saturated heterocycloalkylene having one or more nitrogen atoms or $Cy^{4A}$ is unsubstituted or substituted 3-10 membered saturated heterocycloalkylene having one or more nitrogen atoms, then $R^2$ is selected from H, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkyl-S—, CN, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^a$, $NR^cC(=O)NR^cR^d$, $C(=NR^e)R^b$, $C(=NR^e)NR^cR^d$, $NR^cC(=NR^e)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$; wherein said $C_{1-6}$ alkyl, $C_{2-6}$ alkenyl, $C_{2-6}$ alkynyl, $C_{1-6}$ alkoxy, and $C_{1-6}$ alkyl-S— are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

each $R^{21}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, C(=NR$^e$)NR$^c$R$^d$, NR$^c$C(=NR$^e$)NR$^c$R$^d$, NR$^c$R$^d$, NR$^c$C(=O)R$^b$, NR$^c$C(=O)OR$^a$, NR$^c$C(=O)NR$^c$R$^d$, NR$^c$S(=O)R$^b$, NR$^c$S(=O)$_2$R$^b$, NR$^c$S(=O)$_2$NR$^c$R$^d$, S(=O)R$^b$, S(=O)NR$^c$R$^d$, S(=O)$_2$R$^b$, and S(=O)$_2$NR$^c$R$^d$;

alternatively, when two R$^{21}$ groups are attached to the same carbon atom, the two R$^{21}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, $C_{1-3}$ alkyl, $C_{1-3}$ alkoxy, and $C_{1-3}$ haloalkyl;

each Cy$^2$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, R$^{22}$, CN, NO$_2$, OR$^a$, SR$^a$, C(=O)R$^b$, C(=O)NR$^c$R$^d$, C(=O)OR$^a$, OC(=O)R$^b$, OC(=O)NR$^c$R$^d$, C(=NR$^e$)NR$^c$R$^d$, NR$^c$C(=NR$^e$)NR$^c$R$^d$, NR$^c$R$^d$, NR$^c$C(=O)R$^b$, NR$^c$C(=O)OR$^a$, NR$^c$C(=O)NR$^c$R$^d$, NR$^c$S(=O)R$^b$, NR$^c$S(=O)$_2$R$^b$, NR$^c$S(=O)$_2$NR$^c$R$^d$, S(=O)R$^b$, S(=O)NR$^c$R$^d$, S(=O)$_2$R$^b$, and S(=O)$_2$NR$^c$R$^d$;

each R$^a$, R$^c$, and R$^d$ are independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(=O)R$^{b1}$, NR$^{c1}$C(=O)OR$^{a1}$, NR$^{c1}$C(=O)NR$^{c1}$R$^{d1}$, NR$^{c1}$S(=O)R$^{b1}$, NR$^{c1}$S(=O)$_2$R$^{b1}$, NR$^{c1}$S(=O)$_2$NR$^{c1}$R$^{d1}$, S(=O)R$^{b1}$, S(=O)NR$^{c1}$R$^{d1}$, S(=O)$_2$R$^{b1}$, and S(=O)$_2$NR$^{c1}$R$^{d1}$;

each R$^b$ is independently selected from $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, CM alkyl, $C_{2-6}$ alkenyl, $C_{2-6}$ alkynyl, $C_{1-6}$ haloalkyl, CN, NO$_2$, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(=O)R$^{b1}$, NR$^{c1}$C(=O)OR$^{a1}$, NR$^{c1}$C(=O)NR$^{c1}$R$^{d1}$, NR$^{c1}$S(=O)R$^{b1}$, NR$^{c1}$S(=O)$_2$R$^{b1}$, NR$^{c1}$S(=O)$_2$NR$^{c1}$R$^{d1}$, S(=O)R$^{b1}$, S(=O)NR$^{c1}$R$^{d1}$, S(=O)$_2$R$^{b1}$, and S(=O)$_2$NR$^{c1}$R$^{d1}$;

each R$^e$ is independently selected from H, CN, OH, $C_{1-4}$ alkyl, $C_{1-4}$alkoxy, NO$_2$, C(O)(C$_{1-4}$ alkyl), and S(=O)$_2$(C$_{1-4}$ alkyl);

each R$^{22}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from Cy$^3$, halo, CN, NO$_2$, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(=O)R$^{b1}$, NR$^{c1}$C(=O)OR$^{a1}$, NR$^{c1}$C(=O)NR$^{c1}$R$^{d1}$, NR$^{c1}$S(=O)R$^{b1}$, NR$^{c1}$S(=O)$_2$R$^{b1}$, NR$^{c1}$S(=O)$_2$NR$^{c1}$R$^{d1}$, S(=O)R$^{b1}$, S(=O)NR$^{c1}$R$^{d1}$, S(=O)$_2$R$^{b1}$, and S(=O)$_2$NR$^{c1}$R$^{d1}$;

each R$^{a1}$, R$^{c1}$, and R$^{d1}$ are independently selected from H, $C_{1-3}$ alkyl, $C_{2-3}$ alkenyl, $C_{2-3}$ alkynyl, and $C_{1-3}$ haloalkyl;

each R$^{b1}$ is independently selected from $C_{1-3}$ alkyl, $C_{2-3}$ alkenyl, $C_{2-3}$ alkynyl, and $C_{1-3}$ haloalkyl;

each R$^{e1}$ is independently selected from H, CN, OH, $C_{1-4}$ alkyl, and $C_{1-4}$ alkoxy;

each Cy$^3$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $C_{1-6}$ alkyl, $C_{2-6}$ alkenyl, $C_{2-6}$ alkynyl, $C_{1-6}$ haloalkyl, halo, CN, NO$_2$, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(=O)R$^{b1}$, NR$^{c1}$C(=O)OR$^{a1}$, NR$^{c1}$C(=O)NR$^{c1}$R$^{d1}$, NR$^{c1}$S(=O)R$^{b1}$, NR$^{c1}$S(=O)$_2$R$^{b1}$, NR$^{c1}$S(=O)$_2$NR$^{c1}$R$^{d1}$, S(=O)R$^{b1}$, S(=O)NR$^{c1}$R$^{d1}$, S(=O)$_2$R$^{b1}$, and S(=O)$_2$NR$^{c1}$R$^{d1}$;

R$^3$ is selected from Cy$^4$, -Cy$^{4A}$-Cy$^5$, -Cy$^{4A}$-Y$^1$-Cy$^5$, -Cy$^{4A}$-Y$^1$-Cy$^{5A}$-Cy$^6$, -Cy$^{4A}$-Cy$^{5A}$-Y$^2$-Cy$^6$, -Cy$^{4A}$-Y$^1$-Cy$^{5A}$-Y$^2$-Cy$^6$, or -Cy$^{4A}$-Y$^3$-Cy$^6$;

Cy$^4$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected R$^{31}$ groups;

Cy$^{4A}$ is selected from $C_{6-10}$ arylene, $C_{3-10}$ cycloalkylene, 5-10 membered heteroarylene, and 3-10 membered heterocycloalkylene, wherein said $C_{6-10}$ arylene, $C_{3-10}$ cycloalkylene, 5-10 membered heteroarylene, and 3-10 membered heterocycloalkylene are optionally substituted with 1, 2, 3, or 4 independently selected R$^{31}$ groups;

Y$^1$ is Y$^{11}$, $C_{1-6}$ alkylene, $C_{2-6}$ alkenylene, $C_{2-6}$ alkynylene, $C_{1-6}$ alkylene-Y$^{11}$, $C_{2-6}$ alkenylene-Y$^{11}$, $C_{2-6}$ alkynylene-Y$^{11}$, Y$^{11}$—$C_{1-6}$ alkylene, Y$^{11}$—$C_{2-6}$ alkenylene, or Y$^{11}$—$C_{2-6}$ alkynylene, wherein said alkylene, alkenylene and alkynylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

Cy$^5$ and Cy$^6$ are each independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected R$^{32}$ groups;

Cy$^{5A}$ is selected from $C_{6-10}$ arylene, $C_{3-10}$ cycloalkylene, 5-10 membered heteroarylene, and 3-10 membered heterocycloalkylene, wherein said $C_{6-10}$ arylene, $C_{3-10}$ cycloalkylene, 5-10 membered heteroarylene, and 3-10 membered heterocycloalkylene are each optionally substituted with 1, 2, 3, or 4 independently selected R$^{32}$ groups;

Y$^2$ is Y$^{21}$, $C_{1-6}$ alkylene, $C_{2-6}$ alkenylene, $C_{2-6}$ alkynylene, $C_{1-6}$ alkylene-Y$^{21}$, $C_{2-6}$ alkenylene-Y$^{21}$, $C_{2-6}$ alkynylene-Y$^{21}$, Y$^{21}$—$C_{1-6}$ alkylene, Y$^{21}$—$C_{2-6}$ alkenylene, or Y$^{21}$—$C_{2-6}$ alkynylene, wherein said alkylene, alkenylene and alkynylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

Y$^3$ is $C_{1-6}$ alkylene-Y$^{31}$—$C_{1-6}$ alkylene, $C_{1-6}$ alkylene-Y$^{31}$—$C_{1-6}$ alkylene-Y$^{31}$, or Y$^{31}$—$C_{1-6}$ alkylene-Y$^{31}$—$C_{1-6}$ alkylene, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

each $Cy^7$ is independently selected from $C_{6-10}$ aryl, $C_{3-10}$cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 independently selected $R^{33}$ groups;

$Y^{11}$, $Y^{21}$, and $Y^{31}$ are each independently selected from O, S, C(=O), C(=O)NR$^f$, C(=O)O, OC(=O), OC(=O)NR$^f$, NR$^f$, NR$^f$C(=O), NR$^f$C(=O)O, NR$^f$C(=O)NR$^f$, NR$^f$S(=O), NR$^f$S(=O)$_2$, NR$^f$S(=O)$_2$NR$^f$, S(=O), S(=O)NR$^f$, S(=O)$_2$, and S(=O)$_2$NR$^f$;

each $R^{31}$ is independently selected from $Cy^7$, $C_{1-6}$ alkyl, $C_{2-6}$ alkenyl, $C_{2-6}$ alkynyl, $C_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each $R^{32}$ is independently selected from $C_{1-6}$ alkyl, $C_{2-6}$ alkenyl, $C_{2-6}$ alkynyl, $C_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each $R^{33}$ is independently selected from halo, OH, NO$_2$, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonyloxy, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

alternatively, when two $R^{33}$ groups are attached to the same carbon atom, the two $R^{33}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, $C_{1-3}$ alkyl, $C_{1-3}$ alkoxy, and $C_{1-3}$ haloalkyl;

each $R^{a2}$, $R^{c2}$, and $R^{d2}$ are independently selected from H, CM alkyl, $C_{2-6}$ alkenyl, $C_{2-6}$ alkynyl, and CM haloalkyl, wherein said $C_{1-6}$ alkyl, $C_{2-6}$ alkenyl, and $C_{2-6}$ alkynyl are each optionally substituted with 1, 2, or 3 substituents independently selected from $R^{33}$;

each $R^{b2}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $R^{33}$;

each $R^{e2}$ is independently selected from H, CN, OH, $C_{1-4}$ alkyl, and $C_{1-4}$ alkoxy;

each $R^f$ is independently selected from H and $C_{1-3}$ alkyl;

$R^4$ is selected from H, halo, CN, NH$_2$, $C_{1-3}$ alkyl, and $C_{1-3}$ haloalkyl; and $R^5$ is selected from H, halo, cyano, hydroxy, amino, ($C_{1-4}$ alkyl)amino, di($C_{1-4}$ alkyl)amino, $C_{1-4}$ alkyl, $C_{1-4}$ haloalkyl, and $C_{1-4}$ alkoxy.

In some embodiments:
the

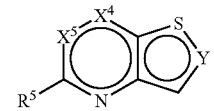

ring system is aromatic;

each ═ is independently selected from a single bond and a double bond;

Y is N or CR$^4$;

$X^1$ is selected from CR$^1$, CR$^3$R$^{1a}$, C(=O), N, NR$^1$, O, and S;

$X^2$ is selected from CR$^2$, C(=O), N, NR$^2$, and C(=NR$^{2a}$);

$X^3$ is selected from CR$^3$ and NR$^3$;

$X^4$ is selected from C and N; and $X^5$ is C; or $X^4$ is C; and $X^5$ is selected from C and N;

provided that:

(i) the selections for each of $X^1$, $X^2$, $X^3$, $X^4$, $X^5$ and ═ maintain proper valency;

(ii) when $X^1$ is O or S, then $X^2$ is not NR$^2$ and $X^2$—$X^3$ is not —C(=O)—CR$^3$—;

(iii) when $X^1$ is NR$^1$, then $X^2$ ═ $X^3$ is not —NR$^2$—NR$^3$—;

(iv) when $X^4$ is N, then $X^1$ ═ $X^2$ ═ $X^3$ is not =N—NR$^2$—NR$^3$—; and (v) when $X^5$ is N, then $X^1$ ═ $X^2$ is not —NR$^1$—NR$^2$— and $X^1$ ═ $X^2$ ═ $X^3$ is not —CR$^1$R$^{1a}$—NR$^2$—CR$^3$═;

$R^1$ is selected from H, halo, CN, NH$_2$, $C_{1-3}$ alkyl, $C_{1-3}$ alkoxy, and $C_{1-3}$ haloalkyl;

$R^{1a}$ is selected from H, halo, CN, NH$_2$, $C_{1-3}$ alkyl, and $C_{1-3}$ haloalkyl;

$R^{2a}$ is selected from CN, OH, OCH$_3$, and NO$_2$;

$R^2$ is selected from H, halo, CM alkyl, $C_{2-6}$ alkenyl, $C_{2-6}$ alkynyl, CM haloalkyl, $C_{1-6}$ alkoxy, $C_{1-6}$ alkyl-S—, CN, OC(=O)R$^b$, OC(=O)NR$^c$R$^d$, NR$^c$R$^d$, NR$^c$C(=O)R$^b$, NR$^c$C(=O)OR$^a$, NR$^c$C(=O)NR$^c$R$^d$, C(=NR$^e$)R$^b$, C(=NR$^e$)NR$^c$R$^d$, NR$^c$C(=NR$^e$)NR$^c$R$^d$, NR$^c$S(=O)R$^b$, NR$^c$S(=O)$_2$R$^b$, NR$^c$S(=O)$_2$NR$^c$R$^d$, S(=O)R$^b$, S(=O)NR$^c$R$^d$, S(=O)$_2$R$^b$, and S(=O)$_2$NR$^c$R$^d$; wherein said CM alkyl, $C_{2-6}$ alkenyl, $C_{2-6}$ alkynyl, CM alkoxy, and $C_{1-6}$ alkyl-S— are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

alternatively, $R^2$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $R^{21}$, $Cy^2$, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

each $R^{21}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

alternatively, when two $R^{21}$ groups are attached to the same carbon atom, the two $R^{21}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, $C_{1-3}$ alkyl, $C_{1-3}$ alkoxy, and $C_{1-3}$ haloalkyl;

each $Cy^2$ is independently selected from $C_{6-10}$ aryl, $C_{3-10}$ cycloalkyl, 5-10 membered heteroaryl, and 3-10 membered heterocycloalkyl wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $R^{22}$, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

each $R^a$, $R^c$, and $R^d$ are independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^b$ is independently selected from $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^e$ is independently selected from H, CN, OH, $C_{1-4}$ alkyl, $C_{1-4}$alkoxy, $NO_2$, $C(O)(C_{1-4}$ alkyl), and $S(=O)_2(C_{1-4}$ alkyl);

each $R^{22}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^{a1}$, $R^{c1}$, and $R^{d1}$ are independently selected from H, $C_{1-3}$ alkyl, $C_{2-3}$ alkenyl, $C_{2-3}$ alkynyl, and $C_{1-3}$ haloalkyl;

each $R^{b1}$ is independently selected from $C_{1-3}$ alkyl, $C_{2-3}$ alkenyl, $C_{2-3}$ alkynyl, and $C_{1-3}$ haloalkyl;

each $R^{e1}$ is independently selected from H, CN, OH, $C_{1-4}$ alkyl, and $C_{1-4}$alkoxy;

each $Cy^3$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $C_{1-6}$ alkyl, $C_{2-6}$ alkenyl, $C_{2-6}$ alkynyl, $C_{1-6}$ haloalkyl, halo, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

$R^3$ is $Cy^4$, $-Cy^{4A}-Cy^5$, $-Cy^{4A}-Y^1-Cy^5$, $-Cy^{4A}-Y^1-Cy^{5A}-Cy^6$, $-Cy^{4A}-Cy^{5A}-Y^2-Cy^6$, $-Cy^{4A}-Y^1-Cy^{5A}-Y^2-Cy^6$, or $-Cy^{4A}-Y^3-Cy^6$;

$Cy^4$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{31}$ groups, wherein said 3-10 membered heterocycloalkyl is not a saturated heterocycloalkyl group having one or more nitrogen ring members;

$Cy^{4A}$ is selected from $C_{6-10}$ arylene, $C_{3-10}$ cycloalkylene, 5-10 membered heteroarylene, and 3-10 membered heterocycloalkylene, wherein said $C_{6-10}$ arylene, $C_{3-10}$ cycloalkylene, 5-10 membered heteroarylene, and 3-10 membered heterocycloalkylene are optionally substituted with 1, 2, 3, or 4 independently selected $R^{31}$ groups, wherein said 3-10 membered heterocycloalkylene is not a saturated heterocycloalkylene group having one or more nitrogen ring members;

$Y^1$ is $Y^{11}$, $C_{1-6}$ alkylene, $C_{2-6}$ alkenylene, $C_{2-6}$ alkynylene, $C_{1-6}$ alkylene-$Y^{11}$, $C_{2-6}$ alkenylene-$Y^{11}$, $C_{2-6}$ alkynylene-$Y^{11}$, $Y^{11}$—$C_{1-6}$ alkylene, $Y^{11}$—$C_{2-6}$ alkenylene, or $Y^{11}$—$C_{2-6}$ alkynylene, wherein said alkylene, alkenylene and alkynylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

$Cy^5$ and $Cy^6$ are each independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{32}$ groups;

$Cy^{5A}$ is selected from $C_{6-10}$ arylene, $C_{3-10}$ cycloalkylene, 5-10 membered heteroarylene, and 3-10 membered heterocycloalkylene, wherein said $C_{6-10}$ arylene, $C_{3-10}$ cycloalkylene, 5-10 membered heteroarylene, and 3-10 membered heterocycloalkylene are each optionally substituted with 1, 2, 3, or 4 independently selected $R^{32}$ groups;

$Y^2$ is $Y^{21}$, $C_{1-6}$ alkylene, $C_{2-6}$ alkenylene, $C_{2-6}$ alkynylene, $C_{1-6}$ alkylene-$Y^{21}$, $C_{2-6}$ alkenylene-$Y^{21}$, $C_{2-6}$ alkynylene-$Y^{21}$, $Y^{21}$—$C_{1-6}$ alkylene, $Y^{21}$—$C_{2-6}$ alkenylene, or $Y^{21}$—$C_{2-6}$ alkynylene, wherein said alkylene, alkenylene and alkynylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

$Y^3$ is $C_{1-6}$ alkylene-$Y^{31}$—$C_{1-6}$ alkylene, $C_{1-6}$ alkylene-$Y^{31}$—$C_{1-6}$ alkylene-$Y^{31}$, or $Y^{31}$—$C_{1-6}$ alkylene-$Y^{31}$—$C_{1-6}$ alkylene, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

each $Cy^7$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 independently selected $R^{33}$ groups;

$Y^{11}$, $Y^{21}$, and $Y^{31}$ are each independently selected from O, S, C(=O), C(=O)NR$^f$, C(=O)O, OC(=O), OC(=O)NR$^f$, NR$^f$, NR$^f$C(=O), NR$^f$C(=O)O, NR$^f$C(=O)NR$^f$, NR$^f$S(=O), NR$^f$S(=O)$_2$, NR$^f$S(=O)$_2$NR$^f$, S(=O), S(=O)NR$^f$, S(=O)$_2$, and S(=O)$_2$NR$^f$;

each $R^{31}$ is independently selected from $Cy^7$, $C_{1-6}$ alkyl, $C_{2-6}$ alkenyl, $C_{2-6}$ alkynyl, $C_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, and S(=O)$_2$NR$^{c2}$R$^{d2}$;

each $R^{32}$ is independently selected from $C_{1-6}$ alkyl, $C_{2-6}$ alkenyl, $C_{2-6}$ alkynyl, $C_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each $R^{33}$ is independently selected from halo, OH, NO$_2$, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$alkoxy-$C_{1-3}$ alkyl, $C_{3-7}$ cycloalkyl, $C_{1-3}$alkoxy, $C_{1-3}$ haloalkoxy, amino, $C_{1-3}$alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$alkyl)carbamyl, carboxy, $C_{1-3}$ alkylcarbonyl, $C_{1-4}$ alkoxycarbonyl, $C_{1-3}$ alkylcarbonyloxy, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$alkylaminocarbonylamino, and di($C_{1-3}$alkyl)aminocarbonylamino;

alternatively, when two $R^{33}$ groups are attached to the same carbon atom, the two $R^{33}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, $C_{1-3}$ alkyl, $C_{1-3}$ alkoxy, and $C_{1-3}$ haloalkyl;

each $R^{a2}$, $R^{c2}$, and $R^{d2}$ are independently selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $R^{33}$;

each $R^{b2}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $R^{33}$;

each $R^{e2}$ is independently selected from H, CN, OH, $C_{1-4}$ alkyl, and $C_{1-4}$ alkoxy;

each $R^f$ is independently selected from H and $C_{1-3}$ alkyl;

$R^4$ is selected from H, halo, CN, NH$_2$, $C_{1-3}$ alkyl, and $C_{1-3}$ haloalkyl; and $R^5$ is selected from H, halo, cyano, hydroxy, amino, ($C_{1-4}$ alkyl)amino, di($C_{1-4}$ alkyl)amino, $C_{1-4}$ alkyl, $C_{1-4}$ haloalkyl, and $C_{1-4}$ alkoxy.

In some embodiments:

$R^2$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkyl-S—, NR$^c$R$^d$, NR$^c$C(=O)R$^b$, NR$^c$C(=O)OR$^a$, NR$^c$C(=O)NR$^c$R$^d$, NR$^c$S(=O)R$^b$, NR$^c$S(=O)$_2$R$^b$, NR$^c$S(=O)$_2$NR$^c$R$^d$, S(=O)$_2$R$^b$, and S(=O)$_2$NR$^c$R$^d$; wherein said $C_{1-6}$ alkyl, $C_{2-6}$ alkenyl, $C_{2-6}$ alkynyl and $C_{1-6}$ alkoxy, and $C_{1-6}$ alkyl-S— are each optionally substituted with 1, 2, or 3 substituents independently selected from halo, CN, OR$^a$, SR$^a$, C(=O)R$^b$, C(=O)NR$^c$R$^d$, C(=O)OR$^a$, OC(=O)R$^b$, OC(=O)NR$^c$R$^d$, C(=NR$^e$)NR$^c$R$^d$, NR$^c$C(=NR$^e$)NR$^c$R$^d$, NR$^c$R$^d$, NR$^c$C(=O)R$^b$, NR$^c$C(=O)OR$^a$, NR$^c$C(=O)NR$^c$R$^d$, NR$^c$S(=O)

$R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

$R^a$, $R^c$, and $R^d$ are independently selected from H, $C_{1-6}$ alkyl, and $C_{1-6}$ haloalkyl, wherein said $C_{1-6}$ alkyl is optionally substituted with 1, 2, or 3 substituents independently selected from halo, CN, $OR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$; and each $R^b$ is independently selected from $C_{1-6}$ alkyl and $C_{1-6}$ haloalkyl, wherein said $C_{1-6}$ alkyl is optionally substituted with 1, 2, or 3 substituents independently selected from halo, $C_{1-6}$ alkyl, CN, $OR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$.

In some embodiments:

$R^2$ is $C_{1-6}$ alkyl, which is optionally substituted with 1, 2, or 3 substituents independently selected from halo, CN, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

$R^a$, $R^c$, and $R^d$ are independently selected from H, $C_{1-6}$ alkyl, and $C_{1-6}$ haloalkyl, wherein said $C_{1-6}$ alkyl is optionally substituted with 1, 2, or 3 substituents independently selected from halo, CN, $OR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^b$ is independently selected from $C_{1-6}$ alkyl and $C_{1-6}$ haloalkyl, wherein said $C_{1-6}$ alkyl is optionally substituted with 1, 2, or 3 substituents independently selected from halo, $C_{1-6}$ alkyl, CN, $OR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$.

In some embodiments, $R^2$ is $C_{1-6}$ alkyl, $C_{1-6}$alkoxy, and $C_{1-6}$alkyl-S—, each of which is optionally substituted with 1, 2, or 3 substituents independently selected from halo, CN, OH, $C_{1-6}$ alkoxy, $S(C_{1-6}$ alkyl), $C(=O)(C_{1-6}$ alkyl), $C(=O)NH_2$, $C(=O)NH(C_{1-6}$ alkyl), $C(=O)N(C_{1-6}$alkyl)$_2$, $C(=O)O(C_{1-6}$ alkyl), $OC(=O)(C_{1-6}$ alkyl), $OC(=O)NH_2$, $OC(=O)NH(C_{1-6}$ alkyl), $OC(=O)N(C_{1-6}$ alkyl)$_2$, $C(=NH)NH_2$, $C(=NH)NH(C_{1-6}$ alkyl), $C(=NH)N(C_{1-6}$alkyl)$_2$, $NHC(=NH)NH_2$, $NHC(=NH)NH(C_{1-6}$ alkyl), $NHC(=NH)N(C_{1-6}$ alkyl)$_2$, $NH_2$, $NH(C_{1-6}$ alkyl), $N(C_{1-6}$ alkyl)$_2$, $NHC(=O)(C_{1-6}$ alkyl), $N(C_{1-6}$ alkyl)$C(=O)$ $(C_{1-6}$ alkyl), $NHC(=O)(C_{1-6}$ alkyl), $NHC(=O)O(C_{1-6}$ alkyl), $N(C_{1-6}$alkyl)$C(=O)O(C_{1-6}$ alkyl), $NHC(=O)NH_2$, $NHC(=O)NH(C_{1-6}$ alkyl), $NHC(=O)N(C_{1-6}$ alkyl)$_2$, $NHS(=O)(C_{1-6}$ alkyl), $N(C_{1-6}$ alkyl)$S(=O)(C_{1-6}$ alkyl), $NHS(=O)_2(C_{1-6}$ alkyl), $N(C_{1-6}$ alkyl)$S(=O)_2(C_{1-6}$ alkyl), $NHS(=O)_2NH_2$, $NHS(=O)_2NH(C_{1-6}$ alkyl), $NHS(=O)_2N(C_{1-6}$alkyl)$_2$, $S(=O)(C_{1-6}$ alkyl), $S(=O)NH_2$, $S(=O)NH(C_{1-6}$ alkyl), $S(=O)N(C_{1-6}$alkyl)$_2$, $S(=O)_2(C_{1-6}$ alkyl), $S(=O)_2NH_2$, $S(=O)_2NH(C_{1-6}$ alkyl), and $S(=O)_2N(C_{1-6}$ alkyl)$_2$.

In some embodiments, $R^2$ is $C_{1-6}$ alkyl, which is optionally substituted with 1, 2, or 3 substituents independently selected from halo, CN, OH, $C_{1-6}$ alkoxy, $S(C_{1-6}$ alkyl), $C(=O)(C_{1-6}$ alkyl), $C(=O)NH_2$, $C(=O)NH(C_{1-6}$ alkyl), $C(=O)N(C_{1-6}$ alkyl)$_2$, $C(=O)O(C_{1-6}$ alkyl), $OC(=O)(C_{1-6}$ alkyl), $OC(=O)NH_2$, $OC(=O)NH(C_{1-6}$ alkyl), $OC(=O)N(C_{1-6}$alkyl)$_2$, $C(=NH)NH_2$, $C(=NH)NH(C_{1-6}$ alkyl), $C(=NH)N(C_{1-6}$ alkyl)$_2$, $NHC(=NH)NH_2$, $NHC(=NH)NH(C_{1-6}$ alkyl), $NHC(=NH)N(C_{1-6}$ alkyl)$_2$, $NH_2$, $NH(C_{1-6}$ alkyl), $N(C_{1-6}$ alkyl)$_2$, $NHC(=O)(C_{1-6}$ alkyl), $N(C_{1-6}$alkyl)$C(=O)$ $(C_{1-6}$ alkyl), $NHC(=O)(C_{1-6}$ alkyl), $NHC(=O)O(C_{1-6}$ alkyl), $N(C_{1-6}$ alkyl)$C(=O)O(C_{1-6}$ alkyl), $NHC(=O)NH_2$, $NHC(=O)NH(C_{1-6}$ alkyl), $NHC(=O)N(C_{1-6}$ alkyl)$_2$, $NHS(=O)(C_{1-6}$ alkyl), $N(C_{1-6}$ alkyl)$S(=O)(C_{1-6}$ alkyl), $NHS(=O)_2(C_{1-6}$ alkyl), $N(C_{1-6}$ alkyl)$S(=O)_2(C_{1-6}$ alkyl), $NHS(=O)_2NH_2$, $NHS(=O)_2NH(C_{1-6}$ alkyl), $NHS(=O)_2N(C_{1-6}$ alkyl)$_2$, $S(=O)(C_{1-6}$ alkyl), $S(=O)NH_2$, $S(=O)NH(C_{1-6}$ alkyl), $S(=O)N(C_{1-6}$ alkyl)$_2$, $S(=O)_2(C_{1-6}$ alkyl), $S(=O)_2NH_2$, $S(=O)_2NH(C_{1-6}$ alkyl), and $S(=O)_2N(C_{1-6}$ alkyl)$_2$.

In some embodiments, $R^2$ is $C_{1-6}$ alkyl, which is optionally substituted with 1, 2, or 3 substituents independently selected from halo, CN, $OR^a$, and $NR^cS(=O)_2R^b$; wherein each $R^a$ and $R^c$ are independently selected from H and $C_{1-3}$ alkyl; and each $R^b$ is independently selected from $C_{1-3}$ alkyl.

In some embodiments, $R^2$ is H or $C_{1-6}$ alkyl, wherein said $C_{1-6}$ alkyl is optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H and $C_{1-3}$ alkyl; and each $R^b$ is independently selected from $C_{1-3}$ alkyl.

In some embodiments, $R^2$ is H, methyl, ethyl, propyl, or isopropyl, wherein said methyl, ethyl, propyl, or isopropyl are each optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl.

In some embodiments, $R^2$ is methyl or ethyl, each of which is optionally substituted with 1, 2, or 3 substituents independently selected from halo, CN, $OR^a$, and $NR^cS(=O)_2 R^b$; wherein each $R^a$ and $R^c$ are independently selected from H, methyl, and ethyl; and each $R^b$ is independently selected from methyl and ethyl.

In some embodiments, $R^2$ is cyclopropyl or an azetidine ring, each of which is optionally substituted with 1, 2, or 3 independently selected $R^{21}$ groups.

In some embodiments, each $R^{21}$ is independently $C_{1-3}$ alkyl.

In some embodiments:

$R^2$ is H, methyl, ethyl, propyl, or isopropyl, wherein said methyl, ethyl, propyl, or isopropyl are each optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl; or alternatively, $R^2$ is cyclopropyl or an azetidine ring, each of which is optionally substituted with 1, 2, or 3 independently selected $R^{21}$ groups; and each $R^{21}$ is independently $C_{1-3}$ alkyl.

In some embodiments, $R^2$ is —$CH_2$—OH, —$CH(CH_3)$—OH, or —$CH_2$—$NHSO_2CH_3$.

In some embodiments, $R^4$ is H.

In some embodiments, $R^5$ is H.

In some embodiments, $R^3$ is selected from $Cy^4$, $-Cy^{4A}$-$Cy^5$, $-Cy^{4A}$-$Cy^{5A}$-$C^6$, $-Cy^{4A}$-$Y^1$-$Cy^5$, $-Cy^{4A}$-$Y^1$-$Cy^{5A}$-$Cy^6$, $-Cy^{4A}$-$Cy^{5A}$-$Y^2$-$Cy^6$, $-Cy^{4A}$-$Y^1$-$Cy^{5A}$-$Y^2$-$Cy^6$, and $-Cy^{4A}$-$Y^3$-$Cy^6$.

In some embodiments:

$Y^1$ is $Y^{11}$, $C_{1-6}$ alkylene, $C_{1-6}$ alkylene-$Y^{11}$, or $Y^{11}$—$C_{1-6}$ alkylene;

$Y^2$ is $Y^{21}$, $C_{1-6}$ alkylene, $C_{1-6}$ alkylene-$Y^{21}$, or $Y^{21}$—$C_{1-6}$ alkylene;

$Y^3$ is $C_{1-6}$ alkylene-$Y^{31}$—$C_{1-6}$ alkylene, $C_{1-6}$ alkylene-$Y^{31}$—$C_{1-6}$ alkylene-$Y^{31}$, or $Y^{31}$—$C_{1-6}$ alkylene-$Y^{31}$—$C_{1-6}$ alkylene; and $Y^{11}$, $Y^{21}$, and $Y^{31}$ are each independently selected from O and $NR^f$.

In some embodiments, $R^3$ is $Cy^4$, $-Cy^{4A}$-$Cy^5$, or $-Cy^{4A}$-$Y^1$-$Cy^5$.

In some embodiments, $R^3$ is $-Cy^{4A}$-$Cy^5$ or $-Cy^{4A}$-$Y^1$-$Cy^5$.

In some embodiments, $R^3$ is $Cy^4$ or $-Cy^{4A}$-$Cy^5$.

In some embodiments, $R^3$ is $Cy^4$.

In some embodiments, $R^3$ is $-Cy^{4A}$-$Cy^5$.

In some embodiments, $R^3$ is $-Cy^{4A}$-$Cy^{5A}$-$Cy^6$.

In some embodiments, $R^3$ is $-Cy^{4A}$-$Y^1$-$Cy^5$.

In some embodiments, $R^3$ is $-Cy^{4A}$-$Y^1$-$Cy^5$; wherein Y is $C_{1-4}$alkylene or $Y^{11}$—$C_{1-4}$ alkylene; and $Y^{11}$ is C(=O).

In some embodiments, $R^3$ is $-Cy^{4A}$-$Y^1$-$Cy^{5A}$-$Cy^6$.

In some embodiments, $R^3$ is $-Cy^{4A}$-$Cy^{5A}$-$Y^2$-$Cy^6$.

In some embodiments, $R^3$ is $-Cy^{4A}$-$Y^1$-$Cy^{5A}$-$Y^2$-$Cy^6$.

In some embodiments, $R^3$ is $-Cy^{4A}$-$Y^3$-$Cy^6$.

In some embodiments, $Y^1$ is $Y^{11}$, CM alkylene, $C_{1-6}$ alkylene-$Y^{11}$, or $Y^{11}$—$C_{1-6}$ alkylene.

In some embodiments, $Y^2$ is $Y^{21}$, CM alkylene, CM alkylene-$Y^{21}$, or $Y^{21}$—$C_{1-6}$ alkylene.

In some embodiments, $Y^3$ is CM alkylene-$Y^{31}$—$C_{1-6}$ alkylene, CM alkylene-$Y^{31}$—$C_{1-6}$ alkylene-$Y^{31}$, or $Y^{31}$—$C_{1-6}$ alkylene-$Y^{31}$—$C_{1-6}$ alkylene.

In some embodiments, $Y^{11}$, $Y^{21}$, and $Y^{31}$ are each independently selected from O and $NR^f$.

In some embodiments, $Cy^4$ is selected from $C_{6-10}$ aryl, $C_{3-10}$ cycloalkyl and 3-10 membered heterocycloalkyl, each of which are optionally substituted with 1, 2, 3, or 4 independently selected $R^{31}$ groups, provided said 3-10 membered heterocycloalkyl is not a saturated heterocycloalkyl group having one or more nitrogen ring members.

In some embodiments, $Cy^4$ is phenyl, cyclohexyl, tetrahydro-2H-pyran ring, a piperidine ring, or a pyrrolidine ring, each which is optionally substituted with 1, 2, 3, or 4 substituents independently selected $R^{31}$ groups.

In some embodiments, $Cy^4$ is selected from $C_{3-10}$ cycloalkyl and 3-10 membered heterocycloalkyl, each of which are optionally substituted with 1, 2, 3, or 4 independently selected $R^{31}$ groups, provided said 3-10 membered heterocycloalkyl is not a saturated heterocycloalkyl group having one or more nitrogen ring members.

In some embodiments, $Cy^4$ is $C_{3-7}$ cycloalkyl, which is optionally substituted with 1, 2, 3, or 4 independently selected $R^{31}$ groups.

In some embodiments, $Cy^4$ is selected from $C_{3-7}$ cycloalkyl, which is optionally substituted with 1, 2, 3, or 4 independently selected $R^{31}$ groups.

In some embodiments, $Cy^4$ is selected from cyclohexyl, each of which is optionally substituted with 1, 2, 3, or 4 independently selected $R^{31}$ groups.

In some embodiments, $Cy^4$ is a tetrahydro-2H-pyran ring, which is optionally substituted with 1 or 2 independently selected $R^{31}$ groups.

In some embodiments, $Cy^4$ is a cyclohexyl, tetrahydro-2H-pyran ring, or a piperidine ring each which is optionally substituted with 1, 2, 3, or 4 substituents independently selected $R^{31}$ groups.

In some embodiments, $Cy^4$ is piperidin-4-yl, which is optionally substituted with 1 or 2 independently selected $R^{31}$ groups.

In some embodiments, $Cy^{4A}$ is selected from $C_{3-10}$ cycloalkylene and 3-10 membered heterocycloalkylene, each of which are optionally substituted with 1, 2, 3, or 4 independently selected $R^{31}$ groups, provided said 3-10 membered heterocycloalkylene is not a saturated heterocycloalkylene group having one or more nitrogen ring members.

In some embodiments, $Cy^{4A}$ is selected from $C_{3-10}$ cycloalkylene, which is optionally substituted with 1, 2, 3, or 4 independently selected $R^{31}$ groups.

In some embodiments, $Cy^{4A}$ is selected from $C_{3-7}$ cycloalkylene, which is optionally substituted with 1, 2, 3, or 4 independently selected $R^{31}$ groups.

In some embodiments, $Cy^{4A}$ is selected from cyclopropylene, cyclobutylene, cyclopentylene, cyclohexylene, and cycloheptylene, each of which is optionally substituted with 1, 2, 3, or 4 independently selected $R^{31}$ groups.

In some embodiments, $Cy^{4A}$ is selected from cyclohexylene, each of which is optionally substituted with 1 or 2 independently selected $R^{31}$ groups.

In some embodiments, $Cy^5$ is 5-10 membered heteroaryl, which is optionally substituted with 1 or 2 independently selected $R^{32}$ groups.

In some embodiments, $Cy^5$ is 1H-1,2,4-triazolyl, which is optionally substituted with 1 or 2 independently selected $R^{32}$ groups.

In some embodiments, $Cy^5$ is 1H-1,2,4-triazolyl.

In some embodiments, $Cy^5$ is $C_{6-10}$ aryl or 5-10 membered heteroaryl, which are each optionally substituted with 1 or 2 independently selected $R^{32}$ groups.

In some embodiments, $Cy^5$ is a pyridine ring, a pyrazole ring, or a triazole ring, each of which is optionally substituted with 1 or 2 independently selected $R^{32}$ groups.

In some embodiments, $R^3$ is $Cy^4$, provided that $Cy^4$ is not 3-10 membered saturated heterocycloalkyl having one or more nitrogen ring members; and $R^2$ is selected from H, halo, cyclopropyl, cyclobutyl, an azetidine ring, $C_{1-6}$ alkyl, $C_{2-6}$ alkenyl, $C_{2-6}$ alkynyl, $C_{1-6}$ haloalkyl, $C_{4-6}$ alkoxy, $C_{1-6}$ alkyl-S—, CN, OC(=O)$R^b$, OC(=O)$NR^cR^d$, $NR^cR^d$, $NR^cC(=O)R^b$, $NR^cC(=O)OR^a$, $NR^cC(=O)NR^cR^d$, C(=$NR^e$)$R^b$, C(=$NR^e$)$NR^cR^d$, $NR^cC(=NR^e)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$; wherein said $C_{1-6}$ alkyl, $C_{2-6}$ alkenyl, $C_{2-6}$ alkynyl, $C_{1-6}$ alkoxy, and $C_{1-6}$ alkyl-S— are each optionally substituted with 1, 2, or 3 substituents independently selected from halo, CN, $NO_2$, $OR^a$, $SR^a$, C(=O)$R^b$, C(=O)$NR^cR^d$, C(=O)$OR^a$, OC(=O)$R^b$, OC(=O)$NR^cR^d$, C(=$NR^e$)$NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$.

In some embodiments:

each $R^{31}$ is independently selected from $C_{1-6}$ alkyl, $C_{1-6}$ haloalkyl, halo, CN, $OR^{a2}$, and $NR^{c2}R^{d2}$; wherein said $C_{1-6}$ alkyl are each optionally substituted with 1, 2, or 3 substituents independently selected from halo, CN, $OR^{a2}$, C(=O)$NR^{c2}R^{d2}$, C(=O)$OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, and $C_{1-6}$ haloalkyl; and each $R^{b2}$ is independently selected from $C_{1-6}$ alkyl and $C_{1-6}$ haloalkyl.

In some embodiments:

each $R^{31}$ is independently selected from $C_{1-6}$ alkyl, $C_{1-6}$ haloalkyl, halo, CN, $OR^{a2}$, $C(=O)R^{b2}$, $C(=O)OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, and $C_{1-6}$ haloalkyl, wherein said $C_{1-6}$ alkyl and $C_{1-6}$ haloalkyl are each optionally substituted by 1, 2, or 3 CN; and each $R^{b2}$ is independently selected from $C_{1-6}$ alkyl and $C_{1-6}$ haloalkyl, which are each optionally substituted by 1, 2, or 3 CN.

In some embodiments:

each $R^{31}$ is independently selected from CN, OH, F, Cl, $C_{1-4}$ alkyl, $C_{1-4}$ haloalkyl, cyano-$C_{1-3}$ alkyl, HO—$C_{1-3}$ alkyl, $C_{1-3}$ alkylcarbonyl, $C_{1-4}$ alkoxycarbonyl, amino, $C_{1-3}$ alkylamino, and di($C_{1-3}$ alkyl)amino, wherein said $C_{1-4}$ alkyl, $C_{1-3}$ alkylcarbonyl, $C_{1-3}$ alkylamino, and di($C_{1-3}$ alkyl) amino are each optionally substituted with 1, 2, or 3 substituents independently selected from F, Cl, CN, carbamyl, $C_{1-3}$ alkylcarbamyl, di($C_{1-3}$ alkyl)carbamyl, $C_{1-3}$ alkylaminosulfonyl, $C_{1-3}$ alkylsulfonyl, amino, $C_{1-3}$ alkylamino, and di($C_{1-3}$alkyl)amino.

In some embodiments, each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl.

In some embodiments:

each $R^{32}$ is independently selected from $C_{1-6}$ alkyl, $C_{1-6}$ haloalkyl, halo, CN, $OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, and $C_{1-6}$ haloalkyl; and each $R^{b2}$ is independently selected from $C_{1-6}$ alkyl and $C_{1-6}$ haloalkyl.

In some embodiments, each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl.

In some embodiments:

$R^2$ is $C_{1-6}$ alkyl, which is optionally substituted with 1, 2, or 3 substituents independently selected from halo, CN, OH, $C_{1-6}$alkoxy, $S(C_{1-6}$ alkyl), $C(=O)(C_{1-6}$ alkyl), $C(=O)NH_2$, $C(=O)NH(C_{1-6}$ alkyl), $C(=O)N(C_{1-6}$alkyl)$_2$, $C(=O)O(C_{1-6}$ alkyl), $OC(=O)(C_{1-6}$ alkyl), $OC(=O)NH_2$, $OC(=O)NH(C_{1-6}$ alkyl), $OC(=O)N(C_{1-6}$alkyl)$_2$, $C(=NH)NH_2$, $C(=NH)NH(C_{1-6}$ alkyl), $C(=NH)N(C_{1-6}$alkyl)$_2$, NHC$(=NH)NH_2$, NHC$(=NH)NH(C_{1-6}$ alkyl), NHC$(=NH)N(C_{1-6}$ alkyl)$_2$, $NH_2$, $NH(C_{1-6}$ alkyl), $N(C_{1-6}$ alkyl)$_2$, NHC$(=O)(C_{1-6}$ alkyl), $N(C_{1-6}$alkyl)C$(=O)$ $(C_{1-6}$ alkyl), NHC$(=O)(C_{1-6}$ alkyl), NHC$(=O)O(C_{1-6}$ alkyl), $N(C_{1-6}$ alkyl)C$(=O)O(C_{1-6}$ alkyl), NHC$(=O)NH_2$, NHC$(=O)NH(C_{1-6}$ alkyl), NHC$(=O)N(C_{1-6}$alkyl)$_2$, NHS$(=O)(C_{1-6}$ alkyl), $N(C_{1-6}$alkyl)S$(=O)(C_{1-6}$ alkyl), NHS$(=O)_2(C_{1-6}$ alkyl), $N(C_{1-6}$ alkyl)S$(=O)_2(C_{1-6}$ alkyl), NHS$(=O)_2NH_2$, NHS$(=O)_2NH(C_{1-6}$ alkyl), NHS$(=O)_2N(C_{1-6}$ alkyl)$_2$, $S(=O)$ $(C_{1-6}$ alkyl), $S(=O)NH_2$, $S(=O)NH(C_{1-6}$ alkyl), $S(=O)N$ $(C_{1-6}$ alkyl)$_2$, $S(=O)_2(C_{1-6}$ alkyl), $S(=O)_2NH_2$, $S(=O)_2$ $NH(C_{1-6}$ alkyl), and $S(=O)_2N(C_{1-6}$ alkyl)$_2$;

$R^3$ is $Cy^4$ or -$Cy^{4A}$-$Cy^5$;

$Cy^4$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{31}$ groups;

$Cy^{4A}$ is selected from $C_{6-10}$ arylene, $C_{3-10}$ cycloalkylene, 5-10 membered heteroarylene, and 3-10 membered heterocycloalkylene, wherein said $C_{6-10}$ aryl, $C_{3-10}$cycloalkyl, 5-10 membered heteroaryl, and 3-10 membered heterocycloalkyl are optionally substituted with 1, 2, 3, or 4 independently selected $R^{31}$ groups;

$Cy^5$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{32}$ groups;

each $R^{31}$ is independently selected from $C_{1-6}$ alkyl, CM haloalkyl, halo, CN, $OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{32}$ is independently selected from $C_{1-6}$ alkyl, CM haloalkyl, halo, CN, $OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, CM alkyl, and $C_{1-6}$ haloalkyl;

each $R^{b2}$ is independently selected from $C_{1-6}$ alkyl and CM haloalkyl;

$R^4$ is H; and $R^5$ is H.

In some embodiments:

$R^2$ is $C_{1-6}$ alkyl, which is optionally substituted with 1, 2, or 3 substituents independently selected from halo, CN, $OR^3$, and $NR^cS(=O)_2R^b$; wherein each $R^a$ and $R^c$ are independently selected from H and $C_{1-3}$ alkyl; and each $R^b$ is independently selected from $C_{1-3}$ alkyl;

$R^3$ is $Cy^4$ or -$Cy^{4A}$-$Cy^5$;

$Cy^4$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{31}$ groups;

$Cy^{4A}$ is selected from $C_{6-10}$ arylene, $C_{3-10}$ cycloalkylene, 5-10 membered heteroarylene, and 3-10 membered heterocycloalkylene, wherein said $C_{6-10}$ aryl, $C_{3-10}$cycloalkyl, 5-10 membered heteroaryl, and 3-10 membered heterocycloalkyl are optionally substituted with 1, 2, 3, or 4 independently selected $R^{31}$ groups;

$Cy^5$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{32}$ groups;

each $R^{31}$ is independently selected from $C_{1-6}$ alkyl, CM haloalkyl, halo, CN, $OR^{a2}$, and $NR^{c2}R^{d2}$; wherein said $C_{1-6}$ alkyl are each optionally substituted with 1, 2, or 3 substituents independently selected from halo, CN, $OR^{a2}$, C(=O)$NR^{c2}R^{d2}$, C(=O)$OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{32}$ is independently selected from $C_{1-6}$ alkyl, CM haloalkyl, halo, CN, $OR^{a2}$, and $NR^{c2}R^{d2}$; wherein said $C_{1-6}$ alkyl are each optionally substituted with 1, 2, or 3 substituents independently selected from halo, CN, $OR^{a2}$, C(=O)$NR^{c2}R^{d2}$, C(=O)$OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, CM alkyl, and $C_{1-6}$ haloalkyl; each $R^{b2}$ is independently selected from $C_{1-6}$ alkyl and CM haloalkyl;

$R^4$ is H; and $R^5$ is H.

In some embodiments:

$R^2$ is $C_{1-6}$ alkyl, which is optionally substituted with 1, 2, or 3 substituents independently selected from halo, CN, $OR^3$, and $NR^cS(=O)_2R^b$; wherein each $R^a$ and $R^c$ are independently selected from H and $C_{1-3}$ alkyl; and each $R^b$ is independently selected from $C_{1-3}$ alkyl;

$R^3$ is $Cy^4$ or -$Cy^{4A}$-$Cy^5$;

$Cy^4$ is selected from $C_{3-10}$ cycloalkyl and 3-10 membered heterocycloalkyl, each of which are optionally substituted with 1, 2, 3, or 4 independently selected $R^{31}$ groups, provided said 3-10 membered heterocycloalkyl is not a saturated heterocycloalkyl group having one or more nitrogen ring members;

$Cy^{4A}$ is selected from $C_{3-10}$ cycloalkylene and 3-10 membered heterocycloalkylene, each of which are optionally substituted with 1, 2, 3, or 4 independently selected $R^{31}$ groups, provided said 3-10 membered heterocycloalkylene is not a saturated heterocycloalkylene group having one or more nitrogen ring members;

$Cy^5$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{32}$ groups;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl;

each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

In some embodiments:

$R^2$ is —$CH_2$—OH, —CH(CH$_3$)—OH, or —$CH_2$—NHSO$_2$CH$_3$;

$R^3$ is $Cy^4$ or -$Cy^{4A}$-$Cy^5$;

$Cy^4$ is selected from $C_{3-10}$ cycloalkyl and 3-10 membered heterocycloalkyl, each of which are optionally substituted with 1, 2, 3, or 4 independently selected $R^{31}$ groups, provided said 3-10 membered heterocycloalkyl is not a saturated heterocycloalkyl group having one or more nitrogen ring members;

$Cy^{4A}$ is selected from $C_{3-10}$ cycloalkylene and 3-10 membered heterocycloalkylene, each of which are optionally substituted with 1, 2, 3, or 4 independently selected $R^{31}$ groups, provided said 3-10 membered heterocycloalkylene is not a saturated heterocycloalkylene group having one or more nitrogen ring members;

$Cy^5$ is selected from 5-10 membered heteroaryl, which is optionally substituted with 1, 2, 3, or 4 independently selected $R^{32}$ groups;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl;

each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

In some embodiments:

$R^2$ is —$CH_2$—OH, —CH(CH$_3$)—OH, or —$CH_2$—NHSO$_2$CH$_3$; $R^3$ is $Cy^4$;

$Cy^4$ is selected from $C_{3-10}$ cycloalkyl and 3-10 membered heterocycloalkyl, each of which are optionally substituted with 1, 2, 3, or 4 independently selected $R^{31}$ groups, provided said 3-10 membered heterocycloalkyl is not a saturated heterocycloalkyl group having one or more nitrogen ring members;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

In some embodiments:

$R^2$ is H, methyl, ethyl, propyl, or isopropyl, wherein said methyl, ethyl, propyl, or isopropyl are each optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl; or alternatively, $R^2$ is cyclopropyl or an azetidine ring, each of which is optionally substituted with 1, 2, or 3 independently selected $R^{21}$ groups;

each $R^{21}$ is independently $C_{1-3}$ alkyl;

$R^3$ is $Cy^4$, -$Cy^{4A}$-$Cy^5$, or -$Cy^{4A}$-$Y^1$-$Cy^5$;

$Y^1$ is $C_{1-4}$alkylene or $Y^{11}$—$C_{1-4}$ alkylene;

$Y^{11}$ is C(=O);

$Cy^4$ is selected from $C_{6-10}$ aryl, $C_{3-10}$ cycloalkyl, and 3-10 membered heterocycloalkyl, each of which are optionally substituted with 1, 2, 3, or 4 independently selected $R^{31}$ group, provided said 3-10 membered heterocycloalkylene is not a saturated heterocycloalkylene group having one or more nitrogen ring members;

$Cy^{4A}$ is selected from $C_{3-10}$ cycloalkylene and 3-10 membered heterocycloalkylene, each of which are optionally substituted with 1, 2, 3, or 4 independently selected $R^{31}$ groups, provided said 3-10 membered heterocycloalkylene is not a saturated heterocycloalkylene group having one or more nitrogen ring members;

$Cy^5$ is $C_{6-10}$ aryl or 5-10 membered heteroaryl, which are each optionally substituted with 1 or 2 independently selected $R^{32}$ groups;

each $R^{31}$ or $R^{32}$ are each independently selected from $C_{1-6}$ alkyl, $C_{1-6}$ haloalkyl, halo, CN, $OR^{a2}$, $C(=O)R^{b2}$, $C(=O)OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, and $C_{1-6}$ haloalkyl, wherein said $C_{1-6}$ alkyl, and $C_{1-6}$ haloalkyl are each optionally substituted by 1, 2, or 3 CN;

each $R^{b2}$ is independently selected from $C_{1-6}$ alkyl and $C_{1-6}$ haloalkyl, which are each optionally substituted by 1, 2, or 3 CN;

$R^4$ is H; and $R^5$ is H.

In some embodiments:

$R^2$ is H, methyl, ethyl, propyl, or isopropyl, wherein said methyl, ethyl, propyl, or isopropyl are each optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl; or alternatively, $R^2$ is cyclopropyl or an azetidine ring, each of which is optionally substituted with 1, 2, or 3 independently selected $R^{21}$ groups;

provided that when $X^1 = X^2 = X^3$ is $-N=CR^2-NR^3-$, $X^4$ is C, and $X^5$ is C; and $Cy^4$ is unsubstituted or substituted 3-10 membered saturated heterocycloalkylene having one or more nitrogen atoms or $Cy^{4A}$ is unsubstituted or substituted 3-10 membered saturated heterocycloalkylene having one or more nitrogen atoms, then $R^2$ is selected from H, methyl, ethyl, propyl, or isopropyl, wherein said methyl, ethyl, propyl, or isopropyl are each optionally optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl;

each $R^{21}$ is independently $C_{1-3}$ alkyl;

$R^3$ is $Cy^4$, $-Cy^{4A}-Cy^5$, or $-Cy^{4A}-Y^1-Cy^5$;

$Y^1$ is $C_{1-4}$alkylene, $Y^{11}-C_{1-4}$ alkylene, or $C_{1-6}$ alkylene-$Y^{11}$;

$Y^{11}$ is $C(=O)$ or $NHC(=O)O$;

$Cy^4$ is selected from phenyl, $C_{3-7}$ cycloalkyl, and 4-6 membered heterocycloalkyl, each of which are optionally substituted with 1, 2, 3, or 4 independently selected $R^{31}$ group; $Cy^{4A}$ is selected from $C_{3-7}$ cycloalkylene and 4-6 membered heterocycloalkylene, each of which are optionally substituted with 1, 2, 3, or 4 independently selected $R^{31}$ groups;

$Cy^5$ is phenyl, 4-6 membered heterocycloalkyl, or 5-6 membered heteroaryl, which are each optionally substituted with 1 or 2 independently selected $R^{32}$ groups;

each $R^{31}$ or $R^{32}$ are each independently selected from $C_{1-6}$ alkyl, CM haloalkyl, halo, CN, $OR^{32}$, $C(=O)R^{b2}$, $C(=O)OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, CM alkyl, CM haloalkyl, and wherein said $C_{1-6}$ alkyl, and $C_{1-6}$ haloalkyl are each optionally substituted by 1, 2, or 3 CN;

each $R^{b2}$ is independently selected from $C_{1-6}$ alkyl and CM haloalkyl, which are each optionally substituted by 1, 2, or 3 CN;

$R^4$ is H; and $R^5$ is H.

In some embodiments:

$R^2$ is H, methyl, ethyl, propyl, or isopropyl, wherein said methyl, ethyl, propyl, or isopropyl are each optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl; or alternatively, $R^2$ is cyclopropyl or an azetidine ring, each of which is optionally substituted with 1, 2, or 3 independently selected $R^{21}$ groups;

provided that when $X^1 = X^2 = X^3$ is $-N=CR^2-NR^3-$, $X^4$ is C, and $X^5$ is C; and $Cy^4$ is unsubstituted or substituted 3-10 membered saturated heterocycloalkylene having one or more nitrogen atoms or $Cy^{4A}$ is unsubstituted or substituted 3-10 membered saturated heterocycloalkylene having one or more nitrogen atoms, then $R^2$ is selected from H, methyl, ethyl, propyl, or isopropyl, wherein said methyl, ethyl, propyl, or isopropyl are each optionally optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl;

each $R^{21}$ is independently $C_{1-3}$ alkyl;

$R^3$ is $Cy^4$, $-Cy^{4A}-Cy^5$, or $-Cy^{4A}-Y^1-Cy^5$;

$Y^1$ is $C_{1-4}$alkylene or $Y^{11}-C_{1-4}$ alkylene;

$Y^{11}$ is $C(=O)$;

$Cy^4$ is selected from $C_{6-10}$ aryl, $C_{3-10}$ cycloalkyl, and 3-10 membered heterocycloalkyl, each of which are optionally substituted with 1, 2, 3, or 4 independently selected $R^{31}$ group;

$Cy^{4A}$ is selected from $C_{3-10}$ cycloalkylene and 3-10 membered heterocycloalkylene, each of which are optionally substituted with 1, 2, 3, or 4 independently selected $R^{31}$ groups;

$Cy^5$ is $C_{6-10}$ aryl or 5-10 membered heteroaryl, which are each optionally substituted with 1 or 2 independently selected $R^{32}$ groups;

each $R^{31}$ or $R^{32}$ are each independently selected from $C_{1-6}$ alkyl, $C_{1-6}$ haloalkyl, halo, CN, $OR^{a2}$, $C(=O)R^{b2}$, $C(=O)OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, and $C_{1-6}$ haloalkyl, wherein said $C_{1-6}$ alkyl, and $C_{1-6}$ haloalkyl are each optionally substituted by 1, 2, or 3 CN;

each $R^{b2}$ is independently selected from $C_{1-6}$ alkyl and $C_{1-6}$ haloalkyl, which are each optionally substituted by 1, 2, or 3 CN;

$R^4$ is H; and $R^5$ is H.

In some embodiments:

$R^2$ is —$CH_2$—OH, —$CH(CH_3)$—OH, or —$CH_2$—$NHSO_2CH_3$;

$R^3$ is -$Cy^{4A}$-$Cy^5$;

$Cy^{4A}$ is selected from $C_{3-10}$ cycloalkylene and 3-10 membered heterocycloalkylene, each of which are optionally substituted with 1, 2, 3, or 4 independently selected $R^{31}$ groups, provided said 3-10 membered heterocycloalkylene is not a saturated heterocycloalkylene group having one or more nitrogen ring members;

$Cy^5$ is selected from 5-10 membered heteroaryl, which is optionally substituted with 1, 2, 3, or 4 independently selected $R^{32}$ groups;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl;

each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

In some embodiments:

$R^2$ is —$CH_2$—OH, —$CH(CH_3)$—OH, or —$CH_2$—$NHSO_2CH_3$;

$R^3$ is $Cy^4$ or -$Cy^{4A}$-$Cy^5$;

$Cy^4$ is selected from cyclohexylene and a 2H-tetrahydrofuran ring, each of which are optionally substituted with 1, 2, 3, or 4 independently selected $R^{31}$ groups;

$Cy^{4A}$ is selected from cyclohexylene and a 2H-tetrahydrofuran ring, each of which are optionally substituted with 1, 2, 3, or 4 independently selected $R^{31}$ groups;

$Cy^5$ is selected from 5-10 membered heteroaryl, which is optionally substituted with 1, 2, 3, or 4 independently selected $R^{32}$ groups;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl;

each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

In some embodiments:

$X^1 \doteq X^2 \doteq X^3$ is =N—$CR^2$=$NR^3$—, $X^4$ is C, $X^5$ is C, and Y is $CR^4$; or $X^1 \doteq X^2 \doteq X^3$ is —$CR^1$=$CR^2$—$NR^3$—, $X^4$ is C, $X^5$ is C, and Y is $CR^4$; or $X^1 \doteq X^2 \doteq X^3$ is —$CR^1R^{1a}$—C(=O)—$NR^3$—, $X^4$ is C, $X^5$ is C, and Y is $CR^4$; or $X^1 \doteq X^2 \doteq X^3$ is —O—C(=O)—$NR^3$—, $X^4$ is C, $X^5$ is C, and Y is $CR^4$; or $X^1 \doteq X^2 \doteq X^3$ is =N—$CR^2$=$CR^3$—, $X^4$ is N, $X^5$ is C, and Y is $CR^4$.

In some embodiments:

$X^1 \doteq X^2 \doteq X^3$ is =N—$CR^2$=$NR^3$—, $X^1$ is C, $X^5$ is C, and Y is $CR^4$; or $X^1 \doteq X^2 \doteq X^3$ is —$CR^1$=$CR^2$—$NR^3$—, $X^1$ is C, $X^5$ is C, and Y is $CR^4$; or $X^1 \doteq X^2 \doteq X^3$ is —$CR^1R^{1a}$—C(=O)—$NR^3$—, $X^1$ is C, $X^5$ is C, and Y is $CR^4$; or $X^1 \doteq X^2 \doteq X^3$ is —O—C(=O)—$NR^3$—, $X^1$ is C, $X^5$ is C, and Y is $CR^4$; or $X^1 \doteq X^2 \doteq X^3$ is =N—$CR^2$=$CR^3$—, $X^1$ is N, $X^5$ is C, and Y is $CR^4$; or $X^1 \doteq X^2 \doteq X^3$ is —N=N—$NR^3$—, $X^1$ is C, $X^5$ is C, and Y is $CR^4$; or $X^1 \doteq X^2 \doteq X^3$ is —$NR^1$—C(=O)—$NR^3$—, $X^1$ is C, $X^5$ is C, and Y is $CR^4$; or $X^1 \doteq X^2 \doteq X^3$ is —N=$CR^2$—$CR^3$=, $X^1$ is C, $X^5$ is N, and Y is $CR^4$; or $X^1 \doteq X^2 \doteq X^3$ is —$CR^1$=$CR^2$—$CR^3$=, $X^1$ is C, $X^5$ is N, and Y is $CR^4$; or $X^1 \doteq X^2 \doteq X^3$ is =N—N=$CR^3$—, $X^1$ is N, $X^5$ is C, and Y is $CR^4$; or $X^1 \doteq X^2 \doteq X^3$ is =$CR^1$—N=$CR^3$—, $X^1$ is N, $X^5$ is C, and Y is $CR^4$; or $X^1 \doteq X^2 \doteq X^3$ is =$CR^1$—$CR^2$=$CR^3$—, $X^1$ is N, $X^5$ is C, and Y is $CR^4$; or $X^1 \doteq X^2 \doteq X^3$ is —$CR^1$=N—$NR^3$—, $X^1$ is C, $X^5$ is C, and Y is $CR^4$; or $X^1 \doteq X^2 \doteq X^3$ is —O—N=$CR^3$—, $X^1$ is C, $X^5$ is C, and Y is $CR^4$; or $X^1 \doteq X^2 \doteq X^3$ is —$NR^1$—N=$CR^3$—, $X^1$ is C, $X^5$ is C, and Y is $CR^4$; or $X^1 \doteq X^2 \doteq X^3$ is —S—N=$CR^3$—, $X^1$ is C, $X^5$ is C, and Y is $CR^4$; or $X^1 \doteq X^2 \doteq X^3$ is —O—$CR^2$=$CR^3$—, $X^1$ is C, $X^5$ is C, and Y is $CR^4$; or $X^1 \doteq X^2 \doteq X^3$ is —S—$CR^2$=$CR^3$—, $X^1$ is C, $X^5$ is C, and Y is $CR^4$; or $X^1 \doteq X^2 \doteq X^3$ is =N—$NR^2$—$CR^3$—, $X^1$ is C, $X^5$ is C, and Y is $CR^4$; or $X^1 \doteq X^2 \doteq X^3$ is —C(=O)—$NR^2$—$CR^3$—, $X^1$ is C, $X^5$ is C, and Y is $CR^4$.

In some embodiments, $X^1 \doteq X^2 \doteq X^3$ is —$CR^1$=$CR^2$—$NR^3$—, $X^1$ is C, and $X^5$ is C.

In some embodiments, $X^1 \doteq X^2 \doteq X^3$ is —$CR^1R^{1a}$—C(=O)—$NR^3$—, $X^1$ is C, and $X^5$ is C.

In some embodiments, $X^1 \doteq X^2 \doteq X^3$ is —O—C(=O)—$NR^3$—, $X^1$ is C, and $X^5$ is C.

In some embodiments, $X^1 \doteq X^2 \doteq X^3$ is =N—$CR^2$=$CR^3$—, $X^1$ is N, and $X^5$ is C.

In some embodiments, the compound is a compound of Formula IIa:

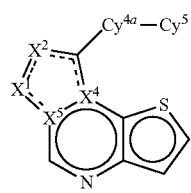

IIa or a pharmaceutically acceptable salt thereof.

In some embodiments, the compound is a compound of Formula IIb:

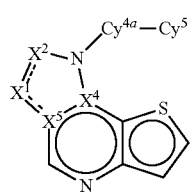

IIb or a pharmaceutically acceptable salt thereof.

In some embodiments, the compound is a compound of Formula IIc:

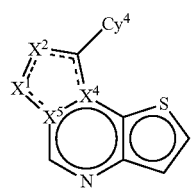

IIc or a pharmaceutically acceptable salt thereof.

In some embodiments, the compound is a compound of Formula IId:

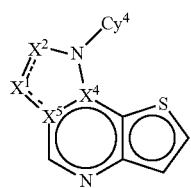

IId or a pharmaceutically acceptable salt thereof.

In some embodiments, the compound is a compound of Formula IIe:

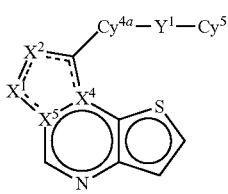

IIe or a pharmaceutically acceptable salt thereof.

In some embodiments, the compound is a compound of Formula IIf:

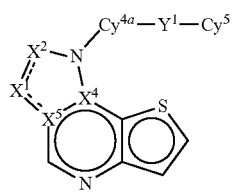

IIf or a pharmaceutically acceptable salt thereof.

In some embodiments, the compound is a compound of Formula IIIa:

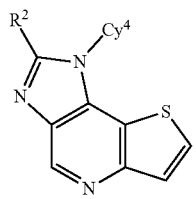

IIIa or a pharmaceutically acceptable salt thereof.

In some embodiments, the compound is a compound of Formula IIIb:

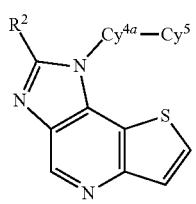

IIIb or a pharmaceutically acceptable salt thereof.

In some embodiments, the compound is a compound of Formula IIIc:

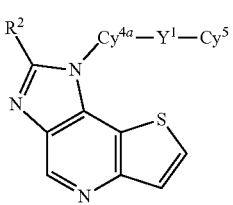

IIIc or a pharmaceutically acceptable salt thereof.

In some embodiments, the compound is a compound of any one of Formulas IV-1 to IV-18:
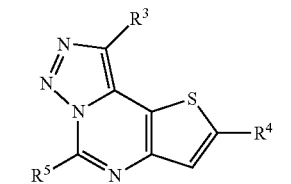 IV-1
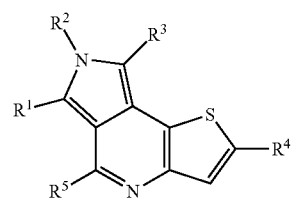 IV-2
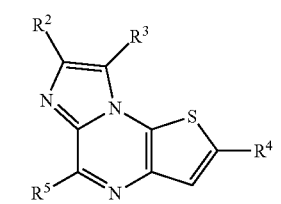 IV-3
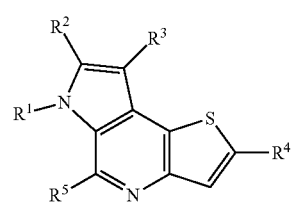 IV-4
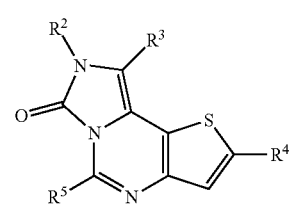 IV-5
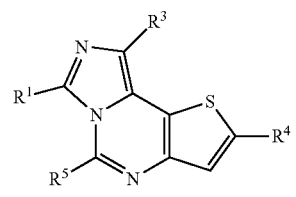 IV-6
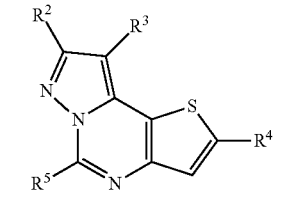 IV-7
-continued
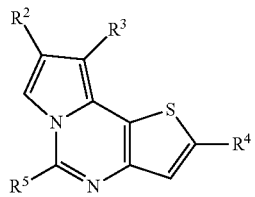 IV-8
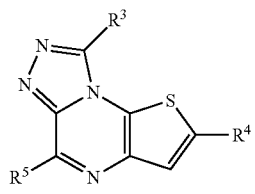 IV-9
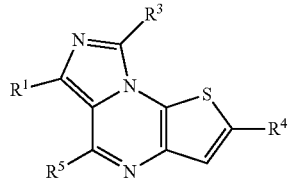 IV-10
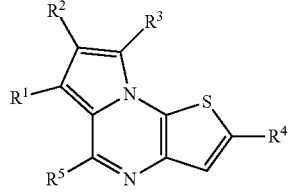 IV-11
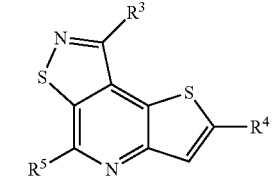 IV-12
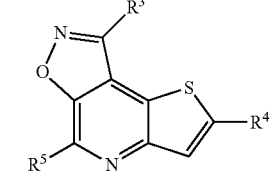 IV-13
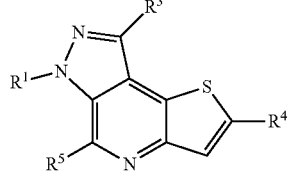 IV-14
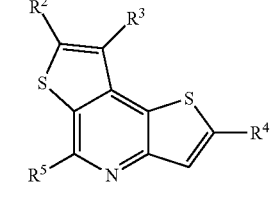 IV-15

-continued
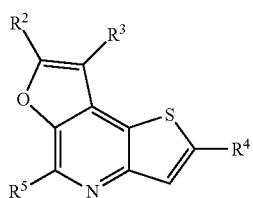
IV-16
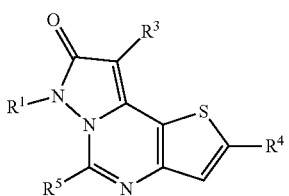
IV-17
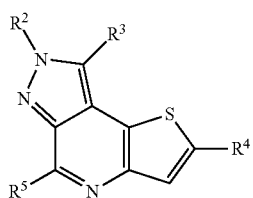
IV-18
or a pharmaceutically acceptable salt thereof.
In some embodiments, the compound is a compound of any one of Formula IV-19 to IV-28:
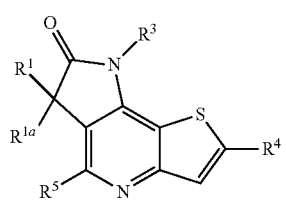
IV-19
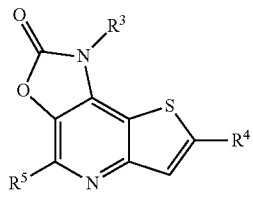
IV-20
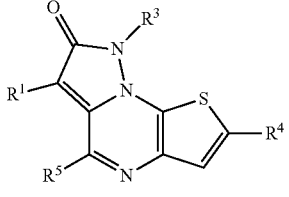
IV-21
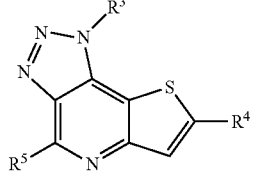
IV-22
-continued
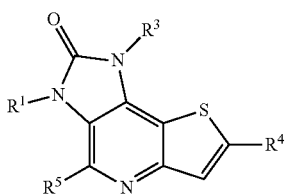
IV-23
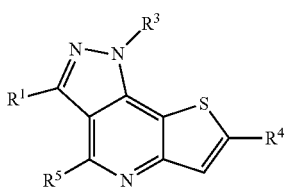
IV-24
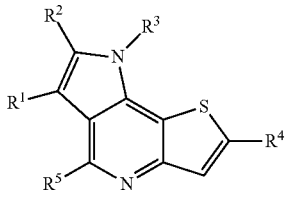
IV-25
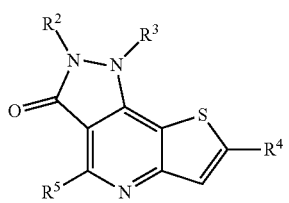
IV-26
IV-27
IV-28
or a pharmaceutically acceptable salt thereof.
In some embodiments, the compound is a compound of Formula V:
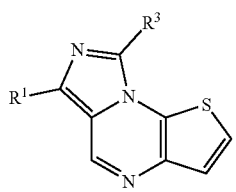
V
or a pharmaceutically acceptable salt thereof.

In some embodiments, the compound is a compound of Formula VI:

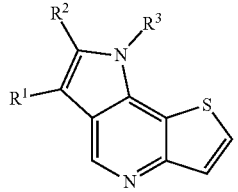

VI or a pharmaceutically acceptable salt thereof.

In some embodiments, the compound is a compound of Formula VII:

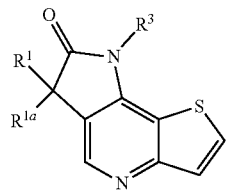

VII or a pharmaceutically acceptable salt thereof.

In some embodiments, the compound is a compound of Formula VIII:

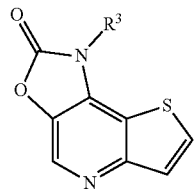

VIII or a pharmaceutically acceptable salt thereof.

In some embodiments, the compound is a compound of Formula IX:

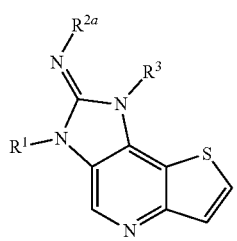

IX or a pharmaceutically acceptable salt thereof.

In some embodiments, the compound is a compound of Formula X:

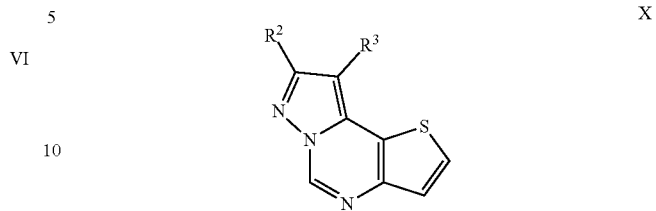

X or a pharmaceutically acceptable salt thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is to be understood that the "alkyl" or "aryl" represents a linking alkylene group or arylene group, respectively.

At various places in the present specification, rings are described (e.g., "a piperidine ring"). Unless otherwise specified, these rings can be attached to the rest of the molecule at any ring member as permitted by valency. For example, the term "a 2H-tetrahydropyran ring" may refer to a 2H-tetrahydropyran-2-yl, 2H-tetrahydropyran-3-yl, 2H-tetrahydropyran-4-yl ring, etc.

The term "n-membered" where n is an integer typically describes the number of ring-forming atoms in a moiety where the number of ring-forming atoms is n. For example, 2H-tetrahydropyran is an example of a 6-membered heterocycloalkyl ring, 1H-1,2,4-triazole is an example of a 5-membered heteroaryl ring, pyridine is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

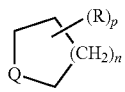

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like.

As used herein, the term "alkylene", employed alone or in combination with other terms, refers to a divalent alkyl linking group, which can be branched or straight-chain, where the two substituents may be attached any position of the alkylene linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl" refers to an alkyl group having one or more double carbon-carbon bonds and having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "alkenylene", employed alone or in combination with other terms, refers to a divalent alkenyl linking group, which can be branched or straight-chain, where the two substituents may be attached any position of the alkenylene linking group.

As used herein, the term "alkynylene", employed alone or in combination with other terms, refers to a divalent alkynyl linking group, which can be branched or straight-chain, where the two substituents may be attached any position of the alkynylene linking group.

As used herein, the term "$C_{1-3}$ alkoxy", employed alone or in combination with other terms, refers to a group of formula —O-alkyl, wherein the alkyl group has 1 to 3 carbons. Example alkoxy groups include methoxy, ethoxy, and propoxy (e.g., n-propoxy and isopropoxy).

As used herein, the term "amino" refers to a group of formula —$NH_2$.

As used herein, the term "$C_{1-3}$ alkylamino" refers to a group of formula —NH(alkyl), wherein the alkyl group 1 to 3 carbon atoms.

As used herein, the term "di($C_{1-3}$-alkyl)amino" refers to a group of formula —N$(alkyl)_2$, wherein the two alkyl groups each has, independently, 1 to 3 carbon atoms.

As used herein, the term "$C_{1-4}$alkoxycarbonyl" refers to a group of formula —C(O)O— alkyl, wherein the alkyl group has 1 to 4 carbon atoms.

As used herein, the term "$C_{1-3}$ alkylcarbonyl" refers to a group of formula —C(O)-alkyl, wherein the alkyl group has 1 to 3 carbon atoms.

As used herein, the term "carboxy" refers to a group of formula —C(O)OH.

As used herein, the term "thio" refers to a group of formula —SH.

As used herein, the term "$C_{1-3}$ alkylthio" refers to a group of formula —S—($C_{1-3}$ alkyl).

As used herein, the term "$C_{1-3}$ alkylsulfinyl" refers to a group of formula —S(O)-alkyl, wherein the alkyl group has 1 to 3 carbon atoms.

As used herein, the term "$C_{1-3}$ alkylsulfonyl" refers to a group of formula —$S(O)_2$-alkyl, wherein the alkyl group has 1 to 3 carbon atoms.

As used herein, the term "$C_{1-3}$ alkylcarbonyloxy" refers to a group of formula —OC(O)— alkyl, wherein the alkyl group has 1 to 3 carbon atoms.

As used herein, the term "$C_{1-3}$ alkylcarbonylamino" refers to a group of formula —NHC(O)-alkyl, wherein the alkyl group has 1 to 3 carbon atoms.

As used herein, the term "aminocarbonylamino" refers to a group of formula —NHC(O)$NH_2$.

As used herein, the term "$C_{1-3}$ alkylaminocarbonylamino," refers to a group of formula —NHC(O)NH(alkyl), wherein said alkyl has 1 to 3 carbon atoms.

As used herein, the term "di($C_{1-3}$ alkylaminocarbonylamino" refers to a group of formula —NHC(O)N$(alkyl)_2$, wherein each alkyl independently has 1 to 3 carbon atoms.

As used herein, the term "carbamyl" refers to a group of formula —C(O)—$NH_2$.

As used herein, the term "$C_{1-3}$ alkylcarbamyl" refers to a group of formula —C(O)—NH(alkyl), wherein the alkyl group has 1 to 3 carbon atoms.

As used herein, the term "di($C_{1-3}$-alkyl)carbamyl" refers to a group of formula —C(O)N$(alkyl)_2$, wherein the two alkyl groups each has, independently, 1 to 3 carbon atoms.

As used herein, the term "$C_{1-3}$ alkylsulfonylamino" refers to a group of formula —NHS$(O)_2$-alkyl, wherein said alkyl has 1 to 3 carbon atoms.

As used herein, the term "aminosulfonyl" refers to a group of formula —$S(O)_2NH_2$.

As used herein, the term "$C_{1-3}$ alkylaminosulfonyl" refers to a group of formula —$S(O)_2$NH(alkyl), wherein said alkyl has 1 to 3 carbon atoms.

As used herein, the term "di($C_{1-3}$ alkylaminosulfonyl" refers to a group of formula —$S(O)_2$N$(alkyl)_2$, wherein each alkyl independently has 1 to 3 carbon atoms.

As used herein, the term "aminosulfonylamino" refers to a group of formula —NHS$(O)_2NH_2$.

As used herein, the term "$C_{1-3}$ alkylaminosulfonylamino," refers to a group of formula —NHS$(O)_2$NH(alkyl), wherein said alkyl has 1 to 3 carbon atoms.

As used herein, the term "di($C_{1-3}$ alkylaminosulfonylamino" refers to a group of formula —NHS$(O)_2$N$(alkyl)_2$, wherein each alkyl independently has 1 to 3 carbon atoms.

As used herein, the term "HO—$C_{n-m}$-alkyl" refers to a group of formula -alkylene-OH, wherein said alkylene group has n to m carbon atoms. In some embodiments, the alkylene group has 1 to 3 carbon atoms.

As used herein, the term "$C_{o-p}$ alkoxy-$C_{n-m}$-alkyl" refers to a group of formula -alkylene-O-alkyl, wherein said alkylene group has n to m carbon atoms and said alkyl group has o to p carbon atoms. In some embodiments, the alkyl and alkylene groups each independently have 1 to 3 carbon atoms.

As used herein, the term "carbonyl", employed alone or in combination with other terms, refers to a —C(O)— group.

As used herein, "halo" or "halogen", employed alone or in combination with other terms, includes fluoro, chloro, bromo, and iodo.

As used herein, the term "$C_{n-m}$ haloalkyl", employed alone or in combination with other terms, refers to an $C_{n-m}$ alkyl group having up to {2(n to m)+1} halogen atoms which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6 or 1 to 4 carbon atoms.

As used herein, the term "cyano-$C_{n-m}$ alkyl" refers to a $C_{n-m}$ alkyl substituted by a cyano group. In some embodiments, the alkyl group has 1 to 3 carbon atoms.

As used herein, the appearance of the term "monocyclic" before the name of a moiety indicates that the moiety has a single ring.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused, spirocyclic, or bridged rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is a 3-10 membered cycloalkyl, which is monocyclic or bicyclic. In some embodiments, cycloalkyl is a 3-6 or 3-7 monocyclic cycloalkyl. Exemplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. In some embodiments, the cycloalkyl group is cyclopropyl, cyclobutyl, cyclopentyl, or cyclohexyl.

As used herein, the term "aryl", employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is a 5-10 membered heteroaryl, which is monocyclic or bicyclic, comprising 1 to 9 carbon atoms and 1, 2, 3, or 4 heteroatom ring members independently selected from nitrogen, sulfur and oxygen. In some embodiments, heteroaryl is a 5-6 membered heteroaryl, which is monocyclic or bicyclic, comprising 1 to 5 carbon atoms and 1, 2, 3, or 4 heteroatom ring members independently selected from nitrogen, sulfur, and oxygen. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like.

A five-membered ring heteroaryl is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heteroarylalkyl" refers to a group of formula -alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen.

As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused, spirocyclic, or bridged rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 5-10 membered heterocycloalkyl, which is monocyclic or bicyclic, comprising 2 to 9 carbon atoms and 1, 2, 3, or 4 heteroatom ring members independently selected from nitrogen, sulfur, and oxygen. Examples of heterocycloalkyl groups include 1,2,3,4-tetrahydro-quinoline, azetidine, azepane, pyrrolidine, piperidine, piperazine, morpholine, thiomorpholine, pyran, and a 2-oxo-1,3-oxazolidine ring.

As used herein, the term "heterocycloalkylalkyl" refers to a group of formula -alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as p-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2, 4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. In some embodiments, 1, 2, or 3 $CH_2$ groups in the azetidine ring of Formula I are replaced by a CHD or $CD_2$ group. In some embodiments, 1, 2, or 3 $CH_2$ or CH groups in the piperidine ring of Formula I are replaced by a CHD, $CD_2$ or CD group, respectively. In some embodiments, 1, 2, 3, 4, or 5 $CH_2$ or CH groups in the piperidine ring of Formula I are replaced by a CHD, $CD_2$ or CD group, respectively.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention.

Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula I can be synthesized by procedures analogous to those in the schemes below. When $X^1$—$X^2$—$X^3$ is —N=$CR^2$—$NR^3$—, $X^4$ is C, and $X^5$ is C, compounds of Formula I can be prepared as illustrated in Scheme 1. Appropriately substituted thienopyridines 1 can be subjected to nitration under conditions such as tetrabutylammonium nitrate and trifluoroacetic anhydride in dichloromethane or nitric acid in sulfuric acid to give compounds of formula 2. Reaction of thienopyridinols 2 in heated POCl$_3$ or other suitable chlorination conditions such as POCl$_3$/PCl$_5$ provides the corresponding chlorides 3. Coupling of compounds 3 with an appropriate $R^3$—NH$_2$ in the presence of a suitable base such as diisopropylethylamine affords compounds 4. Reduction of nitro compounds 4 using catalytic hydrogenation conditions with catalyst such as palladium or nickel or using iron or other suitable reducing conditions yields the corresponding diamines 5. Condensation of compounds 5 with an appropriate amide (activated with triethyloxonium tetrafluoroborate) generates the desired compounds 6. The diamine can also react with an appropriate acid $R^2CO_2H$ under coupling conditions to give an amide intermediate which subsequently can be transformed compounds 6 via an intermolecular condensation. The $R^2$ and $R^3$ can be further modified to desired groups. Alternatively, the $R^3$ can be further transformed to groups disclosed in the invention via modification on compounds 4 and 5.

Scheme 1

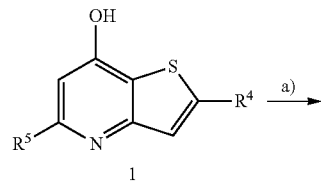

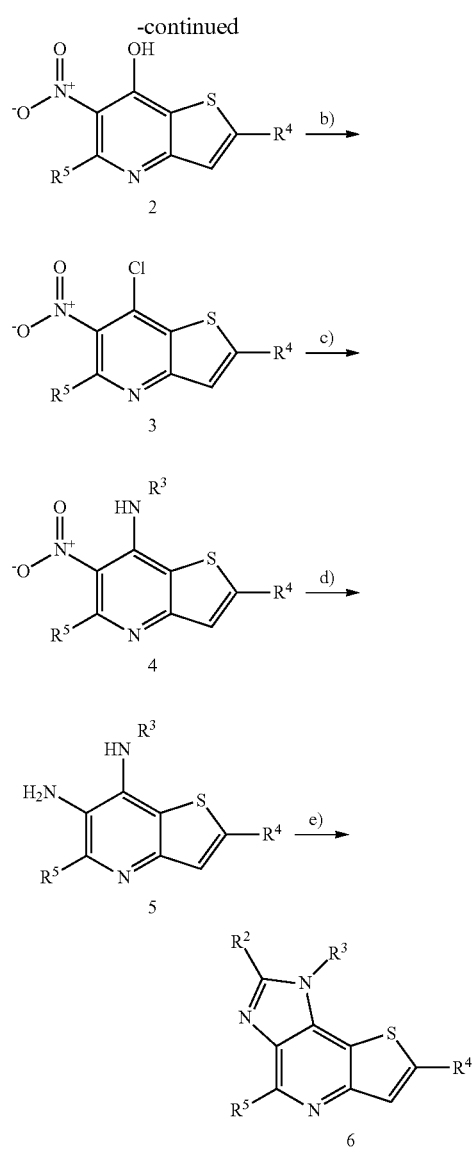

When $X^1$—$X^2$—$X^3$ is —$CR^1$=$CR^2$—$NR^3$—, $X^4$ is C, and $X^5$ is C, compounds of Formula I can be prepared as illustrated in Scheme 2. Appropriately substituted thienopyridines 1 can react with TV-iodosuccinimide to give compounds 7. Reaction of thienopyridinols 7 in heated POCl$_3$ or other suitable chlorination conditions such as POCl$_3$/PCl$_5$ provides the corresponding chlorides 8. Reaction of the iodo compounds 8 with an appropriate alkyne compound catalyzed by a suitable palladium and copper catalyst such as bis(triphenylphosphine)palladium(II) chloride and copper(I) iodide affords compounds 9. Condensation of 9 with $R^3$—NH$_2$ in the presence of suitable coupling conditions such as palladium acetate, (9,9-dimethyl-9H-xanthene-4,5-diyl)bis(diphenylphosphine) and cesium carbonate in toluene generates an amine coupling intermediate which cyclizes in situ with alkyne to furnish compounds of formula 10. The substitution $R^2$ can be introduced by halogenation, nitration or nucleophilic addition of the pyrrole ring. Further modifications of $R^1$, $R^2$, $R^3$, $R^4$, and $R^5$ can be achieved in each step using methods known to one skilled in the art.

Scheme 2

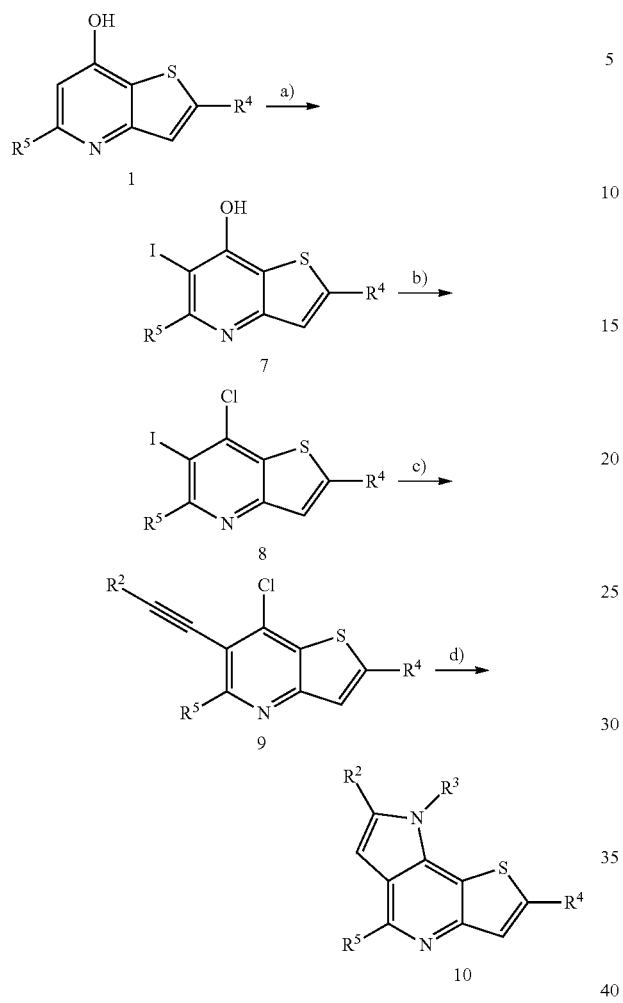

When $X^3$—$X^2$—$X^3$ is —O—C(O)—$NR^3$—, $X^4$ is C, and $X^5$ is C, compounds of Formula I can be prepared as illustrated in Scheme 3. Thienopyridines 11 can be reacted with NaOCl to yield the corresponding chlorinated compounds 12. Alternatively, 11 can be converted to N-oxide which subsequently can be converted to 12 in the HCl or POCl$_3$ conditions. Protection of the hydroxyl group in 12 using conditions known to one skilled in the art gives ether compound 13. Reaction 13 with $R^3NH_2$ under coupling conditions such as palladium acetate, (9,9-dimethyl-9H-xanthene-4,5-diyl)bis(diphenylphosphine) and cesium carbonate in toluene can generate compounds 14. Deprotection of 14 with boron tribromide gives compounds 15. Treatment of 15 with triphosgene or carbonyl diimidazole then provides compounds of formula 16.

Scheme 3

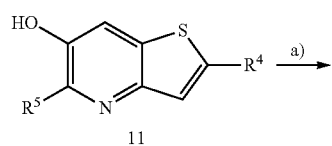

When $X^1$—$X^2$—$X^3$ is =N—$CR^2$=$CR^3$—, $X^4$ is N, and $X^5$ is C, compounds of Formula I can be prepared as illustrated in Scheme 4. Reaction of thienopyrazines 17 with hydrogen peroxide in acetic acid gives an N-oxide intermediate which upon treatment with phosphorous oxychloride provides compounds 18. Substitution of chloride with Boc-NH$_2$ under Buchwald conditions yields compounds 19. Alkylation of carbamates 19 with appropriately substituted 2-halomethyl ketone [halo-CH$_2$C(O)R$^3$] by methods known to one skilled in the art gives compounds 20. The later can be further converted to corresponding substituted compounds 21 under standard alkylation or aldo-condensation conditions if necessary. The deprotection of 21 to 22 can be accomplished using conditions such as trifluoroacetic acid in dichloromethane or HCl in dioxane. Cyclization of 22 to compounds 23 can be accomplished by methods known to one skilled in the art, for example treatment with trifluoroacetic anhydride and trifluoroacetic acid mixture. Further functionalization of R$^2$, R$^3$, R$^4$, R$^5$ can be performed, if desired, using reactions know to one skilled in the art (for example, Larock, R. C. *Comprehensive Organic Transformation*).

Scheme 4

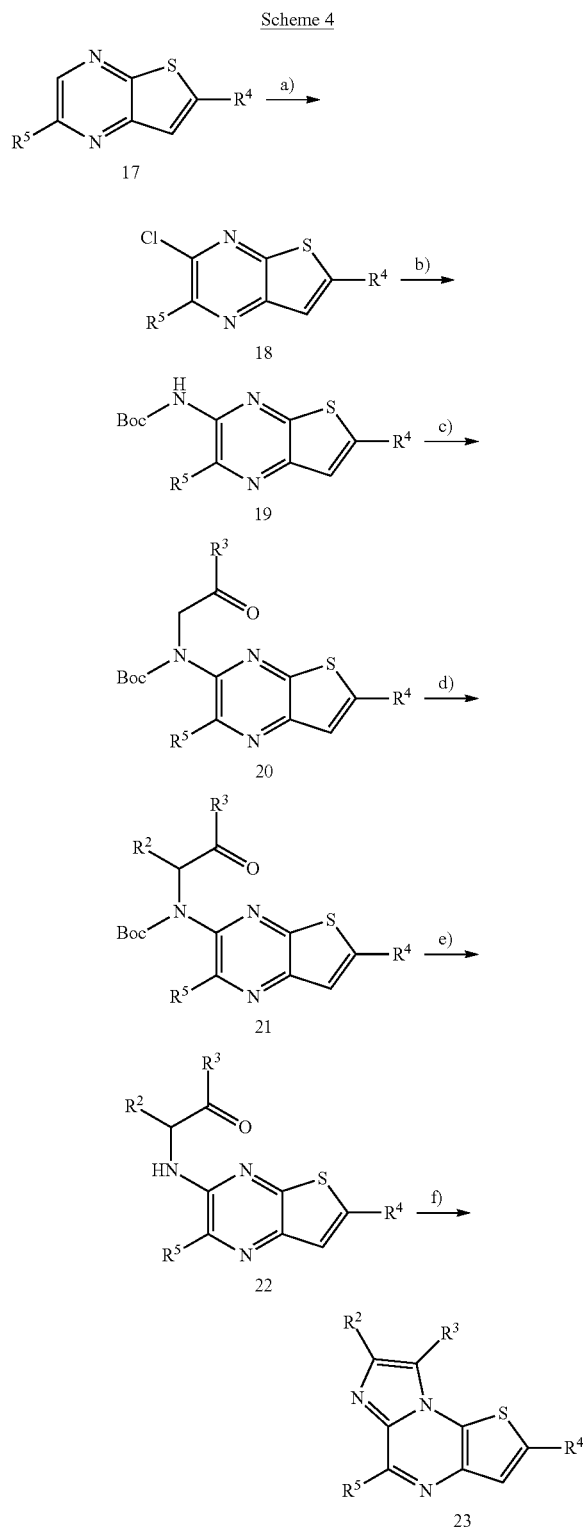

Alternatively, compounds of formula 23 can be synthesized as shown in Scheme 5. Compounds 19 from Scheme 4 can be treated with trifluoroacetic acid or HCl in dioxane to give deprotected compounds 24. Condensation of 24 with alpha-halo-ketone in the presence of a suitable base then affords the desired compounds 23.

Scheme 5

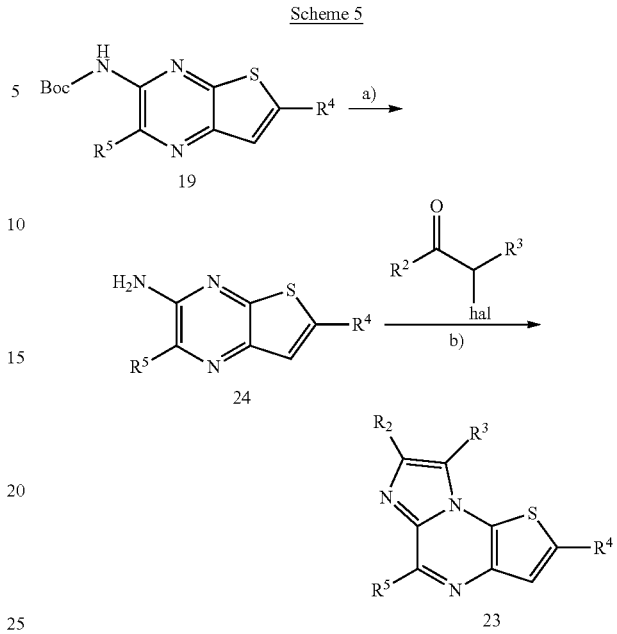

When $X^1$—$X^2$—$X^3$ is —N=N—$NR^3$—, $X^4$ is C, and $X^5$ is C, compounds of Formula I can be prepared by reacting compounds 5 from Scheme 1 with a diazoniation reagent such as butyl nitrite in the presence of copper(II) bromide, as illustrated in Scheme 6.

Scheme 6

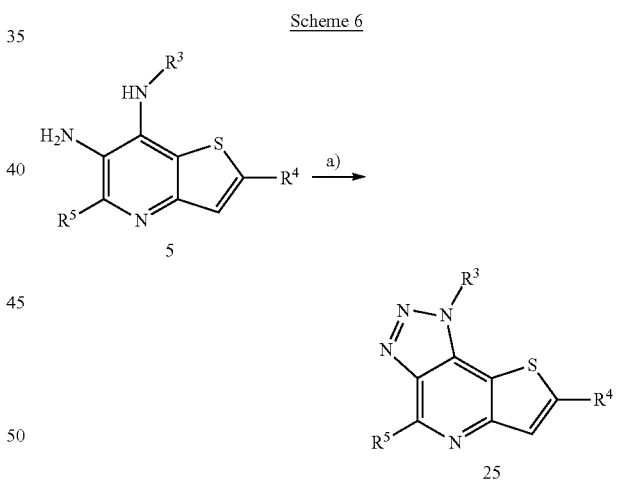

When $X^1$—$X^2$—$X^3$ is —N=$CR^2$—$CR^3$=, $X^4$ is C, and $X^5$ is N, compounds of formula I can be prepared as illustrated in Scheme 7. Tribromopyrazoles 28 can be protected with a suitable protective group such as SEM to give corresponding compounds 29. Lithium-halogen exchange of 29 with butyl lithium then quenched with a suitable alkylation reagent (for example $R^2$-halo) or electrophile (for example an aldehyde) provides compounds 30. Reaction of 30 with a lithium reagent such as butyl lithium followed by aqueous work up affords monobromo-pyrazoles 31. Suzuki reaction of 31 with borates 27 (prepared from bromide 26 by reacting with pinacol borate in the presence of a suitable palladium catalyst) can give coupling compounds 32. Bromination of 32 can yield compounds 33, which can be reduced with iron to provide amines 34. Deprotection of SEM can be achieved using methods known to one skilled in the art, such as reacting with trifluoroacetic acid followed by treatment with ammonium hydroxide. Condensation of 35 with ortho esters then generates tricyclic compounds 36. The later can be subjected to coupling conditions such as Suzuki coupling conditions to provide compounds of formula 37. Further modifications of substitutions, if desired, may be performed by methods known by one skilled in the art.

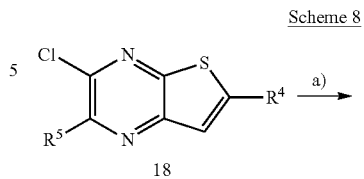

Scheme 8

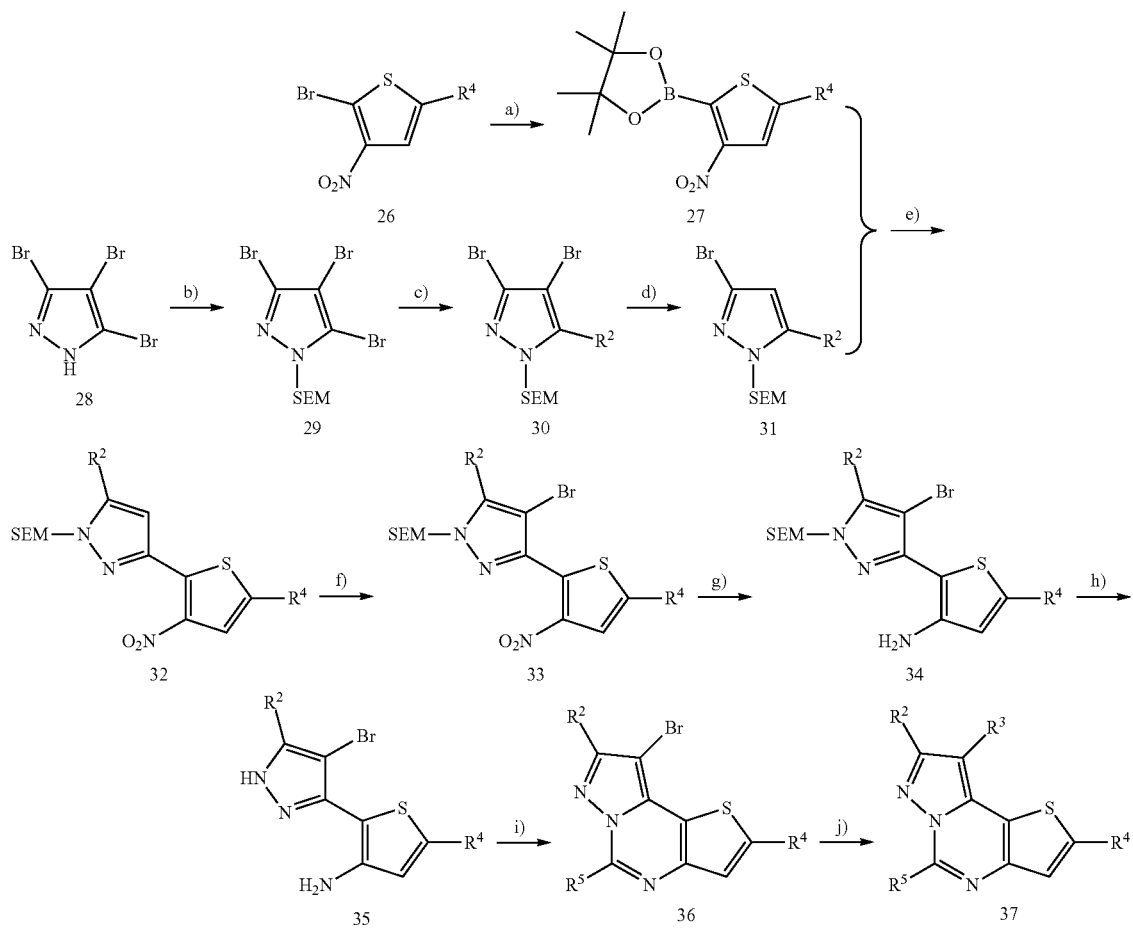

Scheme 7

When $X^1$—$X^2$—$X^3$ is =N—N=$CR^3$—, $X^4$ is N, and $X^5$ is C, compounds of Formula I can be prepared as illustrated in Scheme 8. Substituted hydrazines 38 can be prepared by reaction of compounds 18 with an appropriately protected hydrazine (for example Boc-NHNH$_2$) under Buchwald-Hartwig amination conditions. Deprotection of compounds 38 can be performed using conditions such as those described in Greene, T. W. and Wats, P. G. M. "Protective Groups in Organic Synthesis, $3^{rd}$ Edition", 1999, Wiley-Interscience. For example when P is Boc, compounds 38 can be deprotected to 39 by treatment with trifluoroacetic acid or HCl in dioxane. The formation of hydrazides 40 from 39 may be accomplished by a variety of methods known to one skilled in the art, such as standard peptide coupling methods. The hydrazides 40 can be cyclized to compounds of formula 41 by reacting with POCl$_3$ or with thionyl chloride in the presence of a suitable base (for example triethylamine).

-continued

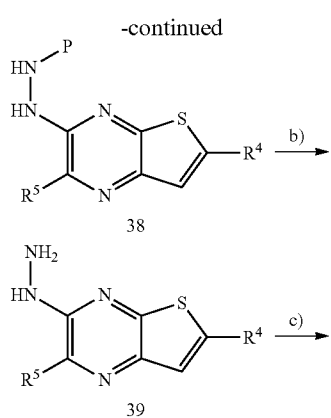

47
-continued

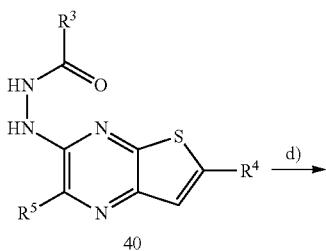
40

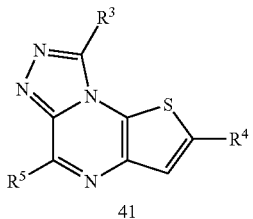
41

48
-continued

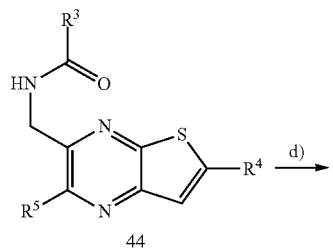
44

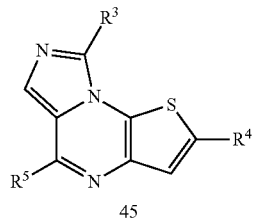
45

When $X^1$—$X^2$—$X^3$ is =$CR^1$—N=$CR^3$—, $X^4$ is N, and $X^5$ is C, compounds of Formula I can be prepared as illustrated in Scheme 9. Thienopyrazines 18 can be converted to cyano compounds 42 via Pd-mediated cyanation, such as zinc cynide in the presence of palladium(II) trifluoroacetate and racemic-2-(di-tert-butylphosphino)-1,1'-binapthyl. Subsequent reduction of nitriles 42 gives amines 43 using well known conditions such as palladium catalyzed hydrogenation in the presence of HCl. The coupling of amines 43 with acids $R^3CO_2H$ can be achieved under standard amide coupling conditions such as HATU/diisopropylethylamine. Cyclization of amides 44 to the tricyclic compounds of formula 45 can be accomplished by conversion to the corresponding thioamide (by reacting with Lawesson's reagent, for example) followed by treatment with an activating agent (such as a mercury salt, a silver salt or a copper salt).

When $X^1$—$X^2$—$X^3$ is —$NR^1$—N=$CR^3$—, $X^4$ is C, and $X^5$ is C, compounds of Formula I can be prepared as illustrated in Scheme 10. Commercially available chlorothieopyridines 46 can be converted to the corresponding iodo analogs 47 through treatment with sodium iodide at elevated temperature. Reaction iodothienopyridines 47 with butyl lithium or other metal reagents followed by treatment with a suitable aldehyde $R^3$CHO provides alcohols 48. Preparation of ketones 49 can be accomplished by treating 48 with an oxidizing agent such as Dess-Martin periodinane. Ketones 49 can then be transformed to hydrazones 50 through reaction with hydrazine. Cyclization of hydrazones 50 to tricyclic compounds 51 can be achieved via an intramolecular Buchwald-Hartwig cyclization. Compounds 51 can be converted to compounds of formula 52 by reacting of 51 with an alkylating reagent such as $R^1$-halogen or $R^1$—OMs/$R^1$—OTs in the presence of a base such as DBU. Alternatively, compounds of formula 53 (Formula I, when $X^1$—$X^2$—$X^3$ is =N—$NR^2$—$CR^3$=, $X^4$ is C, and $X^5$ is C) can be prepared by treating 51 with an alkylating reagent $R^2$-leaving group (leaving group is halo, OTs, OMs, OTf, etc.) in the presence of a suitable base such as sodium hydride.

Scheme 9

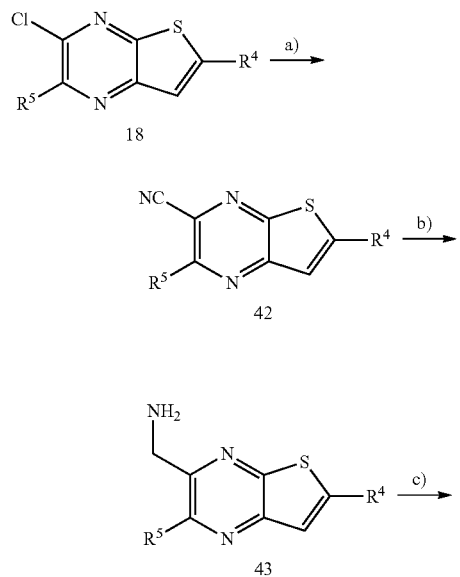

Scheme 10

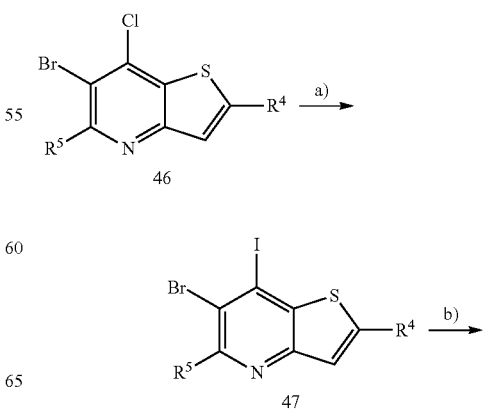

Scheme 11

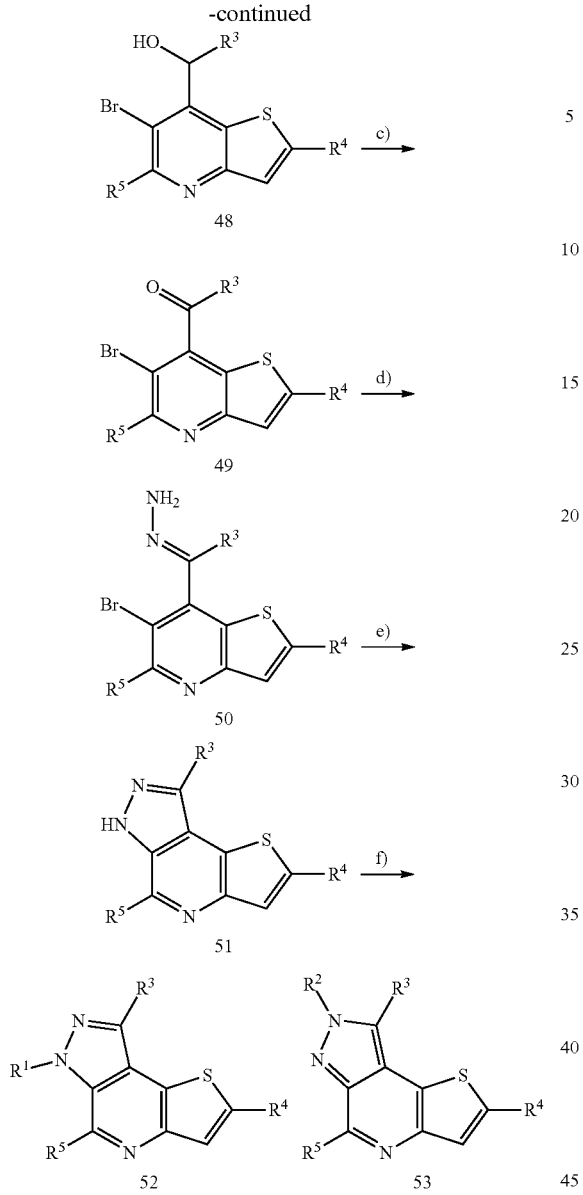

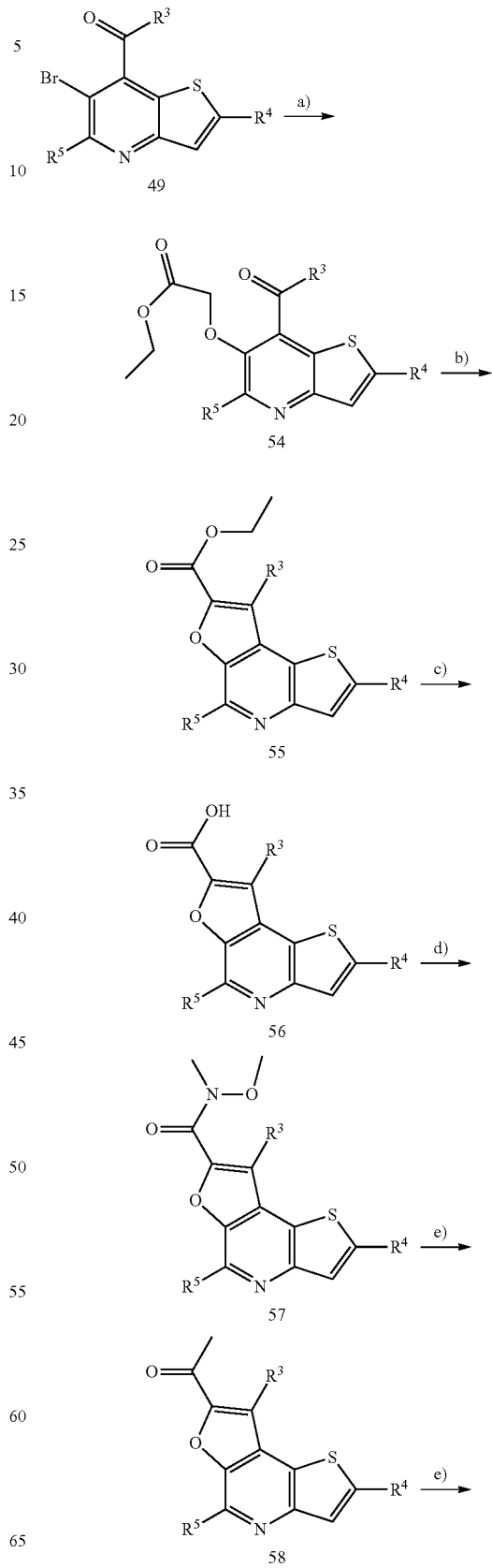

When $X^1$—$X^2$—$X^3$ is —O=$CR^2$=$CR^3$—, $X^4$ is C, and $X^5$ is C, compounds of Formula I can be prepared as illustrated in Scheme 11. Compounds 49 from Scheme 10 can be reacted with glycolic acid ester under Buchwald-Hartwig coupling conditions to generate compounds 54. Cyclization of 54 under basic conditions such as potassium tert-butoxide can provide tricyclic compounds 55. Further functionalization of the substitutions on 55 can be performed, in desired, using reactions known to one skilled in the art. For example, the esters 55 can be hydrolyzed to acids 56, which can then be transformed to amides 57 under standard coupling conditions such as BOP or HATU coupling. Reaction of amides 57 with a nucleophile such as methyl magnesium bromide affords ketones 58, which can then be reduced to give compounds of formula 59. When $X^1$—$X^2$—$X^3$ is —S=$CR^2$=$CR^3$—, $X^4$ is C, and $X^5$ is C, compounds of Formula I can be prepared in analogy to the methods illustrated in Scheme 11, with thioglycolic ester replacing glycolic ester.

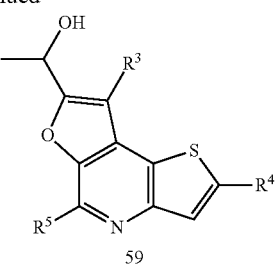

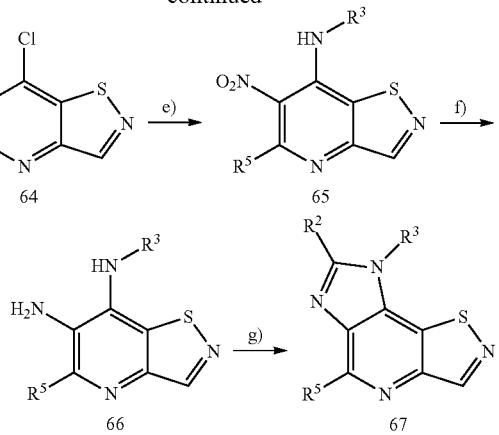

When Y is N, $X^1$—$X^2$—$X^3$ is —N=$CR^2$—$NR^3$—, $X^4$ is C, and $X^5$ is C, compounds of formula I of the invention can be prepared as illustrated in Scheme 12. Appropriately substituted fluoropyridines 60 can be reacted with a thiol such as benzylthiol in the presence of a suitable base such as sodium tert-butoxide to give compounds of formula 61. Reaction of pyridine thioethers 61 with sulfuryl chloride followed by treatment with ammonia provides cyclized products 62. Alternatively, compounds 62 can be synthesized by reacting compounds 60 with hydroxylamine and sulfur. Nitration of compounds 63 gives compounds of formula 64. Coupling of compounds 64 with an appropriate $R^3$—$NH_2$ in the presence of a suitable base such as diisopropylethylamine affords compounds 65. Reduction of nitro compounds 65 using catalytic hydrogenation conditions with catalyst such as palladium or nickel or using iron or other suitable reducing conditions yields the corresponding diamines 66. Condensation of compounds 66 with an appropriate amide (activated with triethyloxonium tetrafluoroborate) generates the desired compounds 67. The diamine can also react with an appropriate acid $R^2CO_2H$ under coupling conditions to give an amide intermediate which subsequently can be transformed compounds 67 via an intermolecular condensation. The $R^2$ and $R^3$ can be further modified to desired groups. Alternatively, $R^3$ can be further transformed to groups disclosed in the invention via modification on compounds 65 and 66.

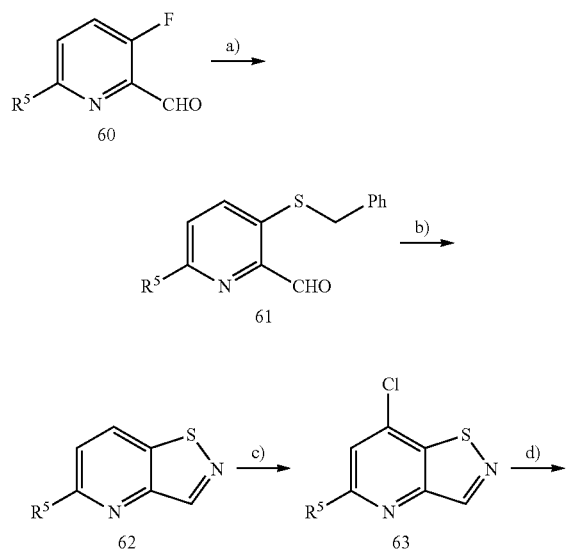

Methods

Compounds of the invention are JAK inhibitors, and the majority of the compounds of the invention, are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 $IC_{50}$ ratio>1). In some embodiments, the compounds are about 10-fold more selective for JAK1 over JAK2. In some embodiments, the compounds are about 3-fold, about 5-fold, about 10-fold, about 15-fold, or about 20-fold more selective for JAK1 over JAK2 as calculated by measuring $IC_{50}$ at 1 mM ATP (e.g., see Example A).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106: 9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chrondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)). In some embodiments, the myeloproliferative disorder is post-essential thrombocythemia myelofibrosis (Post-ET MF). In some embodiments, the myeloproliferative disorder is post polycythemia vera myelofibrosis (Post-PV MF).

JAK-associated disease further include myelodysplastic syndrome (MDS).

The present invention further provides methods of treating psoriasis or other skin disorders by administration of a topical formulation containing a compound of the invention.

In some embodiments, JAK inhibitors described herein can be used to treat pulmonary arterial hypertension.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

The JAK inhibitors described herein can further be used to treat ischemia reperfusion injuries or a disease or condition related to an inflammatory ischemic event such as stroke or cardiac arrest. The JAK inhibitors described herein can further be used to treat endotoxin-driven disease state (e.g., complications after bypass surgery or chronic endotoxin states contributing to chronic cardiac failure). The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19): 19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface*, 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted subepithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compounds of the invention, or in combination with other JAK inhibitors, such as those reported in U.S. Ser. No. 11/637,545, which is incorporated herein by reference in its entirety, can be used to treat respiratory dysfunction or failure associated wth viral infection, such as influenza and SARS.

In some embodiments, the present invention provides a compound of Formula I, pharmaceutically acceptable salt thereof, as described in any of the embodiments herein, for use in a method of treating any of the diseases or disorders described herein. In some embodiments, the present invention provides the use of a compound of Formula I as described in any of the embodiments herein, for the preparation of a medicament for use in a method of treating any of the diseases or disorders described herein.

In some embodiments, the present invention provides a compound of Formula I as described herein, or a pharmaceutically acceptable salt thereof, for use in a method of modulating JAK1. In some embodiments, the present invention also provides use of a compound of Formula I as described herein, or a pharmaceutically acceptable salt thereof, for the preparation of a medicament for use in a method of modulating JAK1.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the therapeutically effective amount is about 5 mg to about 1000 mg, or about 10 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, a suitable chemotherapeutical agent can be selected from antimetabolite agents, topoisomerase 1 inhibitors, platinum analogs, taxanes, anthracyclines, and EGFR inhibitors, and combinations thereof.

In some embodiments, antimetabolite agents include capecitabine, gemcitabine, and fluorouracil (5-FU).

In some embodiments, taxanes include paclitaxel, Abraxane® (paclitaxel protein-bound particles for injectable suspension), and Taxotere® (docetaxel).

In some embodiments, platinum analogs include oxaliplatin, cisplatin, and carboplatin.

In some embodiments, topoisomerase 1 inhibitors include irinotecan and topotecan.

In some embodiment, anthracyclines include doxorubicin or liposomal formulations of doxorubicin.

In some embodiments, the chemotherapeutic is FOFFIRINOX (5-FU, lecovorin, irinotecan and oxaliplatin). In some embodiments, the chemotherapeutic agent is gemcitabine and Abraxane® (paclitaxel protein-bound particles for injectable suspension).

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holies Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DEO 11, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline). In some embodiments, the additional therapeutic agent binds to FKBP12.

In some embodiments, the additional therapeutic agent is an alkylating agent or DNA cross-linking agent; an antimetabolite/demethylating agent (e.g., 5-flurouracil, capecitabine or azacitidine); an anti-hormone therapy (e.g., hormone receptor antagonists, SERMs, or aromotase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGER inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate or cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is a topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethyl siloxane), polyethylene oxide, poly(lactide-co-glycolide), poly(2-hydroxyethylmethacrylate), poly(vinyl alcohol), or polypropylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic fdm. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic composition comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro JAK labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

EXAMPLES

Example 1. (1R)-1-{1-[(3S)-Tetrahydro-2H-pyran-3-yl]-1H-imidazo[4,5-d]thieno[3,2-b]pyridin-2-yl}ethanol

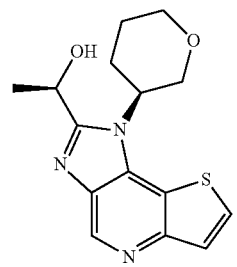 [SMILES: C[C@@H](O)c1nc2cnc3ccsc3c2n1[C@H]1CCCOC1]

Step 1. 6-Nitrothieno[3,2-b]pyridin-7-ol

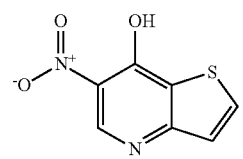

N,N,N-Tributylbutan-1-aminium nitrate (from Aldrich, 9.1 g, 30 mmol) dissolved in methylene chloride (100 mL) was added dropwise to a stirred solution of thieno[3,2-b]pyridin-7-ol (from Aldrich, 3.0 g, 20 mmol) in methylene chloride (100 mL) at −5° C. Trifluoroacetic anhydride (4.5 mL, 32 mmol) was added while maintaining the temperature below 0° C. The resulting mixture was then stirred at −5° C.

for 30 min and at room temperature overnight. The reaction mixture was concentrated, diluted with ether, filtered. The solid collected was washed with water and then ether/methanol (MeOH) mixture (1:1), and air-dried to give the desired product (3.3 g, 85%). LCMS calculated for $C_7H_5N_2O_3S$ (M+H)$^+$: m/z=197.0; Found: 196.9.

Step 2. 7-Chloro-6-nitrothieno[3,2-b]pyridine

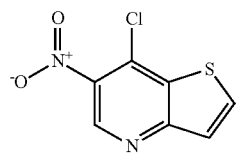

6-Nitrothieno[3,2-b]pyridin-7-ol (3.3 g, 17 mmol) was suspended in phosphoryl chloride (30 mL, 400 mmol) and heated at reflux for 1 h (dissolution was apparent after 45 min). The solvent was removed. Toluene was added to the residue and the volatiles were removed in vacuo. Dichloromethane and sat. NaHCO, solution were added (Caution: gas evolution), and the layers separated. The organic layer was washed with water, dried over MgSO$_4$ and concentrated to give the desired product (2.7 g, 75%). LCMS calculated for $C_7H_4ClN_2O_2S$ (M+H)$^+$: m/z=215.0; Found: 214.9.

Step 3. 6-Nitro-N-[(3S)-tetrahydro-2H-pyran-3-yl]thieno[3,2-b]pyridin-7-amine

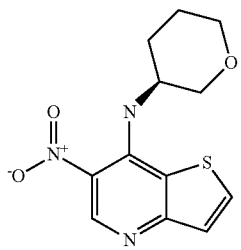

A mixture of 7-chloro-6-nitrothieno[3,2-b]pyridine (0.060 g, 0.28 mmol), (3S)-tetrahydro-2H-pyran-3-amine hydrochloride (from J&W Pharmatech, 0.059 g, 0.43 mmol) and N,N-diisopropylethylamine (0.15 mL, 0.84 mmol) in isopropyl alcohol (0.95 mL) was heated at 60° C. overnight. The resulting mixture was concentrated and purified on silica gel (eluting with 0 to 50% ethyl acetate (EtOAc) in hexanes) to give the desired product (30 mg, 38%). LCMS calculated for $C_{12}H_{14}N_3O_3S$ (M+H)$^+$: m/z=280.1; Found: 280.0.

Step 4. N7-[(3S)-Tetrahydro-2H-pyran-3-yl]thieno[3,2-b]pyridine-6,7-diamine

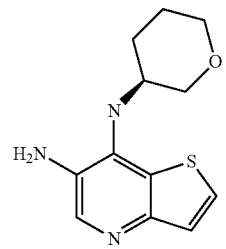

A mixture of 6-nitro-N-[(3S)-tetrahydro-2H-pyran-3-yl]thieno[3,2-b]pyridin-7-amine (30 mg, 0.1 mmol), iron (18 mg, 0.32 mmol) and ammonium chloride (29 mg, 0.54 mmol) in ethanol (0.8 mL)/water (0.3 mL) was heated at reflux for 4 h. The resulting mixture was filtered. The filtrate was diluted with EtOAc, washed with sat. NaHCO$_3$ solution, dried over MgSO$_4$, and concentrated. The residue was purified on silica gel (eluting with 0 to 5% MeOH in dichloromethane) to give the desired product. LCMS calculated for $C_{12}H_{16}N_3OS$ (M+H)$^+$: m/z=250.1; Found: 250.0.

Step 5. (1R)-1-{1-[(3S)-Tetrahydro-2H-pyran-3-yl]-1H-imidazo[4,5-d]thieno[3,2-b]pyridin-2-yl}ethanol A mixture of (2R)-2-hydroxypropanamide (from Aldrich, 5.4 mg, 0.060 mmol) and triethyloxonium tetrafluoroborate (12 mg, 0.062 mmol) in tetrahydrofuran (0.1 mL) became a solution after stirred for 15 min. After another 45 min, this solution was added to a mixture of N7-[(3S)-tetrahydro-2H-pyran-3-yl]thieno[3,2-b]pyridine-6,7-diamine (7.5 mg, 0.030 mmol) in ethanol (0.24 mL) and the resultant mixture was heated at reflux for 2 h. The crude mixture was purified on RP-HPLC (XBridge C18 column, eluting with a gradient of acetonitrile/water containing 0.1% ammonium hydroxide, at flow rate of 30 mL/min) to give the desired product (5.9 mg, 65%). LCMS calculated for $C_{15}H_{18}N_3O_2S$ (M+H)$^+$: m/z=304.1; Found: 304.0.

Example 2. (trans-4-{2-[(1R)-1-Hydroxyethyl]-1H-imidazo[4,5-d]thieno[3,2-b]pyridin-1-yl}cyclohexyl)acetonitrile

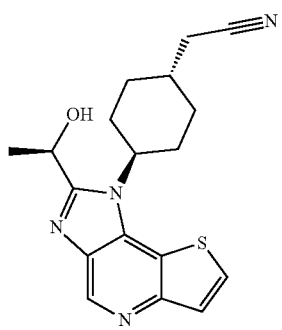 [SMILES: C[C@@H](O)c1nc2cnc3ccsc3c2n1[C@H]1CC[C@H](CC#N)CC1]

Step 1. {trans-4-[(6-Nitrothieno[3,2-b]pyridin-7-yl)amino]cyclohexyl}methanol

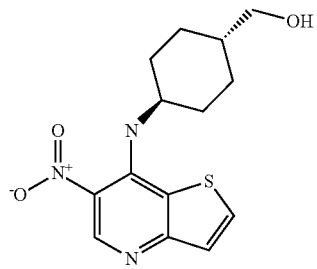

A mixture of 7-chloro-6-nitrothieno[3,2-b]pyridine (0.21 g, 0.98 mmol) (Example 1, Step 2), (trans-4-aminocyclohexyl)methanol (from J&W Pharmatech, 0.25 g, 2.0 mmol) and N,N-diisopropylethylamine (0.51 mL, 2.9 mmol) in isopropyl alcohol (3.3 mL) was heated at 90° C. for 2 h. The resulting mixture was concentrated and purified on silica gel (eluting with 0 to 60% EtOAc in hexanes) to give the desired product (0.26 g, 86%). LCMS calculated for $C_{14}H_{18}N_3O_3S$ (M+H)$^+$: m/z=308.1; Found: 308.0.

Step 2. {trans-4-[(6-Nitrothieno[3,2-b]pyridin-7-yl)amino]cyclohexyl}methyl methane sulfonate

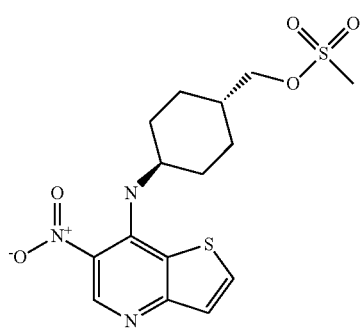

To a mixture of {trans-4-[(6-nitrothieno[3,2-b]pyridin-7-yl)amino]cyclohexyl}methanol (0.26 g, 0.84 mmol) and N,A-diisopropylethylamine (0.30 mL, 1.7 mmol) in methylene chloride (3 mL) was added methanesulfonyl chloride (0.085 mL, 1.1 mmol). The resulting mixture was stirred at room temperature for 2 h. After diluting with water, the mixture was extracted with dichloromethane. The organic layers were concentrated and purified on silica gel (eluting with 0 to 70% EtOAc in hexanes) to give the desired product (0.2 g, 61%). LCMS calculated for $C_{15}H_{20}N_3O_5S_2$ (M+H)$^+$: m/z=386.1; Found: 386.0.

Step 3. {trans-4-[(6-Nitrothieno[3,2-b]pyridin-7-yl)amino]cyclohexyl}acetonitrile

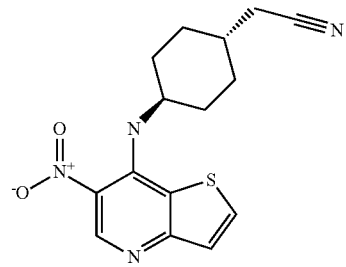

A mixture of {trans-4-[(6-nitrothieno[3,2-b]pyridin-7-yl)amino]cyclohexyl}methyl methanesulfonate (0.20 g, 0.52 mmol) and sodium cyanide (0.057 g, 1.2 mmol) in dimethyl sulfoxide (2 mL) was stirred at 90° C. for 4 h. After diluting with EtOAc, the resulting mixture was washed with sat. NaHCO, solution, water and brine, then concentrated. The residue was purified on silica gel (eluting with 0 to 5% MeOH in dichloromethane) to give the desired product. LCMS calculated for $C_{15}H_{17}N_4O_2S$ (M+H)$^+$: m/z=317.1; Found: 317.0.

Step 4. {trans-4-[(6-Aminothieno[3,2-b]pyridin-7-yl)amino]cyclohexyl}acetonitrile

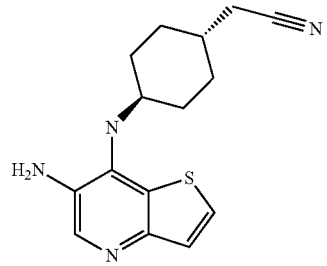 [SMILES: N#CC[C@H]1CC[C@H](Nc2c(N)cnc3ccsc23)CC1]

A mixture of {tram-4-[(6-nitrothieno[3,2-b]pyridin-7-yl)amino]cyclohexyl}acetonitrile (0.16 g, 0.50 mmol) and 10% palladium on carbon (20 mg) in methanol (5 mL) was hydrogenated under balloon pressure of $H_2$ at room temperature for 2 h. The reaction mixture was filtered and the filtrate concentrated to give the desired product (0.124 g, 86%), which was used directly in the next step. LCMS calculated for $C_{15}H_{19}N_4S$ (M+H)$^+$: m/z=287.1; Found: 287.1.

Step 5. (trans-4-{2-[(1R)-1-Hydroxyethyl]-1H-imidazo[4,5-d]thieno[3,2-b]pyridin-1-yl}cyclohexyl)acetonitrile

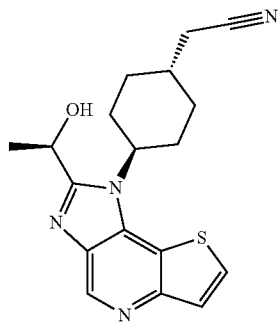 [SMILES: C[C@@H](O)c1nc2cnc3ccsc3c2n1[C@H]1CC[C@H](CC#N)CC1]

A mixture of (2R)-2-hydroxypropanamide (0.12 g, 1.3 mmol) and triethyloxonium tetrafluoroborate (0.25 g, 1.3 mmol) in tetrahydrofuran (2 mL) became a solution after stirred for 15 min. After another 45 min, this solution was added to a mixture of {trans-4-[(6-aminothieno[3,2-b]pyridin-7-yl)amino]cyclohexyl}acetonitrile (124 mg, 0.433 mmol) in ethanol (3.4 mL) and the resultant mixture was heated at reflux for 2 h. The crude mixture was purified on RP-HPLC (XBridge C18 column, eluting with a gradient of acetonitrile/water containing 0.1% ammonium hydroxide, at flow rate of 30 mL/min) to give the desired product (65 mg, 44%). LCMS calculated for $C_{18}H_{21}N_4OS$ (M+H)$^+$: m/z=341.1; Found: 341.1. $^1$H NMR (DMSO-$d_6$, 400 MHz) δ 8.98 (1H, s), 8.00 (1H, d, J=5.2 Hz), 7.66 (1H, d, J=5.2 Hz), 5.86 (1H, d, J=6.4 Hz), 5.19 (1H, m), 4.92 (1H, m), 2.61 (2H, d, J=6.0 Hz), 2.43 (2H, m), 2.01 (5H, m), 1.64 (3H, d, J=6.4 Hz), 1.40 (2H, m) ppm.

Example 3. trans-4-{2-[(1R)-1-Hydroxyethyl]-1Z-imidazo[4,5-d]thieno[3,2-b]pyridin-1-yl}cyclohexanol

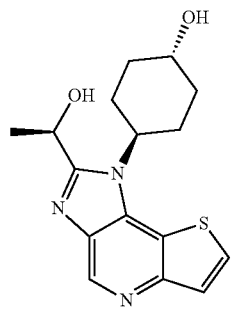 [SMILES: C[C@@H](O)c1nc2cnc3ccsc3c2n1[C@H]1CC[C@H](O)CC1]

Step 1. trans-4-[(6-Nitrothieno[3,2-b]pyridin-7-yl)amino]cyclohexanol

A mixture of 7-chloro-6-nitrothieno[3,2-b]pyridine (0.47 g, 2.2 mmol) (Example 1, step 2), trans-4-aminocyclohexanol (from Aldrich, 0.50 g, 4.4 mmol) and N,N-diisopropylethylamine (1.1 mL, 6.6 mmol) in isopropyl alcohol (7.4 mL) was heated at 90° C. for 2 h. The reaction mixture was concentrated and purified on silica gel (eluting with 0 to 5% MeOH in dichloromethane) to give the desired product (0.266 g, 41%). LCMS calculated for $C_{13}H_{16}N_3O_3S$ (M+H)$^+$: m/z=294.1; Found: 294.0.

Step 2. trans-4-[(6-Aminothieno[3,2-b]pyridin-7-yl)amino]cyclohexanol

A mixture of trans-4-[(6-nitrothieno[3,2-b]pyridin-7-yl)amino]cyclohexanol (50 mg, 0.2 mmol) and 10% palladium on carbon (7 mg) in methanol (2 mL) was hydrogenated under balloon pressure of $H_2$ at room temperature for 2 h. The reaction mixture was filtered. The filtrate was concentrated to give the desired product, which was used directly in the next step. LCMS calculated for $C_{13}H_{18}N_3OS$ (M+H)$^+$: m/z=264.1; Found: 264.1.

Step 3. trans-4-{2-[(1R)-1-Hydroxyethyl]-1H-imidazo[4,5-d]thieno[3,2-b]pyridin-1-yl}cyclohexanol A mixture of (2R)-2-hydroxypropanamide (96 mg, 1.1 mmol) and triethyloxonium tetrafluoroborate (0.20 g, 1.1 mmol) in tetrahydrofuran (2 mL) became a solution after stirred for 15 min. After another 45 min, this solution was added to a mixture of trans-4-[(6-aminothieno[3,2-b]pyridin-7-yl)amino]cyclohexanol (95 mg, 0.36 mmol) in ethanol (2.9 mL) and heated at reflux for 2 h. The resulting mixture was purified on RP-HPLC (XBridge C18 column, eluting with a gradient of acetonitrile/water containing 0.1% ammonium hydroxide, at flow rate of 30 mL/min) to give the desired product (0.9 mg, 0.8%). LCMS calculated for $C_{16}H_{20}N_3O_2S$ (M+H)$^+$: m/z=318.1; Found: 318.0.

Example 4. (1R)-1-(1-{trans-4-[(2,2,2-Trifluoroethyl)amino]cyclohexyl}-1H-imidazo[4,5-d]thieno[3,2-b]pyridin-2-yl)ethanol

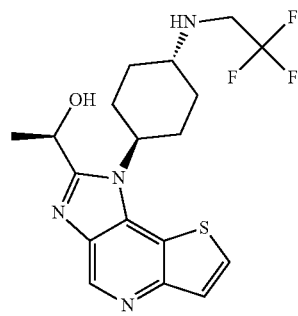 [SMILES: C[C@@H](O)c1nc2cnc3ccsc3c2n1[C@H]1CC[C@H](NCC(F)(F)F)CC1]

Step 1. trans-N-(6-Nitrothieno[3,2-b]pyridin-7-yl)cyclohexane-1,4-diamine

A mixture of 7-chloro-6-nitrothieno[3,2-b]pyridine (0.21 g, 0.98 mmol) (Example 1, step 2), trans-cyclohexane-1,4-diamine (from Aldrich, 0.13 g, 1.2 mmol) and N,N-diisopropylethylamine (0.34 mL, 2.0 mmol) in isopropyl alcohol (3.3 mL) was heated at 90° C. for 2 h. The solvent in the resulting mixture was removed to give the desired product, which was used directly in the next step. LCMS calculated for $C_{13}H_{17}N_4O_2S$ (M+H)$^+$: m/z=293.1; Found: 293.0.

Step 2. trans-N-(6-Nitrothieno[3,2-b]pyridin-7-yl)-N'-(2,2,2-trifluoroethyl)cyclohexane-1,4-diamine To a mixture of trans-N-(6-nitrothieno[3,2-b]pyridin-7-yl)cyclohexane-1,4-diamine (120 mg, 0.41 mmol) and N,N- diisopropylethylamine (0.36 mL, 2.0 mmol) in methylene chloride (2 mL)/N,N-dimethylformamide (2 mL) was added 2,2,2-trifluoroethyl trifluoromethanesulfonate (0.18 mL, 1.2 mmol). The reaction was stirred at room temperature for 4 h. The resulting mixture was diluted with water, extracted with dichloromethane. The organic layers were concentrated and purified on silica gel (eluting with 0 to 5% MeOH in dichloromethane) to give the desired product (34 mg, 22%). LCMS calculated for $C_{15}H_{18}F_3N_4O_2S$ (M+H)$^+$: m/z=375.1; Found: 375.0.

Step 3. N7-{trans-4-[(2,2,2-Trifluoroethyl)amino]cyclohexyl}thieno[3,2-b]pyridine-6,7-diamine A mixture of trans-N-(6-nitrothieno[3,2-b]pyridin-7-yl)-N-(2,2,2-trifluoroethyl)cyclohexane-1,4-diamine (34 mg, 0.091 mmol) and 10% palladium on carbon (4 mg) in methanol (0.9 mL) was hydrogenated under balloon pressure of H$_2$ at room temperature for 2 h. The reaction mixture was filtered and the filtrate was concentrated to give the desired product (27 mg, 86%), which was used directly in the next step. LCMS calculated for $C_{15}H_{20}F_3N_4S$ (M+H)$^+$: m/z=345.1; Found: 345.0.

Step 4. (1R)-1-(1-{trans-4-[(2,2,2-Trifluoroethyl)amino]cyclohexyl}-1H-imidazo[4,5-d]thieno[3,2-b]pyridin-2-yl)ethanol A mixture of (2R)-2-hydroxypropanamide (21 mg, 0.24 mmol) and triethyloxonium tetrafluoroborate (45 mg, 0.24 mmol) in tetrahydrofuran (0.3 mL) became a solution after stirring for 15 min. After another 45 min, this solution was added to a mixture of N7-{trans-4-[(2,2,2-trifluoroethyl)amino]cyclohexyl}thieno[3,2-b]pyridine-6,7-diamine (27 mg, 0.078 mmol) in ethanol (0.62 mL) and heated at reflux for 2 h. The resulting mixture was purified on RP-HPLC (XBridge C18 column, eluting with a gradient of acetonitrile/water containing 0.1% ammonium hydroxide, at flow rate of 30 mL/min) to give the desired product (3.2 mg, 10%). LCMS calculated for $C_{18}H_{22}F_3N_4OS$ (M+H)$^+$: m/z=399.1; Found: 399.2.

Example 5. (1R)-1-(1-{trans-4-[2-(Methylsulfonyl)ethyl]cyclohexyl}-1H-imidazo[4,5-d]thieno[3,2-b]pyridin-2-yl)ethanol

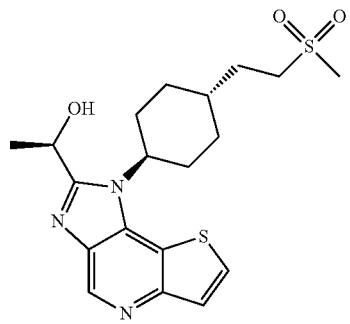 [SMILES: C[C@@H](O)c1nc2cnc3ccsc3c2n1[C@H]1CC[C@H](CCS(C)(=O)=O)CC1]

Step 1. tert-Butyl (trans-4-formylcyclohexyl)carbamate

A solution of tert-butyl [trans-4-(hydroxymethyl)cyclohexyl]carbamate (from Aldrich, 0.61 g, 2.7 mmol) in methylene chloride (10 mL) at 0° C. was added Dess-Martin periodinane (1.35 g, 3.19 mmol). The resulting mixture was stirred at room temperature overnight. The reaction was quenched with aq. 1 N NaOH solution, extracted with dichloromethane. The combined organic layers were washed with water and brine, dried over MgSO$_4$, and concentrated. The residue was purified on silica gel (eluting with 0 to 5% MeOH in dichloromethane) to give the desired product (0.3 g, 50%). LCMS calculated for $C_{12}H_{21}NO_3Na$ (M+Na)+: m/z=250.2; Found: 250.1.

Step 2. tert-Butyl {trans-4-[2-(methylsulfonyl)vinyl]cyclohexyl}carbamate

To a solution of 1.0 M potassium tert-butoxide in tetrahydrofuran (THF) (1.0 mL, 1.0 mmol) was added diethyl [(methylsulfonyl)methyl]phosphonate (0.21 g, 0.92 mmol) dropwise at 0° C. and the resulting mixture was stirred at 0° C. for 1 h. A solution of tert-butyl (trans-4-formylcyclohexyl)carbamate (0.15 g, 0.66 mmol) in tetrahydrofuran (4.6 mL) was added dropwise, then cooling bath was removed and the mixture was stirred at room temperature for 1 h. The reaction mixture was diluted with EtOAc, washed with water, concentrated and purified on silica gel (eluting with 0 to 5% MeOH in dichloromethane) to give the desired product (0.14 g, 70%) as a mixture of E- and Z-isomers. LCMS calculated for $C_{14}H_{25}NO_4SNa$ (M+Na)+: m/z=326.2; Found: 326.1.

Step 3. trans-4-(2-(Methylsulfonyl)ethyl)cyclohexanamine Trifluoroacetate

A mixture of tert-butyl {trans-4-[2-(methylsulfonyl)vinyl]cyclohexyl}carbamate (140 mg, 0.46 mmol) and 10% of palladium on carbon (49 mg) in methanol (4 mL) was hydrogenated under balloon pressure of H$_2$ at room temperature overnight. The reaction mixture was filtered and the filtrate was concentrated to give tert-butyl {trans-4-[2-(methylsulfonyl)ethyl]cyclohexyl}carbamate. LCMS calculated for $C_9H_{20}NO_2S$ (M-Boc+2H)$^+$: m/z=206.1; Found: 206.1. The Boc-intermediate was treated with trifluoroacetic acid (0.2 mL, 3 mmol) in methylene chloride (0.5 mL) at room temperature for 1 h. The resulting mixture was concentrated to give the desired product as trifluoroacetic acid (TFA) salt. LCMS calculated for $C_9H_{20}NO_2S$ (M+H)$^+$: m/z=206.1; Found: 206.1.

Step 4. N-{trans-4-[2-(Methylsulfonyl)ethyl]cyclohexyl}-6-nitrothieno[3,2-b]pyridin-7-amine A mixture of 7-chloro-6-nitrothieno[3,2-b]pyridine (0.10 g, 0.46 mmol), trans-4-[2-(methylsulfonyl)ethyl]cyclohexanamine TFA salt (0.12 g, 0.60 mmol) and N,N-diisopropylethylamine (0.40 mL, 2.3 mmol) in isopropyl alcohol (1.0 mL) was heated at 90° C. for 2 h. The reaction mixture was concentrated and purified on silica gel (eluting with 0 to 45% EtOAc in dichloromethane) to give the desired product. LCMS calculated for $C_{16}H_{22}N_3O_4S_2$ (M+H)$^+$: m/z=384.1; Found: 384.0.

Step 5. N7-{trans-4-[2-(Methylsulfonyl)ethyl]cyclohexyl}thieno[3,2-b]pyridine-6,7-diamine A mixture of N-{trans-4-[2-(methylsulfonyl)ethyl]cyclohexyl}-6-nitrothieno[3,2-b]pyridin-7-amine (220 mg, 0.57 mmol) and 10% palladium on carbon (60 mg, 0.06 mmol) in methanol (4 mL) was hydrogenated under balloon pressure of H$_2$ at room temperature for 2 h. The reaction mixture was filtered and the filtrate was concentrated to give the desired product, which was used in the next step directly. LCMS calculated for C$_{16}$H$_{24}$N$_3$O$_2$S$_2$(M+H)$^+$: m/z=354.1; Found: 354.0.

Step 6. (1R)-1-(1-{trans-4-[2-(Methylsulfonyl)ethyl] cyclohexyl}-1H-imidazo[4,5-d]thieno[3,2-b]pyridin-2-yl)ethanol A mixture of (2R)-2-hydroxypropanamide (52 mg, 0.59 mmol) and triethyloxonium tetrafluoroborate (0.11 g, 0.59 mmol) in tetrahydrofuran (1 mL) became a solution after stirring for 15 min. After another 45 min, this solution was added to a mixture of N7-{trans-4-[2-(methylsulfonyl)ethyl] cyclohexyl}thieno[3,2-b]pyridine-6,7-diamine (83 mg, 0.23 mmol) in ethanol (2 mL) and heated at reflux overnight. The resulting mixture was purified on RP-HPLC (XBridge C18 column, eluting with a gradient of acetonitrile/water containing 0.1% ammonium hydroxide, at flow rate of 30 mL/min) to give the desired product (1.1 mg, 1.1%). LCMS calculated for C$_{19}$H$_{26}$N$_3$O$_3$S$_2$(M+H)$^+$: m/z=408.1; Found: 408.1.

Example 6. (1R)-1-{1-[cis-4-(1H-1,2,4-Triazol-1-yl) cyclohexyl]-1H-imidazo[4,5-d]thieno[3,2-b]pyridin-2-yl}ethanol

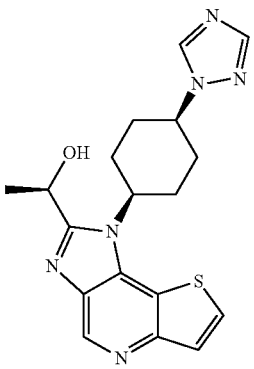 [SMILES: C[C@@H](O)c1nc2cnc3ccsc3c2n1[C@H]1CC[C@@H](n2cncn2)CC1]

Step 1. trans-4-[(tert-Butoxycarbonyl)amino]cyclohexyl Methanesulfonate

To a mixture of tert-butyl (trans-4-hydroxycyclohexyl) carbamate (from AstaTech, 0.133 g, 0.618 mmol) and triethylamine (0.12 mL, 0.86 mmol) in methylene chloride (1 mL) was added methanesulfonyl chloride (0.057 mL, 0.74 mmol). The reaction mixture was stirred at room temperature for 2 h. After dilution with sat. aq. NaHCO$_3$ solution, the mixture was extracted with dichloromethane. The combined organic layers were washed with brine, dried over MgSO$_4$ and concentrated to give the desired product (0.18 g, 99%).

Step 2. cis-4-(1H-1,2,4-Triazol-1-yl)cyclohexanamine trifluoroacetate

Sodium hydride (60%, 0.034 g, 0.86 mmol) was added portionwise to a solution of 1H-1,2,4-triazole (0.064 g, 0.92 mmol) in N,N-dimethylformamide (2 mL). After stirred for 5 min, trans-4-[(tert-butoxycarbonyl)amino]cyclohexyl methanesulfonate (0.18 g, 0.61 mmol) was added. The resulting mixture was stirred at 65° C. over weekend. The cooled mixture was poured into ice-cold water, extracted with EtOAc. The organic layers were concentrated and purified on silica gel (eluting with 0 to 5% MeOH in EtOAc) to give tert-butyl [cis-4-(1H-1,2,4-triazol-1-yl)cyclohexyl] carbamate (0.14 g, 86%). LCMS calculated for C$_{13}$H$_{23}$N$_4$O$_2$ (M+H)$^+$: m/z=267.2; Found: 267.1. This carbamate intermediate was treated with trifluoroacetic acid (0.28 mL, 3.7 mmol) in methylene chloride (1 mL) at room temperature for 1 h and then concentrated to give the desired product as TFA salt. LCMS calculated for C$_8$H$_{15}$N$_4$(M+H)$^+$: m/z=167.1; Found: 167.2.

Step 3. 6-Nitro-N-[cis-4-(1H-1,2,4-triazol-1-yl)cyclohexyl]thieno[3,2-b]pyridin-7-amine A mixture of 7-chloro-6-nitrothieno[3,2-b]pyridine (0.10 g, 0.46 mmol), cis-4-(1H-1,2,4-triazol-1-yl)cyclohexanamine TFA salt (0.10 g, 0.60 mmol) and N,N-diisopropylethylamine (0.40 mL, 2.3 mmol) in isopropyl alcohol (1.0 mL) was heated at 90° C. for 2 h. The resulting mixture was concentrated and purified on silica gel (eluting with 0 to 10% EtOAc in dichloromethane) to give the desired product (32 mg, 20%). LCMS calculated for C$_{15}$H$_{17}$N$_6$O$_2$S (M+H)$^+$: m/z=345.1; Found: 345.0.

Step 4. N7-[cis-4-(1H-1,2,4-Triazol-1-yl)cyclohexyl]thieno[3,2-b]pyridine-6,7-diamine A mixture of 6-nitro-N-[cis-4-(1H-1,2,4-triazol-1-yl)cyclohexyl]thieno[3,2-b]pyridin-7-amine (32 mg, 0.093 mmol) and 10% palladium on carbon (4 mg) in methanol (0.9 mL) was hydrogenated under balloon pressure of H$_2$ at room temperature for 2 h. The reaction was filtered and the resultant filtrate was concentrated to give the desired product, which was used directly in the next step. LCMS calculated for C$_{15}$H$_{19}$N$_6$S (M+H)$^+$: m/z=315.1; Found: 315.1.

Step 5. (1R)-1-{1-[cis-4-(1H-1,2,4-Triazol-1-yl) cyclohexyl]-1H-imidazo[4,5-d]thieno[3,2-b]pyridin-2-yl}ethanol A mixture of (2R)-2-hydroxypropanamide (28 mg, 0.32 mmol) and triethyloxonium tetrafluoroborate (60 mg, 0.32 mmol) in tetrahydrofuran (0.4 mL) became a solution after stirring for 15 min. After another 45 min, this solution was added to a mixture of N7-[cis-4-(1H-1,2,4-triazol-1-yl)cyclohexyl]thieno[3,2-b]pyridine-6,7-diamine (25 mg, 0.080 mmol) in ethanol (0.8 mL) and heated at reflux overnight. The resulting mixture was purified on RP-HPLC (XBridge C18 column, eluting with a gradient of acetonitrile/water containing 0.1% ammonium hydroxi de, at flow rate of 30 mL/min) to give the desired product (1.7 mg, 5.8%). LCMS calculated for C$_{18}$H$_{21}$N$_6$OS (M+H)$^+$: m/z=369.1; Found: 369.1.

Example 7. cis-4-{2-[(1R)-1-Hydroxyethyl]-1H-imidazo[4,5-d]thieno[3,2-b]pyridin-1-yl}cyclohexanecarbonitrile

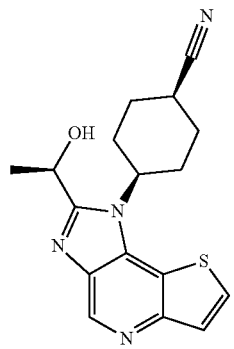 [SMILES: C[C@@H](O)c1nc2cnc3ccsc3c2n1[C@H]1CC[C@@H](C#N)CC1]

Step 1. trans-4-[(6-Nitrothieno[3,2-b]pyridin-7-yl)amino]cyclohexyl Methanesulfonate To a mixture of trans-4-[(6-nitrothieno[3,2-b]pyridin-7-yl)amino]cyclohexanol (0.21 g, 0.72 mmol) (Example 3, Step 1) and N,N-diisopropylethylamine (0.25 mL, 1.4 mmol) in methylene chloride (2 mL) was added methanesulfonyl chloride (0.083 mL, 1.1 mmol). The reaction was stirred at room temperature for 2 h. After dilution with sat. aq. NaHCO$_3$ solution, the resulting mixture was extracted with dichloromethane. The organic layers were concentrated and purified on silica gel (eluting with 0 to 5% MeOH in dichloromethane) to give the desired product (0.24 g, 90%). LCMS calculated for C$_{14}$H$_{18}$N$_3$O$_5$S$_2$(M+H)$^+$: m/z=372.1; Found: 372.0.

Step 2. cis-4-[(6-Nitrothieno[3,2-b]pyridin-7-yl)amino]cyclohexanecarbonitrile A mixture of trans-4-[(6-nitrothieno[3,2-b]pyridin-7-yl)amino]cyclohexyl methanesulfonate (0.12 g, 0.32 mmol) and sodium cyanide (0.061 g, 1.2 mmol) in dimethyl sulfoxide (1 mL) was stirred at 90° C. for 6 h. After dilution with EtOAc, the resulting mixture was washed with sat. NaHCO$_3$ solution, water and brine, and then concentrated. The residue was purified on silica gel (eluting with 0 to 5% MeOH in dichloromethane) to give the desired product (32 mg). LCMS calculated for C$_{14}$H$_{15}$N$_4$O$_2$S (M+H)$^+$: m/z=303.1; Found: 303.0.

Step 3. cis-4-[(6-Aminothieno[3,2-b]pyridin-7-yl)amino]cyclohexanecarbonitrile A mixture of cis-4-[(6-nitrothieno[3,2-b]pyridin-7-yl)amino]cyclohexanecarbonitrile (32 mg, 0.10 mmol) and 10% palladium on carbon (4 mg) in methanol (1 mL) was hydrogenated under balloon pressure of H$_2$ at room temperature for 4 h. The mixture was filtered and the filtrate was concentrated to give the desired product, which was used directly in the next step. LCMS calculated for C$_{14}$H$_{17}$N$_4$S (M+H)$^+$: m/z=273.1; Found: 273.1.

Step 4. cis-4-{2-[(1R)-1-Hydroxyethyl]-1H-imidazo[4,5-d]thieno[3,2-b]pyridin-1-yl}cyclohexanecarbonitrile A mixture of (2R)-2-hydroxypropanamide (40 mg, 0.4 mmol) and triethyloxonium tetrafluoroborate (89 mg, 0.47 mmol) in tetrahydrofuran (0.4 mL) became a solution after stirring for 15 min. After another 45 min, this solution was added to a mixture of cis-4-[(6-aminothieno[3,2-b]pyridin-7-yl)amino]cyclohexanecarbonitrile (32 mg, 0.12 mmol) in ethanol (0.74 mL) and heated at reflux overnight. The resulting mixture was purified on RP-HPLC (XBridge C18 column, eluting with a gradient of acetonitrile/water containing 0.1% ammonium hydroxide, at flow rate of 30 mL/min) to give the desired product (1.1 mg, 2.9%). LCMS calculated for C$_{17}$H$_{19}$N$_4$OS (M+H)$^+$: m/z=327.1; Found: 327.0.

Example 8. 3-(trans-4-{2-[(1R)-1-Hydroxyethyl]-1H-imidazo[4,5-d]thieno[3,2-b]pyridin-1-yl}cyclohexyl)propanenitrile

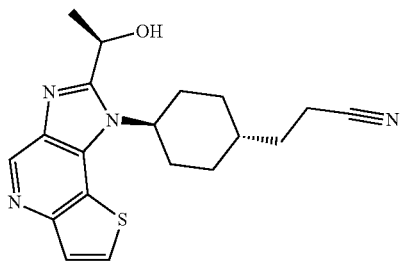 [SMILES: C[C@@H](O)c1nc2cnc3ccsc3c2n1[C@H]1CC[C@H](CCC#N)CC1]

Step 1. tert-Butyl {trans-4-[2-cyanovinyl]cyclohexyl}carbamate

To a solution of 1.0 M potassium tert-butoxide in THF (1.0 mL, 1.0 mmol) was added diethyl cyanomethylphosphonate (0.15 mL, 0.92 mmol) dropwise at 0° C. and the resulting mixture was stirred at 0° C. for 1 h. A solution of tert-butyl (trans-4-formylcyclohexyl)carbamate (0.15 g, 0.66 mmol) (Example 5, Step 1) in tetrahydrofuran (4.6 mL) was added dropwise, then cooling bath was removed and the reaction mixture was stirred at room temperature for 1 h. The reaction was diluted with EtOAc, washed with water. The organic layers were concentrated and purified on silica gel (eluting with 0 to 5% MeOH in dichloromethane) to give the desired product as a mixture of E- and Z-isomers (0.14 g, 70%). LCMS calculated for C$_{14}$H$_{22}$N$_2$O$_2$Na (M+Na)$^+$: m/z=273.2; Found: 273.0.

Step 2. 3-(trans-4-Aminocyclohexyl)propanenitrile Trifluoroacetate

A mixture of tert-butyl {trans-4-[2-cyanovinyl]cyclohexyl}carbamate (0.13 g, 0.52 mmol) and 10% palladium on carbon (52 mg) in ethanol (2 mL) was hydrogenated under balloon pressure of H$_2$ over weekend. The mixture was filtered, and the filtrate was concentrated to give tert-butyl [trans-4-(2-cyanoethyl)cyclohexyl]carbamate. LCMS calculated for C$_{10}$H$_{17}$N$_2$O$_2$ (M-$^t$Bu+H)$^+$: m/z=197.1; Found: 197.1. This carbamate intermediate was treated with trifluoroacetic acid (0.4 mL, 5 mmol) in methylene chloride (1 mL) at room temperature for 1 h, and then the solvent removed to give the desired product as TFA salt. LCMS calculated for C$_9$H$_{17}$N$_2$(M+H)$^+$: m/z=153.1; Found: 153.2.

Step 3. 3-{trans-4-[(6-Nitrothieno[3,2-b]pyridin-7-yl)amino]cyclohexyl}propanenitrile A mixture of 7-chloro-6-nitrothieno[3,2-b]pyridine (0.087 g, 0.41 mmol), 3-(trans-4-aminocyclohexyl)propanenitrile (0.080 g, 0.52 mmol) TFA salt and N,N-diisopropylethylamine (0.35 mL, 2.0 mmol) in isopropyl alcohol (0.89 mL) was heated at 90° C. for 2 h. The resulting mixture was concentrated and purified on silica gel (eluting with 0 to 20% EtOAc in dichloromethane) to give the desired product (63 mg, 47%). LCMS calculated for $C_{16}H_{19}N_4O_2S$ (M+H)$^+$: m/z=331.1; Found: 331.0.

Step 4. 3-{trans-4-[(6-Aminothieno[3,2-b]pyridin-7-yl)amino]cyclohexyl}propanenitrile A mixture of 3-{trans-4-[(6-nitrothieno[3,2-b]pyridin-7-yl)amino]cyclohexyl}propanenitrile (63 mg, 0.19 mmol) and 10% palladium on carbon (20 mg) in methanol (1 mL) was hydrogenated under balloon pressure of $H_2$ at room temperature for 2 h. The reaction mixture was filtered and the filtrate was concentrated to give the desired product (48 mg, 84%), which was used directly in the next step. LCMS calculated for $C_{16}H_{21}N_4S$ (M+H)$^+$: m/z=301.1; Found: 301.1.

Step 5. 3-(trans-4-{2-[(1R)-1-Hydroxyethyl]-1H-imidazo[4,5-d]thieno[3,2-b]pyridin-1-yl}cyclohexyl)propanenitrile To a mixture of 3-{trans-4-[(6-aminothieno[3,2-b]pyridin-7-yl)amino]cyclohexyl}propanenitrile (0.048 g, 0.16 mmol) and (R)-2-hydroxypropanoic acid (0.019 g, 0.21 mmol) in methylene chloride (0.96 mL) was added N,N-diisopropylethylamine (60 µL, 0.35 mmol) and N,N,N',N'-tetramethyl-O-(7-azabenzotriazol-1-yl)uronium hexafluorophosphate (66 mg, 0.17 mmol). The resulting mixture was stirred at room temperature overnight. The mixture was washed with water. The organic layers were concentrated and purified on silica gel (eluting with 0 to 10% MeOH in dichloromethane) to give (2R)—N-(7-{[trans-4-(2-cyanoethyl)cyclohexyl]amino}thieno[3,2-b]pyridin-6-yl)-2-hydroxypropanamide. LCMS calculated for $C_{19}H_{25}N_4O_2S$ (M+H)$^+$: m/z=373.2; Found: 373.0. A solution of the amide intermediate in acetic acid (0.3 mL) was stirred at 105° C. for 5 h. The solvent in the reaction mixture was removed in vacuo, diluted with MeOH and purified on RP-HPLC (XBridge C18 column, eluting with a gradient of acetonitrile/water containing 0.1% ammonium hydroxide, at flow rate of 30 mL/min) to give the desired product (6 mg, 10%). LCMS calculated for $C_{19}H_{23}N_4OS$ (M+H)$^+$: m/z=355.2; Found: 355.1.

Example 9. (1R)-1-[1-(3-Fluoropiperidin-4-yl)-1H-imidazo[4,5-d]thieno[3,2-b]pyridin-2-yl]ethanol

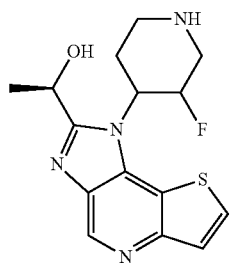 [SMILES: C[C@@H](O)c1nc2cnc3ccsc3c2n1C1CCNCC1F]

Step 1. tert-Butyl 3-hydroxy-4-[(6-nitrothieno[3,2-b]pyridin-7-yl)amino]piperidine-1-carboxylate A mixture of 7-chloro-6-nitrothieno[3,2-b]pyridine (0.61 g, 2.8 mmol) (Example 1, Step 2), tert-butyl 4-amino-3-hydroxypiperidine-1-carboxylate (from Aurora, 0.95 g, 4.4 mmol) and N,N-diisopropylethylamine (0.99 mL, 5.7 mmol) in isopropyl alcohol (7.4 mL) was heated at 90° C. for 2 h. The resulting mixture was diluted with water. The precipitate was collected by filtration, washed with water and air-dried to give the desired product (1 g, 89%). LCMS calculated for $C_{17}H_{23}N_4O_5S$ (M+H)$^+$: m/z=395.1; Found: 395.0.

Step 2. tert-Butyl 3-fluoro-4-[(6-nitrothieno[3,2-b]pyridin-7-yl)amino]piperidine-1-carboxylate To a solution of tert-butyl 3-hydroxy-4-[(6-nitrothieno[3,2-b]pyridin-7-yl)amino]piperidine-1-carboxylate (716 mg, 1.82 mmol) in methylene chloride (4 mL) cooled at 0° C. was added slowly 2-methoxy-N-(2-methoxyethyl)-N-(trifluoro-λ(4)-sulfanyl)ethanamine (0.50 mL, 2.7 mmol). The reaction was stirred at room temperature for 4 h. The mixture was diluted with dichloromethane, washed with water, and concentrated. The residue was purified on silica gel (eluting with 0 to 30% EtOAc in dichloromethane) to give the desired product (0.32 g, 44%) as a mixture of cis- and trans-isomers mixture. LCMS calculated for $C_{17}H_{22}FN_4O_4S$ (M+H)$^+$: m/z=397.1; Found: 397.1.

Step 3. tert-Butyl 4-[(6-aminothieno[3,2-b]pyridin-7-yl)amino]-3-fluoropiperidine-1-carboxylate A mixture of tert-butyl 3-fluoro-4-[(6-nitrothieno[3,2-b]pyridin-7-yl)amino]piperidine-1-carboxylate (0.32 g, 0.81 mmol) and 10% palladium on carbon (80 mg) in methanol (8 mL) was hydrogenated under balloon pressure of $H_2$ at room temperature for 5 h. The reaction mixture was filtered, and the filtrate was concentrated to give the desired product (0.23 g, 78%) as a mixture of cis- and trans-isomers mixture. LCMS calculated for $C_{17}H_{24}FN_4O_2S$ (M+H)$^+$: m/z=367.2; Found: 367.1.

Step 4. (1R)-1-[1-(3-Fluoropiperidin-4-yl)-1H-imidazo[4,5-d]thieno[3,2-b]pyridin-2-yl]ethanol To a mixture of tert-butyl 4-[(6-aminothieno[3,2-b]pyridin-7-yl)amino]-3-fluoropiperidine-1-carboxylate (0.21 g, 0.57 mmol) and (R)-2-hydroxypropanoic acid (0.059 g, 0.65 mmol) in methylene chloride (5 mL) was added N,N-diisopropylethylamine (0.23 mL, 1.3 mmol) and N,N,N',N'-tetramethyl-O-(7-azabenzotriazol-1-yl)uronium hexafluorophosphate (0.23 g, 0.60 mmol). The resulting mixture was stirred at room temperature overnight. The reaction mixture was washed with water, concentrated and purified on silica gel (eluting with 0 to 10% MeOH in dichloromethane) to give tert-butyl 3-fluoro-4-[(6-{[(2R)-2-hydroxypropanoyl]amino}thieno[3,2-b]pyridin-7-yl)amino]piperidine-1-carboxylate (0.155 g, 62%). LCMS calculated for $C_{20}H_{28}FN_4O_4S$ (M+H)$^+$: m/z=439.2; Found: 439.1. A solution of the amide intermediate in acetic acid (1 mL) was heated at reflux for 2 h. The resulting mixture was purified on silica gel (eluting with 0-10% MeOH in dichloromethane) to give tert-butyl 3-fluoro-4-{2-[(1R)-1-hydroxyethyl]-1H-imidazo[4,5-d]thieno[3,2-b]pyridin-1-yl}piperidine-1-carboxylate (16 mg, 10%). LCMS calculated for $C_{20}H_{26}FN_4O_3S$ (M+H)$^+$: m/z=421.2; Found: 421.1. The Boc protected intermediate was treated with trifluoroacetic acid (0.1 mL, 1 mmol) in methylene chloride (0.2 mL) at room temperature for 1 h. The mixture was concentrated and purified on RP-HPLC (XBridge C18 column, eluting with a gradient of acetonitrile/water containing 0.1% ammonium hydroxide, at flow rate of 30 mL/min) to give two desired products. First peak retention time 0.253 min. LCMS calculated for $C_{15}H_{18}FN_4OS$ (M+H)$^+$: m/z=321.1; Found: 321.1. Second peak retention time 0.514 min. LCMS calculated for $C_{15}H_{18}FN_4OS$ (M+H)$^+$: m/z=321.1; Found: 321.1.

Example 10. (trans-4-{2-[(1R)-1-Hydroxyethyl]-1H-imidazo[4,5-d]thieno[3,2-b]pyridin-1-yl}cyclohexyl)acetonitrile HCl Salt

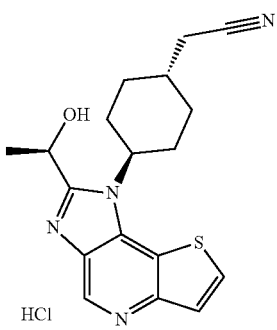 [SMILES: C[C@@H](O)c1nc2cnc3ccsc3c2n1[C@H]1CC[C@H](CC#N)CC1 ; Cl]

Step 1. {trans-4-[(tert-Butoxycarbonyl)amino]cyclohexyl}methyl Methanesulfonate A mixture of tert-butyl [trans-4-(hydroxymethyl)cyclohexyl]carbamate (from Albany Molecular, 1.5 g, 6.5 mmol) in methylene chloride (20 mL) was treated with pyridine (2.14 mL, 26.5 mmol). The mixture was cooled to 0° C. and methanesulfonyl chloride (1.01 mL, 13.1 mmol) was added dropwise over 5 min. The reaction was stirred at room temperature for 5 h. The resulting mixture was then concentrated and partitioned between EtOAc and water. The organic phases were concentrated and purified on silica gel (eluting with 50% EtOAc in hexanes) to give the desired product (1.48 g, 74%). LCMS calculated for $C_{13}H_{25}NO_5SNa$ (M+Na)$^+$: m/z=330.2; Found: 330.0.

Step 2. (trans-4-Aminocyclohexyl)acetonitrile Trifluoroacetate

A mixture of {trans-4-[(tert-butoxycarbonyl)amino]cyclohexyl}methyl methanesulfonate (1.48 g, 4.81 mmol) and sodium cyanide (0.46 g, 9.4 mmol) in dimethyl sulfoxide (20 mL) was stirred at 90° C. for 4 h. After cooling, the mixture was partitioned between EtOAc and brine. The organic layer was washed with water, concentrated and purified on silica gel (eluting with 50% EtOAc in hexanes) to give tert-butyl [trans-4-(cyanomethyl)cyclohexyl]carbamate. LCMS calculated for $C_{13}H_{22}N_2O_2Na$ (M+Na)$^+$: m/z=261.2; Found: 261.1. A solution of the Boc-protected intermediate in methylene chloride (20 mL) was treated with trifluoroacetic acid (3 mL, 40 mmol) and the resulting mixture was stirred at room temperature for 2 h, then concentrated to give the desired product as TFA salt. LCMS calculated for $C_8H_{15}N_2$(M+H)$^+$: m/z=139.1; Found: 139.1.

Step 3. {trans-4-[(6-Nitrothieno[3,2-b]pyridin-7-yl)amino]cyclohexyl}acetonitrile To a stirred suspension of 7-chloro-6-nitrothieno[3,2-b]pyridine (0.88 g, 4.1 mmol) in isopropyl alcohol (14 mL), (trans-4-aminocyclohexyl)acetonitrile TFA salt (0.68 g, 4.9 mmol) and N,N-diisopropylethylamine (3.0 mL, 17 mmol) were added. The reaction was stirred at 90° C. for 2 h. The mixture was concentrated and purified on silica gel (eluting with 0 to 60% EtOAc in dichloromethane) to give the desired product (1 g, 77%). LCMS calculated for $C_{15}H_{17}N_4O_2S$ (M+H)$^+$: m/z=317.1; Found: 317.0.

Step 4. {trans-4-[(6-Aminothieno[3,2-b]pyridin-7-yl)amino]cyclohexyl}acetonitrile A mixture of {trans-4-[(6-nitrothieno[3,2-b]pyridin-7-yl)amino]cyclohexyl}acetonitrile (1.0 g, 3.2 mmol) and 10% palladium on carbon (0.3 g, 0.3 mmol) in methanol (30 mL) was hydrogenated under balloon pressure of $H_2$ at room temperature for 5 h. The reaction mixture was filtered. The filtrate was concentrated, diluted with dichlormethane, dried over $MgSO_4$, and concentrated. The residue was purified on silica gel (eluting with 0 to 5% MeOH in dichloromethane) to give the desired product. (0.63 g, 70%). LCMS calculated for $C_{15}H_{19}N_4S$ (M+H)$^+$: m/z=287.1; Found: 287.1.

Step 5. (trans-4-{2-[(1R)-1-hydroxyethyl]-1H-imidazo[4,5-d]thieno[3,2-b]pyridin-1-yl}cyclohexyl)acetonitrile A mixture of (2R)-2-hydroxypropanamide (0.630 g, 7.07 mmol) and triethyloxonium tetrafluoroborate (1.26 g, 6.66 mmol) in tetrahydrofuran (9.7 mL) was stirred at room temperature for 2 h. The solvent was removed, and the residue dissolved in ethanol (4.1 mL) and added to a suspension of {trans-4-[(6-aminothieno[3,2-b]pyridin-7-yl)amino]cyclohexyl}acetonitrile (0.63 g, 2.2 mmol) in ethanol (15 mL). The reaction was stirred at 80° C. for 2 h. The solvent was removed and the residue was partitioned between EtOAc and sat. $NaHCO_3$ solution. The organic phase was washed with brine, dried over $MgSO_4$, and concentrated. The residue was purified on silica gel (eluting with 0 to 10% MeOH in dichloromethane), then further purified on RP-HPLC (XBridge C18 column, eluting with a gradient of acetonitrile/water containing 0.1% ammonium hydroxide, at flow rate of 30 mL/min) to give the desired product (0.55 g, 73%). LCMS calculated for $C_{18}H_{21}N_4OS$ (M+H)$^+$: m/z=341.1; Found: 341.1.

Step 6. (trans-4-{2-[(1R)-1-Hydroxyethyl]-1H-imidazo[4,5-d]thieno[3,2-b]pyridin-1-yl}cyclohexyl)acetonitrile HCl Salt (trans-4-{2-[(1R)-1-Hydroxyethyl]-1H-imidazo[4,5-d]thieno[3,2-b]pyridin-1-yl}cyclohexyl)acetonitrile (0.154 g, 0.451 mmol) was dissolved in acetonitrile (10 mL). 1.0 M Hydrogen chloride in water (0.480 mL, 0.480 mmol) was added slowly with stirring, followed by addition of water (10 mL). The mixture was stirred at room temperature until becoming homogeneous. The resulting solution was lyophilized to give the desired product as HCl salt. (0.169 g, 99.5%). LCMS calculated for $C_{18}H_{21}N_4OS$ (M+H)$^+$: m/z=341.1; Found: 341.1. $^1$H NMR (DMSO-d$_6$, 500 MHz) δ 9.55 (1H, s), 8.47 (1H, d, J=5.5 Hz), 8.00 (1H, d, J=5.5

Hz), 5.32 (1H, m), 5.07 (1H, m), 2.62 (2H, d, J=6.0 Hz), 2.43 (2H, m), 2.12 (2H, m), 2.04 (3H, m), 1.68 (3H, d, J=6.0 Hz), 1.46 (2H, m) ppm.

Example 11. (1R)-1-{1-[trans-4-(Hydroxymethyl)cyclohexyl]-1H-imidazo[4,5-d]thieno[3,2-b]pyridin-2-yl}ethanol

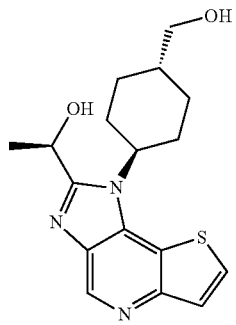 [SMILES: C[C@@H](O)c1nc2cnc3ccsc3c2n1[C@H]1CC[C@H](CO)CC1]

Step 1. {trans-4-[(6-Aminothieno[3,2-b]pyridin-7-yl)amino]cyclohexyl}methanol

A mixture of {trans-4-[(6-nitrothieno[3,2-b]pyridin-7-yl)amino]cyclohexyl}methanol (0.080 g, 0.26 mmol) (Example 2, Step 1) and 10% palladium on carbon (0.03 g) in methanol (3 mL) was hydrogenated under balloon pressure of $H_2$ at room temperature for 1 h. The mixture was filtered. The filtrate was concentrated, diluted with dichloromethane, then dried over $MgSO_4$, and concentrated. The residue was purified on silica gel (eluting with 10% MeOH in dichloromethane) to give the desired product (41 mg, 57%). LCMS calculated for $C_{14}H_{20}N_3OS$ $(M+H)^+$: m/z=278.1; Found: 278.1.

Step 2. (1R)-1-{1-[trans-4-(Hydroxymethyl)cyclohexyl]-1H-imidazo[4,5-d]thieno[3,2-b]pyridin-2-yl}ethanol A mixture of (2R)-2-hydroxypropanamide (42 mg, 0.48 mmol) and triethyloxonium tetrafluoroborate (85 mg, 0.45 mmol) in tetrahydrofuran (0.65 mL) was stirred at room temperature for 2 h. The solvent was removed, and the residue dissolved in ethanol (0.27 mL) and added to a suspension of {trans-4-[(6-aminothieno[3,2-b]pyridin-7-yl)amino]cyclohexyl}methanol (41 mg, 0.15 mmol) in ethanol (0.99 mL). The resulting mixture was stirred at 85° C. for 1 h. The solvent was removed and the residue was purified on RP-HPLC (XBridge C18 column, eluting with a gradient of acetonitrile/water containing 0.1% ammonium hydroxide, at flow rate of 30 mL/min) to give the desired product (2.3 mg, 4.7%). LCMS calculated for $C_{17}H_{22}N_3O_2S$ $(M+H)^+$: m/z=332.1; Found: 332.1.

Example 12. (1R)-1-{1-[trans-4-(Fluoromethyl)cyclohexyl]-1H-imidazo[4,5-d]thieno[3,2-b]pyridin-2-yl}ethanol

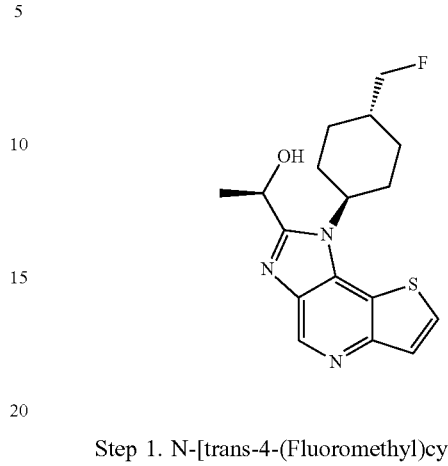

Step 1. N-[trans-4-(Fluoromethyl)cyclohexyl]-6-nitrothieno[3,2-b]pyridin-7-amine To a solution of {trans-4-[(6-nitrothieno[3,2-b]pyridin-7-yl)amino]cyclohexyl}methanol (0.30 g, 0.98 mmol) in methylene chloride (2 mL) cooled at 0° C. was added slowly 2-methoxy-N-(2-methoxyethyl)-N-(trifluoro-λ(4)-sulfanyl)ethanamine (0.27 mL, 1.5 mmol). The resulting mixture was stirred at room temperature for 4 h. The mixture was diluted with dichloromethane, washed with water, and concentrated. The residue was purified on silica gel (eluting with 0-30% EtOAc in dichloromethane) to give the desired product (0.2 g, 70%). LCMS calculated for $C_{14}H_{17}FN_3O_2S$ $(M+H)^+$: m/z=310.1; Found: 310.0.

Step 2. N7-[trans-4-(Fluoromethyl)cyclohexyl]thieno[3,2-b]pyridine-6,7-diamine

A mixture of N-[trans-4-(fluoromethyl)cyclohexyl]-6-nitrothieno[3,2-b]pyridin-7-amine (0.20 g, 0.65 mmol) and 10% palladium on carbon (0.07 g) in methanol (7 mL) was hydrogenated under balloon pressure of $H_2$ at room temperature for 1 h. The mixture was filtered. The filtrate was concentrated, diluted with dichloromethane, and then dried over $MgSO_4$ and concentrated to give the desired product (0.11 g, 61%). LCMS calculated for $Cl_4H_{19}FN_3S$ $(M+H)^+$: m/z=280.1; Found: 280.1.

Step 3. (1R)-1-{1-[trans-4-(Fluoromethyl)cyclohexyl]-1H-imidazo[4,5-d]thieno[3,2-b]pyridin-2-yl}ethanol A mixture of (2R)-2-hydroxypropanamide (0.184 g, 2.07 mmol) and triethyloxonium tetrafluoroborate (0.371 g, 1.95 mmol) in tetrahydrofuran (2.8 mL) was stirred at room temperature for 2 h. The solvent was removed and the residue dissolved in ethanol (1.2 mL) and added to a suspension of N7-[trans-4-(fluoromethyl)cyclohexyl]thieno[3,2-b]pyridine-6,7-diamine (0.18 g, 0.64 mmol) in ethanol (4.3 mL). The resulting mixture was stirred at 80° C. for 1 h. The solvent was removed and the residue was purified on RP-HPLC (XBridge C18 column, eluting with a gradient of acetonitrile/water containing 0.1% ammonium hydroxide, at flow rate of 30 mL/min) to give the desired product (0.10 g, 50%). LCMS calculated for $C_{17}H_{21}FN_3OS$ $(M+H)^+$: m/z=334.1; Found: 334.1

Example 13. (1R)-1-(1-Cyclohexyl-1H-imidazo[4,5-d]thieno[3,2-b]pyridin-2-yl)ethanol

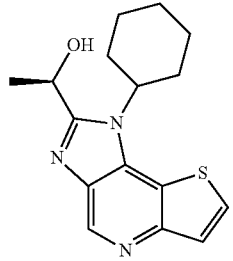 [SMILES: C[C@@H](O)c1nc2cnc3ccsc3c2n1C1CCCCC1]

Step 1. N-Cyclohexyl-6-nitrothieno[3,2-b]pyridin-7-amine

A mixture of 7-chloro-6-nitrothieno[3,2-b]pyridine (0.055 g, 0.26 mmol) (Example 1, Step 2), cyclohexanamine (59 μL, 0.51 mmol) and N,N-diisopropylethylamine (0.13 mL, 0.77 mmol) in isopropyl alcohol (0.87 mL) was heated at 90° C. for 2 h. The resulting mixture was concentrated to give the desired product, which was used directly in the next step. LCMS calculated for $C_{13}H_{16}N_3O_2S$ $(M+H)^+$: m/z=278.1; Found: 278.0.

Step 2. N7-Cyclohexylthieno[3,2-b]pyridine-6,7-diamine

A mixture of N-cyclohexyl-6-nitrothieno[3,2-b]pyridin-7-amine (0.065 g, 0.23 mmol) and 10% palladium on carbon (0.02 g) in methanol (3 mL) was hydrogenated under balloon pressure of $H_2$ at room temperature for 1 h. The reaction mixture was filtered. The filtrate was concentrated, diluted with dichloromethane, dried over $MgSO_4$, and concentrated. The residue was purified on silica gel (eluting with 0 to 10% MeOH in dichloromethane) to give the desired product (42 mg, 72%). LCMS calculated for $C_{13}H_{18}N_3S$ $(M+H)^+$: m/z=248.1; Found: 248.1.

Step 3. (1R)-1-(1-Cyclohexyl-1H-imidazo[4,5-d]thieno[3,2-b]pyridin-2-yl)ethanol A mixture of (2R)-2-hydroxypropanamide (49 mg, 0.55 mmol) and triethyloxonium tetrafluoroborate (98 mg, 0.51 mmol) in tetrahydrofuran (0.75 mL) was stirred at room temperature for 2 h. The solvent was removed and the residue dissolved in ethanol (0.32 mL) and added to a suspension of N7-cyclohexylthieno[3,2-b]pyridine-6,7-diamine (42 mg, 0.17 mmol) in ethanol (1.1 mL). The reaction mixture was stirred at 80° C. for 1 h. The solvent was removed, and the residue was purified on RP-HPLC (XBridge C18 column, eluting with a gradient of acetonitrile/water containing 0.1% ammonium hydroxide, at flow rate of 30 mL/min) to give the desired product (1 mg, 2%). LCMS calculated for $C_{16}H_{20}N_3OS$ $(M+H)^+$: m/z=302.1; Found: 302.1.

Example 14. 1-(trans-4-{2-[(1R)-1-hydroxyethyl]-1H-imidazo[4,5-d]thieno[3,2-b]pyridin-1-yl}cyclohexyl)-N-methylmethanesulfonamide

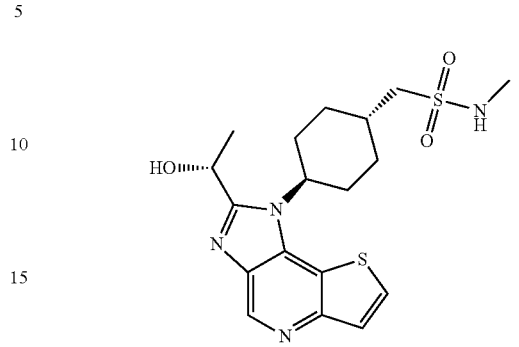

Step 1. {trans-4-[(tert-Butoxycarbonyl)amino]cyclohexyl}methyl 4-methylbenzenesulfonate To a solution of tert-butyl [trans-4-(hydroxymethyl)cyclohexyl]carbamate (0.50 g, 2.2 mmol) (Supplier: ChemImpex) in methylene chloride (15 mL) was added triethylamine (1.29 mL, 9.27 mmol), 4-dimethylaminopyridine (53 mg, 0.44 mmol), and p-toluenesulfonyl chloride (0.89 g, 4.7 mmol). The resulting mixture was stirred at room temperature for 2 h before adding more p-toluenesulfonyl chloride (0.42 g, 2.2 mmol). The mixture was stirred overnight. Water and dichloromethane were added and the layers separated. The aqueous was extracted with dichloromethane. The combined organics were washed with water and brine, dried (MgSO4), filtered, and concentrated. The residue was purified on Biotage Isolera (40 g Agela cartridge, eluted with 5-50% EtOAc/hexanes over 15 min) to give the desired product (0.72 g, 86%) as a white crystalline solid. LCMS calculated for $C_{19}H_{29}NO_5SNa$ $(M+Na)^+$: m/z=406.2; Found: 406.0.

Step 2. S-({trans-4-[(tert-Butoxycarbonyl)amino]cyclohexyl}methyl) ethanethioate To a mixture of {trans-4-[(tert-butoxycarbonyl)amino]cyclohexyl}methyl 4-methylbenzenesulfonate (0.72 g, 1.9 mmol) in dimethyl sulfoxide (6.0 mL) was added a solution of potassium thioacetate (0.242 g, 2.12 mmol) in dimethyl sulfoxide (1.0 mL). The resulting mixture was stirred at 55° C. for 3 h. After cooling, the reaction was quenched by adding sat. $NaHCO_3$. After stirring briefly, the solids that formed were filtered and washed with water to give 0.52 g (96%) of the desired product. LCMS calculated for $C_9H_{18}NOS$ $(M+H-Boc+H)^+$: m/z=188.1; Found: 188.2.

Step 3. S-[(trans-4-Aminocyclohexyl)methyl] ethanethioate Triluoroacetate

A mixture of S-({trans-4-[(tert-Butoxycarbonyl)amino]cyclohexyl}methyl) ethanethioate (0.20 g, 0.70 mmol) in methylene chloride (1.6 mL) was treated with trifluoroacetic acid (0.54 mL, 7.0 mmol) at room temperature for 2 h. The reaction mixture was evaporated to dryness to give the desired product (0.21 g, 100%). LCMS calculated for $C_9H_{18}NOS$ $(M+H)^+$: m/z=188.1; Found: 188.1.

Step 4. S-({trans-4-[(6-Nitrothieno[3,2-b]pyridin-7-yl)amino]cyclohexyl}methyl) ethanethioate A mixture of S-[(trans-4-Aminocyclohexyl)methyl] ethanethioate trifluoroacetate (0.21 g, 0.70 mmol), 7-chloro-6-nitrothieno[3,2-b]pyridine (0.11 g, 0.51 mmol), and N,N-diisopropylethylamine (0.27 mL, 1.5 mmol) in isopropyl alcohol (1.6 mL) was heated at 90° C. for 2 h. The mixture was concentrated under reduced pressure. The residue was treated with water to form a solid which was collected by filtration and washed with water to give the desired product (0.12 g, 64%). LCMS calculated for $C_{16}H_{20}N_3O_3S_2$(M+H)$^+$: m/z=366.1; Found: 366.1. $^1$H NMR (DMSO-$d_6$, 400 MHz) δ 9.07 (1H, s), 9.03 (1H, d, J=8.8 Hz), 8.35 (1H, d, J=5.6 Hz), 7.51 (1H, d, J=5.6 Hz), 4.13 (1H, m), 2.83 (2H, d, J=6.4 Hz), 2.34 (3H, s), 2.13 (2H, m), 1.83 (2H, m), 1.51 (3H, m), 1.19 (2H, m) ppm.

Step 5. {trans-4-[(6-Nitrothieno[3,2-b]pyridin-7-yl)amino]cyclohexyl}methanesulfonic Acid A mixture of hydrogen peroxide (30%, 110 μL, 1.1 mmol) was added to formic acid (0.43 mL), and the resulting mixture stirred for 30 min before adding S-({trans-4-[(6-nitrothieno[3,2-b]pyridin-7-yl)amino]cyclohexyl}methyl) ethanethioate (67 mg, 0.18 mmol). The resulting mixture was stirred at room temperature overnight. The reaction was quenched with a small amount of 0.3 M sodium metabisulfite solution. The pH of the mixture was adjusted to ~5 by adding 50% NaOH, which caused a solid to crash out. The solid was filtered and washed with ether to give the desired product (68 mg) which was used directly in the next step without further purification. LCMS calculated for $C_{14}H_{18}N_3O_5S_2$(M+H)$^+$: m/z=372.1; Found: 372.1.

Step 6. N-Methyl-1-{trans-4-[(6-nitrothieno[3,2-b]pyridin-7-yl)amino]cyclohexyl}methanesulfonamide To a mixture of {trans-4-[(6-nitrothieno[3,2-b]pyridin-7-yl)amino]cyclohexyl}methanesulfonic acid (34 mg, 0.092 mmol) in methylene chloride (0.30 mL) was added 1 drop of DMF and thionyl chloride (33 μL, 0.46 mmol). The resulting mixture was stirred at 42° C. for 1 h, then the solvents were evaporated to give the crude {trans-4-[(6-Nitrothieno[3,2-b]pyridin-7-yl)amino]cyclohexyl} methanesulfonyl chloride. To the crude sulfonyl chloride made above was added 2.0 M methylamine in THF (0.30 mL, 0.60 mmol). The mixture was stirred at room temperature for 30 h. LCMS showed a small amount of starting material remaining. More 2.0 M methylamine in THF (0.15 mL) was added and stirred for 30 min, to give a complete reaction. The solvents were evaporated and the resultant residue was dried in vacuo to give the crude product which was used in the next step without further purification. LCMS calculated for $C_{15}H_{21}N_4O_4S_2$(M+H)$^+$: m/z=385.1; Found: 385.1.

Step 7. 1-{trans-4-[(6-Aminothieno[3,2-b]pyridin-7-yl)amino]cyclohexyl}-N-methylmethanesulfonamide A mixture of N-methyl-1-{trans-4-[(6-nitrothieno[3,2-b]pyridin-7-yl)amino]cyclohexyl}methanesulfonamide (35 mg, 0.091 mmol) and 10% palladium on carbon (10 mg) in methanol (1.0 mL) was stirred under an atmosphere of H$_2$ for 10 h. The mixture was filtered through Celite. The filtrate was concentrated under reduced pressure to give the desired product (32 mg). LCMS calculated for $C_{15}H_{23}N_4O_2S_2$(M+H)$^+$: m/z=355.1; Found: 355.1.

Step 8. 1-(trans-4-{2-[(1R)-1-hydroxyethyl]-1H-imidazo[4,5-d]thieno[3,2-b]pyridin-1-yl}cyclohexyl)-N-methylmethanesulfonamide A mixture of (2R)-2-hydroxypropanamide (25.8 mg, 0.290 mmol) and triethyloxonium tetrafluoroborate (51.9 mg, 0.273 mmol) in tetrahydrofuran (0.40 mL) was stirred at room temperature for 1 h. After evaporated to dry under reduced pressure, the clear oil was mixed with ethanol (0.20 mL, 3.4 mmol) and added to a solution of 1-{trans-4-[(6-aminothieno[3,2-b]pyridin-7-yl)amino]cyclohexyl}-N-methylmethanesulfonamide (32 mg, 0.090 mmol) in ethanol (0.60 mL) in a microwave vial. The mixture was then heated at 80° C. for 1 h. The mixture was concentrated under reduced pressure. The resultant residue was purified using prep-LCMS (XBridge C18 column, eluting with a gradient of acetonitrile/water containing 0.1% ammonium hydroxide, at flow rate of 30 mL/min) to give the desired product (9.8 mg, 26%). LCMS calculated for $C_{18}H_{25}N_4O_3S_2$(M+H)$^+$: m/z=409.1; Found: 409.1.

Example 15. (1R)-1-{1-[1-(2,2,2-Trifluoroethyl)piperidin-4-yl]-1H-imidazo[4,5-d]thieno[3,2-b]pyridin-2-yl}ethanol

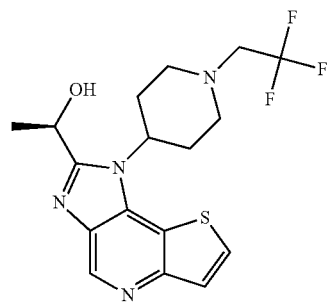 [SMILES: C[C@@H](O)c1nc2cnc3ccsc3c2n1C1CCN(CC(F)(F)F)CC1]

Step 1. tert-Butyl 4-[(6-nitrothieno[3,2-b]pyridin-7-yl)amino]piperidine-1-carboxylate A mixture of 7-chloro-6-nitrothieno[3,2-b]pyridine (0.48 g, 2.2 mmol) (Example 1, Step 2), tert-butyl 4-aminopiperidine-1-carboxylate (from Aldrich, 0.67 g, 3.4 mmol) and N,N-diisopropylethylamine (1.2 mL, 6.7 mmol) in isopropyl alcohol (7.6 mL) was heated at 90° C. for 2 h. The precipitate was washed with isopropyl alcohol to give the desired product (0.70 83%). LCMS calculated for $C_{17}H_{23}N_4O_4S$ (M+H): m/z=379.1; Found: 379.2.

Step 2. Tert-Butyl 4-[(6-aminothieno[3,2-b]pyridin-7-yl)amino]piperidine-1-carboxylate A mixture of tert-butyl 4-[(6-nitrothieno[3,2-b]pyridin-7-yl)amino]piperidine-1-carboxylate (0.70 g, 1.8 mmol) and 10% palladium on carbon (0.2 g) in methanol (20 mL) was subjected to balloon pressure of H$_2$ at room temperature for 5 h. The reaction mixture was filtered and concentrated and to give the desired product (0.64 g, 100%). LCMS calculated for $C_{17}H_{25}N_4O_2S$ (M+H)$^+$: m/z=349.2; Found: 349.1.

Step 3. tert-Butyl 4-{2-[(1R)-1-hydroxyethyl]-1H-imidazo[4,5-d]thieno[3,2-b]pyridin-1-yl}piperidine-1-carboxylate A mixture of (2R)-2-hydroxypropanamide (0.468 g, 5.26 mmol) and triethyloxonium tetrafluoroborate (0.941 g, 4.95 mmol) in tetrahydrofuran (7.2 mL) was stirred at room temperature for 2 h. The solvent was removed and the residue dissolved in ethanol (3.0 mL) and added to a suspension of tert-butyl 4-[(6-aminothieno[3,2-b]pyridin-7-yl)amino]piperidine-1-carboxylate (0.57 g, 1.6 mmol) in ethanol (11 mL). The mixture was stirred at 80° C. for 1 h. The solvent was removed and the residue was purified on RP-HPLC (XBridge C18 column, eluting with a gradient of acetonitrile/water containing 0.1% ammonium hydroxide, at flow rate of 60 mL/min) to give the desired product (85 mg, 13%). LCMS calculated for $C_{20}H_{27}N_4O_3S$ (M+H)$^+$: m/z=403.2; Found: 403.2.

Step 4. (1R)-1-(1-Piperidin-4-yl-1H-imidazo[4,5-d]thieno[3,2-b]pyridin-2-yl)ethanol Hydrochloride To a solution of tert-butyl 4-{2-[(1R)-1-hydroxyethyl]-1H-imidazo[4,5-d]thieno[3,2-b]pyridin-1-yl}piperidine-1-carboxylate (71 mg, 0.18 mmol) in methylene chloride (1.2 mL) was added 4.0 M hydrogen chloride in dioxane (0.35 mL, 1.4 mmol). The reaction solution was stirred at room temperature for 6 h. The solvent was removed to give the desired product as white solid (60 mg, 100%). LCMS calculated for $C_{15}H_{19}N_4OS$ (M+H)$^+$: m/z=303.1; Found: 303.1.

Step 5. (1R)-1-{1-[1-(2,2,2-Trifluoroethyl)piperidin-4-yl]-1H-imidazo[4,5-d]thieno[3,2-b]pyridin-2-yl}ethanol To a mixture of (1R)-1-(1-piperidin-4-yl-1H-imidazo[4,5-d]thieno[3,2-b]pyridin-2-yl)ethanol hydrochloride (21.6 mg, 0.0637 mmol) and triethylamine (40.0 μL, 0.287 mmol) in methylene chloride (0.78 mL) was added 2,2,2-trifluoroethyl trifluoromethanesulfonate (17.8 mg, 0.0765 mmol). The resulting mixture was stirred overnight at room temperature. The solvents were evaporated, and the crude residue purified on RP-HPLC (XBridge C18 column, eluting with a gradient of acetonitrile/water containing 0.1% ammonium hydroxide, at flow rate of 30 mL/min) to give 6.5 mg (26%) of the desired product. LCMS calculated for $C_{17}H_{20}F_3N_4OS$ (M+H)$^+$: m/z=385.1; Found: 385.0.

Example 16. 3-(4-{2-[(1R)-1-Hydroxyethyl]-1H-imidazo[4,5-d]thieno[3,2-b]pyridin-1-yl}piperidin-1-yl)propanenitrile

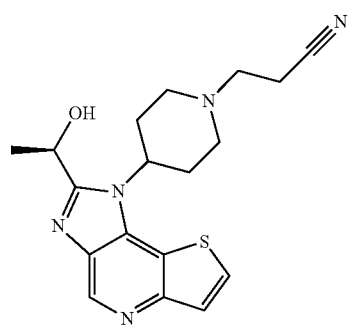 [SMILES: C[C@@H](O)c1nc2cnc3ccsc3c2n1C1CCN(CCC#N)CC1]

To a solution of (1R)-1-(1-piperidin-4-yl-1H-imidazo[4,5-d]thieno[3,2-b]pyridin-2-yl)ethanol hydrochloride (21.7 mg, 0.0640 mmol) (Example 15, Step 4) in acetonitrile (0.40 mL) was added 2-propenenitrile (8.4 μL, 0.13 mmol), followed by 1,8-diazabicyclo[5.4.0]undec-7-ene (38 μL, 0.26 mmol). The resulting mixture was stirred at room temperature overnight. After evaporating to dryness, the residue was purified on RP-HPLC (XBridge C18 column, eluting with a gradient of acetonitrile/water containing 0.1% ammonium hydroxide, at flow rate of 30 mL/min) to give the desired product (11 mg, 48%). LCMS calculated for $C_{18}H_{22}N_5OS$ (M+H)$^+$: m/z=356.2; Found: 356.0.

Example 17. {trans-4-[2-(Hydroxymethyl)-1H-imidazo[4,5-d]thieno[3,2-b]pyridin-1-yl]cyclohexyl}acetonitrile

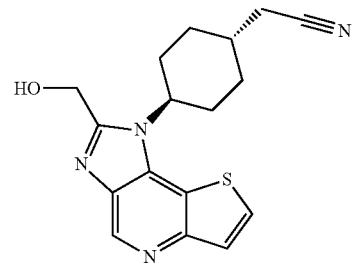 [SMILES: N#CC[C@H]1CC[C@H](n2c(CO)nc3cnc4ccsc4c32)CC1]

A mixture of {trans-4-[(6-aminothieno[3,2-b]pyridin-7-yl)amino]cyclohexyl}acetonitrile (51.9 mg, 0.181 mmol) (Example 2, Step 4) and 2-chloro-1,1,1-triethoxyethane (from Aldrich, 0.105 mL, 0.549 mmol) in acetic acid (0.5 mL) was stirred at 120° C. for 30 min. The solvent was removed and the resultant residue dissolved in dichloromethane and purified on silica gel (eluting with 0-5% MeOH in dichloromethane) to give 22 mg (35.5%) of {trans-4-[2-(Chloromethyl)-1H-imidazo[4,5-d]thieno[3,2-b]pyridin-1-yl]cyclohexyl}acetonitrile. LCMS calculated for $C_{17}H_{18}ClN_4S$ (M+H)$^+$: m/z=345.1; Found: 345.0. Also eluted was 8 mg (12%) of {1-[trans-4-(cyanomethyl)cyclohexyl]-1H-imidazo[4,5-d]thieno[3,2-b]pyridin-2-yl}methyl acetate, LCMS calculated for $C_{19}H_{21}N_4O_2S$ (M+H)$^+$: m/z=369.1; Found: 369.0. The acetate compound was treated with lithium hydroxide to give compound the desired product after HPLC purification (XBridge C18 column, eluting with a gradient of acetonitrile/water containing 0.1% ammonium hydroxide, at flow rate of 30 mL/min). LCMS calculated for $C_{17}H_{19}N_4OS$ (M+H)$^+$: m/z=327.1; Found: 327.1. H NMR (500 MHz, DMSO-d$_6$) δ 8.96 (s, 1H), 8.01 (d, J=5.5 Hz, 1H), 7.67 (d, J=5.5 Hz, 1H), 5.80 (t, J=5.6 Hz, 1H), 4.85 (d, J=5.3 Hz, 2H), 4.74 (m, 1H), 2.61 (d, J=6.1 Hz, 2H), 2.42 (m, 2H), 2.09-1.99 (m, 5H), 1.41 (m, 2H) ppm.

93

Example 18. N-({1-[trans-4-(Cyanomethyl)cyclohexyl]-1H-imidazo[4,5-d]thieno[3,2-b]pyridin-2-yl}methyl)methanesulfonamide

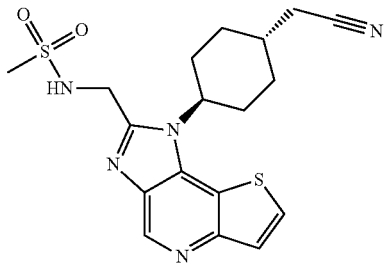 [SMILES: CS(=O)(=O)NCc1nc2cnc3ccsc3c2n1[C@H]1CC[C@H](CC#N)CC1]

Step 1. tert-Butyl (methylsulfonyl)carbamate

Triethylamine (2.2 mL, 16 mmol), di-tert-butyldicarbonate (2.65 g, 12.1 mmol) and 4-dimethylaminopyridine (0.096 g, 0.79 mmol) were added sequentially to a solution of methanesulfonamide (0.75 g, 7.9 mmol) in methylene chloride (20 mL) at room temperature. The reaction was stirred at room temperature for 2 h and then concentrated. EtOAc was added, and the resultant mixture was washed with 1N aq. HCl solution, dried over MgSO$_4$ and concentrated to give the desired product (1 g) to be used in the next step directly.

Step 2. N-({1-[trans-4-(Cyanomethyl)cyclohexyl]-1H-imidazo[4,5-d]thieno[3,2-b]pyridin-2-yl}methyl)methanesulfonamide To a solution of {trans-4-[2-(chloromethyl)-1H-imidazo[4,5-d]thieno[3,2-b]pyridin-1-yl]cyclohexyl}acetonitrile (from example 17, 22.2 mg, 0.0644 mmol) dissolved in N,N-dimethylformamide (0.2 mL) was added tert-butyl (methylsulfonyl)carbamate (19 mg, 0.096 mmol) and potassium carbonate (18 mg, 0.13 mmol). The reaction was stirred at 50° C. overnight. The mixture was diluted with water, extracted with EtOAc. The combined organic layers were dried over MgSO$_4$ and concentrated to give tert-butyl ({1-[trans-4-(cyanomethyl)cyclohexyl]-1H-imidazo[4,5-d]thieno[3,2-b]pyridin-2-yl}methyl)(methylsulfonyl)carbamate. LCMS calculated for C$_{23}$H$_{30}$N$_5$O$_4$S$_2$(M+H)$^+$: m/z=504.2; Found: 504.1. This crude intermediate was treated with trifluoroacetic acid (0.1 mL, 1 mmol) in methylene chloride (0.1 mL) at room temperature for 30 min, and then the solvent was removed in vacuo. The residue was then dissolved in MeOH and purified on prep-LCMS (XBridge C18 column, eluting with a gradient of acetonitrile/water containing 0.1% ammonium hydroxide, at flow rate of 30 mL/min) to give the desired product (9.5 mg, 36%). LCMS calculated for C$_{18}$H$_{22}$N$_5$O$_2$S$_2$(M+H)$^+$: m/z=404.1; Found: 404.0.

94

Example 19. (1R)-1-{1-[(3S)-6-(Hydroxymethyl)tetrahydro-2H-pyran-3-yl]-1H-imidazo[4,5-d]thieno[3,2-b]pyridin-2-yl}ethanol

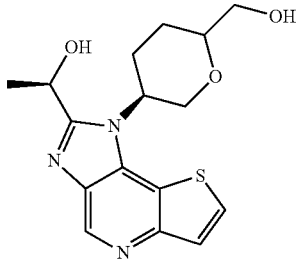 [SMILES: C[C@@H](O)c1nc2cnc3ccsc3c2n1[C@H]1CCC(CO)OC1]

Step 1. Tert-Butyl (4S)-2,2-dimethyl-4-vinyl-1,3-oxazolidine-3-carboxylate

To a suspension of methyl triphenylphosphonium bromide (5.63 g, 15.8 mmol) in tetrahydrofuran (140 mL) was added 2.5 M n-butyllithium in hexane (7.35 mL, 18.4 mmol). The deep red solution was stirred at 0° C. for 1 h. Then a solution of tert-butyl (4R)-4-formyl-2,2-dimethyl-1,3-oxazolidine-3-carboxylate (from Aldrich, 3.01 g, 13.1 mmol) in tetrahydrofuran (7.3 mL) was added drop wise at 0° C. The red solution was warmed to room temperature and stirred for 12 h. Hexanes was added to the reaction mixture in 4:1 (v/v) ratio. The suspension was filtered through Celite and the filtrate concentrated. The resultant residue was purified by flash chromatography (eluting with 10% ethyl acetate in hexanes) to give the desired compound as colorless oil (1.92 g, 64%).

Step 2. tert-Butyl [(1S)-1-(hydroxymethyl)prop-2-en-1-yl]carbamate

To a solution of tert-butyl (4S)-2,2-dimethyl-4-vinyl-1,3-oxazolidine-3-carboxylate (1.90 g, 8.36 mmol) in methanol (83 mL) was added p-toluenesulfonic acid monohydrate (0.80 g, 4.2 mmol) at 0° C. The mixture was slowly warmed to room temperature overnight. The reaction mixture was diluted with saturated NaHCO$_3$ solution, concentrated, and then diluted with ethyl acetate. The organic layer was washed with sat. NaHCO$_3$ (2×) and brine, dried over Na$_2$SO$_4$, filtered and concentrated to give the desired product as colorless oil (1.187 g, 76%). $^1$H NMR (400 MHz, CDCl$_3$) δ 5.81 (1H, m), 5.25 (2H, m), 4.90 (1H, m), 4.25 (1H, br s), 3.67 (2H, m), 1.45 (9H, s) ppm.

Step 3. tert-Butyl [(1S)-1-({[1-(hydroxymethyl)prop-2-en-1-yl]oxy}methyl)prop-2-en-1-yl]carbamate To a flask was charged with tert-butyl [(1S)-1-(hydroxymethyl)prop-2-en-1-yl]carbamate (0.401 g, 2.14 mmol), tris(dibenzylideneacetone)dipalladium(0) (59 mg, 0.064 mmol), N,N'-(1S,2S)-cyclohexane-1,2-diylbis[2-(diphenylphosphino)-1-naphthamide] (150 mg, 0.19 mmol), and 4-dimethylaminopyridine (78 mg, 0.64 mmol). The reaction mixture was purged with N$_2$ three times, and then methylene chloride (21.3 mL), and 1.0 M triethylborane in THF (130 μL, 0.13 mmol) was added sequentially. After stirring for 10 min, 2-vinyloxirane (0.150 g, 2.14 mmol) was added and the resulting mixture was stirred overnight. The reaction was diluted with dichloromethane and sat. NaHCO₃ solution. The organic layer was separated and dried over Na₂SO₄, filtered and concentrated. The crude residue was purified with flash chromatography (eluting with 0-50% ethyl acetate/hexanes) to give the desired product (0.271 g, 49%). ¹H NMR (300 MHz, CDCl₃) δ 5.85 (1H, m), 5.67 (1H, m), 5.84-5.17 (4H, m), 4.83 (1H, m), 4.30 (1H, br s), 3.83 (1H, m), 3.69 (1H, dd, J=4.5 and 6.9 Hz), 3.54 (2H, m), 3.36 (1H, dd, J=4.5 and 6.9 Hz), 1.45 (9H, s) ppm.

Step 4. 2-({(2S)-2-[(tert-Butoxycarbonyl)amino]but-3-en-1-yl}oxy)but-3-en-1-yl acetate To a mixture of tert-butyl [(1S)-1-({[1-(hydroxymethyl)prop-2-en-1-yl]oxy}methyl)prop-2-en-1-yl]carbamate (268 mg, 1.04 mmol) in methylene chloride (10 mL) was added with triethylamine (435 µL, 3.12 mmol). The mixture was cooled to 0° C., and acetyl chloride (150 µL, 2.1 mmol) was added drop wise. The reaction was stirred at room temperature for 2 h, then quenched with water. The organic layer was concentrated and the resultant residue purified on silica gel (eluting with 20% ethyl acetate/hexanes) to give the desired product (0.26 g, 85%). LCMS calculated for C₁₀H₁₈NO₃ (M-100+H)⁺: m/z=200.1; Found: 200.1.

Step 5. {(5S)-5-[(tert-Butoxycarbonyl)amino]-5,6-dihydro-2H-pyran-2-yl}methyl Acetate To a 500 mL 2-neck round bottom flask, benzylidene (dichloro)(1,3-dimesitylimidazolidin-2-id-2-yl)(tricyclohexylphosphoranyl)ruthenium (38 mg, 0.044 mmol) was added. After purged with nitrogen for 3 times, dichloromethane (anhydrous, 8 mL) was added followed by 2-({(2S)-2-[(tert-butoxycarbonyl)amino]but-3-en-1-yl}oxy)but-3-en-1-yl acetate (265 mg, 0.885 mmol). The reaction mixture was stirred at room temperature for 15 h. The mixture was concentrated in vacuo. The residue was purified via flash chromatography (eluting with hexanes to 25% EtOAc in hexanes) to give the desired product as a brown oil (0.205 g, 85%). LCMS calculated for C₉H₁₄NO₅ (M+H-Bu+H)⁺: m/z=216.1; Found: 216.1. ¹H NMR (300 MHz, CDCl₃) δ 5.94 (0.17H, m), 5.84 (0.83H, m), 5.69 (1H, m), 4.89 (0.13H, m), 4.70 (0.83H, m), 4.25 (1H, m), 4.05 (4H, m), 3.56 (0.13H, m), 3.38 (0.87H, m), 2.04 (2.49H, s), 2.03 (0.51H, m), 1.38 (9H, s) ppm (The product was a ~5:1 mixture of trans- and cis-isomers).

Step 6. [(5S)-5-Amino-5,6-dihydro-2H-pyran-2-yl]methyl Acetate

To a solution of {(5S)-5-[(tert-butoxycarbonyl)amino]-5,6-dihydro-2H-pyran-2-yl}methyl acetate (205 mg, 0.756 mmol) in methylene chloride (5.2 mL) was added 4.0 M hydrogen chloride in dioxane (1.5 mL, 6.0 mmol). The reaction solution was stirred at room temperature for 6 h. The solvent was removed under reduced pressure to give the desired product as white solid. LCMS calculated for C₈H₁₄NO₃ (M+H)⁺: m/z=172.1; Found: 172.1.

Step 7. {(5S)-5-[(6-Nitrothieno[3,2-b]pyridin-7-yl)amino]-5,6-dihydro-2H-pyran-2-yl}methyl Acetate A mixture of 7-chloro-6-nitrothieno[3,2-b]pyridine (156 mg, 0.727 mmol), [(5S)-5-amino-5,6-dihydro-2H-pyran-2-yl]methyl acetate (129 mg, 0.754 mmol) and N,N-diisopropylethylamine (0.26 mL, 1.5 mmol) in isopropyl alcohol (1.7 mL) was heated at 90° C. for 2 h. The reaction mixture was concentrated and purified with flash chromatography to give the desired product (0.21 g 83%). LCMS calculated for C₁₅H₁₆N₃O₅S (M+H)⁺: m/z=350.1; Found: 350.0.

Step 8. {(5S)-5-[(6-Aminothieno[3,2-b]pyridin-7-yl)amino]tetrahydro-2H-pyran-2-yl}methyl Acetate A mixture of {(5S)-5-[(6-nitrothieno[3,2-b]pyridin-7-yl)amino]-5,6-dihydro-2H-pyran-2-yl}methyl acetate (210 mg, 0.600 mmol) and 10% palladium on carbon (0.21 g) in methanol (4.0 mL) was subjected to balloon pressure of H₂ at room temperature for 2 h. The mixture was filtered, and the filtrate was concentrated and purified with flash chromatography (eluting with 15% methanol in dichloromethane) to give the desired product (145 mg, 75%). LCMS calculated for C₁₅H₂₀N₃O₃S (M+H)⁺: m/z=322.1; Found: 322.0.

Step 9. (1R)-1-{1-[(3S)-6-(Hydroxymethyl)tetrahydro-2H-pyran-3-yl]-1H-imidazo[4,5-d]thieno[3,2-b]pyridin-2-yl}ethanol A mixture of (2R)-2-hydroxypropanamide (131 mg, 1.47 mmol) and triethyloxonium tetrafluoroborate (263 mg, 1.38 mmol) in THF (2 mL) was stirred at room temperature for 2 h. The solvent was removed and the residue dissolved in ethanol (0.85 mL) and added to a suspension of {(5S)-5-[(6-aminothieno[3,2-b]pyridin-7-yl)amino]tetrahydro-2H-pyran-2-yl}methyl acetate (145 mg, 0.451 mmol) in ethanol (3.1 mL). The mixture was stirred at 80° C. for 1 h. The reaction was cooled to room temperature and diluted with water (1.0 mL). Lithium hydroxide (32.4 mg, 1.35 mmol) was added, and the mixture was stirred for 2 h. The reaction mixture was diluted with methanol and purified with prep-LCMS (XBridge C18 column, eluting with a gradient of acetonitrile/water containing 0.1% ammonium hydroxide, at flow rate of 60 mL/min) to give the desired product as white solid (95 mg, 63%). LCMS calculated for C₁₆H₂₀N₃O₃S (M+H)⁺: m/z=334.1; Found: 334.0.

Example 20. ((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile

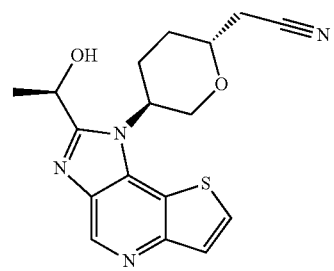 [SMILES: C[C@@H](O)c1nc2cnc3ccsc3c2n1[C@H]1CC[C@H](CC#N)OC1]

Step 1: ((2R,5S)-5-{2-[(1R)-1-Hydroxyethyl]-1H-imidazo[4,5-d]thieno[3,2-b]pyridin-1-yl}tetrahydro-2H-pyran-2-yl)methyl 4-methylbenzenesulfonate and ((2S,5S)-5-{2-[(1R)-1-hydroxyethyl]-1H-imidazo[4,5-d]thieno[3,2-b]pyridin-1-yl}tetrahydro-2H-pyran-2-yl)methyl 4-methylbenzenesulfonate To a solution of (1R)-1-{1-[(3S)-6-(hydroxymethyl)tetrahydro-2H-pyran-3-yl]-1H-imidazo[4,5-d]thieno[3,2-b]pyridin-2-yl}ethanol (100 mg, 0.300 mmol) (Example 19, Step 9) in methylene chloride (3.4 mL) and pyridine (0.146 mL, 1.80 mmol) was added p-toluenesulfonyl chloride (57.2 mg, 0.300 mmol) and 4-dimethylaminopyridine (1.8 mg, 0.015 mmol) at 0° C. The reaction mixture was allowed to warm to room temperature overnight. The reaction mixture was concentrated, diluted with methanol, and purified with prep-LCMS (XBridge C18 column, eluting with a gradient of acetonitrile/water containing 0.1% ammonium hydroxide, at flow rate of 60 mL/min) to give two peaks. On analytic HPLC (Waters SunFire C18, 2.1×50 mm, 5 μM; Flow rate 3 mL/min; Injection volume 2 μL; At gradient from 2 to 80% B in 3 minutes (A=water with 0.025% TFA, B= acetonitrile)): First peak (45.3 mg, 31%) retention time 1.81 min, LCMS calculated for $C_{23}H_{26}N_3O_5S_2(M+H)^+$: m/z=488.1; Found: 488.1. Second peak (8.5 mg, 5.8%) retention time 1.88 min, LCMS calculated for $C_{23}H_{26}N_3O_5S_2(M+H)^+$: m/z=488.1; Found: 488.1.

Step 2. ((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile A mixture of ((2R,5S)-5-{2-[(1R)-1-hydroxyethyl]-1H-imidazo[4,5-d]thieno[3,2-b]pyridin-1-yl}tetrahydro-2H-pyran-2-yl)methyl 4-methylbenzenesulfonate (from 1st peak of previous step, 27 mg, 0.055 mmol) and sodium cyanide (4.5 mg, 0.092 mmol) in dimethyl sulfoxide (0.4 mL) was stirred at 50° C. for 4 h. After cooling, the mixture was diluted with methanol and purified with prep-LCMS (XBridge C18 column, eluting with a gradient of acetonitrile/water containing 0.1% ammonium hydroxide, at flow rate of 30 mL/min) to give the desired product (14.5 mg, 76%). LCMS calculated for $C_{17}H_{19}N_4O_2S$ $(M+H)^+$: m/z=343.1; Found: 343.0. $^1$H NMR (DMSO-$d_6$, 500 MHz) δ 9.51 (1H, s), 8.45 (1H, d, J=5.5 Hz), 7.97 (1H, d, J=5.5 Hz), 5.31 (1H, m), 5.20 (1H, m), 4.31 (1H, m), 4.23 (1H, m), 4.02 (1H, m), 2.96 (1H, dd, J=17.0 and 4.5 Hz), 2.85 (1H, dd, J=17.0 and 4.5 Hz), 2.66 (1H, m), 2.26 (1H, m), 2.09 (1H, m), 1.73 (1H, m), 1.69 (3H, d, J=6.5 Hz) ppm.

Example 20a. ((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile Hydrate

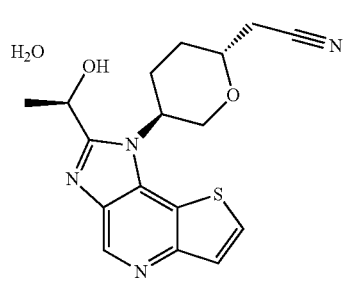

((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile (52 mg, 0.15 mmol) from Example 20 was crystallized from a mixture of acetonitrile (8 mL) and water (4 mL). The resulting colorless prism crystal collected was suitable for X-ray crystal structure analysis.

Crystal data shows: ~0.520×0.180×0.100 mm, orthorhombic, P212121, a=6.962(3) Å, b=11.531(4) Å, c=20.799 (7) Å, Vol=1669.6(10) Å$^3$, Z=4, T=–100.° C., Formula weight=359.42, Density=1.430 g/cm$^3$, μ(Mo)=0.22 mm$^{-1}$ Data collection was done on a Bruker SMART APEX-II CCD system, MoKalpha radiation, standard focus tube, anode power=50 kV×42 mA, crystal to plate distance=5.0 cm, 512×512 pixels/frame, beam center=(256.13,253.14), total frames=1151, oscillation/frame=0.50°, exposure/frame=10.1 sec/frame, SAINT integration, hkl min/max=(–9, 9, –15, 15, –27, 27), data input to shelx=17025, unique data=3975, two-theta range=3.92 to 55.720, completeness to two-theta 55.72=99.80%, R(int-xl)=0.0681, SADABS correction applied.

Structure was solved using XS(Shelxtl), refined using shelxtl software package, refinement by full-matrix least squares on F$^2$, scattering factors from Int. Tab. Vol C Tables 4.2.6.8 and 6.1.1.4, number of data=3975, number of restraints=0, number of parameters=235, data/parameter ratio=16.91, goodness-of-fit on F$^2$=1.04, R indices [I>4sigma(I)] R1=0.0505, wR2=0.1242, R indices(all data) R1=0.0769, wR2=0.1401, max difference peak and hole=0.724 and –0.277 e/Å$^3$, refined flack parameter=–0.12 (13), All of the CH hydrogen atoms were refined using a riding model. The OH hydrogens were found from a difference map and fully refined.

Results showed that the asymmetric unit contains one molecule and one water as shown with thermal ellipsoids drawn to the 50% probability level. The stereochemistry at each of three stereocenters (as indicated in the name and structure of the compound above) was confirmed. The flack parameter refined to 0.28(24) indicating the correct enantiomeric setting.

Example 21. ((2S,5S)-5-{2-[(1R)-1-Hydroxyethyl]-1H-imidazo[4,5-d]thieno[3,2-b]pyridin-1-yl}tetrahydro-2H-pyran-2-yl)acetonitrile

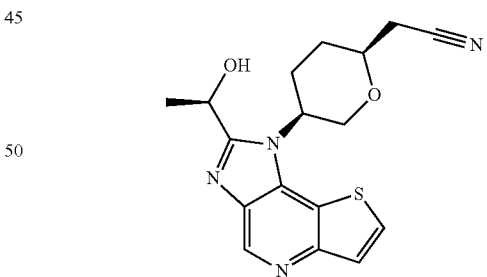

This compound was prepared according to the procedure described in Example 20, Step 2, using ((2S,5S)-5-{2-[(1R)-1-hydroxyethyl]-1H-imidazo[4,5-d]thieno[3,2-b]pyridin-1-yl}tetrahydro-2H-pyran-2-yl)methyl 4-methylbenzenesulfonate (from Example 20, step 1, 2nd peak) instead of ((2R,5S)-5-{2-[(1R)-1-Hydroxyethyl]-1H-imidazo[4,5-d] thieno[3,2-b]pyridin-1-yl}tetrahydro-2H-pyran-2-yl)methyl 4-methylbenzenesulfonate as starting material. LCMS calculated for $C_{17}H_{19}N_4O_2S$ $(M+H)^+$: m/z=343.1; Found: 343.0.

Example 22. N-((1-((2S)-Bicyclo[2.2.1]heptan-2-yl)-1H-imidazo[4,5-d]thieno[3,2-b]pyridin-2-yl)methyl)methanesulfonamide

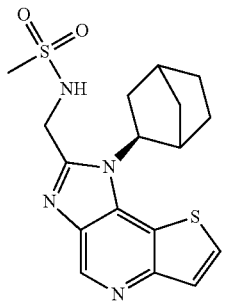 [SMILES: CS(=O)(=O)NCc1nc2cnc3ccsc3c2n1[C@H]1CC2CCC1C2]

Step 1. N-[(2S)-Bicyclo[2.2.1]hept-2-yl]-6-nitrothieno[3,2-b]pyridin-7-amine A mixture of 7-chloro-6-nitrothieno[3,2-b]pyridine (0.064 g, 0.30 mmol) (Example 1, Step 2), bicyclo[2.2.1]heptan-2-amine (from Aldrich, 0.050 g, 0.45 mmol) and triethylamine (0.083 mL, 0.60 mmol) in isopropyl alcohol (1.4 mL) was heated at 90° C. for 2 h. The mixture was concentrated to give the desired product, which was used in the next step without further purification. LCMS calculated for $C_{14}H_{16}N_3O_2S$ (M+H)$^+$: m/z=290.1; Found: 290.0.

Step 2. N7-[(2S)-Bicyclo[2.2.1]hept-2-yl]thieno[3,2-b]pyridine-6,7-diamine

A mixture of N-[(2S)-bicyclo[2.2.1]hept-2-yl]-6-nitrothieno[3,2-b]pyridin-7-amine (0.080 g, 0.28 mmol) and 10% palladium on carbon (0.03 g) in methanol (3 mL) was subjected to balloon pressure of $H_2$ at room temperature for 1 h. The mixture was filtered and the filtrate concentrated to give the desired product, which was used directly in the next step without further purification. LCMS calculated for $C_{14}H_{18}N_3S$ (M+H)$^+$: m/z=260.1; Found: 260.0.

Step 3. 1-[(2S)-Bicyclo[2.2.1]hept-2-yl]-2-(chloromethyl)-1H-imidazo[4,5-d]thieno[3,2-b]pyridine A mixture of N7-[(2S)-bicyclo[2.2.1]hept-2-yl]thieno[3,2-b]pyridine-6,7-diamine (0.060 g, 0.23 mmol) and 2-chloro-1,1,1-triethoxyethane (0.134 mL, 0.700 mmol) in acetic acid (0.2 mL) was stirred at 120° C. for 30 min. The solvent was removed and the resultant residue was dissolved in dichloromethane and purified on silica gel (eluting with 0-5% MeOH in dichloromethane) to give the desired product. LCMS calculated for $C_{16}H_{17}ClN_3S$ (M+H)$^+$: m/z=318.1; Found: 318.0.

Step 4. N-((1-((2S)-Bicyclo[2.2.1]heptan-2-yl)-1H-imidazo[4,5-d]thieno[3,2-b]pyridin-2-yl)methyl)methanesulfonamide To a solution of 1-[(2S)-bicyclo[2.2.1]hept-2-yl]-2-(chloromethyl)-1H-imidazo[4,5-d]thieno[3,2-b]pyridine (0.10 g, 0.31 mmol) dissolved in N,N-dimethylformamide (1 mL) was added tert-butyl (methylsulfonyl)carbamate (0.092 g, 0.47 mmol) and potassium carbonate (0.087 g, 0.63 mmol). The mixture was stirred at 50° C. overnight, then diluted with water and extracted with EtOAc. The combined organic layers were dried over $MgSO_4$ and concentrated to give crude tert-butyl ({1-[(2S)-bicyclo[2.2.1]hept-2-yl]-1H-imidazo[4,5-d]thieno[3,2-b]pyridin-2-yl}methyl)(methylsulfonyl)carbamate. LCMS calculated for $C_{22}H_{29}N_4O_4S_2$(M+H)$^+$: m/z=477.2; Found: 477.1. The crude intermediate was treated with trifluoroacetic acid (0.5 mL, 6 mmol) in methylene chloride (0.5 mL) at room temperature for 30 min, then the solvent was removed in vacuo. The residue was re-dissolved in MeOH and purified on prep-LCMS (XBridge C18 column, eluting with a gradient of acetonitrile/water containing 0.1% ammonium hydroxide, at flow rate of 30 mL/min) to give the desired product (30 mg, 25%). LCMS calculated for $C_{17}H_{21}N_4O_2S_2$(M+H)$^+$: m/z=377.1; Found: 377.0.

Example 23. (trans-4-{7-[(1R)-1-Hydroxyethyl]-8H-pyrrolo[2,3-d]thieno[3,2-b]pyridin-8-yl}cyclohexyl)acetonitrile

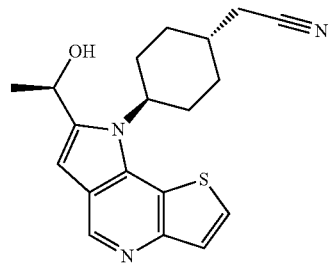 [SMILES: C[C@@H](O)c1cc2cnc3ccsc3c2n1[C@H]1CC[C@H](CC#N)CC1]

Step 1. 6-Iodothieno[3,2-b]pyridin-7-ol

A mixture of thieno[3,2-b]pyridin-7-ol (from Aldrich) (0.54 g, 3.6 mmol) and N-iodosuccinimide (0.88 g, 3.9 mmol) in acetonitrile (10 mL) was heated at reflux overnight. The mixture was concentrated under reduced pressure to give the desired product which was used in the next step without further purification. LCMS calculated for $C_7H_5INOS$ (M+H)$^+$: m/z=277.9; Found: 277.8.

Step 2. 7-Chloro-6-iodothieno[3,2-b]pyridine

A mixture of the crude 6-iodothieno[3,2-b]pyridin-7-ol (0.99 g, 3.6 mmol) in phosphoryl chloride (20 mL) was heated at 120° C. for 2 h. The reaction was cooled to room temperature, concentrated under reduced pressure. The residue was co-evaporated with toluene, then diluted with dichloromethane and neutralized carefully with sat. $NaHCO_3$ solution. The black tar was filtered off and the filtrate was transferred to a separation funnel. The organic layer was concentrated and purified on silica gel (eluting with 0-35% EtOAc/hexanes) to give the desired product (44% in 2 steps). LCMS calculated for $C_7H_4ClNS$ (M+H)$^+$: m/z=295.9; Found: 295.8.

Step 3. (2R)-4-(7-Chlorothieno[3,2-b]pyridin-6-yl)but-3-yn-2-ol

A mixture of 7-chloro-6-iodothieno[3,2-b]pyridine (0.46 g, 1.6 mmol), bis(triphenylphosphine)palladium(II) chloride (0.11 g, 0.16 mmol) and copper(I) iodide (30 mg, 0.16 mmol) was purged with $N_2$. (2R)-but-3-yn-2-ol (0.13 g, 1.9 mmol) and triethylamine (4.5 mL, 33 mmol) was added via syringe. The reaction mixture was heated at reflux for 2 h. The mixture was concentrated under reduced pressure, and the resultant residue was purified on silica gel (eluting with 0-85% EtOAc/hexanes) to give the desired product. LCMS calculated for $C_{11}H_9ClNOS$ (M+H)$^+$: m/z=238.0; Found: 238.0.

Step 4. (trans-4-{7-[(1R)-1-Hydroxyethyl]-8H-pyrrolo[2,3-d]thieno[3,2-b]pyridin-8-yl}cyclohexyl)acetonitrile A mixture of (2R)-4-(7-chlorothieno[3,2-b]pyridin-6-yl)but-3-yn-2-ol (0.055 g, 0.23 mmol), (trans-4-aminocyclohexyl)acetonitrile hydrochloride (0.040 g, 0.23 mmol), cesium carbonate (0.19 g, 0.58 mmol), palladium acetate (5.2 mg, 0.023 mmol) and (9,9-dimethyl-9H-xanthene-4,5-diyl)bis(diphenylphosphine) (27 mg, 0.046 mmol) in toluene (1.1 mL) was purged with $N_2$ for 3 times. The resulting mixture was stirred at 100° C. for 2 h, then at 120° C. for 2 h. The mixture was filtered. The filtrate was concentrated under reduced pressure, diluted with MeOH and purified on prep-LCMS (XBridge C18 column, eluting with a gradient of acetonitrile/water containing 0.1% ammonium hydroxide, at flow rate of 30 mL/min) to give the desired product (1.4 mg, 1.8%). LCMS calculated for $C_{19}H_{22}N_3OS$ (M+H)$^+$: m/z=340.1; Found: 340.1.

Example 24. (1-Hydroxy-4-{2-[(1R)-1-hydroxyethyl]-1H-imidazo[4,5-d]thieno[3,2-b]pyridin-1-yl}cyclohexyl)acetonitrile

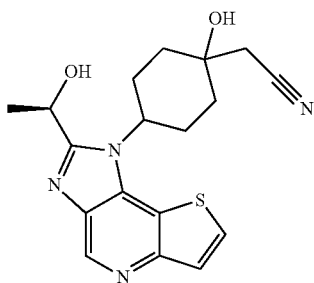 [SMILES: C[C@@H](O)c1nc2cnc3ccsc3c2n1C1CCC(O)(CC#N)CC1]

Step 1. N-1,4-Dioxaspiro[4,5]dec-8-yl-6-nitrothieno[3,2-b]pyridin-7-amine

A mixture of 1,4-dioxaspiro[4,5]decan-8-amine (from J&W PharmLab, 0.40 g, 2.5 mmol), 7-chloro-6-nitrothieno[3,2-b]pyridine (0.29 g, 1.4 mmol) and triethylamine (0.38 mL, 2.7 mmol) in isopropyl alcohol (4.4 mL) was stirred at 90° C. for 2 h. The mixture was concentrated to give the desired product to be used in the next step directly. LCMS calculated for $C_{15}H_{18}N_3O_4S$ (M+H)$^+$: m/z=336.1; Found: 336.0.

Step 2. 4-[(6-Nitrothieno[3,2-b]pyridin-7-yl)amino]cyclohexanone

A mixture of N-1,4-dioxaspiro[4,5]dec-8-yl-6-nitrothieno[3,2-b]pyridin-7-amine (0.45 g, 1.3 mmol) and 3.0 M hydrogen chloride in water (9 mL, 30 mmol) in acetone (20 mL) was stirred at room temperature for 20 min and then at 60° C. for 1 h. The mixture was basified with aq. 5M NaOH solution at 0° C., then extracted with EtOAc. The combined organic layers were dried over sodium sulfate, concentrated and purified on silica gel column (eluting with 0-30% of EtOAc in methylene chloride) to give the desired product (0.2 g, 51% in 2 steps). LCMS calculated for $C_{13}H_{14}N_3O_3S$ (M+H)$^+$: m/z=292.1; Found: 292.0.

Step 3. {1-Hydroxy-4-[(6-nitrothieno[3,2-b]pyridin-7-yl)amino]cyclohexyl}acetonitrile A solution of N,N-diisopropylamine (0.19 mL, 1.4 mmol) in tetrahydrofuran (3 mL) was cooled to 0° C. 1.6 M n-butyllithium in hexanes (0.86 mL, 1.4 mmol) was added dropwise, keeping the temperature below 5° C. After the addition was complete, the mixture was stirred for 20 min at 0° C. The mixture was then cooled to −78° C. and acetonitrile (0.072 mL, 1.4 mmol) was added, keeping the temperature below −70° C. After the addition was complete, the mixture was stirred for 20 min at −78° C. and a mixture of 4-[(6-nitrothieno[3,2-b]pyridin-7-yl)amino]cyclohexanone (0.20 g, 0.69 mmol) in tetrahydrofuran (3 mL)/hexamethylphosphoramide (3 mL) was added, keeping the temperature below −70° C. After the addition was complete, the mixture was stirred for 30 min at −78° C. and then stirred at room temperature for 5 h. The mixture was partitioned between methylene chloride and sat. aq. $NH_4Cl$ solution. The organic phase was washed with water, dried over sodium sulfate, concentrated and purified on silica gel column (eluting with 0-30% EtOAc in methylene chloride) to give the desired product (0.11 g, 48%). LCMS calculated for $C_{15}H_{17}N_4O_3S$ (M+H)$^+$: m/z=333.1; Found: 333.0.

Step 4. {4-[(6-Aminothieno[3,2-b]pyridin-7-yl)amino]-1-hydroxycyclohexyl}acetonitrile A mixture of {1-hydroxy-4-[(6-nitrothieno[3,2-b]pyridin-7-yl)amino]cyclohexyl}acetonitrile (0.11 g, 0.33 mmol) and 10% Pd/C (0.050 g) in methanol (7 mL) was hydrogenated under balloon pressure of $H_2$ at room temperature for 2 h. The mixture was filtered, concentrated and purified on silica gel column (eluting with 0-10% MeOH in methylene chloride) to give the desired product as a mixture of cis- and trans-isomer mixtures (38 mg, 38%). LCMS calculated for $C_{15}H_{19}N_4OS$ (M+H)$^+$: m/z=303.1; Found: 303.0.

Step 5. (trans-1-Hydroxy-4-{2-[(1R)-1-hydroxyethyl]-1H-imidazo[4,5-d]thieno[3,2-b]pyridin-1-yl}cyclohexyl)acetonitrile A mixture of (2R)-2-hydroxypropanamide (57 mg, 0.64 mmol) and triethyloxonium tetrafluoroborate (119 mg, 0.626 mmol) in tetrahydrofuran (0.8 mL) was stirred at room temperature for 2 h. The solvent was removed and the residue dissolved in ethanol (0.23 mL) and added to a suspension of {4-[(6-aminothieno[3,2-b]pyridin-7-yl)amino]-1-hydroxycyclohexyl}acetonitrile (38 mg, 0.12 mmol) in ethanol (0.84 mL). The mixture was stirred at 85° C. for 2 h and then purified on prep-HPLC (XBridge C18 column, eluting with a gradient of acetonitrile/water containing 0.1% ammonium hydroxide, at flow rate of 60 mL/min) to give 2 peaks. On analytic HPLC (Waters SunFire C18, 2.1×50 mm, 5 μM; Flow rate 3 mL/min; Injection volume 2 μL; At gradient from 2 to 80% B in 3 minutes (A=water with 0.025% TFA, B=acetonitrile)): First peak (5 mg, 10%) retention time 0.952 min, LCMS calculated for $C_{18}H_{21}N_4O_2S$ (M+H)$^+$: m/z=357.1; Found: 357.1. $^1$H NMR (DMSO-$d_6$, 400 MHz) δ 8.94 (1H, s), 8.00 (1H, d, J=5.6 Hz), 7.60 (1H, d, J=5.6 Hz), 5.78 (1H, d, J=6.8 Hz), 5.22

(1H, s), 5.13 (1H, m), 4.82 (1H, m), 2.65 (4H, m), 1.86 (2H, m), 1.73-1.63 (4H, m), 1.59 (1H, d, J=6.8 Hz) ppm. Second peak (15 mg, 33%) retention time 0.977 min, LCMS calculated for $C_{18}H_{21}N_4O_2S$ (M+H)$^+$: m/z=357.1; Found: 357.1. H NMR (DMSO-d$_6$, 400 MHz) δ 8.93 (1H, s), 7.99 (1H, d, J=5.6 Hz), 7.63 (1H, d, J=5.6 Hz), 5.82 (1H, d, J=6.8 Hz), 5.33 (1H, s), 5.15 (1H, m), 4.88 (1H, m), 3.05 (2H, m), 2.23 (2H, m), 1.93 (4H, m), 1.74 (2H, m), 1.61 (1H, d, J=6.8 Hz) ppm.

Example 25. {(2E)-1-[trans-4-(Cyanomethyl)cyclohexyl]-1,3-dihydro-2H-imidazo[4,5-d]thieno[3,2-b]pyridin-2-ylidene}cyanamide Trifluoroacetate

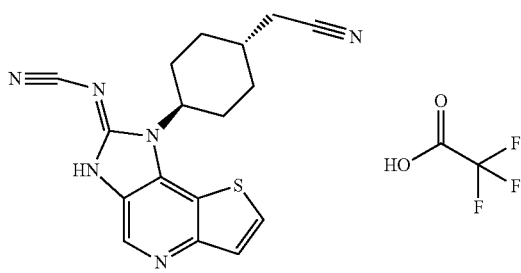 [SMILES: N#CC[C@H]1CC[C@H](n2/c(=N/C#N)[nH]c3cnc4ccsc4c32)CC1 ; O=C(O)C(F)(F)F]

A solution of {trans-4-[(6-aminothieno[3,2-b]pyridin-7-yl)amino]cyclohexyl}acetonitrile (0.028 g, 0.098 mmol), diphenyl cyanocarbonimidate (0.046 g, 0.20 mmol) and N,N-diisopropylethylamine (0.17 mL, 0.98 mmol) in acetonitrile (1 mL) was heated at 100° C. for 2 h. The mixture was stripped to dryness, diluted with methanol (MeOH) and then purified by prep-HPLC (XBridge C18 column, eluting with a gradient of acetonitrile/water containing 0.05% TFA, at flow rate of 60 mL/min) to give the desired product as TFA salt (2.5 mg, 7.6%). LCMS calculated for $C_7H_{17}N_6S$ (M+H)$^+$: m/z=337.1; Found: 337.1.

Example 26. [trans-4-(2-Cyclopropyl-1H-imidazo[4,5-d]thieno[3,2-b]pyridin-1-yl)cyclohexyl]acetonitrile

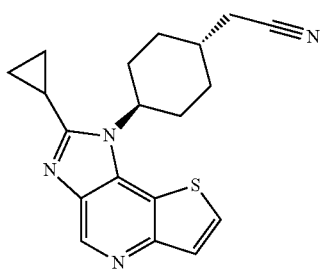 [SMILES: N#CC[C@H]1CC[C@H](n2c(C3CC3)nc3cnc4ccsc4c32)CC1]

A mixture of cyclopropanecarboxamide (65.0 mg, 0.764 mmol) and triethyloxonium tetrafluoroborate (145 mg, 0.763 mmol) in tetrahydrofuran (0.4 mL) was stirred at room temperature for 1 h and then concentrated. A mixture of {trans-4-[(6-aminothieno[3,2-b]pyridin-7-yl)amino]cyclohexyl}acetonitrile (22 mg, 0.077 mmol), and the above made reagent in ethanol (0.70 mL) was heated at reflux for 2 h. The mixture was purified on prep-HPLC (XBridge C18 column, eluting with a gradient of acetonitrile/water containing 0.1% ammonium hydroxide, at flow rate of 60 mL/min) to give the desired product (2.5 mg, 9.7%). LCMS calculated for $C_{19}H_{21}N_4S$ (M+H)$^+$: m/z=337.1; Found: 337.0.

Example 27. [trans-4-(2-Isopropyl-1H-imidazo[4,5-d]thieno[3,2-b]pyridin-1-yl)cyclohexyl]acetonitrile

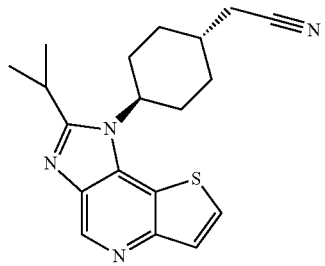 [SMILES: CC(C)c1nc2cnc3ccsc3c2n1[C@H]1CC[C@H](CC#N)CC1]

A mixture of 2-methylpropanamide (80 mg, 0.9 mmol) and triethyloxonium tetrafluoroborate (170 mg, 0.89 mmol) in tetrahydrofuran (0.4 mL) was stirred at room temperature for 1 h and then concentrated. A mixture of {trans-4-[(6-aminothieno[3,2-b]pyridin-7-yl)amino]cyclohexyl}acetonitrile (22 mg, 0.077 mmol) and the above made reagent in ethanol (0.70 mL) was heated at reflux for 2 h. The mixture was purified on prep-HPLC (XBridge C18 column, eluting with a gradient of acetonitrile/water containing 0.1% ammonium hydroxide, at flow rate of 60 mL/min) to give the desired product (2.9 mg, 11%). LCMS calculated for $C_{19}H_{23}N_4S$ (M+H)$^+$: m/z=339.2; Found: 339.0.

Example 28. [trans-4-(2-Azetidin-3-yl-1H-imidazo[4,5-d]thieno[3,2-b]pyridin-1-yl)cyclohexyl]acetonitrile

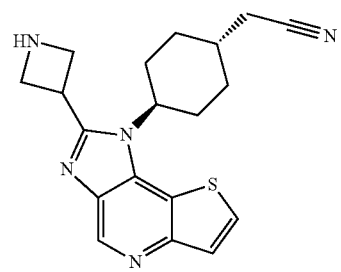 [SMILES: N#CC[C@H]1CC[C@H](n2c(C3CNC3)nc3cnc4ccsc4c32)CC1]

Step 1. tert-Butyl 3-(aminocarbonyl)azetidine-1-carboxylate

To a solution of 1-(tert-butoxycarbonyl)azetidine-3-carboxylic acid (from Activate Scientific. 0.25 g, 1.2 mmol), ammonium acetate (0.14 g, 1.9 mmol) and N,N,N',N'-tetramethyl-O-(7-azabenzotriazol-1-yl)uronium hexafluorophosphate (0.71 g, 1.9 mmol) in N,N-dimethylformamide (4 mL) was added N,N-diisopropylethylamine (0.43 mL, 2.5 mmol). The mixture was stirred at room temperature overnight. The mixture was diluted with MeOH and purified on prep-LCMS (XBridge C18 column, eluting with a gradient of acetonitrile/water containing 0.1% ammonium hydroxide, at flow rate of 60 mL/min) to give the desired product (0.156 g, 63%). LCMS calculated for $C_9H_6N_2O_3Na$ (M+Na)$^+$: m/z=223.1; Found: 223.0.

Step 2. tert-Butyl 3-{1-[trans-4-(cyanomethyl)cyclohexyl]-1H-imidazo[4,5-d]thieno[3,2-b]pyridin-2-yl}azetidine-1-carboxylate A mixture of tert-butyl 3-(aminocarbonyl)azetidine-1-carboxylate (156 mg, 0.779 mmol) and triethyloxonium tetrafluoroborate (280 mg, 1.5 mmol) in tetrahydrofuran (0.4 mL) was stirred at room temperature for 1 h and then concentrated. A mixture of {trans-4-[(6-aminothieno[3,2-b]pyridin-7-yl)amino]cyclohexyl}acetonitrile (39 mg, 0.14 mmol) and the above made reagent in ethanol (0.70 mL) was heated at reflux for 2 h. The mixture was cooled to room temperature, diluted with EtOAc, washed with sat. NaHCO$_3$ solution, dried over MgSO$_4$, concentrated and purified on silica gel column (0-5% MeOH in methylene chloride) to give the desired product. LCMS calculated for $C_{24}H_{30}N_5O_2S$ (M+H)$^+$: m/z=452.2; Found: 452.1.

Step 3. [trans-4-(2-Azetidin-3-yl-1H-imidazo[4,5-d]thieno[3,2-b]pyridin-1-yl)cyclohexyl]acetonitrile 3-{1-[trans-4-(Cyanomethyl)cyclohexyl]-1H-imidazo[4,5-d]thieno[3,2-b]pyridin-2-yl}azetidine-1-carboxylate (14 mg, 0.031 mmol) was treated with trifluoroacetic acid (1 mL) in methylene chloride (1 mL) at room temperature for 1 h. The mixture was stripped to dryness, diluted with MeOH and purified on prep-HPLC (XBridge C18 column, eluting with a gradient of acetonitrile/water containing 0.1% ammonium hydroxide, at flow rate of 60 mL/min) to give the desired product. LCMS calculated for $C_{19}H_{22}N_5S$ (M+H)$^+$: m/z=352.2; Found: 352.0.

Example 29. {trans-4-[2-(1-Methylazetidin-3-yl)-1H-imidazo[4,5-d]thieno[3,2-b]pyridin-1-yl]cyclohexyl}acetonitrile

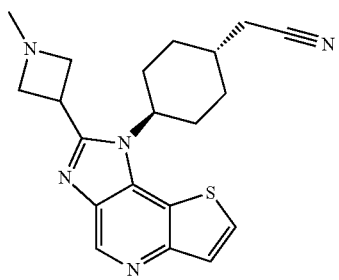 [SMILES: CN1CC(c2nc3cnc4ccsc4c3n2[C@H]2CC[C@H](CC#N)CC2)C1]

To a solution of [trans-4-(2-azetidin-3-yl-1H-imidazo[4,5-d]thieno[3,2-b]pyridin-1-yl)cyclohexyl]acetonitrile (14 mg, 0.038 mmol) in methanol (0.5 mL)/tetrahydrofuran (0.5 mL)/acetonitrile (0.5 mL) was added 37% aq. formaldehyde solution (12 µL, 0.16 mmol). The resulting mixture was stirred at room temperature for 10 min before sodium triacetoxyborohydride (16 mg, 0.077 mmol) was added. The mixture was stirred at room temperature for 1 h and then diluted with MeOH and purified by prep-HPLC (XBridge C18 column, eluting with a gradient of acetonitrile/water containing 0.1% ammonium hydroxide, at flow rate of 60 mL/min) to give the desired product (0.8 mg, 6%). LCMS calculated for $C_{20}H_{24}N_5S$ (M+H)$^+$: m/z=366.2; Found: 366.1.

Example 30. 3-[(cis-4-{2-[(1R)-1-Hydroxyethyl]-1H-imidazo[4,5-d]thieno[3,2-b]pyridin-1-yl}cyclohexyl)amino]propanenitrile

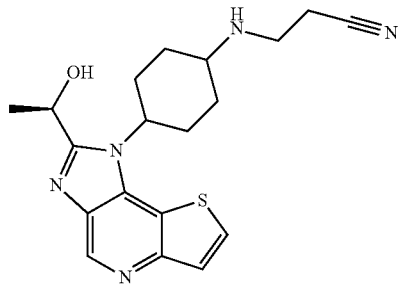 [SMILES: C[C@@H](O)c1nc2cnc3ccsc3c2n1C1CCC(NCCC#N)CC1]

Step 1. tert-Butyl {4-[(6-nitrothieno[3,2-b]pyridin-7-yl)amino]cyclohexyl}carbamate A mixture of 7-chloro-6-nitrothieno[3,2-b]pyridine (118 mg, 0.550 mmol), tert-butyl (4-aminocyclohexyl)carbamate (140 mg, 0.66 mmol) and triethylamine (0.23 mL, 1.6 mmol) in isopropyl alcohol (5 mL) was heated at 100° C. for 1 h. The mixture was concentrated to give the desired product as a mixture of cis- & trans-isomer mixtures to be used in the next step directly. LCMS calculated for $C_{18}H_{25}N_4O_4S$ (M+H)$^+$: m/z=393.2; Found: 393.1.

Step 2. tert-Butyl {4-[(6-aminothieno[3,2-b]pyridin-7-yl)amino]cyclohexyl}carbamate tert-Butyl {4-[(6-nitrothieno[3,2-b]pyridin-7-yl)amino]cyclohexyl}carbamate (216 mg, 0.550 mmol) and 10% Pd/C (20 mg) in methanol (5 mL) was subjected to balloon pressure of H$_2$ at room temperature for 2 h. The mixture was filtered, concentrated and purified on silica gel column (eluting with 0-10% MeOH in methylene chloride) to give the desired product. LCMS calculated for $C_{18}H_{27}N_4O_2S$ (M+H)$^+$: m/z=363.2; Found: 363.1.

Step 3. tert-Butyl (4-{2-[(1R)-1-hydroxyethyl]-1H-imidazo[4,5-d]thieno[3,2-b]pyridin-1-yl}cyclohexyl)carbamate A mixture of (2R)-2-hydroxypropanamide (320 mg, 3.6 mmol) and triethyloxonium tetrafluoroborate (0.69 g, 3.6 mmol) in tetrahydrofuran (3 mL) was stirred at room temperature for 1 h and then concentrated. A mixture of tert-butyl {4-[(6-aminothieno[3,2-b]pyridin-7-yl)amino]cyclohexyl}carbamate (191 mg, 0.527 mmol) and the above made reagent in ethanol (4.8 mL) was heated at reflux for 2 h. The mixture was concentrated and purified on silica gel column (eluting with 0-10% MeOH in methylene chloride) to give the desired product. LCMS calculated for $C_{21}H_{29}N_4O_3S$ (M+H)$^+$: m/z=417.2; Found: 417.0.

Step 4. (1R)-1-[1-(4-Aminocyclohexyl)-1H-imidazo[4,5-d]thieno[3,2-b]pyridin-2-yl]ethanol Dihydrochloride tert-Butyl (4-{2-[(1R)-1-hydroxyethyl]-1H-imidazo[4,5-d]thieno[3,2-b]pyridin-1-yl}cyclohexyl)carbamate (0.22 g, 0.53 mmol) was treated with 4.0 M hydrogen chloride in dioxane (0.66 mL, 2.6 mmol) in methylene chloride (3 mL) at room temperature overnight. The mixture was concentrated to give the desired product as HCl salt (0.22 g, 94%). LCMS calculated for $C_{16}H_{21}N_4OS$ (M+H)$^+$: m/z=317.1; Found: 317.0.

Step 5. 3-[(trans-4-{2-[(1R)-1-Hydroxyethyl]-1H-imidazo[4,5-d]thieno[3,2-b]pyridin-1-yl}cyclohexyl) amino]propanenitrile To a solution of (1R)-1-[1-(4-aminocyclohexyl)-1H-imidazo[4,5-d]thieno[3,2-b]pyridin-2-yl]ethanol dihydrochloride (26 mg, 0.067 mmol) in acetonitrile (0.45 mL) was added 1,8-diazabicyclo[5.4.0]undec-7-ene (50 µL, 0.33 mmol) followed by 2-propenenitrile (8.78 µL, 0.134 mmol). The resulting mixture was stirred at room temperature overnight. After evaporated to dry, the residue was purified by prep-HPLC (XBridge C18 column, eluting with a gradient of acetonitrile/water containing 0.1% ammonium hydroxide, at flow rate of 60 mL/min) to give 2 peaks. On analytic HPLC (Waters SunFire C18, 2.1×50 mm, 5 µM; Flow rate 3 mL/min; Injection volume 2 µL; At gradient from 2 to 80% B in 3 minutes (A=water with 0.025% TFA, B=acetonitrile)): First peak (4.3 mg, 17%) retention time 0.683 min, LCMS calculated for $C_{19}H_{24}N_5OS$ (M+H)$^+$: m/z=370.2; Found: 370.1. Second peak from the prep-HPLC (4.3 mg, 17%) retention time is 0.598 min on the analytic HPLC, LCMS calculated for $C_{19}H_{24}N_5OS$ (M+H)$^+$: m/z=370.2; Found: 370.1.

Example 31. N-Ethyl-2-(trans-4-{2-[(1R)-1-hydroxyethyl]-1H-imidazo[4,5-d]thieno[3,2-b]pyridin-1-yl}cyclohexyl)acetamide

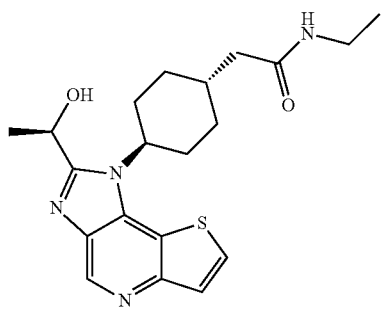 [SMILES: CCNC(=O)C[C@H]1CC[C@H](n2c([C@@H](C)O)nc3cnc4ccsc4c32)CC1]

Step 1. Ethyl {trans-4-[(6-nitrothieno[3,2-b]pyridin-7-yl)amino]cyclohexyl}acetate A mixture of 7-chloro-6-nitrothieno[3,2-b]pyridine (97 mg, 0.45 mmol), ethyl (trans-4-aminocyclohexyl)acetate hydrochloride (from Activate Scientific, 120 mg, 0.54 mmol) and triethylamine (0.19 mL, 1.4 mmol) in isopropyl alcohol (4 mL) was heated at 100° C. for 1 h. The mixture was concentrated to give the desired product to be used in the next step directly. LCMS calculated for $C_{17}H_{22}N_3O_4S$ (M+H)$^+$: m/z=364.1; Found: 364.1.

Step 2. Ethyl {trans-4-[(6-aminothieno[3,2-b]pyridin-7-yl)amino]cyclohexyl}acetate Ethyl {trans-4-[(6-nitrothieno[3,2-b]pyridin-7-yl)amino] cyclohexyl}acetate (160 mg, 0.44 mmol) and 10% Pd/C (20 mg) in methanol (4 mL) was subjected to balloon pressure of H$_2$ at room temperature for 2 h. The mixture was filtered. The filtrate was concentrated and purified on silica gel column (eluting with 0-10% MeOH in methylene chloride) to give the desired product. LCMS calculated for $C_{17}H_{24}N_3O_2S$ (M+H)$^+$: m/z=334.2; Found: 334.1.

Step 3. Ethyl (trans-4-{2-[(1R)-1-hydroxyethyl]-1H-imidazo[4,5-d]thieno[3,2-b]pyridin-1-yl}cyclohexyl) acetate A mixture of (2R)-2-hydroxypropanamide (170 mg, 1.9 mmol) and triethyloxonium tetrafluoroborate (0.36 g, 1.9 mmol) in tetrahydrofuran (2 mL) was stirred at room temperature for 1 h and then concentrated. A mixture of ethyl {trans-4-[(6-aminothieno[3,2-b]pyridin-7-yl)amino] cyclohexyl}acetate (150 mg, 0.45 mmol) and the above made reagent in ethanol (4.8 mL) was heated at reflux for 2 h. The mixture was concentrated and purified on silica gel column (eluting with 0-5% MeOH in methylene chloride) to give the desired product (0.15 g, 86%). LCMS calculated for $C_{20}H_{26}N_3O_3S$ (M+H)$^+$: m/z=388.2; Found: 388.1.

Step 4. (trans-4-{2-[(1R)-1-Hydroxyethyl]-1H-imidazo[4,5-d]thieno[3,2-b]pyridin-1-yl}cyclohexyl) acetic Acid A mixture of ethyl (trans-4-{2-[(1R)-1-hydroxyethyl]-1H-imidazo[4,5-d]thieno[3,2-b]pyridin-1-yl}cyclohexyl) acetate (0.15 g, 0.39 mmol) and lithium hydroxide, monohydrate (0.079 g, 1.9 mmol) in water (0.7 mL)/methanol (1.7 mL)/tetrahydrofuran (1.7 mL) was stirred at room temperature overnight. The reaction was acidified with 1N aq. HCl solution to pH=4, extracted with methylene chloride. The combined organic layers were dried over MgSO$_4$ and concentrated to give the desired product (0.11 g, 79%) to be used in the next step directly. LCMS calculated for $C_{18}H_{22}N_3O_3S$ (M+H)$^+$: m/z=360.1; Found: 360.1.

Step 5. N-Ethyl-2-(trans-4-{2-[(R)-1-hydroxyethyl]-1H-imidazo[4,5-d]thieno[3,2-b]pyridin-1-yl}cyclohexyl)acetamide To a solution of (trans-4-{2-[(1R)-1-hydroxyethyl]-1H-imidazo[4,5-d]thieno[3,2-b]pyridin-1-yl}cyclohexyl)acetic acid (11 mg, 0.031 mmol), 2.0 M ethylamine in THF (23 µL, 0.046 mmol) and benzotriazol-1-yloxytris(dimethylamino) phosphonium hexafluorophosphate (23 mg, 0.052 mmol) in N,N-dimethylformamide (0.4 mL) was added N,N-diisopropylethylamine (0.016 mL, 0.092 mmol). The mixture was stirred at room temperature for 2 h. The mixture was diluted with MeOH and purified on prep-HPLC (XBridge C18 column, eluting with a gradient of acetonitrile/water containing 0.1% ammonium hydroxide, at flow rate of 30 mL/min) to give the desired product (1.8 mg, 15%). LCMS calculated for $C_{20}H_{27}N_4O_2S$ (M+H)$^+$: m/z=387.2; Found: 387.1.

Example 32. 3-(3-{2-[(1R)-1-Hydroxyethyl]-1H-imidazo[4,5-d]thieno[3,2-b]pyridin-1-yl}cyclohexyl)propanenitrile

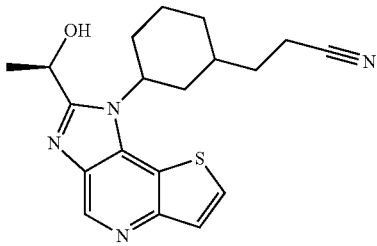 [SMILES: C[C@@H](O)c1nc2cnc3ccsc3c2n1C1CCCC(CCC#N)C1]

Step 1. Tert-Butyl [3-(hydroxymethyl)cyclohexyl]carbamate

To a mixture of 3-[(tert-butoxycarbonyl)amino]cyclohexanecarboxylic acid (from Alfa Aesar, 3.3 g, 14 mmol) and triethylamine (3.8 mL, 27 mmol) in tetrahydrofuran (40 mL) at 0° C. was added dropwise ethyl chloroformate (1.9 mL, 20 mmol). The mixture was stirred at 0° C. for 10 min and then at room temperature for 20 min. The mixture was filtered to remove the white solid and then cooled to 0° C. A mixture of sodium tetrahydroborate (1.0 g, 27 mmol) and methanol (1 mL) was added slowly. The mixture was stirred at room temperature for 1 h. The mixture was quenched with 1N aq. HCl solution and extracted with EtOAc. The extracts were concentrated and purified on silica gel column (eluting with 75% EtOAc in hexanes) to give the desired product (2.88 g, 92%). LCMS calculated for $C_{13}H_{23}NO_3Na$ $(M+Na)^+$: m/z=252.2; Found: 252.1.

Step 2. Tert-Butyl (3-formylcyclohexyl)carbamate

To a solution of tert-butyl [3-(hydroxymethyl)cyclohexyl]carbamate (0.51 g, 2.2 mmol) in methylene chloride (10 mL) at 0° C. was added Dess-Martin periodinane (1.1 g, 2.7 mmol). The mixture was stirred at room temperature for 2 h. The reaction was quenched with aq. 1N NaOH solution and extracted with methylene chloride. The combined organic layers were washed with water and then brine, dried over $MgSO_4$, concentrated, and then purified on silica gel column (eluting with 20-50% EtOAc in hexanes) to give the desired product (0.3 g, 59%). LCMS calculated for $C_{12}H_{21}NO_3Na$ $(M+Na)^+$: m/z=250.2; Found: 250.1.

Step 3. tert-Butyl {3-[2-cyanovinyl]cyclohexyl}carbamate

To 1.0 M potassium tert-butoxide in THF (2.0 mL, 2.0 mmol) was added diethyl cyanomethylphosphonate (0.30 mL, 1.8 mmol) dropwise at 0° C. and the mixture was stirred at 0° C. for 1 h. A solution of tert-butyl (3-formylcyclohexyl)carbamate (0.30 g, 1.3 mmol) in tetrahydrofuran (9.3 mL) was added dropwise, then cooling bath was removed, and the mixture was stirred at room temperature overnight. The mixture was diluted with EtOAc, washed with water, concentrated and purified on silica gel column (eluting with 0-30% EtOAc in hexanes) to give the desired product as a mixture of cis- and trans-isomer mixtures (0.12 g, 36%). LCMS calculated for $C_{14}H_{22}N_2O_2Na$ $(M+Na)^+$: m/z=273.2; Found: 273.1.

Step 4. 3-(3-Aminocyclohexyl)acrylonitrile Hydrochloride tert-Butyl {3-[2-cyanovinyl]cyclohexyl}carbamate was treated with 4.0 M hydrogen chloride in dioxane (1.6 mL, 6.6 mmol) in methylene chloride (2 mL) at room temperature for 2 h. The mixture was stripped to dryness to give the desired product as a mixture of cis- and trans-isomers. LCMS calculated for $C_9H_{15}N_2(M+H)^+$: m/z=151.1; Found: 151.1.

Step 5. 3-{3-[(6-Nitrothieno[3,2-b]pyridin-7-yl)amino]cyclohexyl}acrylonitrile A mixture of 3-(3-aminocyclohexyl)acrylonitrile hydrochloride (0.090 g, 0.48 mmol), 7-chloro-6-nitrothieno[3,2-b]pyridine (0.085 g, 0.40 mmol) and triethylamine (0.22 mL, 1.6 mmol) in isopropyl alcohol (0.9 mL) was heated at 90° C. for 1 h. The mixture was concentrated to give the desired product to be used in the next step directly. LCMS calculated for $C_{16}H_{17}N_4O_2$ $(M+H)^+$: m/z=329.1; Found: 329.1.

Step 6. 3-{3-[(6-Aminothieno[3,2-b]pyridin-7-yl)amino]cyclohexyl}propanenitrile A mixture of 3-{3-[(6-nitrothieno[3,2-b]pyridin-7-yl)amino]cyclohexyl}acrylonitrile (0.13 g, 0.40 mmol) and 10% Pd/C (0.05 g) in methanol (10 mL) was hydrogenated under balloon pressure of $H_2$ at room temperature over weekend. The mixture was filtered, concentrated and purified on silica gel column (eluting with 0-10% MeOH in methylene chloride) to give the desired product. LCMS calculated for $C_{16}H_{21}N_4S$ $(M+H)^+$: m/z=301.1; Found: 301.0.

Step 7. 3-(3-{2-[(1R)-1-Hydroxyethyl]-1H-imidazo[4,5-d]thieno[3,2-b]pyridin-1-yl}cyclohexyl)propanenitrile A mixture of (2R)-2-hydroxypropanamide (194 mg, 2.18 mmol) and triethyloxonium tetrafluoroborate (0.41 g, 2.2 mmol) in tetrahydrofuran (2 mL) was stirred at room temperature for 1 h and then concentrated. A mixture of 3-{3-[(6-aminothieno[3,2-b]pyridin-7-yl)amino]cyclohexyl}propanenitrile (131 mg, 0.436 mmol) and the above made reagent in ethanol (4.7 mL) was heated at reflux for 2 h. The mixture was filtered, diluted with MeOH and purified on prep-HPLC (XBridge C18 column, eluting with a gradient of acetonitrile/water containing 0.1% ammonium hydroxide, at flow rate of 60 mL/min) to give the desired product (60 mg, 39%). LCMS calculated for $C_{19}H_{23}N_4OS$ $(M+H)^+$: m/z=355.2; Found: 355.0.

Example 33. [4-(7-Methylimidazo[1,2-a]thieno[3,2-e]pyrazin-8-yl)phenyl]acetonitrile

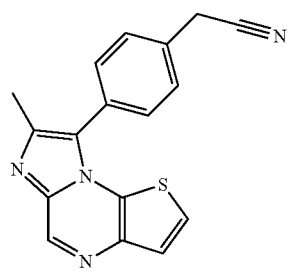 [SMILES: Cc1nc2cnc3ccsc3n2c1-c1ccc(CC#N)cc1]

Step 1. 6-Bromo-5-chloro-2-methylimidazo[1,2-a]pyrazine

Into a 1-neck round-bottom flask N,N-diisopropylamine (0.50 mL, 3.6 mmol) was dissolved in tetrahydrofuran (4.0 mL) and cooled at −78° C. 1.6 M n-butyllithium in hexane (1.9 mL, 3.1 mmol) was added. The reaction was stirred at −78° C. for 30 min and 6-bromo-2-methylimidazo[1,2-a]pyrazine (from Ark Pharm, 0.500 g, 2.36 mmol) in tetrahydrofuran (6.0 mL) was added dropwise. The reaction mixture was stirred at −78° C. for 45 min and hexachloroethane (0.72 g, 3.1 mmol) was added. The resulting mixture was stirred at −78° C. for 1 h. The reaction was quenched with NH$_4$Cl solution and then partitioned between EtOAc and water. The EtOAc extract was washed with brine, dried (MgSO4), and stripped in vacuo. The residue was chromatographed on silica gel eluting with 40% EtOAc in hexanes to give the desired product (0.25 g, 43%). LCMS calculated for C$_7$H$_6$BrClN$_3$ (M+H)$^+$: m/z=245.9; Found: 245.9. $^1$H NMR (CDCl$_3$, 400 MHz) δ 8.72 (1H, s), 7.68 (1H, s), 2.56 (3H, s) ppm.

Step 2. 5-Chloro-2-methyl-6-[(trimethylsilyl)ethynyl]imidazo[1,2-a]pyrazine

A mixture of 6-bromo-5-chloro-2-methylimidazo[1,2-a]pyrazine (0.710 g, 2.88 mmol), bis(triphenylphosphine)palladium(II) chloride (0.1 g, 0.1 mmol), (trimethylsilyl)acetylene (0.90 mL, 6.3 mmol), copper(I) iodide (0.04 g, 0.2 mmol), and triethylamine (0.803 mL, 5.76 mmol) in N,N-dimethylformamide (8.5 mL) was heated in an oil bath at 45° C. and stirring for 14 h. The reaction was quenched with water (20 ml) and was extracted with ethyl acetate (2×100 ml). The combined organic extracts were washed with water (10 ml), saturated NaCl (10 ml), dried over Na$_2$SO$_4$ and the solvent removed in vacuo. The product was purified by silica gel chromatography eluting with 10-20% EtOAc in hexanes to give the desired product (0.39 g, 76%). LCMS calculated for C$_{12}$H$_{15}$ClN$_3$Si (M+H)$^+$: m/z=264.1; Found: 264.0.

Step 3. 7-Methylimidazo[1,2-a]thieno[3,2-e]pyrazine

A mixture of 5-chloro-2-methyl-6-[(trimethylsilyl)ethynyl]imidazo[1,2-a]pyrazine (0.400 g, 1.52 mmol), and sodium sulfide nonahydrate (1.09 g, 4.55 mmol) in N,N-dimethylformamide (6.0 mL) was heated in a preheated oil bath at 100° C. with stirring for 1 h. The reaction was cooled and partitioned between EtOAc and water. The organic layer was washed with water, brine, dried and the solvent was removed in vacuo. The residue was chromatographed on silica gel eluting with EtOAc and 3% MeOH in EtOAc to give the desired product (0.15 g, 52%). LCMS calculated for C$_9$H$_8$N$_3$S (M+H)$^+$: m/z=190.0; Found: 190.0.

Step 4. 8-Iodo-7-methylimidazo[1,2-a]thieno[3,2-e]pyrazine

A mixture of 7-methylimidazo[1,2-a]thieno[3,2-e]pyrazine (30 mg, 0.16 mmol), and N-iodosuccinimide (39 mg, 0.17 mmol) in methylene chloride (1.2 mL) was stirred at 25° C. for 16 h. The product was purified by prep-HPLC (XBridge C18 column, eluting with a gradient of acetonitrile/water containing 0.1% ammonium hydroxide, at flow rate of 60 mL/min) to give the desired product (15 mg, 30%). LCMS calculated for C$_9$H$_7$IN$_3$S (M+H)$^+$: m/z=315.9; Found: 316.0. $^1$H NMR (CDCl$_3$, 400 MHz) δ 8.89 (1H, s), 7.55 (1H, d, J=5.6 Hz), 7.35 (1H, d, J=5.6 Hz), 2.55 (3H, s) ppm.

Step 5. [4-(7-Methylimidazo[1,2-a]thieno[3,2-e]pyrazin-8-yl)phenyl]acetonitrile A mixture of [4-(cyanomethyl)phenyl]boronic acid (from Aldrich, 9.3 mg, 0.058 mmol), 8-iodo-7-methylimidazo[1,2-a]thieno[3,2-e]pyrazine (12 mg, 0.038 mmol), and potassium carbonate (16 mg, 0.12 mmol), in acetonitrile (0.6 mL) and water (0.2 mL) was degassed. Into the mixture was added tetrakis(triphenylphosphine)palladium(0) (2.2 mg, 0.0019 mmol). The reaction mixture was heated at 160° C. for 10 min in a microwave reactor. The reaction was diluted with methanol, filtered. The filtrate was purified by prep-HPLC (XBridge C18 column, eluting with a gradient of acetonitrile/water containing 0.1% ammonium hydroxide, at flow rate of 60 mL/min) to give the desired product. LCMS calculated for C$_{17}$H$_{13}$N$_4$S (M+H)$^+$: m/z=305.1; Found: 305.0. $^1$H NMR (CDCl$_3$, 400 MHz) δ 9.01 (1H, s), 7.55 (4H, m), 7.49 (1H, d, J=6.0 Hz), 7.14 (1H, d, J=6.0 Hz), 3.93 (2H, s), 2.48 (3H, s) ppm.

Example 34. Mixture of [(1R, 2R, 4S)-2-hydroxy-4-(2-methyl-1H-imidazo[4,5-d]thieno[3,2-b]pyridin-1-yl)cyclohexyl]acetonitrile Trifluoroacetate and [(1S, 2S, 4R)-2-hydroxy-4-(2-methyl-1H-imidazo[4,5-d]thieno[3,2-b]pyridin-1-yl)cyclohexyl]acetonitrile Trifluoroacetate

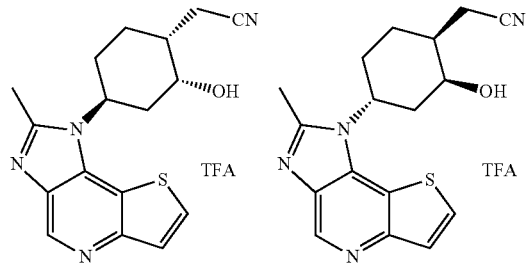 [SMILES: Cc1nc2cnc3ccsc3c2n1[C@H]1CC[C@H](CC#N)[C@H](O)C1 ; Cc1nc2cnc3ccsc3c2n1[C@@H]1CC[C@@H](CC#N)[C@@H](O)C1]

Step 1. Methyl-2-methoxy-4-[(trimethylsilyl)oxy]cyclohex-3-ene-1-carboxylate A mixture of methyl acrylate (5.23 mL, 58.0 mmol) and 1-methoxy-3-(trimethylsiloxy)-1,3-butadiene (from Aldrich, 10.0 g, 58.0 mmol) in toluene (100 mL) was heated at 80° C. for 2 d. The reaction solution was concentrated and purified on silica gel column to give the desired product as a mixture of trans- and cis-isomers (8.3 g, 55%). H NMR (500 MHz, CDCl$_3$) δ 5.16 (1H, m), 4.97 (1H, m), 4.22 (1H, m), 4.08 (1H, m), 3.68 (3H, s), 3.67 (3H, s), 3.32 (3H, s), 3.24 (3H, s), 2.59 (1H, m), 2.51 (1H, m), 1.80-2.14 (8H, m), 0.18 (18H, s) ppm.

Step 2. Methyl (1S, 2R)-2-methoxy-4-oxocyclohexanecarboxylate (Racemic) and methyl (1S, 2S)-2-methoxy-4-oxocyclohexanecarboxylate (Racemic)

To a solution of methyl-2-methoxy-4-[(trimethylsilyl)oxy]cyclohex-3-ene-1-carboxylate (8.3 g, 32 mmol) in methanol (200 mL) was added potassium carbonate (2.2 g, 16 mmol) at 0° C. After stirring for 20 min, the reaction was diluted with saturated NH₄Cl solution and ethyl acetate. The aqueous layer was extracted with ethyl acetate. The combined organic layers were washed with brine, dried over Na₂SO₄, concentrated in vacuo. The crude was purified with flash chromatography (eluting with 0 to 50% ethyl acetate in hexanes) to give trans-isomer (first elute, 1.5 g, 25%), and cis-isomer (last elute, 1.35 g, 22%). For the trans-isomer: $^1$H NMR (400 MHz, CDCl₃) δ 3.89 (1H, m), 3.75 (3H, s), 3.33 (3H, s), 2.85 (1H, m), 2.78 (1H, m), 2.44 (2H, m), 2.32 (1H, m), 2.15 (1H, m), 1.96 (1H, m) ppm. For the cis-isomer: $^1$H NMR (400 MHz, CDCl₃) δ 4.18 (1H, m), 3.72 (3H, s), 3.30 (3H, s), 2.85 (2H, m), 2.46 (2H, m), 2.28 (1H, m), 2.12 (1H, m) ppm.

Step 3. Methyl (1S, 2R, 4R)-4-hydroxy-2-methoxycyclohexanecarboxylate (Racemic)

To a solution of methyl (1S,2R)-2-methoxy-4-oxocyclohexanecarboxylate (racemic, cis-isomer from last step) (1.35 g, 7.25 mmol) in methanol (30 mL) was added sodium tetrahydroborate (270 mg, 7.2 mmol) at −78° C. After stirring for 1 h, the reaction was diluted with sat. NH₄Cl solution and ethyl acetate. The aqueous layer was extracted with ethyl acetate. The combined organic layers were washed with brine, dried over Na₂SO₄, concentrated and purified with flash chromatography (eluting with 70% ethyl acetate in hexanes) to give the desired product (1.26 g, 92%). $^1$H NMR (500 MHz, CDCl₃) δ 3.96 (2H, m), 3.72 (3H, s), 3.38 (3H, s), 2.45 (1H, m), 2.31 (1H, m), 2.11 (1H, m), 1.97 (1H, m), 1.77 (1H, m), 1.50 (2H, m) ppm.

Step 4. Methyl (1S, 2R, 4R)-2-methoxy-4-[(methylsulfonyl)oxy]cyclohexanecarboxylate (Racemic)

A solution of methyl (1S, 2R, 4R)-4-hydroxy-2-methoxycyclohexanecarboxylate (racemic) (1.14 g, 6.06 mmol) in dichloromethane (30 mL) was treated with methanesulfonyl chloride (0.938 mL, 12.1 mmol) dropwise at 0° C. The mixture was stirred at 0° C. for 2 h and partitioned between ethyl acetate and water. The organic phase was concentrated and purified on silica gel (eluting with 50% ethyl acetate in hexanes) to give the desired product (1.48 g, 93%). $^1$H NMR (400 MHz, CDCl₃) δ 4.89 (1H, m), 3.70 (3H, s), 3.62 (1H, m), 3.36 (3H, s), 3.02 (3H, s), 2.78 (1H, m), 2.42 (1H, m), 2.01 (2H, m), 1.98 (1H, m), 1.80 (1H, m), 1.62 (1H, m) ppm.

Step 5. Methyl (1S,2R,4S)-4-azido-2-methoxycyclohexanecarboxylate (Racemic)

To a solution of methyl (1S,2R,4R)-2-methoxy-4-[(methylsulfonyl)oxy]cyclohexanecarboxylate (racemic) (1.48 g, 5.56 mmol) in DMF (19 mL) sodium azide (1.4 g, 22 mmol) was added. The reaction mixture was stirred and heated at 80° C. for 4 h. The reaction mixture was poured into sat. NaHCO₃ solution and extracted with ethyl acetate (2×30 mL). The combined extracts were washed with brine, dried over Na₂SO₄, concentrated. The crude was purified by flash chromatography (eluting with a gradient of 0-35% ethyl acetate in hexanes) to give the desired product as colorless oil (1.02 g, 86%). $^1$H NMR (300 MHz, CDCl₃) δ 3.98 (1H, m), 3.76 (3H, s), 3.58 (1H, m), 3.36 (3H, s), 2.38 (2H, m), 2.06 (1H, m), 1.90 (2H, m), 1.36 (2H, m) ppm.

Step 6. Methyl (1S,2R,4S)-4-[(tert-butoxycarbonyl)amino]-2-methoxycyclohexanecarboxylate (Racemic)

To a solution of methyl (1S,2R,4S)-4-azido-2-methoxycyclohexanecarboxylate (racemic) (901 mg, 4.22 mmol) in methanol (26 mL) was added di-tert-butyldicarbonate (1.11 g, 5.07 mmol) followed by 10% palladium on carbon (720 mg, 0.68 mmol). The resulting mixture was stirred under balloon pressure of hydrogen overnight. The reaction mixture was filtered through a pad of Celite and washed with methanol. The solvent was removed and residue was purified with flash chromatography (eluting with 0-40% ethyl acetate in hexanes) to give the desired product as colorless oil (0.96 g, 79%). $^1$H NMR (300 MHz, CDCl₃) δ 4.38 (1H, m), 3.92 (1H, m), 3.66 (3H, s), 3.28 (3H, s), 2.35 (2H, m), 2.07-1.76 (3H, m), 1.40 (9H, s), 1.08 (2H, m) ppm.

Step 7. tert-Butyl [(1S,3R,4R)-4-(hydroxymethyl)-3-methoxycyclohexyl]carbamate (Racemic)

Methyl (1S,2R,4S)-4-[(tert-butoxycarbonyl)amino]-2-methoxycyclohexanecarboxylate (racemic) (0.87 g, 3.0 mmol) were dissolved in ether (27 mL) and cooled to 0° C. Lithium tetrahydroaluminate (138 mg, 3.63 mmol) was added and the resulting reaction mixture was stirred for 4 h. The reaction was quenched with 5 mL water at 0° C., then diluted with 5 mL 15% NaOH and 15 mL water after stirring for 30 min. The reaction mixture was filtered through a pad of Celite and washed with ethyl acetate. The aqueous layer was extracted with ethyl acetate (2×). The combined organic layers were washed with brine, dried over Na₂SO₄, filtered and concentrated. The crude was purified with flash chromatography (eluting with a gradient of 0-80% ethyl acetate in hexanes) to give the desired product as white foam.

Step 8. {(1R,2R,4S)-4-[(tert-Butoxycarbonyl)amino]-2-methoxycyclohexyl}methyl methanesulfonate (Racemic)

To a solution of tert-butyl [(1S,3R,4R)-4-(hydroxymethyl)-3-methoxycyclohexyl]carbamate (racemic) (671 mg, 2.59 mmol) in dichloromethane (8 mL) was added methanesulfonyl chloride (0.401 mL, 5.18 mmol) at 0° C. The mixture was stirred at 0° C. for 1 h, then concentrated and partitioned between ethyl acetate and water. The organic phase was concentrated and purified by flash chromatography (eluting with a gradient of 50% ethyl acetate in hexanes) to give the desired product (0.87 g, 100%). LCMS calculated for $C_9H_{16}NO_5S$ (M+H-t-Bu-MeOH)⁺: m/z=250.1; Found: 250.0.

Step 9. [(1R,2R,4S)-4-Amino-2-methoxycyclohexyl]acetonitrile trifluoroacetate (Racemic)

A mixture of {(1R,2R,4S)-4-[(tert-butoxycarbonyl)amino]-2-methoxycyclohexyl}methyl methanesulfonate (racemic) (703 mg, 2.08 mmol) and sodium cyanide (120 mg, 2.5 mmol) in DMSO (7 mL) was stirred at 90° C. overnight. After cooling, the mixture was partitioned between ethyl acetate and brine. The organic layer was washed with water and brine, and concentrated to give the Boc-protected azide intermediate. A solution of the intermediate in dichloromethane (9 mL) was treated with TFA (9 mL) and stirred at room temperature for 2 h. The reaction solution was concentrated to give the desired product as TFA salt. LCMS calculated for $C_9H_{17}N_2O$ (M+H)$^+$: m/z=169.1; Found: 169.2.

Step 10. {(1R,2R,4S)-2-Methoxy-4-[(6-nitrothieno [3,2-b]pyridin-7-yl)amino]cyclohexyl}acetonitrile (Racemic)

A mixture of 7-chloro-6-nitrothieno[3,2-b]pyridine (381 mg, 1.78 mmol), [(1R,2R,4S)-4-amino-2-methoxycyclohexyl]acetonitrile (racemic) (310 mg, 1.8 mmol) and N,N-diisopropylethylamine (1.2 mL, 7.1 mmol) in isopropyl alcohol (4.2 mL) was heated at 90° C. for 2 h. The crude was concentrated and purified with flash chromatography to give the desired product (485 mg, 78%). LCMS calculated for $C_{15}H_{19}N_4O_3S$ (M+H)$^+$: m/z=347.1; Found: 347.0.

Step 11. {(1R,2R,4S)-4-[(6-Aminothieno[3,2-b] pyridin-7-yl)amino]-2-methoxycyclohexyl}acetonitrile (Racemic)

A mixture of {(1R,2R,4S)-2-methoxy-4-[(6-nitrothieno [3,2-b]pyridin-7-yl)amino]cyclohexyl}acetonitrile (racemic) (380 mg, 1.1 mmol) and 10% palladium on carbon (0.38 g, 0.36 mmol) in methanol (7.3 mL) was subjected to balloon pressure of H$_2$ at room temperature for 2 h. The mixture was filtered and the filtrate was concentrated and purified with flash chromatography (eluting with 15% methanol in dichloromethane) to give the desired product (310 mg, 89%). LCMS calculated for $C_{16}H_{21}N_4OS$ (M+H)$^+$: m/z=317.1; Found: 317.1.

Step 12. [(1R,2R,4S)-2-Methoxy-4-(2-methyl-1H-imidazo[4,5-d]thieno[3,2-b]pyridin-1-yl)cyclohexyl] acetonitrile (Racemic)

A mixture of {(1R,2R,4S)-4-[(6-aminothieno[3,2-b]pyridin-7-yl)amino]-2-methoxycyclohexyl}acetonitrile (racemic) (45 mg, 0.14 mmol) and triethyl orthoacetate (79 µL, 0.43 mmol) in acetic acid (0.4 mL, 7 mmol) was stirred at 120° C. for 30 min. The solvent was removed, and the residue dissolved in methanol and purified with prep-LCMS (XBridge C18 column, eluting with a gradient of acetonitrile/water containing 0.1% ammonium hydroxide, at flow rate of 60 mL/min) to give the desired product (28 mg, 58%). LCMS calculated for $C_{18}H_{21}N_4OS$ (M+H)$^+$: m/z=341.1; Found: 341.0.

Step 13. Mixture of [(1R, 2R, 4S)-2-hydroxy-4-(2-methyl-1H-imidazo[4,5-d]thieno[3,2-b]pyridin-1-yl) cyclohexyl]acetonitrile trifluoroacetate and [(1S,2S, 4R)-2-hydroxy-4-(2-methyl-1H-imidazo[4,5-d] thieno[3,2-b]pyridin-1-yl)cyclohexyl]acetonitrile Trifluoroacetate To a microwave vial charged with [(1R,2R,4S)-2-methoxy-4-(2-methyl-1H-imidazo[4,5-d]thieno[3,2-b]pyridin-1-yl)cyclohexyl]acetonitrile (racemic) (28 mg, 0.082 mmol) was added acetonitrile (1 mL) and iodotrimethylsilane (0.60 mL, 4.2 mmol). The reaction solution was heated at 80° C. for 6 h. The reaction mixture was diluted with methanol and purified with HPLC purification (XBridge C18 column, eluting with a gradient of acetonitrile/water containing 0.1% TFA, at flow rate of 60 mL/min) to give the desired product as a racemic mixture. LCMS calculated for $C_{17}H_{19}N_4OS$ (M+H)$^+$: m/z=327.1; Found: 327.1.

Example 35. Mixture of [(1R,2R,4S)-4-(2-ethyl-1H-imidazo[4,5-d]thieno[3,2-b]pyridin-1-yl)-2-methoxycyclohexyl]acetonitrile Trifluoroacetate and [(1S,2S,4R)-4-(2-ethyl-1H-imidazo[4,5-d]thieno[3, 2-b]pyridin-1-yl)-2-methoxycyclohexyl]acetonitrile Trifluoracetate

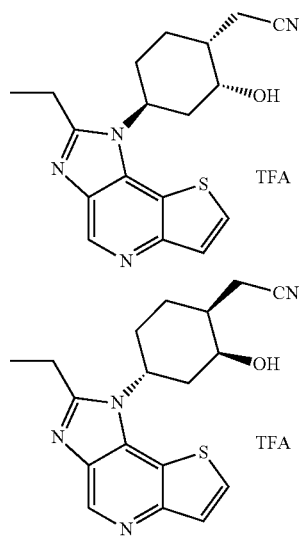

Step 1. [(1R,2S,4S)-4-(2-Ethyl-1H-imidazo[4,5-d] thieno[3,2-b]pyridin-1-yl)-2-methoxycyclohexyl] acetonitrile (Racemic)

The desired compound was prepared according to the procedure of Example 34, steps 12, using 1,1,1-triethoxy-{(1R,2R,4S)-4-[(6-aminothieno[3,2-b]pyridin-7-yl)amino]-2-methoxycyclohexyl}acetonitrile (racemic) and propane as the starting material. LCMS calculated for $C_{19}H_{23}N_4OS$ (M+H)$^+$: m/z=355.2; Found: 355.1.

Step 2. Mixture of [(1R,2R,4S)-4-(2-ethyl-1H-imidazo[4,5-d]thieno[3,2-b]pyridin-1-yl)-2-methoxycyclohexyl]acetonitrile Trifluoroacetate and [(1S,2S, 4R)-4-(2-ethyl-1H-imidazo[4,5-d]thieno[3,2-b] pyridin-1-yl)-2-methoxycyclohexyl]acetonitrile Trifluoracetate The desired compound was prepared according to the procedure of Example 34, steps 13, using [(1R,2S,4S)-4-(2-ethyl-1H-imidazo[4,5-d]thieno[3,2-b]pyridin-1-yl)-2-methoxycyclohexyl]acetonitrile (racemic) as the starting material. LCMS calculated for $C_{18}H_{21}N_4OS$ (M+H)$^+$: m/z=341.1; Found: 341.1.

Example 36. ((1R,2R,4S)-2-Hydroxy-4-{2-[(1R)-1-hydroxyethyl]-1H-imidazo[4,5-d]thieno[3,2-b]pyridin-1-yl}cyclohexyl)acetonitrile and ((1S,2S,4R)-2-hydroxy-4-{2-[(1R)-1-hydroxyethyl]-1H-imidazo[4,5-d]thieno[3,2-b]pyridin-1-yl}cyclohexyl)acetonitrile

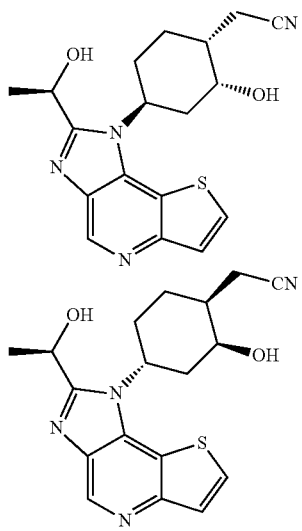

Step 1. Mixture of ((1R,2R,4S)-4-{2-[(1R)-1-Hydroxyethyl]-1H-imidazo[4,5-d]thieno[3,2-b]pyridin-1-yl}-2-methoxycyclohexyl)acetonitrile and ((1R,2R,4S)-4-{2-[(1R)-1-hydroxyethyl]-1H-imidazo[4,5-d]thieno[3,2-b]pyridin-1-yl}-2-methoxycyclohexyl)acetonitrile A mixture of (2R)-2-hydroxypropanamide (82.2 mg, 0.922 mmol) and triethyloxonium tetrafluoroborate (160 mg, 0.87 mmol) in THF (4.6 mL) was stirred at room temperature for 2 h. The solvent was removed and the residue dissolved in ethanol (2.0 mL) and added to a suspension of {(1R,2R,4S)-4-[(6-aminothieno[3,2-b]pyridin-7-yl)amino]-2-methoxycyclohexyl}acetonitrile (racemic) (89 mg, 0.28 mmol) in ethanol (0.9 mL). The mixture was stirred at 80° C. for 1 h. The reaction mixture was diluted with methanol and purified with prep-LCMS (XBridge C18 column, eluting with a gradient of acetonitrile/water containing 0.1% ammonium hydroxide, at flow rate of 60 mL/min) to give the desired product as white solid (65 mg, 62%). LCMS calculated for $C_{19}H_{23}N_4O_2S$ (M+H)$^+$: m/z=371.2; Found: 371.0.

Step 2. ((1R,2R,4S)-2-Hydroxy-4-{2-[(1R)-1-hydroxyethyl]-1H-imidazo[4,5-d]thieno[3,2-b]pyridin-1-yl}cyclohexyl)acetonitrile and ((1S,2S,4R)-2-hydroxy-4-{2-[(1R)-1-hydroxyethyl]-1H-imidazo[4,5-d]thieno[3,2-b]pyridin-1-yl}cyclohexyl)acetonitrile To a solution of ((1R,2R,4S)-4-{2-[(1R)-1-hydroxyethyl]-1H-imidazo[4,5-d]thieno[3,2-b]pyridin-1-yl}-2-methoxycyclohexyl)acetonitrile (diastereoisomer mixture) (40.2 mg, 0.108 mmol) in acetonitrile (2.5 mL) was added iodotrimethylsilane (772 μL, 5.42 mmol). The resulting mixture was heated at 90° C. for 4 h. The reaction was quenched with methanol and purified with prep-LCMS (XBridge C18 column, eluting with a gradient of acetonitrile/water containing 0.1% TFA, at flow rate of 60 mL/min) to give the desired product as mixture of two diastereomers. The racemic mixture was separated by chiral column (Phenomenex Lux Cellulose A-2, 5 um, 21.2×250 mm, 15% ethanol/85% hexanes, flow rate: 18 ml/min, 2 mg/injection) to give two peaks. Isomer 1 (first to elute): LCMS calculated for $C_{18}H_{21}N_4O_2S$ (M+H)$^+$: m/z=357.1; Found: 357.0. Isomer 2 (second to elute): LCMS calculated for $C_{18}H_{21}N_4O_2S$ (M+H)$^+$: m/z=357.1; Found: 357.0.

Example 37. ((1R,2S,4S)-2-Hydroxy-4-{2-[(1R)-1-hydroxyethyl]-1H-imidazo[4,5-d]thieno[3,2-b]pyridin-1-yl}cyclohexyl)acetonitrile Trifluoracetate and ((1S,2R,4R)-2-hydroxy-4-{2-[(1R)-1-hydroxyethyl]-1H-imidazo[4,5-d]thieno[3,2-b]pyridin-1-yl}cyclohexyl)acetonitrile Trifluoracetate

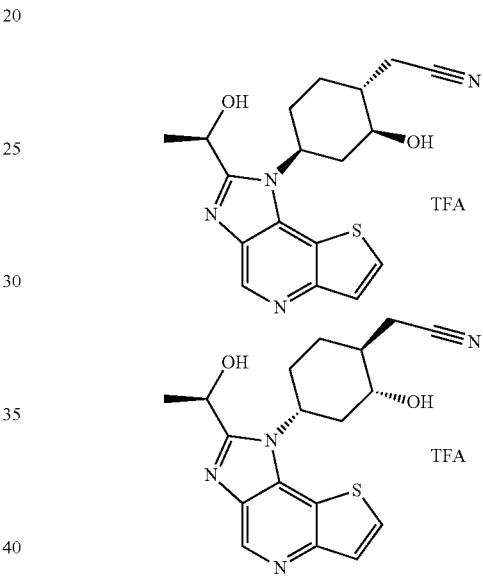

Step 1. Methyl (1S,2S,4R)-4-hydroxy-2-methoxycyclohexanecarboxylate (Racemic)

To a solution of methyl (1S,2S)-2-methoxy-4-oxocyclohexanecarboxylate (trans-isomer from example 34 step 2, first elute, racemic) (1.5 g, 8.0 mmol) in THF (20 mL) at −78° C. was added 1.0 M L-Selectride in THF (12 mL). After stirring at the same temperature for 2 h, the reaction was diluted with sat. NaHCO$_3$ solution and ethyl acetate. The aqueous layer was extracted with ethyl acetate (3×). The combined organic layers were washed with brine, dried over Na$_2$SO$_4$, filtered and concentrated. The crude was purified with flash chromatography (eluting with 0-65% ethyl acetate in hexanes) to give the desired product as colorless oil (1.5 g, 100%). $^1$H NMR (400 MHz, CDCl$_3$) δ 4.18 (1H, m), 3.82 (1H, m), 3.70 (3H, s), 3.32 (3H, s), 2.43 (1H, m), 2.10 (1H, m), 1.96 (1H, m), 1.76 (1H, m), 1.71-1.48 (2H, m), 1.40 (1H, m) ppm.

Step 2. Methyl (1R,2R,4S)-2-methoxy-4-[(methylsulfonyl)oxy]cyclohexanecarboxylate (Racemic)

A solution of methyl (1R,2R,4S)-4-hydroxy-2-methoxycyclohexanecarboxylate (racemic) (1.50 g, 7.97 mmol) in dichloromethane (40 mL) was treated with methanesulfonyl chloride (1.23 mL, 15.9 mmol) dropwise at 0° C. The mixture was stirred at 0° C. for 2 h and partitioned between ethyl acetate and water. The organic phase was concentrated and purified on silica gel (eluting with 50% ethyl acetate in hexanes) to give the desired product (2.12 g, 91%). $^1$H NMR (400 MHz, CDCl$_3$) δ 4.62 (1H, m), 3.71 (3H, s), 3.48 (1H, m), 3.33 (3H, s), 3.02 (3H, s), 2.64 (1H, m), 2.32 (1H, m), 2.19 (1H, m), 2.00 (1H, m), 1.60-1.42 (3H, m) ppm.

Step 3. Methyl (1R,2R,4R)-4-azido-2-methoxycyclohexanecarboxylate (Racemic)

To a solution of methyl (1R,2R,4S)-2-methoxy-4-[(methylsulfonyl)oxy]cyclohexanecarboxylate (racemic) (1.92 g, 7.21 mmol) in DMF (24 mL) sodium azide (1.9 g, 29 mmol) was added. The reaction mixture was stirred and heated at 80° C. for 4 h. The reaction mixture was poured into sat. NaHCO$_3$ solution and extracted with ethyl acetate (2×30 mL). The combined extracts were washed with brine, dried over Na$_2$SO$_4$, concentrated. The crude was purified by flash chromatography (eluting with a gradient 0-35% ethyl acetate in hexanes) to give the desired product as colorless oil (1.22 g, 79%). $^1$H NMR (500 MHz, CDCl$_3$) δ 3.70 (3H, s), 3.44 (1H, m), 3.32 (3H, s), 3.30 (1H, m), 2.48 (1H, m), 2.32 (1H, m), 2.00 (2H, m), 1.48 (1H, m), 1.28 (2H, m) ppm.

Step 4. Methyl (1S,2S,4S)-4-[(tert-butoxycarbonyl)amino]-2-methoxycyclohexanecarboxylate (Racemic)

A solution of methyl (1S,2S,4S)-4-azido-2-methoxycyclohexanecarboxylate (racemic) (1.2 g, 5.6 mmol) in methanol (34 mL) was added di-tert-butyldicarbonate (1.47 g, 6.75 mmol), followed by 10% palladium on carbon (960 mg). The resulting mixture was stirred under H$_2$ balloon overnight. The reaction mixture was filtered through a pad of Celite and washed with methanol. The solvent was removed and residue was purified with flash chromatography (eluting with a gradient 0-40% ethyl acetate in hexanes) to give the desired product as colorless oil (1.02 g, 63%). $^1$H NMR (400 MHz, CDCl$_3$) δ 4.54 (1H, m), 3.68 (3H, s), 3.48 (1H, m), 3.32 (3H, s), 2.43 (1H, m), 2.31 (1H, m), 1.94 (2H, m), 1.54 (1H, m), 1.43 (9H, s), 1.08 (2H, m) ppm.

Step 5. tert-Butyl [(1S,3S,4R)-4-(hydroxymethyl)-3-methoxycyclohexyl]carbamate (Racemic)

Methyl (1S,2S,4S)-4-[(tert-butoxycarbonyl)amino]-2-methoxycyclohexanecarboxylate (racemic) (1.02 g, 3.55 mmol) were dissolved in ether (32 mL) and cooled to 0° C. Lithium tetrahydroaluminate (162 mg, 4.26 mmol) was added and the resulting mixture was stirred for 4 h. The reaction was quenched with 5 mL water at 0° C., then diluted with 5 mL 15% NaOH and 15 mL water after stirring for 30 min. The reaction mixture was filtered through a pad of Celite and washed with ethyl acetate. The aqueous layer was extracted with ethyl acetate (2×). The combined organic layers were washed with brine, dried over Na$_2$SO$_4$, filtered and concentrated. The crude was purified with flash chromatography (eluting with a gradient of 0-80% ethyl acetate in hexanes) to give the desired product as white foam. LCMS calculated for C$_8$H$_{18}$NO$_2$ (M+H-Boc)$^+$: m/z=160.1; Found: 160.2. H NMR (300 MHz, CDCl$_3$) δ 4.46 (1H, brs), 3.71-3.40 (3H, m), 3.37 (3H, s), 3.12 (2H, m), 2.48 (1H, m), 1.94 (1H, m), 1.71-1.50 (3H, m), 1.41 (9H, s), 1.05 (2H, m) ppm.

Step 6. {(1R,2S,4S)-4-[(tert-Butoxycarbonyl)amino]-2-methoxycyclohexyl}methyl Methanesulfonate To a solution of tert-butyl [(1S,3S,4R)-4-(hydroxymethyl)-3-methoxycyclohexyl]carbamate (racemic) (720 mg, 2.8 mmol) in dichloromethane (9 mL) was added methanesulfonyl chloride (0.430 mL, 5.56 mmol) at 0° C. The mixture was stirred at 0° C. for 1 h. The mixture was then concentrated and partitioned between ethyl acetate and water. The organic phase was concentrated and purified by flash chromatography (eluting with a gradient of 50% ethyl acetate in hexanes) to give the desired product (0.859 g, 92%). LCMS calculated for C$_9$H$_{20}$NO$_4$S (M+H-Boc)$^+$: m/z=238.1; Found: 238.0.

Step 7. [(1R,2S,4S)-4-amino-2-methoxycyclohexyl] acetonitrile (Racemic)

A mixture of {(1R,2S,4S)-4-[(tert-butoxycarbonyl)amino]-2-methoxycyclohexyl}methyl methanesulfonate (661 mg, 1.96 mmol) and sodium cyanide (115 mg, 2.35 mmol) in DMSO (6 mL) was stirred at 90° C. overnight. After cooling to room temperature, the mixture was partitioned between ethyl acetate and brine. The organic layer was washed with water and brine, and concentrated to give the Boc-protected azide: LCMS [M+Na] 261.1. A solution of the intermediate in dichloromethane (9 mL) was treated with TFA (9 mL) and stirred at room temperature for 2 h. The reaction solution was concentrated to give the desired product as TFA salt. LCMS calculated for C$_9$H$_{17}$N$_2$O (M+H)$^+$: m/z=169.1; Found: 169.1.

Step 8. {(1R,2S,4S)-2-Methoxy-4-[(6-nitrothieno[3,2-b]pyridin-7-yl)amino]cyclohexyl}acetonitrile (Racemic)

A mixture of 7-chloro-6-nitrothieno[3,2-b]pyridine (381 mg, 1.78 mmol), [(1R,2S,4S)-4-amino-2-methoxycyclohexyl]acetonitrile (racemic) (310 mg, 1.8 mmol) and N,N-diisopropylethylamine (1.2 mL, 7.1 mmol) in isopropyl alcohol (4.2 mL) was heated at 90° C. for 2 h. The crude was concentrated and purified with flash chromatography to give the desired product (469 mg, 76%). LCMS calculated for C$_{15}$H$_{19}$N$_4$O$_3$S (M+H)$^+$: m/z=347.1; Found: 347.0.

Step 9. {(1R,2S,4S)-4-[(6-Aminothieno[3,2-b]pyridin-7-yl)amino]-2-methoxycyclohexyl}acetonitrile (Racemic)

A mixture of {(1R,2S,4S)-2-methoxy-4-[(6-nitrothieno[3,2-b]pyridin-7-yl)amino]cyclohexyl}acetonitrile (racemic) (401 mg, 1.16 mmol) and 10% palladium on carbon (0.20 g) in methanol (7.7 mL) was subjected to balloon pressure of H$_2$ at room temperature for 2 h. The mixture was filtered and the filtrate was concentrated and purified with flash chromatography (eluting with 15% methanol in dichloromethane) to give the desired product (342 mg, 93%). LCMS calculated for C$_{16}$H$_{21}$N$_4$OS (M+H)$^+$: m/z=317.1; Found: 317.1.

Step 10. ((1R,2S,4S)-4-{2-[(1R)-1-Hydroxyethyl]-1H-imidazo[4,5-d]thieno[3,2-b]pyridin-1-yl}-2-methoxycyclohexyl)acetonitrile and ((1S,2R,4R)-4-{2-[(1R)-1-hydroxyethyl]-1H-imidazo[4,5-d]thieno[3,2-b]pyridin-1-yl}-2-methoxycyclohexyl)acetonitrile A mixture of (2R)-2-hydroxypropanamide (40.6 mg, 0.456 mmol) and triethyloxonium tetrafluoroborate (82 mg, 0.43 mmol) in THF (2.3 mL) was stirred at room temperature for 2 h. The solvent was removed and the residue dissolved in ethanol (0.45 mL) and added to a suspension of {(1R,2S,4S)-4-[(6-aminothieno[3,2-b]pyridin-7-yl)amino]-2-methoxycyclohexyl}acetonitrile (racemic) (44 mg, 0.14 mmol) in ethanol (0.45 mL). The resulting mixture was stirred at 80° C. for 1 h. The reaction mixture was diluted with methanol and purified with prep-LCMS (XBridge C18 column, eluting with a gradient of acetonitrile/water containing 0.1% ammonium hydroxide, at flow rate of 60 mL/min) to give the desired product as white solid (26 mg, 50%). LCMS calculated for $C_{19}H_{23}N_4O_2S$ $(M+H)^+$: m/z=371.2; Found: 371.0.

Step 11. ((1R,2S,4S)-2-Hydroxy-4-{2-[(1R)-1-hydroxyethyl]-1H-imidazo[4,5-d]thieno[3,2-b]pyridin-1-yl}cyclohexyl)acetonitrile Trifluoracetate and ((1S,2R,4R)-2-hydroxy-4-{2-[(1R)-1-hydroxyethyl]-1H-imidazo[4,5-d]thieno[3,2-b]pyridin-1-yl}cyclohexyl)acetonitrile Trifluoracetate To a solution of ((1R,2S,4S)-4-{2-[(1R)-1-hydroxyethyl]-1H-imidazo[4,5-d]thieno[3,2-b]pyridin-1-yl}-2-methoxycyclohexyl)acetonitrile (diastereoisomer mixture) (23.0 mg, 0.0621 mmol) in acetonitrile (0.9 mL) was added iodotrimethylsilane (0.45 mL, 3.2 mmol). After stirring at 80° C. for 6 h, the reaction mixture was diluted with methanol and water and purified with prep-LCMS (XBridge C18 column, eluting with a gradient of acetonitrile/water containing 0.1% TFA, at flow rate of 60 mL/min) to give two peaks (isomer 1, 2.1 mg, 9.5%; isomer 2, 2.5 mg, 11%). Isomer 1 (first to elute): LCMS calculated for $C_{18}H_{21}N_4O_2S$ $(M+H)^+$: m/z=357.1; Found: 357.0. Isomer 2 (second to elute): LCMS calculated for $C_{18}H_{21}N_4O_2S$ $(M+H)^+$: m/z=357.1; Found: 357.0.

Example 38. [(2R,5S)-5-(2-Methyl-1H-imidazo[4,5-d]thieno[3,2-b]pyridin-1-yl)tetrahydro-2H-pyran-2-yl]acetonitrile

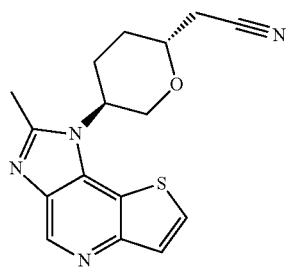 [SMILES: Cc1nc2cnc3ccsc3c2n1[C@H]1CC[C@H](CC#N)OC1]

Step 1. {(2R,5S)-5-[(6-Aminothieno[3,2-b]pyridin-7-yl)amino]tetrahydro-2H-pyran-2-yl}methanol A mixture of {(5S)-5-[(6-nitrothieno[3,2-b]pyridin-7-yl)amino]-5,6-dihydro-2H-pyran-2-yl}methyl acetate (366 mg, 1.05 mmol) and 10% palladium on carbon (0.18 g) in methanol (7.0 mL) was subjected to balloon pressure of $H_2$ at room temperature for 2 h. The mixture was filtered and treated with 1 M NaOH (1 mL) for 1 h. The mixture was diluted with methanol and purified with prep-LCMS (XBridge C18 column, eluting with a gradient of acetonitrile/water containing 0.1% ammonium hydroxide, at flow rate of 60 mL/min) to give two peaks in 5:1 ratio. The major peak is the title compound (154 mg, 58%). LCMS calculated for $C_{13}H_{18}N_3O_2S$ $(M+H)^+$: m/z=280.1; Found: 280.1.

Step 2. [(2R,5S)-5-(2-Methyl-1H-imidazo[4,5-d]thieno[3,2-b]pyridin-1-yl)tetrahydro-2H-pyran-2-yl]methanol To a solution of {(2R,5S)-5-[(6-aminothieno[3,2-b]pyridin-7-yl)amino]tetrahydro-2H-pyran-2-yl}methanol (131 mg, 0.469 mmol) in acetic acid (1.3 mL) was added triethyl orthoacetate (275 μL, 1.50 mmol). The mixture was stirred at 120° C. for 30 min. After cooling to room temperature, the mixture was diluted with methanol and purified with prep-LCMS (XBridge C18 column, eluting with a gradient of acetonitrile/water containing 0.1% ammonium hydroxide, at flow rate of 60 mL/min) to give the desired product as white solid (60 mg, 42%). LCMS calculated for $C_{15}H_{18}N_3O_2S$ $(M+H)^+$: m/z=304.1; Found: 304.1.

Step 3: [(2R,5S)-5-(2-Methyl-1H-imidazo[4,5-d]thieno[3,2-b]pyridin-1-yl)tetrahydro-2H-pyran-2-yl]methyl 4-methylbenzenesulfonate To a solution of [(2R,5S)-5-(2-methyl-1H-imidazo[4,5-d]thieno[3,2-b]pyridin-1-yl)tetrahydro-2H-pyran-2-yl]methanol (60.1 mg, 0.198 mmol) in methylene chloride (2.3 mL) and pyridine (51 μL, 0.62 mmol) was added p-toluenesulfonyl chloride (38.7 mg, 0.203 mmol) and 4-dimethylaminopyridine (1.2 mg, 0.010 mmol) at 0° C. The reaction mixture was allowed to warm to room temperature overnight. The reaction mixture was concentrated, diluted with methanol, and purified with prep-LCMS (XBridge C18 column, eluting with a gradient of acetonitrile/water containing 0.1% ammonium hydroxide, at flow rate of 60 mL/min) to give the desired product (50 mg, 55%). LCMS calculated for $C_{22}H_{24}N_3O_4S_2$ $(M+H)^+$: m/z=458.1; Found: 458.1.

Step 4. [(2R,5S)-5-(2-Methyl-1H-imidazo[4,5-d]thieno[3,2-b]pyridin-1-yl)tetrahydro-2H-pyran-2-yl]acetonitrile To a mixture of [(2R,5S)-5-(2-methyl-1H-imidazo[4,5-d]thieno[3,2-b]pyridin-1-yl)tetrahydro-2H-pyran-2-yl]methyl 4-methylbenzenesulfonate (50.2 mg, 0.110 mmol) and sodium cyanide (9.1 mg, 0.19 mmol) in DMF (1.1 mL) was added 1.0 M sulfuric acid in DMF (9 μL, 0.009 mmol). The reaction solution was stirred at 50° C. overnight. After cooling, the mixture was diluted with methanol and purified with prep-LCMS (XBridge C18 column, eluting with a gradient of acetonitrile/water containing 0.1% ammonium hydroxide, at flow rate of 30 mL/min) to give the desired product (15.2 mg, 44%). LCMS calculated for $C_{16}H_{17}N_4OS$ $(M+H)^+$: m/z=313.1; Found: 313.0.

Example 39. [(2R,5S)-5-(2-Ethyl-1H-imidazo[4,5-d]thieno[3,2-b]pyridin-1-yl)tetrahydro-2H-pyran-2-yl]acetonitrile

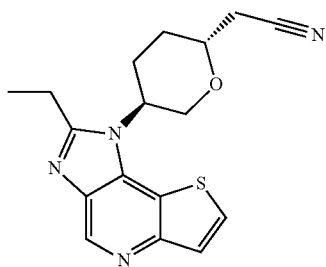 [SMILES: CCc1nc2cnc3ccsc3c2n1[C@H]1CC[C@H](CC#N)OC1]

Step 1. [(2R,5S)-5-(2-Ethyl-1H-imidazo[4,5-d]thieno[3,2-b]pyridin-1-yl)tetrahydro-2H-pyran-2-yl]methanol To a solution of {(2R,5S)-5-[(6-aminothieno[3,2-b]pyridin-7-yl)amino]tetrahydro-2H-pyran-2-yl}methanol (115 mg, 0.412 mmol) in acetic acid (1.1 mL) was added propane, 1,1,1-triethoxy- (265 µL, 1.32 mmol). The resulting mixture was stirred at 120° C. for 30 min. After cooling to room temperature, the mixture was diluted with methanol and purified with prep-LCMS (XBridge C18 column, eluting with a gradient of acetonitrile/water containing 0.1% ammonium hydroxide, at flow rate of 60 mL/min) to give the desired product as white solid (74.8 mg, 57%). LCMS calculated for $C_{16}H_{20}N_3O_2S$ (M+H)$^+$: m/z=318.1; Found: 318.1.

Step 2: [(2R,5S)-5-(2-Ethyl-1H-imidazo[4,5-d]thieno[3,2-b]pyridin-1-yl)tetrahydro-2H-pyran-2-yl]methyl 4-methylbenzenesulfonate This compound was prepared according to the procedure described in Example 38, Step 3, using [(2R,5S)-5-(2-ethyl-1H-imidazo[4,5-d]thieno[3,2-b]pyridin-1-yl)tetrahydro-2H-pyran-2-yl]methanol instead of [(2R,5S)-5-(2-methyl-1H-imidazo[4,5-d]thieno[3,2-b]pyridin-1-yl)tetrahydro-2H-pyran-2-yl]methanol as starting material. LCMS calculated for $C_{23}H_{26}N_3O_4S_2$ (M+H)$^+$: m/z=472.1; Found: 472.0.

Step 3. [(2R,5S)-5-(2-Ethyl-1H-imidazo[4,5-d]thieno[3,2-b]pyridin-1-yl)tetrahydro-2H-pyran-2-yl]acetonitrile This compound was prepared according to the procedure described in Example 38, Step 4, using [(2R,5S)-5-(2-ethyl-1H-imidazo[4,5-d]thieno[3,2-b]pyridin-1-yl)tetrahydro-2H-pyran-2-yl]methyl 4-methylbenzenesulfonate instead of [(2R,5S)-5-(2-methyl-1H-imidazo[4,5-d]thieno[3,2-b]pyridin-1-yl)tetrahydro-2H-pyran-2-yl]methyl 4-methylbenzenesulfonate as starting material. LCMS calculated for $C_{17}H_{19}N_4OS$ (M+H)$^+$: m/z=327.1; Found: 327.0. $^1$H NMR (DMSO-d$_6$, 300 MHz) δ 8.88 (1H, s), 7.95 (1H, d, J=5.5 Hz), 7.61 (1H, d, J=5.5 Hz), 4.64 (1H, m), 4.21 (1H, m), 4.09 (1H, m), 3.93 (1H, m), 3.04 (2H, m), 2.83 (2H, m), 2.53 (1H, m), 2.13 (1H, m), 1.97 (1H, m), 1.67 (1H, m), 1.31 (3H, t, J=7.4 Hz) ppm.

Example 40. [(1R,2S,4S)-4-(2-Ethyl-1H-imidazo[4,5-d]thieno[3,2-b]pyridin-1-yl)-2-hydroxycyclohexyl]acetonitrile and [(1S,2R,4R)-4-(2-ethyl-1H-imidazo[4,5-d]thieno[3,2-b]pyridin-1-yl)-2-hydroxycyclohexyl]acetonitrile

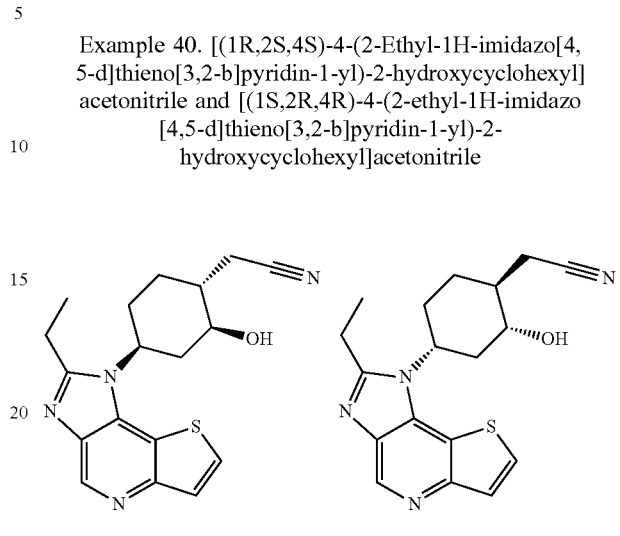

Step 1. [(1R,2S,4S)-4-(2-Ethyl-1H-imidazo[4,5-d]thieno[3,2-b]pyridin-1-yl)-2-methoxycyclohexyl]acetonitrile (Racemic)

This compound was prepared according to the procedure of Example 34, steps 12, using {(1R,2S,4S)-4-[(6-aminothieno[3,2-b]pyridin-7-yl)amino]-2-methoxycyclohexyl}acetonitrile (racemic) and propane, 1,1,1-triethoxy- as the starting material. LCMS calculated for $C_{19}H_{23}N_4OS$ (M+H)$^+$: m/z=355.2; Found: 355.1.

Step 2. [(1R,2S,4S)-4-(2-Ethyl-1H-imidazo[4,5-d]thieno[3,2-b]pyridin-1-yl)-2-hydroxycyclohexyl]acetonitrile and [(1S,2R,4R)-4-(2-ethyl-1H-imidazo[4,5-d]thieno[3,2-b]pyridin-1-yl)-2-hydroxycyclohexyl]acetonitrile In a microwave vial, iodotrimethylsilane (0.20 mL, 1.4 mmol) was added to a solution of [(1R,2S,4S)-4-(2-ethyl-1H-imidazo[4,5-d]thieno[3,2-b]pyridin-1-yl)-2-methoxycyclohexyl]acetonitrile (racemic) (10 mg, 0.03 mmol) in acetonitrile (0.3 mL). The vial was capped, and the mixture heated at 80° C. overnight. The reaction was quenched with a few drops of water. The mixture was then further diluted and purified using prep-LCMS (XBridge C18 column, eluting with a gradient of acetonitrile/water containing 0.1% ammonium hydroxide, at flow rate of 30 mL/min) to give desired product as racemic mixture. The racemic mixture was separated by chiral column (Chiralcel AD-H, 5 uM, 20×250 mm, 80% EtOH/hexanes, flow rate: 18 mL/min) to give two peaks. Isomer 1 (first to elute): LCMS calculated for $C_{18}H_{21}N_4OS$ (M+H)$^+$: m/z=341.1; Found: 341.1. Isomer 2 (second to elute): LCMS calculated for $C_{18}H_{21}N_4OS$ (M+H)$^+$: m/z=341.1; Found: 341.1.

Example 41. [(1R,2S,4S)-4-(2-Methyl-1H-imidazo[4,5-d]thieno[3,2-b]pyridin-1-yl)-2-hydroxycyclohexyl]acetonitrile and [(1S,2R,4R)-4-(2-methyl-1H-imidazo[4,5-d]thieno[3,2-b]pyridin-1-yl)-2-hydroxycyclohexyl]acetonitrile

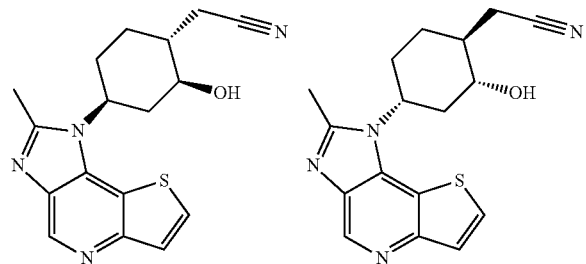 [SMILES: Cc1nc2cnc3ccsc3c2n1[C@H]1CC[C@H](CC#N)[C@@H](O)C1 ; Cc1nc2cnc3ccsc3c2n1[C@@H]1CC[C@@H](CC#N)[C@H](O)C1]

Step 1. [(1R,2S,4S)-4-(2-Methyl-1H-imidazo[4,5-d]thieno[3,2-b]pyridin-1-yl)-2-methoxycyclohexyl]acetonitrile (Racemic)

This compound was prepared according to the procedure of Example 34, steps 12, using {(1R,2S,4S)-4-[(6-aminothieno[3,2-b]pyridin-7-yl)amino]-2-methoxycyclohexyl}acetonitrile (racemic) and triethyl orthoacetate as the starting material. LCMS calculated for $C_{18}H_{21}N_4OS$ (M+H)$^+$: m/z=341.1; Found: 341.1.

Step 2. [(1R,2S,4S)-4-(2-Methyl-1H-imidazo[4,5-d]thieno[3,2-b]pyridin-1-yl)-2-hydroxycyclohexyl]acetonitrile and [(1S,2R,4R)-4-(2-methyl-1H-imidazo[4,5-d]thieno[3,2-b]pyridin-1-yl)-2-hydroxycyclohexyl]acetonitrile This compound was prepared according to the procedure described in Example 40, Step 2, using [(1R,2S,4S)-4-(2-methyl-1H-imidazo[4,5-d]thieno[3,2-b]pyridin-1-yl)-2-methoxycyclohexyl]acetonitrile (racemic) instead of [(1R,2S,4S)-4-(2-ethyl-1H-imidazo[4,5-d]thieno[3,2-b]pyridin-1-yl)-2-methoxycyclohexyl]acetonitrile (racemic) as starting material. The racemic mixture was separated by chiral column (Chiralcel AD-H, 5 uM, 20×250 mm, 80% EtOH/hexanes, flow rate: 18 mL/min) to give two peaks. Isomer 1 (first to elute): LCMS calculated for $C_{17}H_{19}N_4OS$ (M+H)$^+$: m/z=327.1; Found: 327.0. Isomer 2 (second to elute): LCMS calculated for $C_{17}H_{19}N_4OS$ (M+H)$^+$: m/z=327.1; Found: 327.0.

Example 42. [(2R,5S)-5-(2-Isopropyl-1H-imidazo[4,5-d]thieno[3,2-b]pyridin-1-yl)tetrahydro-2H-pyran-2-yl]acetonitrile

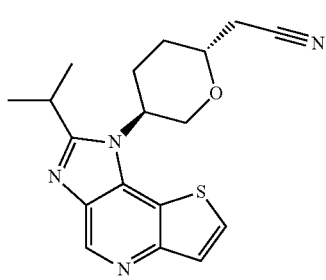

Step 1: [(2R,5S)-5-(2-Isopropyl-1H-imidazo[4,5-d]thieno[3,2-b]pyridin-1-yl)tetrahydro-2H-pyran-2-yl]methanol A mixture of 2-methylpropanamide (71.4 mg, 0.820 mmol) and triethyloxonium tetrafluoroborate (154 mg, 0.812 mmol) in THF (2 mL) was stirred at room temperature for 2 h. The solvent was removed and the residue dissolved in ethanol (0.5 mL) and added to a suspension of {(2R,5S)-5-[(6-aminothieno[3,2-b]pyridin-7-yl)amino]tetrahydro-2H-pyran-2-yl}methanol (69.2 mg, 0.248 mmol) in ethanol (1.7 mL). The mixture was stirred at 80° C. for 1 h. The reaction mixture was cooled to room temperature, diluted with methanol, and purified with prep-LCMS (XBridge C18 column, eluting with a gradient of acetonitrile/water containing 0.1% ammonium hydroxide, at flow rate of 60 mL/min) to give the desired product. LCMS calculated for $C_{17}H_{22}N_3O_2S$ (M+H)$^+$: m/z=332.1; Found: 332.1.

Step 2 [(2R,5S)-5-(2-Isopropyl-1H-imidazo[4,5-d]thieno[3,2-b]pyridin-1-yl)tetrahydro-2H-pyran-2-yl]methyl 4-methylbenzenesulfonate This compound was prepared according to the procedure described in Example 38, Step 3, using [(2R,5S)-5-(2-isopropyl-1H-imidazo[4,5-d]thieno[3,2-b]pyridin-1-yl)tetrahydro-2H-pyran-2-yl]methanol instead of [(2R,5S)-5-(2-methyl-1H-imidazo[4,5-d]thieno[3,2-b]pyridin-1-yl)tetrahydro-2H-pyran-2-yl]methanol as starting material. LCMS calculated for $C_{24}H_{28}N_3O_4S_2$ (M+H)$^+$: m/z=486.1; Found: 486.0.

Step 3. [(2R,5S)-5-(2-Isopropyl-1H-imidazo[4,5-d]thieno[3,2-b]pyridin-1-yl)tetrahydro-2H-pyran-2-yl]acetonitrile This compound was prepared according to the procedure described in Example 38, Step 4, using [(2R,5S)-5-(2-isopropyl-1H-imidazo[4,5-d]thieno[3,2-b]pyridin-1-yl)tetrahydro-2H-pyran-2-yl]methyl 4-methylbenzenesulfonate instead of [(2R,5S)-5-(2-methyl-1H-imidazo[4,5-d]thieno[3,2-b]pyridin-1-yl)tetrahydro-2H-pyran-2-yl]methyl 4-methylbenzenesulfonate as starting material. $^1$H NMR (CDCl$_3$, 300 MHz) δ 9.06 (1H, s), 7.64 (1H, d, J=5.5 Hz), 7.54 (1H, d, J=5.5 Hz), 4.59 (2H, m), 4.04 (2H, m), 3.28 (1H, m), 2.85 (1H, m), 2.64 (2H, m), 2.13 (2H, m), 1.81 (1H, m), 1.44 (6H, m) ppm. LCMS calculated for $C_{18}H_{21}N_4OS$ (M+H)$^+$: m/z=341.1; Found: 341.0.

Example 43. [(2R,5S)-5-(2-Cyclopropyl-1H-imidazo[4,5-d]thieno[3,2-b]pyridin-1-yl)tetrahydro-2H-pyran-2-yl]acetonitrile

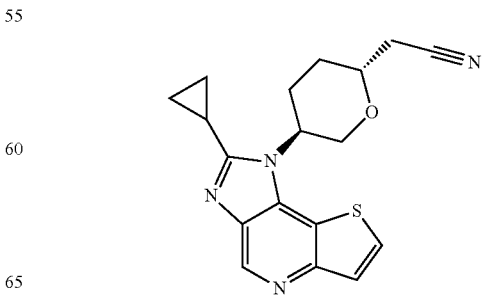

Step 1: [(2R,5S)-5-(2-Cyclopropyl-1H-imidazo[4,5-d]thieno[3,2-b]pyridin-1-yl)tetrahydro-2H-pyran-2-yl]methanol A mixture of cyclopropanecarboxamide (72.6 mg, 0.853 mmol) and triethyloxonium tetrafluoroborate (0.161 g, 0.845 mmol) in THF (2 mL) was stirred at room temperature for 2 h. The solvent was removed and the residue dissolved in ethanol (0.48 mL) and added to a suspension of {(2R,5S)-5-[(6-aminothieno[3,2-b]pyridin-7-yl)amino]tetrahydro-2H-pyran-2-yl}methanol (72.0 mg, 0.258 mmol) in ethanol (1.8 mL). The mixture was stirred at 80° C. for 1 h. The reaction mixture was cooled to room temperature, diluted with methanol, and purified with prep-LCMS (XBridge C18 column, eluting with a gradient of acetonitrile/water containing 0.1% ammonium hydroxide, at flow rate of 60 mL/min) to give the desired product. LCMS calculated for $C_{17}H_{20}N_3O_2S$ $(M+H)^+$: m/z=330.1; Found: 330.0.

Step 2 [(2R,5S)-5-(2-Cyclopropyl-1H-imidazo[4,5-d]thieno[3,2-b]pyridin-1-yl)tetrahydro-2H-pyran-2-yl]methyl 4-methylbenzenesulfonate This compound was prepared according to the procedure described in Example 38, Step 3, using [(2R,5S)-5-(2-cyclopropyl-1H-imidazo[4,5-d]thieno[3,2-b]pyridin-1-yl)tetrahydro-2H-pyran-2-yl]methanol instead of [(2R,5S)-5-(2-methyl-1H-imidazo[4,5-d]thieno[3,2-b]pyridin-1-yl)tetrahydro-2H-pyran-2-yl]methanol as starting material. LCMS calculated for $C_{24}H_{26}N_3O_4S_2$ $(M+H)^+$: m/z=484.1; Found: 484.0.

Step 3. [(2R,5S)-5-(2-Cyclopropyl-1H-imidazo[4,5-d]thieno[3,2-b]pyridin-1-yl)tetrahydro-2H-pyran-2-yl]acetonitrile This compound was prepared according to the procedure described in Example 38, Step 4, using [(2R,5S)-5-(2-cyclopropyl-1H-imidazo[4,5-d]thieno[3,2-b]pyridin-1-yl)tetrahydro-2H-pyran-2-yl]methyl 4-methylbenzenesulfonate instead of [(2R,5S)-5-(2-methyl-1H-imidazo[4,5-d]thieno[3,2-b]pyridin-1-yl)tetrahydro-2H-pyran-2-yl]methyl 4-methylbenzenesulfonate as starting material. LCMS calculated for $C_{18}H_{19}N_4OS$ $(M+H)^+$: m/z=339.1; Found: 339.0.

Example 44. ((2S,5R)-5-{2-[(1R)-1-Hydroxyethyl]-1H-imidazo[4,5-d]thieno[3,2-b]pyridin-1-yl}tetrahydro-2H-pyran-2-yl)acetonitrile

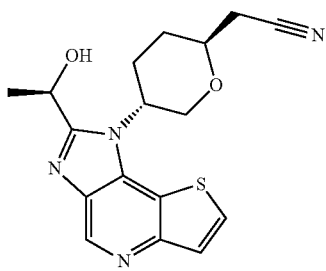 [SMILES: C[C@@H](O)c1nc2cnc3ccsc3c2n1[C@@H]1CC[C@@H](CC#N)OC1]

Step 1: tert-Butyl [(1R)-1-(hydroxymethyl)prop-2-en-1-yl]carbamate

To a solution of (2R)-2-aminobut-3-en-1-ol hydrochloride (0.94 g, 7.6 mmol) (from Astatech Inc.) in ethanol (30 mL) was added triethylamine (1.27 mL, 9.13 mmol) and di-tert-butyldicarbonate (1.99 g, 9.13 mmol). The reaction solution was stirred at room temperature overnight, then concentrated and purified with flash chromatography (eluting with a gradient of 0-50% ethyl acetate in hexanes) to give the desired product as colorless oil.

Step 2: tert-Butyl [(1R)-1-({[1-(hydroxymethyl)prop-2-en-1-yl]oxy}methyl)prop-2-en-1-yl]carbamate A flask charged with tert-butyl [(1R)-1-(hydroxymethyl)prop-2-en-1-yl]carbamate (1.88 g, 10.0 mmol), tris(dibenzylideneacetone)dipalladium(0) (134 mg, 0.146 mmol), N,N'-(1R,2R)-cyclohexane-1,2-diylbis[2-(diphenylphosphino)-1-naphthamide] (350 mg, 0.44 mmol), 4-dimethylaminopyridine (370 mg, 3.0 mmol) was purged with $N_2$ three times, and then filled with methylene chloride (100 mL), followed by addition of 1.0 M triethylborane in THF (0.294 mL, 0.294 mmol). After stirring for 10 min. 2-vinyloxirane (0.704 g, 10.0 mmol) was added, and the resulting mixture was stirred overnight. The reaction was diluted with dichloromethane and sat. $NaHCO_3$ solution. The organic layer was separated and dried over $Na_2SO_4$, filtered and concentrated. The crude residue was purified with flash chromatography (eluting with 0-50% ethyl acetate/hexanes) to give the desired product (0.271 g, 49%). $^1$H NMR (300 MHz, $CDCl_3$) δ 5.85 (1H, m), 5.67 (1H, m), 5.84-5.17 (4H, m), 4.83 (1H, m), 4.30 (1H, br s), 3.83 (1H, m), 3.69 (1H, dd, J=4.5 and 6.9 Hz), 3.54 (2H, m), 3.36 (1H, dd, J=4.5 and 6.9 Hz), 1.45 (9H, s) ppm.

Step 3: 2-({(2R)-2-[(tert-Butoxycarbonyl)amino]but-3-en-1-yl}oxy)but-3-en-1-yl Acetate This compound was prepared according to the procedure described in Example 19, Step 4, using tert-butyl [(1R)-1-({[1-(hydroxymethyl)prop-2-en-1-yl]oxy}methyl)prop-2-en-1-yl]carbamate instead of tert-butyl [(1S)-1-({[1-(hydroxymethyl)prop-2-en-1-yl]oxy}methyl)prop-2-en-1-yl]carbamate as starting material.

Step 4. {(5S)-5-[(tert-Butoxycarbonyl)amino]-5,6-dihydro-2H-pyran-2-yl}methyl Acetate This compound was prepared according to the procedure described in Example 19, Step 5, using 2-({(2R)-2-[(tert-butoxycarbonyl)amino]but-3-en-1-yl}oxy)but-3-en-1-yl acetate instead of 2-({(2S)-2-[(tert-butoxycarbonyl)amino]but-3-en-1-yl}oxy)but-3-en-1-yl acetate as starting material.

Step 5. [(5R)-5-Amino-5,6-dihydro-2H-pyran-2-yl]methyl Acetate

This compound was prepared according to the procedure described in Example 19, Step 6, using {(5R)-5-[(tert-butoxycarbonyl)amino]-5,6-dihydro-2H-pyran-2-yl}methyl acetate instead of {(5S)-5-[(tert-butoxycarbonyl)amino]-5,6-dihydro-2H-pyran-2-yl}methyl acetate as starting material. LCMS calculated for $C_8H_{14}NO_3$ $(M+H)^+$: m/z=172.1; Found: 172.1.

Step 6. {(5R)-5-[(6-Nitrothieno[3,2-b]pyridin-7-yl)amino]-5,6-dihydro-2H-pyran-2-yl}methyl Acetate This compound was prepared according to the procedure described in Example 19, Step 7, using [(5R)-5-amino-5,6- dihydro-2H-pyran-2-yl]methyl acetate instead of [(5S)-5-amino-5,6-dihydro-2H-pyran-2-yl]methyl acetate as starting material. LCMS calculated for $C_{15}H_{16}N_3O_5S$ (M+H)$^+$: m/z=350.1; Found: 350.0.

Step 7. {(5R)-5-[(6-Aminothieno[3,2-b]pyridin-7-yl)amino]tetrahydro-2H-pyran-2-yl}methyl Acetate This compound was prepared according to the procedure described in Example 19, Step 8, using {(5R)-5-[(6-nitrothieno[3,2-b]pyridin-7-yl)amino]-5,6-dihydro-2H-pyran-2-yl}methyl acetate instead of {(5S)-5-[(6-nitrothieno[3,2-b]pyridin-7-yl)amino]-5,6-dihydro-2H-pyran-2-yl}methyl acetate as starting material. LCMS calculated for $C_{15}H_{20}N_3O_3S$ (M+H)$^+$: m/z=322.1; Found: 322.0.

Step 8. (1R)-1-{1-[(3R)-6-(Hydroxymethyl)tetrahydro-2H-pyran-3-yl]-1H-imidazo[4,5-d]thieno[3,2-b]pyridin-2-yl}ethanol This compound was prepared according to the procedure described in Example 19, Step 9, using {(5R)-5-[(6-aminothieno[3,2-b]pyridin-7-yl)amino]tetrahydro-2H-pyran-2-yl}methyl acetate instead of {(5S)-5-[(6-aminothieno[3,2-b]pyridin-7-yl)amino]tetrahydro-2H-pyran-2-yl}methyl acetate as starting material. LCMS calculated for $C_{16}H_{20}N_3O_3S$ (M+H)$^+$: m/z=334.1; Found: 334.0.

Step 9: ((2S,5R)-5-{2-[(1R)-1-Hydroxyethyl]-1H-imidazo[4,5-d]thieno[3,2-b]pyridin-1-yl}tetrahydro-2H-pyran-2-yl)methyl 4-methylbenzenesulfonate and ((2R,5S)-5-{2-[(1R)-1-hydroxyethyl]-1H-imidazo[4,5-d]thieno[3,2-b]pyridin-1-yl}tetrahydro-2H-pyran-2-yl)methyl 4-methylbenzenesulfonate This compound was prepared according to the procedure described in Example 20, Step 1, using (1R)-1-{1-[(3R)-6-(hydroxymethyl)tetrahydro-2H-pyran-3-yl]-1H-imidazo[4,5-d]thieno[3,2-b]pyridin-2-yl}ethanol instead of (1R)-1-{1-[(3S)-6-(hydroxymethyl)tetrahydro-2H-pyran-3-yl]-1H-imidazo[4,5-d]thieno[3,2-b]pyridin-2-yl}ethanol as starting material. LCMS calculated for $C_{23}H_{26}N_3O_5S_2$(M+H)$^+$: m/z=488.1; Found: 488.1.

Step 10: ((2S,5R)-5-{2-[(1R)-1-Hydroxyethyl]-1H-imidazo[4,5-d]thieno[3,2-b]pyridin-1-yl}tetrahydro-2H-pyran-2-yl)acetonitrile This compound was prepared according to the procedure described in Example 20, Step 2, using ((2S,5R)-5-{2-[(1R)-1-hydroxyethyl]-1H-imidazo[4,5-d]thieno[3,2-b]pyridin-1-yl}tetrahydro-2H-pyran-2-yl)methyl 4-methylbenzenesulfonate instead of ((2R,5S)-5-{2-[(1R)-1-hydroxyethyl]-1H-imidazo[4,5-d]thieno[3,2-b]pyridin-1-yl}tetrahydro-2H-pyran-2-yl)methyl 4-methylbenzenesulfonate as starting material. LCMS calculated for $C_{17}H_{19}N_4O_2S$ (M+H)$^+$: m/z=343.1; Found: 343.0.

Example 45: ((2R,5S)-5-{2-[(1S)-1-Hydroxyethyl]-1H-imidazo[4,5-d]thieno[3,2-b]pyridin-1-yl}tetrahydro-2H-pyran-2-yl)acetonitrile

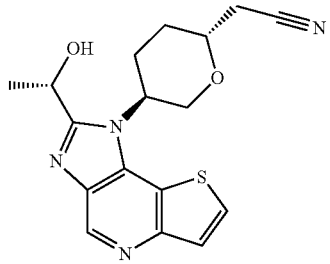 [SMILES: C[C@H](O)c1nc2cnc3ccsc3c2n1[C@H]1CC[C@H](CC#N)OC1]

Step 1: (1S)-1-{1-[(3S,6R)-6-(Hydroxymethyl)tetrahydro-2H-pyran-3-yl]-1H-imidazo[4,5-d]thieno[3,2-b]pyridin-2-yl}ethanol A mixture of (2S)-2-hydroxypropanamide (86.6 mg, 0.972 mmol) and triethyloxonium tetrafluoroborate (185 mg, 0.972 mmol) in THF (2 mL) was stirred at room temperature for 2 h. The solvent was removed and the residue dissolved in ethanol (0.50 mL) and added to a suspension of {(2R,5S)-5-[(6-aminothieno[3,2-b]pyridin-7-yl)amino]tetrahydro-2H-pyran-2-yl}methanol (65.0 mg, 0.233 mmol) in ethanol (1.8 mL). The mixture was stirred at 80° C. for 1 h.

The mixture was cooled to room temperature, diluted with methanol, and purified with prep-LCMS (XBridge C18 column, eluting with a gradient of acetonitrile/water containing 0.1% ammonium hydroxide, at flow rate of 60 mL/min) to give the desired product as white solid (45 mg, 58%). LCMS calculated for $C_{16}H_{20}N_3O_3S$ (M+H)$^+$: m/z=334.1; Found: 334.

Step 2: ((2R,5S)-5-{2-[(1S)-1-Hydroxyethyl]-1H-imidazo[4,5-d]thieno[3,2-b]pyridin-1-yl}tetrahydro-2H-pyran-2-yl)methyl 4-methylbenzenesulfonate To a solution of (1S)-1-{1-[(3S,6R)-6-(hydroxymethyl)tetrahydro-2H-pyran-3-yl]-1H-imidazo[4,5-d]thieno[3,2-b]pyridin-2-yl}ethanol (48.0 mg, 0.144 mmol) in methylene chloride (2.09 mL) and pyridine (70.4 µL, 0.871 mmol) was added p-toluenesulfonyl chloride (35.0 mg, 0.184 mmol) and 4-dimethylaminopyridine (1.1 mg, 0.0092 mmol). The reaction mixture was stirred at room temperature overnight. The reaction mixture was concentrated, diluted with methanol, and purified with prep-LCMS (XBridge C18 column, eluting with a gradient of acetonitrile/water containing 0.1% ammonium hydroxide, at flow rate of 60 mL/min) to give the desired product as white solid (42 mg, 60%). LCMS calculated for $C_{23}H_{26}N_3O_5S_2$(M+H)$^+$: m/z=488.1; Found: 488.1.

Step 3. ((2R,5S)-5-{2-[(1S)-1-Hydroxyethyl]-1H-imidazo[4,5-d]thieno[3,2-b]pyridin-1-yl}tetrahydro-2H-pyran-2-yl)acetonitrile This compound was prepared according to the procedure described in Example 20, Step 2, using ((2R,5S)-5-{2-[(1S)-1-hydroxyethyl]-1H-imidazo[4,5-d]thieno[3,2-b]pyridin-1-yl}tetrahydro-2H-pyran-2-yl)methyl 4-methylbenzenesulfonate instead of ((2R,5S)-5-{2-[(1R)-1-hydroxyethyl]-1H-imidazo[4,5-d]thieno[3,2-b]pyridin-1-yl}tetrahydro- 2H-pyran-2-yl)methyl 4-methylbenzenesulfonate as starting material. LCMS calculated for $C_{17}H_{19}N_4O_2S$ (M+H)$^+$: m/z=343.1; Found: 343.0.

Example 46: [4-(8-Methylpyrazolo[1,5-c]thieno[2,3-e]pyrimidin-9-yl)phenyl]acetonitrile

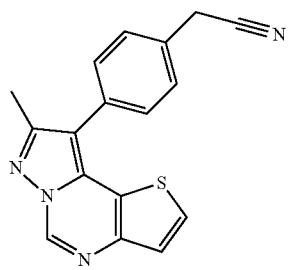 [SMILES: Cc1nn2cnc3ccsc3c2c1-c1ccc(CC#N)cc1]

Step 1: 3-Bromo-5-methyl-1-{[2-(trimethylsilyl)ethoxy]methyl}-1H-pyrazole

To a solution of 3-bromo-5-methyl-1H-pyrazole (from Ark Pharm, 6.4 g, 40 mmol) in tetrahydrofuran (263 mL) at 0° C. was added sodium hydride (3.2 g, 80 mmol). After stirring for 30 min, [β-(trimethylsilyl)ethoxy]methyl chloride (8.4 mL, 48 mmol) was added and the reaction mixture was allowed to warm to room temperature over 2 h. The reaction mixture was diluted with ethyl acetate and water. The aqueous layer was extracted with ethyl acetate. The combined organic layers were washed with brine, dried over $Na_2SO_4$, filtered and concentrated. The crude was purified with flash chromatography (eluting with a gradient of 0-15% ethyl acetate in hexanes) to give the desired product as colorless oil (12 g, 100%). LCMS calculated for $CloH_{20}BrN_2OSi$ (M+H)$^+$: m/z=291.1; Found: 291.0.

Step 2: tert-Butyl (2-bromo-3-thienyl)carbamate

To a solution of tert-butyl 3-thienylcarbamate (from Ark Pharm, 3.97 g, 19.9 mmol) in methylene chloride (190 mL) was added N-bromosuccinimide (3.54 g, 19.9 mmol) portionwise. The resulting mixture was heated at 40° C. for 20 min. The reaction solution was concentrated and the precipitate was filtered and the filtrate was purified with flash chromatography (eluting with a gradient of 0-10% ethyl acetate in hexanes) to give the desired product as white solid. LCMS calculated for $C_5H_5BrNO_2S$ (M+H-t-Bu)$^+$: m/z=221.9; Found: 221.8.

Step 3: tert-Butyl [2-(trimethylstannyl)-3-thienyl]carbamate

To a solution of tert-butyl (2-bromo-3-thienyl)carbamate (4.81 g, 17.3 mmol) in THF (42 mL) was added 2.5 M n-butyllithium in hexanes (15.2 mL, 38.0 mmol) dropwise at −78° C. After stirring for 45 min, 1.0 M chlorotrimethylstannane in THF (19.0 mL, 19.0 mmol) was added. The resulting mixture was allowed to warm to room temperature. The reaction was quenched with brine (70 mL) and extracted with ethyl acetate (2×). The combined organic layers were washed with brine, dried over $MgSO_4$, filtered and concentrated to give the desired product. $^1$H NMR (300 MHz, $CDCl_3$) δ 7.49 (1H, d, J=4.8 Hz), 7.13 (1H, d, J=4.8 Hz), 6.39 (1H, brs), 1.50 (9H, s), 0.36 (9H, s) ppm.

Step 4: tert-Butyl [2-(5-methyl-1-{[2-(trimethylsilyl)ethoxy]methyl}-1H-pyrazol-3-yl)-3-thienyl]carbamate A microwave vial charge with 3-bromo-5-methyl-1-{[2-(trimethylsilyl)ethoxy]methyl}-1H-pyrazole (2.99 g, 10.3 mmol), tert-butyl [2-(trimethylstannyl)-3-thienyl]carbamate (4.40 g, 11.3 mmol), cesium fluoride (3.4 g, 23 mmol) and pre-milled palladium acetate and dicyclohexyl(2',4',6'-triisopropylbiphenyl-2-yl)phosphine (190 mg, 0.20 mmol) was purged with nitrogen three times. 1,2-Dimethoxyethane (10 mL) was added and resulting suspension was heated at 80° C. overnight. After cooling to room temperature, the mixture was diluted with ethyl acetate and filtered through a pad of silica gel. The silica gel pad was washed with ethyl acetate. The solvent was removed in vacuo and the residue was purified with flash chromatography (eluting with a gradient of 0-20% ethyl acetate in hexanes) to give the desired product. LCMS calculated for $C_{19}H_{32}N_3O_3SSi$ (M+H)$^+$: m/z=410.2; Found: 410.2.

Step 5: 8-Methylpyrazolo[1,5-c]thieno[2,3-e]pyrimidine

To a solution of tert-butyl [2-(5-methyl-1-{[2-(trimethylsilyl)ethoxy]methyl}-1H-pyrazol-3-yl)-3-thienyl]carbamate (3.2 g, 7.8 mmol) in methylene chloride (23 mL) was added trifluoroacetic acid (23 mL). After stirring at room temperature for 5 h, the solvent was removed. The residue was dissolved in THF (40 mL) and treated with 1,1-dimethoxy-N,N-dimethylmethanamine (1.56 mL, 11.7 mmol). The resulting solution was heated at 80° C. for 1 h. The solvent was removed under reduced pressure. The crude was purified with flash chromatography (eluting with a gradient of 0-20% ethyl acetate in hexanes) to give the desired product as white solid. $^1$H NMR (300 MHz, $CD_3OD$) δ 9.09 (1H, s), 7.81 (1H, d, J=5.3 Hz), 7.45 (1H, d, J=5.3 Hz), 6.60 (1H, s), 2.49 (3H, s) ppm. LCMS calculated for $C_9H_8N_3S$ (M+H)$^+$: m/z=190.0; Found: 190.0.

Step 6: 9-Bromo-8-methylpyrazolo[1,5-c]thieno[2,3-e]pyrimidine

To a solution of 8-methylpyrazolo[1,5-c]thieno[2,3-e]pyrimidine (1.01 g, 5.34 mmol) in methylene chloride (30 mL) was added N-bromosuccinimide (0.959 g, 5.39 mmol). After stirring for 1 h, the reaction solution was concentrated, and the resultant residue was purified with flash chromatography (eluting with a gradient of 0-20% ethyl acetate in hexanes) to give the desired product as whited solid. $^1$H NMR (300 MHz, $CD_3OD$) δ 9.11 (1H, s), 7.94 (1H, d, J=5.3 Hz), 7.52 (1H, d, J=5.3 Hz), 2.48 (3H, s) ppm. LCMS calculated for $C_9H_7BrN_3S$ (M+H)$^+$: m/z=268.0; Found: 267.9.

Step 7: [4-(8-Methylpyrazolo[1,5-c]thieno[2,3-e]pyrimidin-9-yl)phenyl]acetonitrile A microwave vial charged with 9-bromo-8-methylpyrazolo[1,5-c]thieno[2,3-e]pyrimidine (48.0 mg, 0.179 mmol), [4-(cyanomethyl)phenyl]boronic acid (from Aldrich, 51.9 mg, 0.322 mmol), sodium carbonate (47.4 mg, 0.448 mmol), [1,1'-bis(diphenylphosphino)ferrocene]dichloropalladium (II), complex with dichloromethane (1:1) (15 mg, 0.018 mmol), DMF (1.3 mL) and water (0.13 mL) was purged with N₂ and then stirred at 95° C. for 10 h. The reaction was diluted with ethyl acetate and water. The organic layer was washed with brine, dried over MgSO₄, filtered and concentrated. The crude was purified with prep-LCMS (XBridge C18 column, eluting with a gradient of acetonitrile/water containing 0.1% ammonium hydroxide, at flow rate of 30 mL/min) to give the desired product (35 mg, 64%). LCMS calculated for $C_{17}H_{13}N_4S$ (M+H)⁺: m/z=305.1; Found: 305.0.

Example 47: [trans-4-(2-Ethyl-1H-imidazo[4,5-d] thieno[3,2-b]pyridin-1-yl)cyclohexyl]acetonitrile

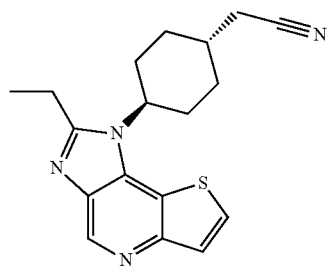 [SMILES: CCc1nc2cnc3ccsc3c2n1[C@H]1CC[C@H](CC#N)CC1]

A mixture of {trans-4-[(6-aminothieno[3,2-b]pyridin-7-yl)amino]cyclohexyl}acetonitrile (20.1 mg, 0.0702 mmol) and 1,1,1-triethoxypropane (0.0428 mL, 0.213 mmol) in acetic acid (0.2 mL) was stirred at 120° C. for 30 min. The mixture was diluted with methanol and purified with prep-LCMS (XBridge C18 column, eluting with a gradient of acetonitrile/water containing 0.1% ammonium hydroxide, at flow rate of 30 mL/min) to give the desired product (13 mg, 57%). LCMS calculated for $C_{18}H_{21}N_4S$ (M+H)⁺: m/z=325.1; Found: 325.1.

Example 48: [trans-4-(2-Methyl-1H-imidazo[4,5-d] thieno[3,2-b]pyridin-1-yl)cyclohexyl]acetonitrile

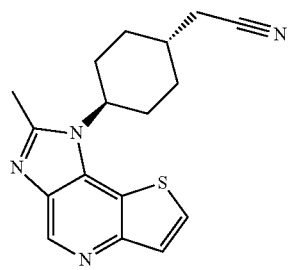 [SMILES: Cc1nc2cnc3ccsc3c2n1[C@H]1CC[C@H](CC#N)CC1]

This compound was prepared according to the procedure described in Example 47, using triethyl orthoacetate instead of propane, 1,1,1-triethoxy-as starting material. LCMS calculated for $C_{17}H_{19}N_4$ (M+H)⁺: m/z=311.1; Found: 311.1.

Example 49. ((1R,3S)-3-{2-[(1R)-1-Hydroxyethyl]-1H-imidazo[4,5-d]thieno[3,2-b]pyridin-1-yl}cyclopentyl)acetonitrile Trifluoroacetate

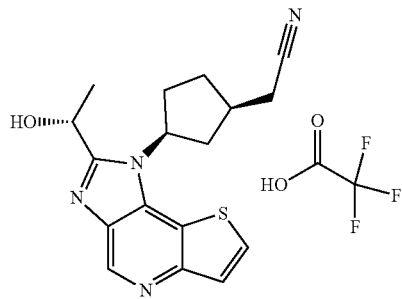

Step 1. Ethyl (1R,3S)-3-aminocyclopentanecarboxylate Trifluoroacetate

To a solution of (1R,3S)-3-[(tert-butoxycarbonyl)amino] cyclopentanecarboxylic acid (from Acros, 0.46 g, 2.0 mmol) in N,N-dimethylformamide (4.6 mL) was added sodium bicarbonate (0.34 g, 4.0 mmol) and iodoethane (0.64 mL, 8.0 mmol). The resulting mixture was stirred overnight at room temperature. The mixture was diluted with ethyl acetate then washed with sat. sodium bicarbonate, water (2×) and brine. The organic was dried (Na2SO4), filtered, and concentrated to give the crude ester. To the crude ester was added methylene chloride (3.0 mL) and trifluoroacetic acid (1.0 mL, 13 mmol). The resulting solution was stirred for 1 h, then concentrated and dried in vacuo to give 0.25 g (46%) of the title compound. LCMS calculated for $C_8H_{16}NO_2$ (M+H)⁺: m/z=158.1; Found: 158.1.

Step 2. Ethyl (1R,3S)-3-[(6-nitrothieno[3,2-b]pyridin-7-yl)amino] cyclopentanecarboxylate To a stirred mixture of 7-chloro-6-nitrothieno[3,2-b]pyridine (0.18 g, 0.84 mmol) and ethyl (1R,3S)-3-aminocyclopentanecarboxylate trifluoroacetate (0.25 g, 0.92 mmol) in isopropyl alcohol (2.3 mL) was added N,N-diisopropylethylamine (0.73 mL, 4.2 mmol). The resulting mixture was stirred at 90° C. for 100 min, and then the solvent was evaporated. The crude residue was purified on silica gel, eluted with 10-60% EtOAc in hexanes to give 0.15 g (55%) of the desired product. LCMS calculated for $C_{15}H_{18}N_3O_4S$ (M+H)⁺: m/z=336.1; Found: 336.0.

Step 3. {(1R,3S)-3-[(6-Nitrothieno[3,2-b]pyridin-7-yl)amino]cyclopentyl}methanol Lithium tetrahydroaluminate (20.4 mg, 0.537 mmol) was added to a solution of ethyl (1R,3S)-3-[(6-nitrothieno[3,2-b]pyridin-7-yl)amino]cyclopentanecarboxylate (0.15 g, 0.45 mmol) in tetrahydrofuran (4.0 mL) with stirring at about 0° C. The resulting mixture was kept cold and stirred for 40 min. Fieser workup was performed followed by filtration through Celite and concentrated. The crude was purified using silica gel, eluted with 40-100% EtOAc in hexanes to give 70 mg (50%) of the desired product. LCMS calculated for $C_{13}H_{16}N_3O_3S$ (M+H)⁺: m/z=294.1; Found: 294.0

Step 4. {(1R,3S)-3-[(6-Nitrothieno[3,2-b]pyridin-7-yl)amino]cyclopentyl}acetonitrile Methanesulfonyl chloride (24.0 µL, 0.310 mmol) was added to a solution of {(1R,3S)-3-[(6-nitrothieno[3,2-b]pyridin-7-yl)amino]cyclopentyl}methanol (70 mg, 0.2 mmol) and triethylamine (66.5 µL, 0.477 mmol) in methylene chloride (2.1 mL) at about 0° C. with stirring. The resulting mixture was allowed to warm to room temperature and stir overnight. The mixture was diluted with dichloromethane then washed with water and brine. The organic was dried (MgSO4), filtered, and concentrated to give a bright yellow gum. To the crude mesylate was added dimethyl sulfoxide (2.0 mL) and sodium cyanide (22 mg, 0.45 mmol). The resulting mixture was stirred at room temperature. After 2 h, the temperature was increased to 80° C. and stirred for 3 h. After cooling, EtOAc and brine were added. The layers were separated and the organic washed with water (2×), dried (Na2SO4), filtered, and concentrated. The crude was purified on silica gel, eluted with 10-70% EtOAc in hexanes to give 8 mg (10%) of the desired product. LCMS calculated for $C_{14}H_{15}N_4O_2S$ $(M+H)^+$: m/z=303.1; Found: 303.0.

Step 5. {(1R,3S)-3-[(6-Aminothieno[3,2-b]pyridin-7-yl)amino]cyclopentyl}acetonitrile A mixture of {(1R,3S)-3-[(6-nitrothieno[3,2-b]pyridin-7-yl)amino]cyclopentyl}acetonitrile (8 mg, 0.03 mmol) and 10% palladium on carbon (4 mg) in methanol (0.3 mL) was stirred under an atmosphere of H2 (balloon) overnight. The mixture was filtered and concentrated to give 7 mg of the desired product. LCMS calculated for $C_{14}H_{17}N_4S$ $(M+H)^+$: m/z=273.1; Found: 273.0.

Step 6. ((1R,3S)-3-{2-[(1R)-1-Hydroxyethyl]-1H-imidazo[4,5-d]thieno[3,2-b]pyridin-1-yl}cyclopentyl)acetonitrile Trifluoroacetate A mixture of (2R)-2-hydroxypropanamide (7.4 mg, 0.083 mmol) and triethyloxonium tetrafluoroborate (14.7 mg, 0.0776 mmol) in tetrahydrofuran (0.15 mL) was stirred at room temperature for 50 min, then concentrated. The residue was dissolved in ethanol (0.1 mL), and this solution was then added to a solution of {(1R,3S)-3-[(6-aminothieno[3,2-b]pyridin-7-yl)amino]cyclopentyl}acetonitrile (7.0 mg, 0.026 mmol) in ethanol (0.1 mL) in a vial. The resulting mixture was stirred at 80° C. for 1 h. After cooling, the mixture was purified using RP-HPLC (XBridge C18 column, eluting with a gradient of acetonitrile/water containing 0.05% TFA, at flow rate of 30 mL/min) to give 3.6 mg (32%) the desired product as the TFA salt. LCMS calculated for $C_{17}H_{19}N_4OS$ $(M+H)^+$: m/z=327.1; Found: 327.0.

Example 50. Ethyl (3S)-3-{2-[(1R)-1-hydroxyethyl]-1H-imidazo[4,5-d]thieno[3,2-b]pyridin-1-yl}piperidine-1-carboxylate

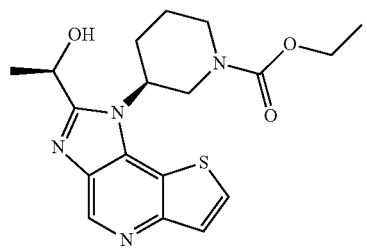 [SMILES: CCOC(=O)N1CCC[C@H](n2c([C@@H](C)O)nc3cnc4ccsc4c32)C1]

Step 1. tert-Butyl (3S)-3-[(6-nitrothieno[3,2-b]pyridin-7-yl)amino]piperidine-1-carboxylate A mixture of 7-chloro-6-nitrothieno[3,2-b]pyridine (166 mg, 0.774 mmol), tert-butyl (3S)-3-aminopiperidine-1-carboxylate (from Aldrich, 186 mg, 0.929 mmol) and triethylamine (0.32 mL, 2.3 mmol) in isopropyl alcohol (1.8 mL) was stirred at 90° C. for 2 h. After cooling to room temperature, solids were observed. Water was added which caused more solids to form. The yellow solids were filtered, washed with water, and dried to give 0.26 g of the desired product. LCMS calculated for $C_{17}H_{23}N_4O_4S$ $(M+H)^+$: m/z=379.1; Found: 379.0. $^1$H NMR (400 MHz, CDCl3) δ 9.40 (s, 1H), 9.29 (s, 1H), 7.84 (d, J=5.5 Hz, 1H), 7.49 (d, J=5.5 Hz, 1H), 4.42 (m, 1H), 3.83 (m, 1H), 3.46 (m, 3H), 2.12 (m, 1H), 1.83 (m, 3H), 1.41 (s, 9H) ppm.

Step 2. tert-Butyl (3S)-3-[(6-aminothieno[3,2-b]pyridin-7-yl)amino]piperidine-1-carboxylate A mixture of tert-butyl (3S)-3-[(6-nitrothieno[3,2-b]pyridin-7-yl)amino]piperidine-1-carboxylate (0.26 g, 0.69 mmol) and 10% palladium on carbon (80 mg) in methanol (5.0 mL) was stirred under an atmosphere of H2 (balloon) overnight. The mixture was filtered through a pad of Celite and concentrated to give 0.24 g of the desired product. LCMS calculated for $C_{17}H_{25}N_4O_2S$ $(M+H)^+$: m/z=349.2; Found: 349.0.

Step 3. tert-Butyl (3S)-3-{2-[(1R)-1-hydroxyethyl]-1H-imidazo[4,5-d]thieno[3,2-b]pyridin-1-yl}piperidine-1-carboxylate A mixture of (2R)-2-hydroxypropanamide (197 mg, 2.21 mmol) and triethyloxonium tetrafluoroborate (395 mg, 2.08 mmol) in tetrahydrofuran (4.0 mL) was stirred at room temperature for 75 min then concentrated. The residue was dissolved in ethanol (1.5 mL) and this solution was then added to a solution of tert-butyl (3S)-3-[(6-aminothieno[3,2-b]pyridin-7-yl)amino]piperidine-1-carboxylate (0.24 g, 0.69 mmol) in ethanol (3.5 mL) in a vial. The resulting mixture was stirred at 80° C. for 2 h. The solvent was evaporated and the crude purified on silica gel, eluted with 0-10% MeOH in dichloromethane to give 250 mg (86%) of the desired product. LCMS calculated for $C_{20}H_{27}N_4O_3S$ $(M+H)^+$: m/z=403.2; Found: 403.1.

Step 4. (1R)-1-{1-[(3S)-Piperidin-3-yl]-1H-imidazo[4,5-d]thieno[3,2-b]pyridin-2-yl}ethanol Hydrochloride To a solution of tert-butyl (3S)-3-{2-[(1R)-1-hydroxyethyl]-1H-imidazo[4,5-d]thieno[3,2-b]pyridin-1-yl}piperidine-1-carboxylate (0.25 g, 0.62 mmol) in methylene chloride (3.5 mL) was added 4.0 M hydrogen chloride in 1,4-dioxane (1.2 mL, 5.0 mmol). A precipitate immediately formed. The reaction was stirred at room temperature for 2 h. The solvents were evaporated and the solids dried in vacuo to give 0.21 g of the product as the HCl salt. LCMS calculated for $C_{15}H_{19}N_4OS$ $(M+H)^+$: m/z=303.1; Found: 303.0.

Step 5. Ethyl (3S)-3-{2-[(1R)-1-hydroxyethyl]-1H-imidazo[4,5-d]thieno[3,2-b]pyridin-1-yl}piperidine-1-carboxylate

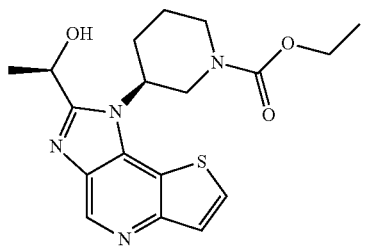 [SMILES: CCOC(=O)N1CCC[C@H](n2c([C@@H](C)O)nc3cnc4ccsc4c32)C1]

To a mixture of (1R)-1-{1-[(3S)-piperidin-3-yl]-1H-imidazo[4,5-d]thieno[3,2-b]pyridin-2-yl}ethanol hydrochloride (15 mg, 0.044 mmol) and triethylamine (18.5 µL, 0.133 mmol) in methylene chloride (0.3 mL) was added ethyl chloroformate (5.1 µL, 0.0531 mmol). The resulting mixture was stirred until completion then the solvent evaporated. The crude residue was purified using RP-HPLC (XBridge C18 column, eluting with a gradient of acetonitrile/water containing 0.1% ammonium hydroxide, at flow rate of 30 mL/min) to give 5.6 mg (34%) of the desired product. LCMS calculated for $C_{18}H_{23}N_4O_3S$ (M+H)$^+$: m/z=375.1; Found: 375.0. $^1$H NMR (300 MHz, CDCl$_3$) δ 9.08 (d, J=1.3 Hz, 1H), 7.69 (dd, J=5.5 and 1.3 Hz, 1H), 7.62 (d, J=5.5 Hz, 1H), 5.21 (d, J=6.7 Hz, 1H), 4.83-4.68 (m, 1H), 4.43-4.23 (m, 2H), 4.15 (q, J=6.9 Hz, 2H), 3.93-3.66 (m, 1H), 3.18-3.01 (m, 1H), 2.76-2.60 (m, 1H), 2.20-2.10 (m, 1H), 2.00 (d, J=13.8 Hz, 1H), 1.79 (d, J=6.4 Hz, 3H), 1.70-1.61 (m, 2H), 1.30-1.16 (m, 3H) ppm.

Example 51. 3-((3S)-3-{2-[(1R)-1-Hydroxyethyl]-1H-imidazo[4,5-d]thieno[3,2-b]pyridin-1-yl}piperidin-1-yl)-3-oxopropanenitrile trifluoroacetate

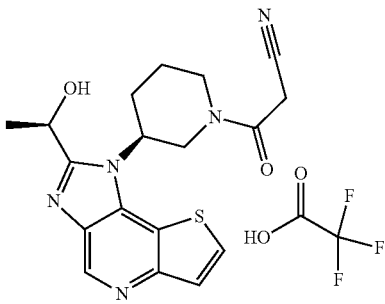

To a mixture of (1R)-1-{1-[(3S)-piperidin-3-yl]-1H-imidazo[4,5-d]thieno[3,2-b]pyridin-2-yl}ethanol hydrochloride (15 mg, 0.044 mmol) (Example 50, step 4), cyanoacetic acid (4.5 mg, 0.053 mmol), and triethylamine (18.5 µL, 0.133 mmol) in methylene chloride (0.3 mL) was added N,N,N',N'-tetramethyl-O-(7-azabenzotriazol-1-yl)uronium hexafluorophosphate (25.2 mg, 0.0664 mmol). The resulting mixture was stirred at room temperature. After 2 h, a second addition of cyanoacetic acid (4.5 mg, 0.053 mmol) was made and stirred overnight. The solvent was evaporated and the residue purified using RP-HPLC (XBridge C18 column, eluting with a gradient of acetonitrile/water containing 0.05% TFA, at flow rate of 30 mL/min) to give 3.4 mg (16%) of the desired product. LCMS calculated for $C_{18}H_{20}N_5O_2S$ (M+H)$^+$: m/z=370.1; Found: 370.0.

Example 52. (1R)-1-{1-[(3S)-1-(4,4,4-Trifluorobutanoyl)piperidin-3-yl]-1H-imidazo[4,5-d]thieno[3,2-b]pyridin-2-yl}ethanol

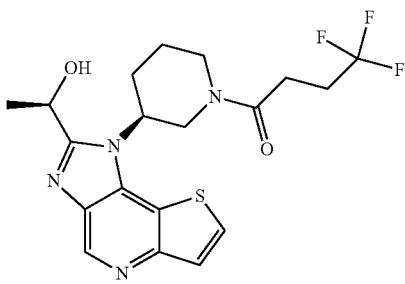 [SMILES: C[C@@H](O)c1nc2cnc3ccsc3c2n1[C@H]1CCCN(C(=O)CCC(F)(F)F)C1]

This compound was prepared using procedures analogous to those for Example 51 with 4,4,4-trifluorobutanoic acid instead of cyanoacetic acid and without the second addition. The crude was purified using RP-HPLC (XBridge C18 column, eluting with a gradient of acetonitrile/water containing 0.1% ammonium hydroxide, at flow rate of 30 mL/min) to give 9.5 mg (50%) of the desired product. LCMS calculated for $C_{19}H_{22}F_3N_4O_2S$ (M+H)$^+$: m/z=427.1; Found: 427.0.

Example 53. (1R)-1-(1-{(3S)-1-[3-(1H-Pyrazol-4-yl)propanoyl]piperidin-3-yl}-1H-imidazo[4,5-d]thieno[3,2-b]pyridin-2-yl)ethanol

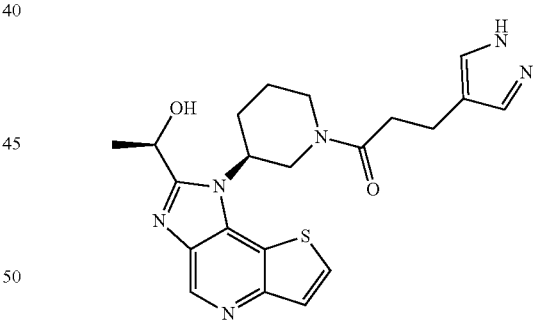

This compound was prepared using procedures analogous to those for Example 52, with 3-(1H-pyrazol-4-yl)propanoic acid (7.9 mg, 0.0567 mmol) instead of 4,4,4-trifluorobutanoic acid. The crude was purified using RP-HPLC (XBridge C18 column, eluting with a gradient of acetonitrile/water containing 0.1% ammonium hydroxide, at flow rate of 30 mL/min) to give 6.5 mg (32%) of the desired product. LCMS calculated for $C_{21}H_{25}N_6O_2S$ (M+H)$^+$: m/z=425.2; Found: 425.1. $^1$H NMR (300 MHz, CDCl$_3$) δ 9.04 (s, 1H), 7.64 (dd, J=11.8 and 6.2 Hz, 1H), 7.57 (d, J=5.6 Hz, 1H), 7.44 (s, 1H), 7.27 (s, 1H), 5.26 (d, J=7.1 Hz, 1H), 4.82 (d, J=8.5 Hz, 2H), 4.07-3.86 (m, 2H), 3.58-3.45 (m, 1H), 3.36-3.24 (m, 1H), 2.96-2.56 (m, 6H), 2.22-1.89 (m, 2H), 1.78 (d, J=6.4 Hz, 4H) ppm.

Example 54. (1R)-1-{1-[(3S)-1-(3-Pyridin-3-ylpropanoyl)piperidin-3-yl]-1H-imidazo[4,5-d]thieno[3,2-b]pyridin-2-yl}ethanol

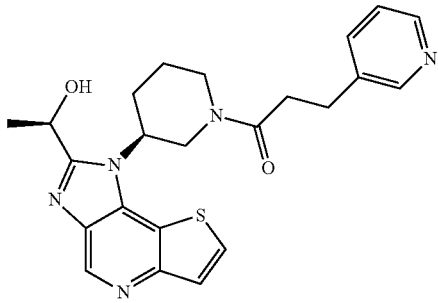 [SMILES: C[C@@H](O)c1nc2cnc3ccsc3c2n1[C@H]1CCCN(C(=O)CCc2cccnc2)C1]

This compound was prepared using procedures analogous to those for Example 52, with 3-pyridin-3-ylpropanoic acid (8.5 mg, 0.057 mmol) instead of 4,4,4-trifluorobutanoic acid. The crude was purified using RP-HPLC (XBridge C18 column, eluting with a gradient of acetonitrile/water containing 0.1% ammonium hydroxide, at flow rate of 30 mL/min) to give 6.8 mg (33%) of the desired product. LCMS calculated for $C_{23}H_{26}N_5O_2S$ (M+H)$^+$: m/z=436.2; Found: 436.0. $^1$H NMR (300 MHz, CDCl$_3$) δ 9.09 (s, 1H), 8.52 (s, 1H), 8.45 (d, J=4.7 Hz, 1H), 8.30 (s, 1H), 7.70-7.56 (m, 2H), 7.29-7.25 (m, 1H), 5.28 (s, 1H), 4.92-4.61 (m, 2H), 4.06-3.81 (m, OH), 3.56 (s, 1H), 3.20-3.09 (m, 1H), 3.00-2.88 (m, 2H), 2.78-2.60 (m, 5H), 2.20-2.00 (m, 1H), 1.86 (d, J=6.2 Hz, 3H), 1.80-1.65 (m, 2H) ppm.

Example 55. (1R)-1-{1-[(3S)-1-(3-Phenylbutanoyl)piperidin-3-yl]-1H-imidazo[4,5-d]thieno[3,2-b]pyridin-2-yl}ethanol

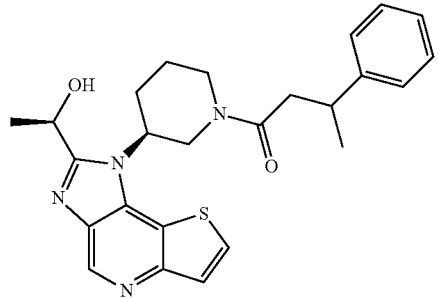 [SMILES: CC(CC(=O)N1CCC[C@H](n2c([C@@H](C)O)nc3cnc4ccsc4c32)C1)c1ccccc1]

This compound was prepared using procedures analogous to those for Example 52, with 3-phenylbutyric acid (9.3 mg, 0.057 mmol) instead of 4,4,4-trifluorobutanoic acid. The crude was purified using RP-HPLC (XBridge C18 column, eluting with a gradient of acetonitrile/water containing 0.1% ammonium hydroxide, at flow rate of 30 mL/min) to give 8.3 mg (39%) of the desired product. LCMS calculated for $C_{25}H_{29}N_4O_2S$ (M+H)$^+$: m/z=449.2; Found: 449.0.

Example 56. 3-((3S)-3-{2-[(1R)-1-Hydroxyethyl]-1H-imidazo[4,5-d]thieno[3,2-b]pyridin-1-yl}piperidin-1-yl)propanenitrile

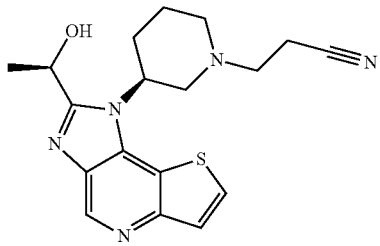 [SMILES: C[C@@H](O)c1nc2cnc3ccsc3c2n1[C@H]1CCCN(CCC#N)C1]

To a solution of (1R)-1-{1-[(3S)-piperidin-3-yl]-1H-imidazo[4,5-d]thieno[3,2-b]pyridin-2-yl}ethanol hydrochloride (15.0 mg, 0.0443 mmol) (Example 50, step 4) in acetonitrile (0.3 mL) was added 1,8-diazabicyclo[5.4.0]undec-7-ene (26 µL, 0.18 mmol), followed by 2-propenenitrile (5.8 µL, 0.089 mmol). The resulting mixture was stirred at room temperature overnight. The solvents were evaporated and the residue was purified by RP-HPLC (XBridge C18 column, eluting with a gradient of acetonitrile/water containing 0.1% ammonium hydroxide, at flow rate of 30 mL/min) to give 5.3 mg (34%) of the desired product. LCMS calculated for $C_{18}H_{22}N_5OS$ (M+H)$^+$: m/z=356.2; Found: 356.1.

Example 57. 1R)-1-{1-[(3S)-1-(3-Phenylpropanoyl)piperidin-3-yl]-1H-imidazo[4,5-d]thieno[3,2-b]pyridin-2-yl}ethanol

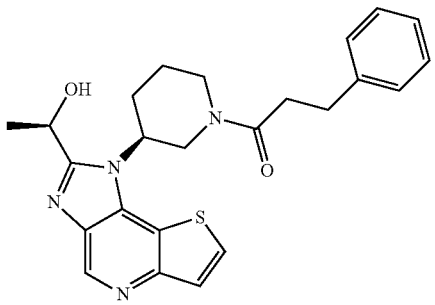 [SMILES: C[C@@H](O)c1nc2cnc3ccsc3c2n1[C@H]1CCCN(C(=O)CCc2ccccc2)C1]

To a mixture of (1R)-1-{1-[(3S)-piperidin-3-yl]-1H-imidazo[4,5-d]thieno[3,2-b]pyridin-2-yl}ethanol hydrochloride (15 mg, 0.044 mmol) (Example 50, step 4) and triethylamine (24.7 µL, 0.177 mmol) in N,N-dimethylformamide (0.3 mL) was added benzenepropanoyl chloride (8.6 µL, 0.058 mmol). The resulting mixture was stirred for 90 min at room temperature. The mixture was purified using RP-HPLC (XBridge C18 column, eluting with a gradient of acetonitrile/water containing 0.1% ammonium hydroxide, at flow rate of 30 mL/min) to give 6.5 mg (34%) of the desired product. LCMS calculated for $C_{24}H_{27}N_4O_2S$ (M+H)$^+$: m/z=435.2; Found: 435.1. $^1$H NMR (300 MHz, CDCl$_3$) δ 9.07 (s, 1H), 7.71-7.66 (m, 1H), 7.65-7.57 (m, 1H), 7.34-7.27 (m, 2H), 7.26-7.16 (m, 2H), 7.12 (d, J=6.9 Hz, 1H), 5.21 (s, 1H), 4.83 (d, J=13.1 Hz, 2H), 4.78-4.64 (m, 1H), 4.04-3.87 (m, 1H), 3.61-3.23 (m, 3H), 3.04-2.85 (m, 2H), 2.77-2.60 (m, 2H), 2.15 (s, 1H), 1.97 (d, J=14.4 Hz, 1H), 1.81 (d, J=6.5 Hz, 2H), 1.50 (d, J=13.1 Hz, 2H) ppm.

Example 58. 4-((3S)-3-{2-[(1R)-1-Hydroxyethyl]-1H-imidazo[4,5-d]thieno[3,2-b]pyridin-1-yl}piperidin-1-yl)-4-oxobutanenitrile

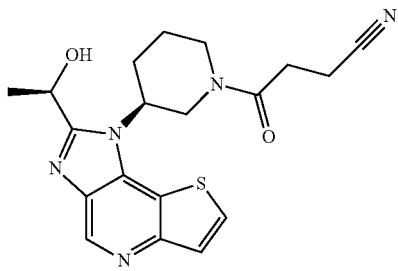 [SMILES: C[C@@H](O)c1nc2cnc3ccsc3c2n1[C@H]1CCCN(C(=O)CCC#N)C1]

Step 1. 4-((3S)-3-{2-[(1R)-1-Hydroxyethyl]-1H-imidazo[4,5-d]thieno[3,2-b]pyridin-1-yl}piperidin-1-yl)-4-oxobutanoic Acid To a solution of (1R)-1-{1-[(3S)-piperidin-3-yl]-1H-imidazo[4,5-d]thieno[3,2-b]pyridin-2-yl}ethanol hydrochloride (30.0 mg, 0.0885 mmol) (Example 50, step 4) and triethylamine (37.0 µL, 0.266 mmol) in methylene chloride (0.5 mL) was added 3-(carbomethoxy)propionyl chloride (12.0 µL, 0.0974 mmol). The resulting mixture was stirred at room temperature for 2 h. Water and dichloromethane were added and the layers separated. The organic was concentrated. The crude residue was taken up in methanol (0.5 mL), tetrahydrofuran (50 µL), and water (40 µL). Lithium hydroxide, monohydrate (18 mg, 0.44 mmol) was added and the mixture stirred at room temperature for 3 h. The mixture was made slightly acidic by adding 1N HCl then concentrated. The mixture was dissolved in dichloromethane, stirred, filtered and concentrated to give 37 mg of clean, crude acid. LCMS calculated for $C_{19}H_{23}N_4O_4S$ (M+H)$^+$: m/z=403.1; Found: 403.2.

Step 2. 4-((3S)-3-{2-[(1R)-1-Hydroxyethyl]-1H-imidazo[4,5-d]thieno[3,2-b]pyridin-1-yl}piperidin-1-yl)-4-oxobutanamide To a mixture of 4-((3S)-3-{2-[(1R)-1-hydroxyethyl]-1H-imidazo[4,5-d]thieno[3,2-b]pyridin-1-yl}piperidin-1-yl)-4-oxobutanoic acid (35 mg, 0.087 mmol), ammonium carbonate (42 mg, 0.43 mmol), and triethylamine (18.2 µL, 0.130 mmol) in N,N-dimethylformamide (0.6 mL) was added benzotriazol-1-yloxytris(dimethylamino)phosphonium hexafluorophosphate (76.9 mg, 0.174 mmol). The resulting mixture was stirred at room temperature for 2.5 h. The mixture was diluted with ethyl acetate then washed with sat. NaHCO$_3$, water, and brine. LCMS showed most of the desired product remained in the aqueous layer. The aqueous layer was concentrated to give white solids. The solids were stirred in ~1:1 MeOH/dichloromethane and then filtered to give 40 mg crude product. The crude was purified using RP-HPLC (XBridge C18 column, eluting with a gradient of acetonitrile/water containing 0.1% ammonium hydroxide, at flow rate of 30 mL/min) to give 6 mg of the desired product. LCMS calculated for $C_{19}H_{24}N_5O_3S$ (M+H)$^+$: m/z=402.2; Found: 402.0.

Step 3. 4-((3S)-3-{2-[(1R)-1-Hydroxyethyl]-1H-imidazo[4,5-d]thieno[3,2-b]pyridin-1-yl}piperidin-1-yl)-4-oxobutanenitrile To a mixture of 4-((3S)-3-{2-[(1R)-1-hydroxyethyl]-1H-imidazo[4,5-d]thieno[3,2-b]pyridin-1-yl}piperidin-1-yl)-4-oxobutanamide (5.5 mg, 0.014 mmol) and triethylamine (9.6 µL, 0.069 mmol) in tetrahydrofuran (0.2 mL) stirring at about 0° C. was added trifluoroacetic anhydride (4.8 µL, 0.034 mmol). The resulting mixture was kept cold and stirred for 2 h. The mixture was concentrated then purified using RP-HPLC (XBridge C18 column, eluting with a gradient of acetonitrile/water containing 0.1% ammonium hydroxide, at flow rate of 30 mL/min) to give 3 mg (57%) of the desired product. LCMS calculated for $C_{19}H_{22}N_5O_2S$ (M+H)$^+$: m/z=384.1; Found: 384.2.

Example 59. 5-((3S)-3-{2-[(1R)-1-Hydroxyethyl]-1H-imidazo[4,5-d]thieno[3,2-b]pyridin-1-yl}piperidin-1-yl)-5-oxopentanenitrile

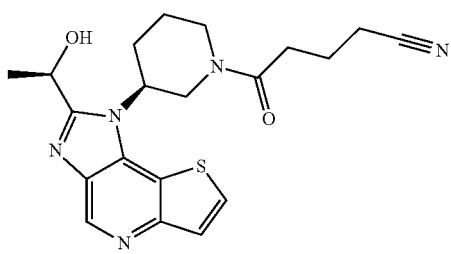 [SMILES: C[C@@H](O)c1nc2cnc3ccsc3c2n1[C@H]1CCCN(C(=O)CCCC#N)C1]

This compound was prepared using procedures analogous to those for Example 58, with 3-carbomethoxybutrylchloride instead of 3-(carbomethoxy)propionyl chloride. Isolated 1.7 mg (31%) of the desired compound. LCMS calculated for $C_{20}H_{24}N_5O_2S$ (M+H)$^+$: m/z=398.2; Found: 398.2.

Example 60. (1R)-1-{1-[1-(4,4,4-Trifluorobutyl)piperidin-4-yl]-1H-imidazo[4,5-d]thieno[3,2-b]pyridin-2-yl}ethanol

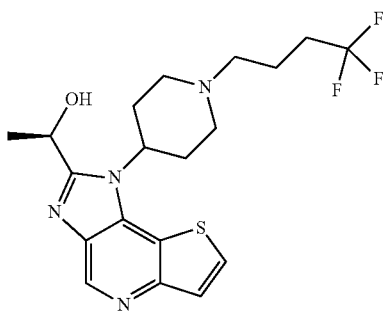 [SMILES: C[C@@H](O)c1nc2cnc3ccsc3c2n1C1CCN(CCCC(F)(F)F)CC1]

Step 1. (1R)-1-(1-Piperidin-4-yl-1H-imidazo[4,5-d]thieno[3,2-b]pyridin-2-yl)ethanol This compound was prepared using procedures analogous to those for Example 50, step 4, with tert-butyl 4-aminopiperidine-1-carboxylate (from Aldrich) instead of tert-butyl (3S)-3-aminopiperidine-1-carboxylate. LCMS calculated for $C_{15}H_{19}N_4OS$ (M+H)$^+$: m/z=303.1; Found: 303.1.

Step 2. (1R)-1-{1-[1-(4,4,4-Trifluorobutyl)piperidin-4-yl]-1H-imidazo[4,5-d]thieno[3,2-b]pyridin-2-yl}ethanol To a mixture of (1R)-1-(1-piperidin-4-yl-1H-imidazo[4,5-d]thieno[3,2-b]pyridin-2-yl)ethanol (15.0 mg, 0.0496 mmol) and 4,4,4-trifluorobutanal (9.4 mg, 0.0744 mmol) in methylene chloride (0.3 mL) and N,N-dimethylformamide (0.2 mL) was added resin of tetramethylammonium triacetoxyborohydride (48.4 mg, 0.0992 mmol). The resulting mixture was stirred overnight. The mixture was filtered and concentrated then purified using RP-HPLC (XBridge C18 column, eluting with a gradient of acetonitrile/water containing 0.1% ammonium hydroxide, at flow rate of 30 mL/min) to give 7 mg (34%) of the desired product. LCMS calculated for $C_{19}H_{24}F_3N_4OS$ (M+H)$^+$: m/z=413.2; Found: 413.1. $^1$H NMR (300 MHz, CDCl$_3$) δ 9.06 (s, 1H), 7.71-7.60 (m, 2H), 5.21 (s, 1H), 4.72-4.58 (m, 1H), 3.70-3.57 (m, 6H), 3.13 (d, J=9.8 Hz, 2H), 2.89-2.66 (m, 1H), 2.49 (t, J=6.9 Hz, 2H), 2.34-2.18 (m, 2H), 1.96 (s, 1H), 1.86-1.74 (m, 2H), 1.67 (s, 2H) ppm.

Example 61. (4-{2-[(1R)-1-Hydroxyethyl]-1H-imidazo[4,5-d]thieno[3,2-b]pyridin-1-yl}piperidin-1-yl)acetonitrile trifluoroacetate

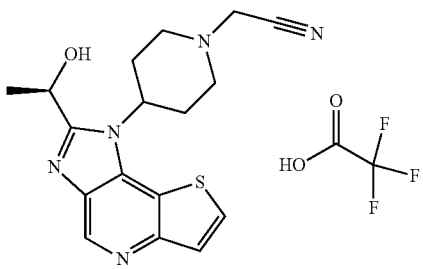 [SMILES: C[C@@H](O)c1nc2cnc3ccsc3c2n1C1CCN(CC#N)CC1 ; O=C(O)C(F)(F)F]

A mixture of (1R)-1-(1-piperidin-4-yl-1H-imidazo[4,5-d]thieno[3,2-b]pyridin-2-yl)ethanol (15 mg, 0.050 mmol) (Example 60, step 1), bromoacetonitrile (4.2 µL, 0.060 mmol) and triethylamine (20.7 µL, 0.149 mmol) in acetonitrile (0.3 mL) was stirred at rt for 4 h. The mixture was diluted and purified using RP-HPLC (XBridge C18 column, eluting with a gradient of acetonitrile/water containing 0.05% TFA, at flow rate of 30 mL/min) to give 4.2 mg (18%) of the desired product. LCMS calculated for $C_{17}H_{20}N_5OS$ (M+H)$^+$: m/z=342.1; Found: 342.0.

Example 62. 3-((3S)-3-{2-[(1R)-1-Hydroxyethyl]-1H-imidazo[4,5-d]thieno[3,2-b]pyridin-1-yl}pyrrolidin-1-yl)propanenitrile

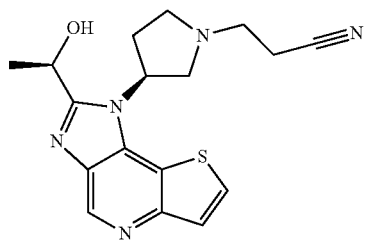 [SMILES: C[C@@H](O)c1nc2cnc3ccsc3c2n1[C@H]1CCN(CCC#N)C1]

Step 1. (1R)-1-{1-[(3S)-Pyrrolidin-3-yl]-1H-imidazo[4,5-d]thieno[3,2-b]pyridin-2-yl}ethanol Hydrochloride This compound was prepared using procedures analogous to those for Example 50, step 4, with tert-butyl (3S)-3-aminopyrrolidine-1-carboxylate (from Aldrich) instead of tert-butyl (3S)-3-aminopiperidine-1-carboxylate. LCMS calculated for $C_{14}H_{17}N_4OS$ (M+H)$^+$: m/z=289.1; Found: 289.0. $^1$H NMR (300 MHz, CD$_3$OD) δ 9.39 (s, 1H), 8.48 (d, J=5.7 Hz, 1H), 7.91 (d, J=5.7 Hz, 1H), 6.10-5.97 (m, 1H), 5.35 (q, J=6.4 Hz, 1H), 4.11-3.91 (m, 3H), 3.68 (dt, 1H), 3.42 (s, 1H), 2.99-2.77 (m, 2H), 1.84 (d, J=6.4 Hz, 2H), 1.60 (s, 1H), 1.32 (dd, J=6.0 and 3.2 Hz, 2H) ppm.

Step 2. 3-((3S)-3-{2-[(1R)-1-Hydroxyethyl]-1H-imidazo[4,5-d]thieno[3,2-b]pyridin-1-yl}pyrrolidin-1-yl)propanenitrile To a solution of (1R)-1-{1-[(3S)-pyrrolidin-3-yl]-1H-imidazo[4,5-d]thieno[3,2-b]pyridin-2-yl}ethanol hydrochloride (15 mg, 0.046 mmol) in acetonitrile (0.3 mL) was added 1,8-diazabicyclo[5.4.0]undec-7-ene (28 µL, 0.18 mmol) followed by 2-propenenitrile (6.1 µL, 0.092 mmol). The resulting mixture was stirred at room temperature for 3 h. The mixture was further diluted and purified using RP-HPLC (XBridge C18 column, eluting with a gradient of acetonitrile/water containing 0.1% ammonium hydroxide, at flow rate of 30 mL/min) to give 5.7 mg (36%) of the desired product. LCMS calculated for $C_{17}H_{20}N_5OS$ (M+H)$^+$: m/z=342.1; Found: 342.1.

Example 63. 3-((3S)-3-{2-[(1R)-1-Hydroxyethyl]-1H-imidazo[4,5-d]thieno[3,2-b]pyridin-1-yl}pyrrolidin-1-yl)-3-oxopropanenitrile

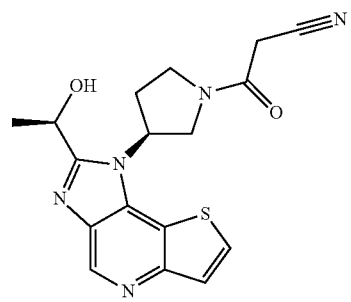 [SMILES: C[C@@H](O)c1nc2cnc3ccsc3c2n1[C@H]1CCN(C(=O)CC#N)C1]

This compound was prepared using procedures analogous to those for Example 51, with (1R)-1-{1-[(3S)-pyrrolidin-3-yl]-1H-imidazo[4,5-d]thieno[3,2-b]pyridin-2-yl}ethanol hydrochloride (Example 62, step 1) instead of (1R)-1-{1-[(3S)-piperidin-3-yl]-1H-imidazo[4,5-d]thieno[3,2-b]pyridin-2-yl}ethanol hydrochloride. The crude product was purified using RP-HPLC (XBridge C18 column, eluting with a gradient of acetonitrile/water containing 0.1% ammonium hydroxide, at flow rate of 30 mL/min) to give 7 mg (43%) of the desired product. LCMS calculated for $C_{17}H_{18}N_5O_2S$ (M+H)$^+$: m/z=356.1; Found: 356.0.

Example 64. (1R)-1-{1-[(3S)-1-(4,4,4-Trifluorobutyl)pyrrolidin-3-yl]-1H-imidazo[4,5-d]thieno[3,2-b]pyridin-2-yl}ethanol

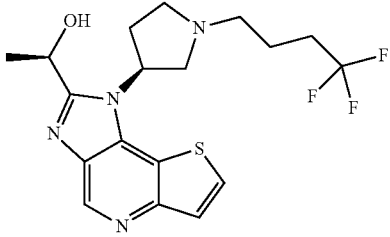 [SMILES: C[C@@H](O)c1nc2cnc3ccsc3c2n1[C@H]1CCN(CCCC(F)(F)F)C1]

This compound was prepared using procedures analogous to those for Example 60, step 2, with (1R)-1-{1-[(3S)-pyrrolidin-3-yl]-1H-imidazo[4,5-d]thieno[3,2-b]pyridin-2-yl}ethanol hydrochloride (Example 62, step 1) instead of (1R)-1-(1-piperidin-4-yl-1H-imidazo[4,5-d]thieno[3,2-b]pyridin-2-yl)ethanol. LCMS calculated for $C_{18}H_{22}F_3N_4OS$ (M+H)$^+$: m/z=399.1; Found: 399.1. H NMR (300 MHz, CDCl$_3$) δ 9.08 (s, 1H), 7.68 (d, J=5.5 Hz, 1H), 7.61 (d, J=5.5 Hz, 1H), 5.59 (dd, J=8.2 and 3.6 Hz, 1H), 5.27 (q, J=6.4 Hz, 1H), 3.49-3.30 (m, 2H), 2.83 (dd, J=10.5 and 8.2 Hz, 1H), 2.74-2.52 (m, 5H), 2.26-2.09 (m, 2H), 1.81 (t, J=7.0 Hz, 6H) ppm.

Example 65. 4-((3S)-3-{2-[(1R)-1-Hydroxyethyl]-1H-imidazo[4,5-d]thieno[3,2-b]pyridin-1-yl}pyrrolidin-1-yl)butanenitrile

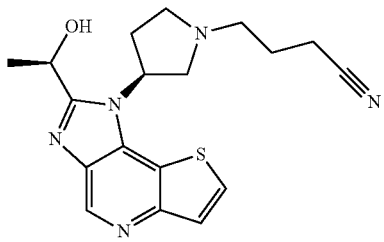 [SMILES: C[C@@H](O)c1nc2cnc3ccsc3c2n1[C@H]1CCN(CCCC#N)C1]

To a mixture of (1R)-1-{1-[(3S)-pyrrolidin-3-yl]-1H-imidazo[4,5-d]thieno[3,2-b]pyridin-2-yl}ethanol hydrochloride (15 mg, 0.046 mmol) and N,N-diisopropylethylamine (24 µL, 0.14 mmol) in acetonitrile (0.2 mL) was added butanenitrile, 4-bromo- (5.1 µL, 0.051 mmol). The resulting mixture was stirred at rt for 4 h. The mixture was diluted and purified using RP-HPLC (XBridge C18 column, eluting with a gradient of acetonitrile/water containing 0.1% ammonium hydroxide, at flow rate of 30 mL/min) to give 6.3 mg (38%) of the desired product. LCMS calculated for $C_{18}H_{22}N_5OS$ (M+H): m/z=356.2; Found: 356.0.

Example 66. 5-((3S)-3-{2-[(1R)-1-Hydroxyethyl]-1H-imidazo[4,5-d]thieno[3,2-b]pyridin-1-yl}pyrrolidin-1-yl)pentanenitrile

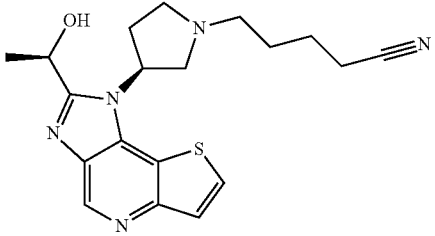 [SMILES: C[C@@H](O)c1nc2cnc3ccsc3c2n1[C@H]1CCN(CCCCC#N)C1]

This compound was prepared using procedures analogous to those for Example 65, with 5-bromovaleronitrile instead of butanenitrile, 4-bromo-. LCMS calculated for $C_{19}H_{24}N_5OS$ (M+H)$^+$: m/z=370.2; Found: 370.1. $^1$H NMR (300 MHz, DMSO-d$_6$) δ 8.98 (s, 1H), 8.02 (d, J=5.5 Hz, 1H), 7.67 (d, J=5.5 Hz, 1H), 5.91 (s, 1H), 5.67-5.57 (m, 1H), 5.29 (s, 1H), 3.26-3.10 (m, 2H), 3.04 (t, J=9.1 Hz, 1H), 2.80 (d, J=8.4 Hz, 1H), 2.70-2.30 (m, 7H) (overlap with solvent), 1.72-1.56 (m, 6H) ppm.

Example 67. ((1R,2R,4S)-2-Amino-4-{2-[(1R)-1-hydroxyethyl]-1H-imidazo[4,5-d]thieno[3,2-b]pyridin-1-yl}cyclohexyl)acetonitrile

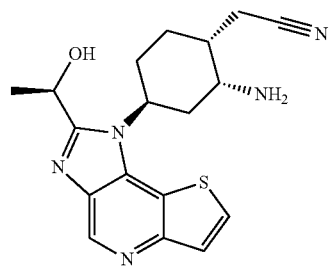 [SMILES: C[C@@H](O)c1nc2cnc3ccsc3c2n1[C@H]1CC[C@H](CC#N)[C@H](N)C1]

Step 1. Methyl (1S,6R)-6-{[(benzyloxy)carbonyl]amino}cyclohex-3-ene-1-carboxylate To a solution of (1R,6S)-6-(methoxycarbonyl)cyclohex-3-ene-1-carboxylic acid (5.0 g, 27 mmol) (from Alfa Aesar) in toluene (50.0 mL) stirring under N$_2$ was added triethylamine (9.1 mL, 65 mmol) followed by diphenylphosphonic azide (5.85 mL, 27.1 mmol). The resulting mixture was stirred at 85° C. overnight (18 h). Benzyl alcohol (2.81 mL, 27.1 mmol) was added and the mixture heated to reflux (135° C.) and stirred overnight. After cooling, the mixture was diluted with EtOAc and then washed with sat. NaHCO$_3$ (2×), water and brine. The organic layer was dried (Na$_2$SO$_4$), filtered, and concentrated. The residue was dried in vacuo to give 7.8 g of yellow oil. LCMS calculated for $C16H_{20}NO_4$ (M+H)$^+$: m/z=290.1; Found: 290.0. $^1$H NMR (300 MHz, CDCl$_3$) δ 7.38-7.27 (m, 5H), 5.62 (q, J=10.1 Hz, 2H), 5.39 (d, J=8.9 Hz, 1H), 5.07 (s, 2H), 4.28-4.19 (m, 1H), 3.66 (s, 3H), 2.81 (d, J=3.2 Hz, 1H), 2.56-2.12 (m, 4H) ppm.

Step 2. Methyl (1R,3S,4R,6S)-4-{[(benzyloxy)carbonyl]amino}-7-oxabicyclo[4.1.0]heptane-3-carboxylate m-Chloroperbenzoic acid (5.56 g, 32.2 mmol) was added to a solution of methyl (1S,6R)-6-{[(benzyloxy)carbonyl]

amino}cyclohex-3-ene-1-carboxylate (7.8 g, 27 mmol) in methylene chloride (150 mL) with stirring at about 0° C. The mixture was slowly warmed to room temperature and stirred overnight. The mixture was diluted with dichloromethane then washed with sat. NaHCO$_3$ (3×). The organic layer was dried (MgSO$_4$), filtered, and concentrated. The crude was purified on silica gel, eluted with 0-50% EtOAc in hexanes to give 4.7 g (57%) of the desired product as a white solid. LCMS calculated for C$_{16}$H$_{20}$NO$_5$ (M+H)$^+$: m/z=306.1; Found: 306.0. $^1$H NMR (300 MHz, CDCl$_3$) δ 7.37-7.29 (m, 5H), 5.75 (d, J=9.9 Hz, 1H), 5.04 (s, 2H), 4.09 (dtd, J=14.0, 6.8, 6.0, and 3.2 Hz, 1H), 3.65 (s, 3H), 3.18 (d, J=5.9 Hz, 2H), 2.60 (dd, J=15.5 and 7.3 Hz, 1H), 2.48 (td, J=7.3, 6.6, and 3.2 Hz, 1H), 2.23-2.01 (m, 3H) ppm.

Step 3. Methyl (1S,2R,4R)-2-{[(benzyloxy)carbonyl]amino}-4-hydroxycyclohexanecarboxylate To a mixture of methyl (1R,3S,4R,6S)-4-{[(benzyloxy)carbonyl]amino}-7-oxabicyclo[4.1.0]heptane-3-carboxylate (1.9 g, 6.2 mmol) in ethanol (30.0 mL) was added sodium tetrahydroborate (0.471 g, 12.4 mmol). The resulting mixture was stirred overnight (22 h) at room temperature. The reaction was quenched with sat. NH$_4$Cl, then most of the solvent evaporated. The residue was taken up in EtOAc and washed with water, dried (Na$_2$SO$_4$), filtered and concentrated. The crude was purified on silica gel, eluted with 40-100% EtOAc in hexanes to give 0.75 g (39%) of the desired product. LCMS calculated for C$_{16}$H$_{22}$NO$_5$ (M+H)$^+$: m/z=308.1; Found: 308.0. $^1$H NMR (300 MHz, CDCl$_3$) δ 7.36-7.28 (m, 5H), 6.02 (d, J=9.0 Hz, 1H), 5.05 (s, 2H), 4.03 (s, 1H), 3.87 (s, 1H), 3.64 (s, 3H), 2.68 (s, 1H), 2.22-2.11 (m, 1H), 1.97-1.67 (m, 5H), 1.42 (s, 1H) ppm.

Step 4. (1S,2R,4R)-2-{[(benzyloxy)carbonyl]amino}-4-[(methylsulfonyl)oxy]cyclohexanecarboxylate Methanesulfonyl chloride (79.6 µL, 1.03 mmol) was added to a mixture of methyl (1S,2R,4R)-2-{[(benzyloxy)carbonyl]amino}-4-hydroxycyclohexanecarboxylate (243 mg, 0.791 mmol) and triethylamine (0.22 mL, 1.6 mmol) in methylene chloride (4.0 mL) with stirring at about 0° C. The resulting mixture was kept cold and stirred for 2 h. The mixture was diluted with dichloromethane then washed with water and brine. The organic layer was dried (MgSO$_4$), filtered, and concentrated to give a white solid. LCMS calculated for C$_{17}$H$_{24}$NO$_7$S (M+H)$^+$: m/z=386.1; Found: 386.0.

Step 5. Methyl (1S,2R,4S)-4-azido-2-{[(benzyloxy)carbonyl]amino}cyclohexanecarboxylate To a solution of methyl (1S,2R,4R)-2-{[(benzyloxy)carbonyl]amino}-4-[(methylsulfonyl)oxy]cyclohexanecarboxylate (0.30 g, 0.78 mmol) in N,N-dimethylformamide (2.6 mL) was added sodium azide (0.20 g, 3.1 mmol). The reaction was heated to 80° C. and stirred for 2.5 h. After cooling, the reaction mixture was poured into sat. NaHCO$_3$/water and extracted with EtOAc (3×). The combined extracts were washed with brine, dried (Na$_2$SO$_4$), and concentrated. The crude was purified on silica gel, eluting with 0-40% EtOAc in hexanes to give 187 mg (72%) of the desired product as a clear gum. LCMS calculated for C$_{16}$H$_{21}$N$_2$O$_4$ (M+H-28)$^+$: m/z=305.2; Found: 305.1.

Step 6. Benzyl [(1R,2R,5S)-5-amino-2-(cyanomethyl)cyclohexyl]carbamate

To a mixture of benzyl [(1R,2R,5S)-5-azido-2-(cyanomethyl)cyclohexyl]carbamate (45 mg, 0.14 mmol) in tetrahydrofuran (1.5 mL) was added water (13 µL, 0.73 mmol) and resin of triphenylphosphine (150 mg, 0.29 mmol). The resulting mixture was stirred overnight at room temperature. The mixture was filtered and dried in vacuo to give 32 mg of crude product. LCMS calculated for C$_{16}$H$_{22}$N$_3$O$_2$ (M+H)$^+$: m/z=288.2; Found: 288.0. The crude was used without further purification.

Step 7. Benzyl {(1R,2R,5S)-2-(cyanomethyl)-5-[(6-nitrothieno[3,2-b]pyridin-7-yl)amino]cyclohexyl}carbamate A mixture of 7-chloro-6-nitrothieno[3,2-b]pyridine (22.0 mg, 0.102 mmol), benzyl [(1R,2R,5S)-5-amino-2-(cyanomethyl)cyclohexyl]carbamate (32 mg, 0.11 mmol) and triethylamine (35.7 µL, 0.256 mmol) in isopropyl alcohol (0.4 mL) was stirred at 90° C. for 2 h. The mixture was cooled and purified on silica gel, eluted with 10-90% EtOAc in hexanes to give 28 mg (59%) of the desired product. LCMS calculated for C$_{23}$H$_{24}$N$_5$O$_4$S (M+H)$^+$: m/z=466.2; Found: 466.1.

Step 8. Benzyl [(1R,2R,5S)-5-[(6-aminothieno[3,2-b]pyridin-7-yl)amino]-2-(cyanomethyl)cyclohexyl]carbamate A mixture of benzyl {(1R,2R,5S)-2-(cyanomethyl)-5-[(6-nitrothieno[3,2-b]pyridin-7-yl)amino]cyclohexyl}carbamate (28 mg, 0.060 mmol) and 10% palladium on carbon (7.0 mg) in methanol (0.44 mL) was stirred under an atmosphere of H$_2$ (balloon) for 3 h. The mixture was filtered and concentrated to give 26 mg of the desired product. LCMS calculated for C$_{23}$H$_{26}$N$_5$O$_2$S (M+H)$^+$: m/z=436.2; Found: 436.0.

Step 9. Benzyl ((1R,2R,5S)-2-(cyanomethyl)-5-{2-[(1R)-1-hydroxyethyl]-1H-imidazo[4,5-d]thieno[3,2-b]pyridin-1-yl}cyclohexyl)carbamate A mixture of (2R)-2-hydroxypropanamide (17.1 mg, 0.192 mmol) and triethyloxonium tetrafluoroborate (34.2 mg, 0.180 mmol) in tetrahydrofuran (0.36 mL) was stirred at room temperature for 75 min and then concentrated. The residue was dissolved in ethanol (0.14 mL), and this solution was then added to a solution of benzyl [(1R,2R,5S)-5-[(6-aminothieno[3,2-b]pyridin-7-yl)amino]-2-(cyanomethyl)cyclohexyl]carbamate (26 mg, 0.060 mmol) in ethanol (0.36 mL) in a vial. The resulting mixture was stirred at 80° C. overnight. After cooling, the mixture was concentrated and purified on silica gel, eluted with 0-10% MeOH in dichloromethane to give 18 mg of the desired product. LCMS calculated for C$_{26}$H$_{28}$N$_5$O$_3$S (M+H)$^+$: m/z=490.2; Found: 490.0.

Step 10. ((1R,2R,4S)-2-Amino-4-{2-[(1R)-1-hydroxyethyl]-1H-imidazo[4,5-d]thieno[3,2-b]pyridin-1-yl}cyclohexyl)acetonitrile A mixture of benzyl ((1R,2R,5S)-2-(cyanomethyl)-5-{2-[(1R)-1-hydroxyethyl]-1H-imidazo[4,5-d]thieno[3,2-b]pyridin-1-yl}cyclohexyl)carbamate (18 mg, 0.037 mmol) and 10% palladium on carbon (24 mg) in methanol (0.27 mL) was stirred under an atmosphere of H$_2$ (balloon) overnight. The mixture was filtered and concentrated. The crude was purified using prep-LCMS (XBridge C18 column, eluting with a gradient of acetonitrile/water containing 0.1% ammonium hydroxide, at flow rate of 30 mL/min) to give 3.2 mg of the desired product. LCMS calculated for C$_{18}$H$_{22}$N$_5$OS (M+H)$^+$: m/z=356.2; Found: 356.1.

Example 68. {(2R,5S)-5-[2-(1-Aminoethyl)-1H-imidazo[4,5-d]thieno[3,2-b]pyridin-1-yl]tetrahydro-2H-pyran-2-yl}acetonitrile Trifluoro Acetate

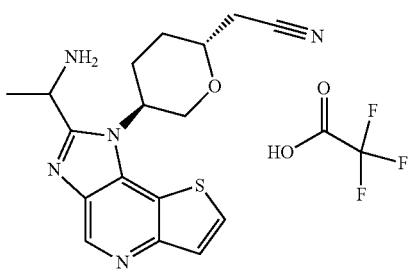

Step 1. [(2R,5S)-5-(2-Acetyl-1H-imidazo[4,5-d]thieno[3,2-b]pyridin-1-yl)tetrahydro-2H-pyran-2-yl]acetonitrile To a solution of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile (154 mg, 0.450 mmol) in methylene chloride (2.0 mL) was added sodium bicarbonate (110 mg, 1.31 mmol) followed by Dess-Martin periodinane (219 mg, 0.517 mmol). The resulting mixture was stirred at room temperature for 3 h. The mixture was diluted with dichloromethane, filtered, and concentrated. The crude was purified on silica gel, eluted with 0-10% MeOH in dichloromethane to give 250 mg of crude product as a white gum. LCMS calculated for C$_{17}$H$_{17}$N$_4$O$_2$S (M+H)$^+$: m/z=341.1; Found: 341.0 (M+H). $^1$H NMR (400 MHz, CDCl$_3$) δ 9.23 (s, 1H), 7.77 (s, 2H), 4.52 (t, J=11.1 Hz, 1H), 4.07 (dd, J=10.1 and 4.4 Hz, 2H), 2.92-2.81 (m, 3H), 2.70-2.64 (m, 2H), 2.21-2.09 (m, 2H), 1.83 (qd, J=13.4 and 4.7 Hz, 1H), 1.62 (s, 2H) ppm.

Step 2. {(2R,5S)-5-[2-(1-Aminoethyl)-1H-imidazo[4,5-d]thieno[3,2-b]pyridin-1-yl]tetrahydro-2H-pyran-2-yl}acetonitrile Trifluoroacetate

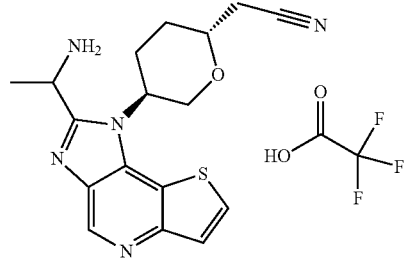 [SMILES: CC(N)c1nc2cnc3ccsc3c2n1[C@H]1CC[C@H](CC#N)OC1 ; O=C(O)C(F)(F)F]

A mixture of [(2R,5S)-5-(2-acetyl-1H-imidazo[4,5-d]thieno[3,2-b]pyridin-1-yl)tetrahydro-2H-pyran-2-yl]acetonitrile (0.10 g, 0.18 mmol), ammonium acetate (136 mg, 1.76 mmol) and sodium cyanoborohydride (28 mg, 0.44 mmol) in methanol (0.4 mL)/acetonitrile (0.4 mL) was heated at 65° C. overnight. The mixture was cooled and purified using RP-HPLC (XBridge C18 column, eluting with a gradient of acetonitrile/water containing 0.05% TFA, at flow rate of 30 mL/min) to give 27 mg (46%) of the desired product. LCMS calculated for C$_{17}$H$_{20}$N$_5$OS (M+H)$^+$: m/z=342.1; Found: 342.0.

Example 69. N-(1-{1-[(3S,6R)-6-(Cyanomethyl)tetrahydro-2H-pyran-3-yl]-1H-imidazo[4,5-d]thieno[3,2-b]pyridin-2-yl}ethyl) acetamide

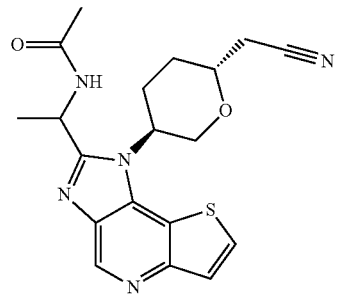 [SMILES: CC(=O)NC(C)c1nc2cnc3ccsc3c2n1[C@H]1CC[C@H](CC#N)OC1]

To a mixture of {(2R,5S)-5-[2-(1-aminoethyl)-1H-imidazo[4,5-d]thieno[3,2-b]pyridin-1-yl]tetrahydro-2H-pyran-2-yl}acetonitrile trifluoroacetate (8.0 mg, 0.018 mmol) (Example 68) and triethylamine (12 μL, 0.088 mmol) in methylene chloride (0.15 mL) was added acetyl chloride (2.0 μL, 0.028 mmol). The resulting mixture was stirred at room temperature for 3 h and then concentrated. The residue was purified using RP-HPLC (XBridge C18 column, eluting with a gradient of acetonitrile/water containing 0.1% ammonium hydroxide, at flow rate of 30 mL/min) to give 3.5 mg (52%) of the desired product. LCMS calculated for C$_{19}$H$_{22}$N$_5$O$_2$S (M+H): m/z=384.1; Found: 384.2.

Example 70. ((2R,5S)-5-{2-[1-(Methylamino)ethyl]-1H-imidazo[4,5-d]thieno[3,2-b]pyridin-1-yl}tetrahydro-2H-pyran-2-yl)acetonitrile

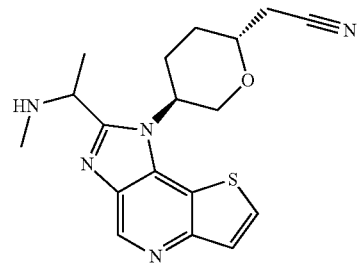 [SMILES: CNC(C)c1nc2cnc3ccsc3c2n1[C@H]1CC[C@H](CC#N)OC1]

To a cooled mixture of {(2R,5S)-5-[2-(1-hydroxyethyl)-1H-imidazo[4,5-d]thieno[3,2-b]pyridin-1-yl]tetrahydro-2H-pyran-2-yl}acetonitrile (10.1 mg, 0.0295 mmol) and triethylamine (12 μL, 0.088 mmol) in methylene chloride (0.18 mL) was added methanesulfonyl chloride (2.7 μL, 0.035 mmol). The resulting mixture was allowed to warm to room temperature and stirred overnight. The mixture was diluted with dichloromethane and washed with water (2×). The layers were separated and the organic concentrated. To the concentrate was added methylene chloride (0.2 mL), triethylamine (18 uL), and methylammonium chloride (6.0 mg, 0.088 mmol). The resulting mixture was stirred at room temperature over the weekend (64 h) then heated to 40° C. for 3 h. The mixture was concentrated then purified using RP-HPLC (XBridge C18 column, eluting with a gradient of acetonitrile/water containing 0.1% ammonium hydroxide, at flow rate of 30 mL/min) to give 2 mg (19%) of the desired product. LCMS calculated for $C_{18}H_{22}N_5OS$ $(M+H)^+$: m/z=356.2; Found: 356.1.

Example 71. {(2R,5S)-5-[2-(1-Fluoroethyl)-1H-imidazo[4,5-d]thieno[3,2-b]pyridin-1-yl]tetrahydro-2H-pyran-2-yl}acetonitrile

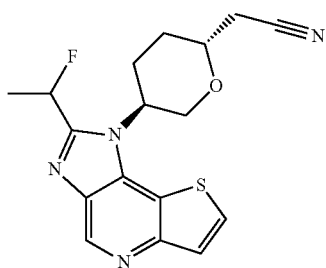

To a cooled mixture of {(2R,5S)-5-[2-(1-hydroxyethyl)-1H-imidazo[4,5-d]thieno[3,2-b]pyridin-1-yl]tetrahydro-2H-pyran-2-yl}acetonitrile (8.0 mg, 0.023 mmol) in methylene chloride (0.2 mL) was added 2-methoxy-N-(2-methoxyethyl)-N-(trifluoro-λ(4)-sulfanyl)ethanamine (4.7 μL, 0.026 mmol) (Deoxo-Fluor). The resulting mixture was warmed to room temperature and stirred overnight. Additional Deoxo-Fluor (5 uL) was added. After 6 h, the reaction was quenched with a few drops of water then concentrated. The residue was purified using RP-HPLC (XBridge C18 column, eluting with a gradient of acetonitrile/water containing 0.1% ammonium hydroxide, at flow rate of 30 mL/min) to give 1.6 mg (20%) of the desired product. LCMS calculated for $C_{17}H_{18}FN_4OS$ (M+H): m/z=345.1; Found: 345.0.

Example 72. [4-(Hydroxymethyl)-4-(1H-imidazo[4,5-d]thieno[3,2-b]pyridin-1-yl)cyclohexyl]acetonitrile

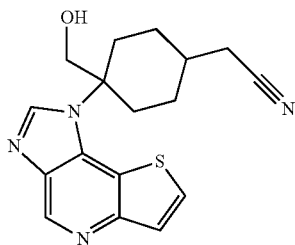 [SMILES: N#CCC1CCC(CO)(n2cnc3cnc4ccsc4c32)CC1]

Step 1. (8-Amino-1,4-dioxaspiro[4,5]dec-8-yl)methanol

Lithium tetrahydroaluminate (189 mg, 4.97 mmol) was added in portions to a solution of 8-amino-1,4-dioxaspiro[4.5]decane-8-carboxylic acid (from Aldrich, 0.50 g, 2.5 mmol) in tetrahydrofuran (20 mL) with stirring at about 0° C. The resulting mixture was slowly warmed to room temperature and stirred overnight. Fieser workup (0.2 mL $H_2O$, 0.2 mL 10% NaOH, 0.6 mL $H_2O$) was performed followed by filtration through Celite and concentrated to give 0.41 g of the desired product to be used without further purifications. LCMS calculated for $C_9H_{18}NO_3$ $(M+H)^+$: m/z=188.1; Found: 188.0.

Step 2. {8-[(6-Nitrothieno[3,2-b]pyridin-7-yl)amino]-1,4-dioxaspiro[4,5]dec-8-yl}methanol A mixture of 7-chloro-6-nitrothieno[3,2-b]pyridine (229 mg, 1.07 mmol), (8-amino-1,4-dioxaspiro[4,5]dec-8-yl)methanol (240 mg, 1.28 mmol) and triethylamine (300 μL, 2 mmol) in isopropyl alcohol (3.5 mL) was stirred at 90° C. overnight. After cooling to room temperature, water was added, which caused more solids to form. The solids were filtered, washed with water, and dried to give 219 mg (56%) of the desired product. LCMS calculated for $C_{16}H_{20}N_3O_5S$ $(M+H)^+$: m/z=366.1; Found: 366.1. $^1H$ NMR (300 MHz, $CDCl_3$) δ 8.93 (s, 1H), 7.78-7.75 (m, 2H), 4.17 (s, 2H), 4.02-3.84 (m, 4H), 2.52 (d, J=13.3 Hz, 2H), 2.12-1.82 (m, 4H), 1.78-1.44 (m, 4H) ppm.

Step 3. {8-[(6-Aminothieno[3,2-b]pyridin-7-yl)amino]-1,4-dioxaspiro[4,5]dec-8-yl}methanol To a mixture of {8-[(6-nitrothieno[3,2-b]pyridin-7-yl)amino]-1,4-dioxaspiro[4,5]dec-8-yl}methanol (219 mg, 0.599 mmol) in methanol (4.5 mL) was added 10% palladium on carbon (76 mg). The mixture was stirred under an atmosphere of $H_2$ (balloon) for 2 d. The mixture was filtered through Celite and concentrated to give 0.20 g of the crude product, which was used directly in the next step without further purifications. LCMS calculated for $C_{16}H_{22}N_3O_3S$ $(M+H)^+$: m/z=336.1; Found: 336.2.

Step 4. [8-(1H-Imidazo[4,5-d]thieno[3,2-b]pyridin-1-yl)-1,4-dioxaspiro[4,5]dec-8-yl]methanol A mixture of {8-[(6-aminothieno[3,2-b]pyridin-7-yl)amino]-1,4-dioxaspiro[4,5]dec-8-yl}methanol (90.0 mg, 0.268 mmol), ethyl orthoformate (112 μL, 0.671 mmol), and p-toluenesulfonic acid monohydrate (5.1 mg, 0.027 mmol) in toluene (3.0 mL) was stirred at 85° C. overnight. The mixture was diluted with EtOAc, then washed with sat. sodium bicarbonate and brine. The organic layer was dried ($Na_2SO_4$), filtered and concentrated to give 50 mg (50%) of the desired product. LCMS calculated for $C_{17}H_{20}N_3O_3S$ $(M+H)^+$: m/z=346.1; Found: 346.0.

Step 5. 4-(Hydroxymethyl)-4-(1H-imidazo[4,5-d]thieno[3,2-b]pyridin-1-yl)cyclohexanone A mixture of [8-(1H-imidazo[4,5-d]thieno[3,2-b]pyridin-1-yl)-1,4-dioxaspiro[4,5]dec-8-yl]methanol (0.13 g, 0.38 mmol) and 3.0 M hydrogen chloride in water (2.0 mL, 6.0 mmol) in acetone (5 mL) was stirred at room temperature for 5 h and then at 60° C. for 1 h. After cooling, the mixture was made slightly basic by the addition of 2.0 N NaOH. The mixture was extracted with EtOAc (3×). The combined extracts were dried ($Na_2SO_4$), filtered, and concentrated. The crude was purified on silica gel, eluted with 0-15% MeOH in dichloromethane to give 56 mg (49%) of the desired product. LCMS calculated for $C_{15}H_6N_3O_2S$ (M+H)$^+$: m/z=302.1; Found: 302.1.

Step 6. [4-(Hydroxymethyl)-4-(1H-imidazo[4,5-d]thieno[3,2-b]pyridin-1-yl)cyclohexylidene]acetonitrile To a solution of diethyl cyanomethylphosphonate (38.6 mg, 0.218 mmol) in tetrahydrofuran (0.5 mL) stirring at about 0° C. was added sodium hydride (10.5 mg, 0.262 mmol). To this was added a solution of 4-(hydroxymethyl)-4-(1H-imidazo[4,5-d]thieno[3,2-b]pyridin-1-yl)cyclohexanone (56 mg, 0.18 mmol) in N,N-dimethylformamide (0.45 mL). The mixture was allowed to warm to room temperature and stirred overnight. The reaction was quenched with water, causing formation of solids. The solids were filtered to give 18 mg of pure desired product. The filtrate was diluted with EtOAc, washed with water, and concentrated to give an additional 39 mg of the crude product. LCMS calculated for $C_{17}H_{17}N_4OS$ (M+H)$^+$: m/z=325.1; Found: 325.0. H NMR (300 MHz, CDCl$_3$) δ 8.37 (s, 1H), 8.15 (s, 1H), 7.47 (d, J=5.6 Hz, 1H), 7.18 (d, J=5.6 Hz, 1H), 5.20 (s, 1H), 4.34 (s, 2H), 2.80 (d, J=4.0 Hz, 3H), 2.59-2.29 (m, 4H), 1.26 (d, J=15.3 Hz, 2H) ppm.

Step 7. [4-(Hydroxymethyl)-4-(1H-imidazo[4,5-d]thieno[3,2-b]pyridin-1-yl)cyclohexyl]acetonitrile A mixture of [4-(hydroxymethyl)-4-(1H-imidazo[4,5-d]thieno[3,2-b]pyridin-1-yl)cyclohexylidene]acetonitrile (18 mg, 0.055 mmol) and 10% palladium on carbon (5.9 mg) in methanol (0.6 mL) was stirred under an atmosphere of H$_2$ (balloon) for 4.5 h. The mixture was filtered through a pad of Celite and concentrated. The crude residue was purified using RP-HPLC (XBridge C18 column, eluting with a gradient of acetonitrile/water containing 0.1% ammonium hydroxide, at flow rate of 30 mL/min) to give two isomers. On analytic HPLC (Waters SunFire C18, 2.1×50 mm, 5 µM; flow rate 3 mL/min; Injection volume 2 µL; at gradient from 2 to 80% B in 3 minutes (A=water with 0.025% TFA, B=acetonitrile)): First peak retention time 1.05 min, LCMS calculated for $C_{17}H_{19}N_4OS$ (M+H)$^+$: m/z=327.1; Found: 327.0. Second peak retention time 1.13 min, LCMS calculated for $C_{17}H_{19}N_4OS$ (M+H)$^+$: m/z=327.1; Found: 327.0.

Example 73. {(2R,5S)-5-[2-(Cyanomethyl)-1H-imidazo[4,5-d]thieno[3,2-b]pyridin-1-yl]tetrahydro-2H-pyran-2-yl}acetonitrile

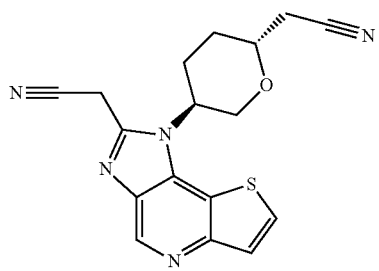 [SMILES: N#CCc1nc2cnc3ccsc3c2n1[C@H]1CC[C@H](CC#N)OC1]

Step 1. Tert-Butyl [(3S)-6-(hydroxymethyl)tetrahydro-2H-pyran-3-yl]carbamate

{(5S)-5-[(tert-Butoxycarbonyl)amino]-5,6-dihydro-2H-pyran-2-yl}methyl acetate (from example 19, step 5) (3.47 g, 12.8 mmol) and 10% palladium on carbon (1.4 g) in methanol (60 mL) was stirred under a H$_2$ balloon at room temperature for 2 h. The reaction mixture was filtered and the filtrate was treated with 1.0 M sodium hydroxide in water (12 mL). After stirring for 4 h, the reaction solution was concentrated and diluted with ethyl acetate. The organic layer was separated and washed with brine, dried over Na$_2$SO$_4$, and concentrated. The residue was purified with prep-LCMS (XBridge C18 column, eluting with a gradient of acetonitrile/water containing 0.1% ammonium hydroxide, at flow rate of 60 mL/min) to give the desired product (0.77 g, 26%). LCMS calculated for $C_6H_{14}NO_2$ (M-100+H)$^+$: m/z=132.1; Found: 132.1.

Step 2. {(5S)-5-[(tert-Butoxycarbonyl)amino]tetrahydro-2H-pyran-2-yl}methyl Methanesulfonate tert-Butyl [(3S)-6-(hydroxymethyl)tetrahydro-2H-pyran-3-yl]carbamate (331 mg, 1.43 mmol) in dichloromethane (5 mL) was treated with methanesulfonyl chloride (0.222 mL, 2.87 mmol) at 0° C. The mixture was stirred at 0° C. for 1 h, then concentrated and partitioned between ethyl acetate and water. The organic phase was concentrated and purified on silica gel (eluting with a gradient of 0 to 50% ethyl acetate in hexanes) to give the desired product (0.38 g, 86%). LCMS calculated for $C_8H_{16}NO_6S$ (M-t-Bu+H)$^+$: m/z=254.1; Found: 254.0.

Step 3. [(5S)-5-Aminotetrahydro-2H-pyran-2-yl]acetonitrile

A mixture of {(5S)-5-[(tert-butoxycarbonyl)amino]tetrahydro-2H-pyran-2-yl}methyl methanesulfonate (308 mg, 0.996 mmol) and sodium cyanide (58 mg, 1.2 mmol) in DMSO (3 mL) was stirred at 90° C. overnight. After cooling to room temperature, the mixture was partitioned between ethyl acetate and brine. The organic layer was washed with water and brine, dried over Na$_2$SO$_4$, and concentrated to give the cyano intermediate. A solution of the intermediate in dichloromethane (4 mL) was treated with 4 M HCl in dioxane (2 mL) and the mixture was stirred at room temperature for 2 h, then concentrated to give the desired product as HCl salt. (42 mg, 30%). LCMS calculated for $C_7H_{13}N_2O$ (M+H)$^+$: m/z=141.1; Found: 141.1.

Step 4. {(2R,5S)-5-[(6-Nitrothieno[3,2-b]pyridin-7-yl)amino]tetrahydro-2H-pyran-2-yl}acetonitrile and {(2S,5S)-5-[(6-nitrothieno[3,2-b]pyridin-7-yl)amino]tetrahydro-2H-pyran-2-yl}acetonitrile 7-Chloro-6-nitrothieno[3,2-b]pyridine (1.18 g, 5.52 mmol), [(5S)-5-aminotetrahydro-2H-pyran-2-yl]acetonitrile hydrochloride (1.01 g, 5.72 mmol) and N,N-diisopropylethylamine (2.0 mL, 12 mmol) in isopropyl alcohol (13 mL) was heated at 50° C. overnight. The solvent was removed and the solid was dissolve in dichloromethane and purified with flash chromatography (20-90% ethyl acetate/hexanes) to give two fractions. On the analytical HPLC (Waters SunFire C18, 2.1×50 mm, 5 uM, with injection volume 2 uL and flow rate 3 mL/min, at gradient from 2 to 80% B in 3 minutes (A=water with 0.025% TFA; B=acetonitrile)): First fraction retention time 1.715 min, LCMS calculated for $C_{14}H_{15}N_4O_3S$ (M+H)$^+$: m/z=319.1; Found: 319.1; Second fraction retention time 1.561 min, LCMS calculated for $C_{14}H_{15}N_4O_3S$ (M+H)$^+$: m/z=319.1; Found: 319.1.

Step 5. {(2R,5S)-5-[(6-Aminothieno[3,2-b]pyridin-7-yl)amino]tetrahydro-2H-pyran-2-yl}acetonitrile {(2R,5S)-5-[(6-Nitrothieno[3,2-b]pyridin-7-yl)amino]tetrahydro-2H-pyran-2-yl}acetonitrile (712 mg, 2.24 mmol) (first fraction from last step) and 10% palladium on carbon (360 mg) in methanol (15 mL) was subjected to balloon pressure of $H_2$ at room temperature for 2 h. The reaction mixture was filtered and concentrated and purified with flash chromatography (15% methanol/dichloromethane) to give the desired product (604 mg, 94%). LCMS calculated for $C_{14}H_{17}N_4OS$ (M+H)$^+$: m/z=289.1; Found: 289.0.

Step 6. {(2R,5S)-5-[2-(Cyanomethyl)-1H-imidazo[4,5-d]thieno[3,2-b]pyridin-1-yl]tetrahydro-2H-pyran-2-yl}acetonitrile A mixture of 2-cyanoacetamide (80.8 mg, 0.960 mmol) and triethyloxonium tetrafluoroborate (181 mg, 0.952 mmol) in THF (2 mL) was stirred at room temperature for 2 h. The solvent was removed and the residue dissolved in ethanol (0.6 mL) and added to a suspension of {(2R,5S)-5-[(6-aminothieno[3,2-b]pyridin-7-yl)amino]tetrahydro-2H-pyran-2-yl}acetonitrile (85.0 mg, 0.295 mmol) in ethanol (2 mL). The resulting mixture was stirred at 55° C. overnight. The reaction was cooled to room temperature and the solid was filtered. The filtrate was purified with preparative LCMS (XBridge C18 column, eluting with a gradient of acetonitrile/water containing 0.05% TFA, at flow rate of 60 mL/min) to give the desired product as TFA salt. LCMS calculated for $C_{17}H_{16}N_5OS$ (M+H)$^+$: m/z=338.1; Found: 338.3. $^1$H NMR (DMSO-$d_6$, 500 MHz) δ 9.24 (s, 1H), 8.22 (d, J=5.5 Hz, 1H), 7.77 (d, J=5.5 Hz, 1H), 4.89 (s, 2H), 4.67 (br s, 1H), 4.20 (m, 2H), 4.00 (s, 1H), 2.96 (dd, J=17.0, 4.3 Hz, 1H), 2.84 (dd, J=17.0, 6.6 Hz, 1H), 2.49 (m, 1H), 2.29 (m, 1H), 2.06 (m, 1H), 1.72 (m, 1H) ppm.

Example 74. {(2S,5S)-5-[2-(Cyanomethyl)-1H-imidazo[4,5-d]thieno[3,2-b]pyridin-1-yl]tetrahydro-2H-pyran-2-yl}acetonitrile

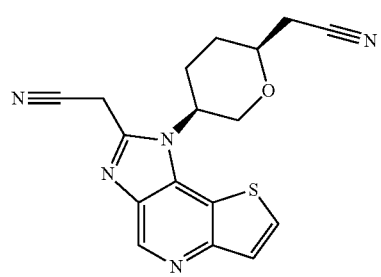 [SMILES: N#CCc1nc2cnc3ccsc3c2n1[C@H]1CC[C@@H](CC#N)OC1]

Step 1. {(2S,5S)-5-[(6-Aminothieno[3,2-b]pyridin-7-yl)amino]tetrahydro-2H-pyran-2-yl}acetonitrile This compound was prepared according to the procedure described in Example 73, Step 5, using {(2S,5S)-5-[(6-nitrothieno[3,2-b]pyridin-7-yl)amino]tetrahydro-2H-pyran-2-yl}acetonitrile (fraction 2, from Example 73, step 4) instead of {(2R,5S)-5-[(6-nitrothieno[3,2-b]pyridin-7-yl)amino]tetrahydro-2H-pyran-2-yl}acetonitrile as starting material. LCMS calculated for $C_{14}H_{17}N_4OS$ (M+H)$^+$: m/z=289.1; Found: 289.0.

Step 2. {(2S,5S)-5-[2-(Cyanomethyl)-1H-imidazo[4,5-d]thieno[3,2-b]pyridin-1-yl]tetrahydro-2H-pyran-2-yl}acetonitrile This compound was prepared according to the procedure described in Example 73, Step 6, using {(2S,5S)-5-[(6-aminothieno[3,2-b]pyridin-7-yl)amino]tetrahydro-2H-pyran-2-yl}acetonitrile instead of {(2R,5S)-5-[(6-aminothieno[3,2-b]pyridin-7-yl)amino]tetrahydro-2H-pyran-2-yl}acetonitrile as starting material. LCMS calculated for $C_{17}H_{16}N_5OS$ (M+H)$^+$: m/z=338.1; Found: 338.3.

Example 75. N-[((2R,5S)-5-{2-[(1R)-1-Hydroxyethyl]-1H-imidazo[4,5-d]thieno[3,2-b]pyridin-1-yl}tetrahydro-2H-pyran-2-yl)methyl]methanesulfonamide

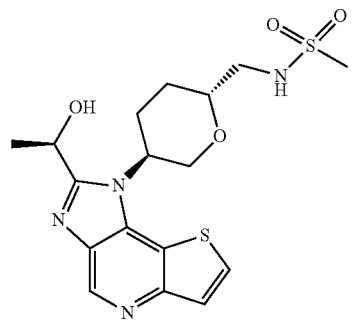 [SMILES: C[C@@H](O)c1nc2cnc3ccsc3c2n1[C@H]1CC[C@H](CNS(C)(=O)=O)OC1]

Step 1. (1R)-1-{1-[(3S,6R)-6-(Azidomethyl)tetrahydro-2H-pyran-3-yl]-1H-imidazo[4,5-d]thieno[3,2-b]pyridin-2-yl}ethanol A mixture of ((2R,5S)-5-{2-[(1R)-1-hydroxyethyl]-1H-imidazo[4,5-d]thieno[3,2-b]pyridin-1-yl}tetrahydro-2H-pyran-2-yl)methyl 4-methylbenzenesulfonate (25 mg, 0.052 mmol) and sodium azide (5.0 mg, 0.077 mmol) in DMF (0.5 mL) was stirred at 60° C. overnight. After cooling to room temperature, the mixture was diluted with methanol and purified with prep-LCMS (XBridge C18 column, eluting with a gradient of acetonitrile/water containing 0.1% ammonium hydroxide, at flow rate of 60 mL/min) to give desired product (12 mg, 65%). LCMS calculated for $C_{16}H_{19}N_6O_2S$ (M+H)$^+$: m/z=359.1; Found: 359.0.

Step 2. (1R)-1-{1-[(3S,6R)-6-(Aminomethyl)tetrahydro-2H-pyran-3-yl]-1H-imidazo[4,5-d]thieno[3,2-b]pyridin-2-yl}ethanol A solution of (1R)-1-{1-[(3S,6R)-6-(azidomethyl)tetrahydro-2H-pyran-3-yl]-1H-imidazo[4,5-d]thieno[3,2-b]pyridin-2-yl}ethanol (12 mg, 0.034 mmol) in methanol (0.2 mL) was added 10% palladium on carbon (5.7 mg). The resulting mixture was stirred under $H_2$ balloon overnight. The reaction mixture was filtered through a pad of Celite and washed with methanol. The solvent was removed under reduced pressure to give the desired product (11 mg, 99%). LCMS calculated for $C_{16}H_{21}N_4O_2S$ (M+H)$^+$: m/z=333.1; Found: 333.1.

Step 3. N-[((2R,5S)-5-{2-[(1R)-1-Hydroxyethyl]-1H-imidazo[4,5-d]thieno[3,2-b]pyridin-1-yl}tetrahydro-2H-pyran-2-yl)methyl]methanesulfonamide To a solution of (1R)-1-{1-[(3S,6R)-6-(aminomethyl)tetrahydro-2H-pyran-3-yl]-1H-imidazo[4,5-d]thieno[3,2-b]

pyridin-2-yl}ethanol (11 mg, 0.033 mmol) in methanol (0.5 mL) was added N,N-diisopropylethylamine (17 μL, 0.099 mmol) and methanesulfonyl chloride (2.8 μL, 0.036 mmol). After stirring for 0.5 h, another equivalent of methanesulfonyl chloride was added. After stirring for 20 min, The reaction solution was diluted with methanol and purified with prep-LCMS (XBridge C18 column, eluting with a gradient of acetonitrile/water containing 0.1% ammonium hydroxide, at flow rate of 30 mL/min) to give the desired product (5 mg, 37%). LCMS calculated for $C_{17}H_{23}N_4O_4S_2$ (M+H)$^+$: m/z=411.1; Found: 411.1.

Example 76. Isopropyl [((2R,5S)-5-{2-[(1R)-1-hydroxyethyl]-1H-imidazo[4,5-d]thieno[3,2-b]pyridin-1-yl}tetrahydro-2H-pyran-2-yl)methyl]carbamate

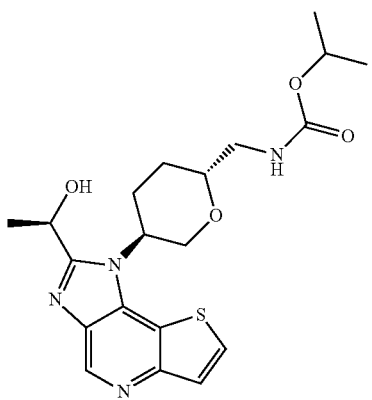 [SMILES: CC(C)OC(=O)NC[C@H]1CC[C@H](n2c([C@@H](C)O)nc3cnc4ccsc4c32)CO1]

To a solution of (1R)-1-{1-[(3S,6R)-6-(aminomethyl)tetrahydro-2H-pyran-3-yl]-1H-imidazo[4,5-d]thieno[3,2-b]pyridin-2-yl}ethanol (11 mg, 0.032 mmol) and triethylamine (22 μL, 0.16 mmol) in methylene chloride (1 mL) was added 1.0 M isopropyl chloroformate in toluene (39 μL). The mixture was stirred at room temperature for 1 h, then stripped to dryness and purified on prep-LCMS (XBridge C18 column, eluting with a gradient of acetonitrile/water containing 0.1% ammonium hydroxide, at flow rate of 30 mL/min) to give the desired product (0.9 mg, 7%). LCMS calculated for $C_{20}H_{27}N_4O_4S$ (M+H)$^+$: m/z=419.2; Found: 419.0.

Example 77. [trans-4-(8-Methylpyrazolo[1,5-c]thieno[2,3-e]pyrimidin-9-yl)cyclohexyl]acetonitrile

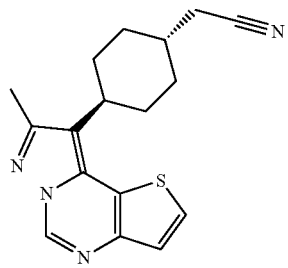 [SMILES: CC(=N)/C(=C1\NC=Nc2ccsc21)[C@H]1CC[C@H](CC#N)CC1]

Step 1. 4-(Hydroxymethyl)cyclohexanol

To a suspension of lithium tetrahydroaluminate (3.11 g, 81.9 mmol) in THF (158 mL) was added a solution of ethyl 4-hydroxycyclohexanecarboxylate (9.40 g, 54.6 mmol) in THF (20 mL) at 0° C. After stirring for 30 min at same temperature, the reaction was quenched with water (10 mL) dropwise, then 15% NaOH solution (10 mL) and water (30 mL). After stirring for 10 min, the reaction mixture was filtered through a pad of Celite, the organic layer was wash with brine, dried over $Na_2SO_4$, filtered and concentrated in vacuo. The residue was purified by flash chromatography (0-100% ethyl acetate/hex) to give the desired product as white solid (6.9 g, 97%).

Step 2. (cis-4-Hydroxycyclohexyl)methyl 4-methylbenzenesulfonate and (trans-4-Hydroxycyclohexyl)methyl 4-methylbenzenesulfonate To a solution of 4-(hydroxymethyl)cyclohexanol (6.80 g, 52.2 mmol) in dichloromethane (400 mL) and pyridine (10.6 mL, 130 mmol) was added p-toluenesulfonyl chloride (11.0 g, 57.4 mmol) and 4-dimethylaminopyridine (410 mg, 3.3 mmol). The reaction mixture was stirred at room temperature overnight. The reaction mixture was diluted with 1 N HCl solution and extracted with dichloromethane. The combined organics were dried over $Na_2SO_4$, filtered and concentrated. The crude was purified with flash chromatography (eluting with a gradient 0-50% ethyl acetate in hexanes) to give two fractions. On the analytical HPLC (Waters SunFire C18, 2.1×50 mm, 5 uM, with injection volume 2 uL and flow rate 3 mL/min, at gradient from 2 to 80% B in 3 minutes (A=water with 0.025% TFA; B=acetonitrile)): First fraction retention time 2.319 min, LCMS calculated for $C_{14}H_{21}O_4S$ (M+H)$^+$: m/z=285.1; Found: 285.0; $^1$H NMR $^1$H NMR (300 MHz, CDCl$_3$) δ 7.77 (d, J=8.3 Hz, 1H), 7.33 (d, J=8.1 Hz, 1H), 3.97 (br s, 1H), 3.83 (d, J=6.8 Hz, 2H), 2.44 (s, 3H), 1.76-1.58 (m, 6H), 1.48 (m, 3H) ppm. Second fraction retention time 2.222 min, LCMS calculated for $C_{14}H_{21}O4S$ (M+H)$^+$: m/z=285.1; Found: 285.0. $^1$H NMR (300 MHz, CDCl$_3$) δ 7.77 (d, J=8.3 Hz, 2H), 7.45 (d, J=8.3 Hz, 2H), 3.82 (d, J=6.4 Hz, 2H), 3.51 (m, 1H), 2.50 (d, J=8.0 Hz, 0H), 2.44 (s, 3H), 2.14-1.90 (m, 2H), 1.80-1.52 (m, 3H), 1.45-1.09 (m, 2H), 1.09-0.87 (m, 2H) ppm.

Step 3. (cis-4-Hydroxycyclohexyl)acetonitrile

A mixture of (cis-4-hydroxycyclohexyl)methyl 4-methylbenzenesulfonate (6.9 g, 24 mmol) (first fraction from last step), sodium cyanide (1.43 g, 29.1 mmol) and DMF (86 mL) was stirred at 80° C. for 1 h. After cooling to room temperature, the mixture was diluted with ethyl acetate and water. The aqueous layer was extracted with ethyl acetate once. The combined organic layers were dried over $Na_2SO_4$ and concentrated. The crude was purified with flash chromatography (eluting with a gradient of 0-50% ethyl acetate in hexanes) to give the desired product (2.5 g, 74%). $^1$H NMR (300 MHz, CDCl$_3$) δ 3.58 (m, 1H), 2.27 (d, J=6.3 Hz, 2H), 2.02 (m, 2H), 1.88 (m, 2H), 1.78-1.45 (m, 2H), 1.42-1.07 (m, 4H) ppm.

Step. 4. (trans-4-Iodocyclohexyl)acetonitrile

To a solution of (cis-4-hydroxycyclohexyl)acetonitrile (2.50 g, 18.0 mmol) in dichloromethane (80 mL) at 0° C. was added 1H-imidazole (1.47 g, 21.6 mmol), triphenylphosphine (5.65 g, 21.6 mmol), and followed by iodine (5.47 g, 21.6 mmol) in several portions over a period of 45 min. The resulting suspension was gradually allowed to warm to room temperature. After stirring at room temperature overnight, the mixture was partitioned between Et$_2$O (100 mL) and water (100 mL). The organic layer was washed with saturated Na$_2$SO$_3$ solution and brine, dried over MgSO$_4$, filtered and concentrated. The residue was purified by flash chromatography (0-20% ethyl acetate/hexanes) to give the desired product as white solid (1.0 g, 22%). H NMR (400 MHz, CDCl$_3$) δ 4.04 (m, 1H), 2.50-2.38 (m, 2H), 2.24 (d, J=6.1 Hz, 2H), 1.99 (m, 2H), 1.77 (m, 3H), 1.22 (m, 2H) ppm.

Step 5. [trans-4-(8-Methylpyrazolo[1,5-c]thieno[2,3-e]pyrimidin-9-yl)cyclohexyl]acetonitrile A microwave tube equipped with a magnetic stir bar and a rubber septum was charged with lithium chloride (44.9 mg, 1.06 mmol). The vial was heated at 140° C. for 10 min under high vacuum and backfilled with nitrogen after cooling to room temperature. Zinc (69.3 mg, 1.06 mmol) was added and the vial was heated at 140° C. for 10 min under high vacuum and backfilled with nitrogen. After cooling to room temperature, THF (0.6 mL) and 1,2-dibromoethane (3.4 μL, 0.040 mmol) was added via syringe. The mixture was heated at 60° C. for 10 min and then cooled to room temperature. Chlorotrimethylsilane (0.99 μL, 0.0078 mmol) and iodine (1.0 mg, 0.0039 mmol) in THF (0.2 mL) was added and stirred at 60° C. for 10 min and cooled to room temperature. (trans-4-Iodocyclohexyl)acetonitrile (132 mg, 0.53 mmol) in THF (0.2 mL) was then added, and the mixture stirred at 50° C. overnight. 9-Bromo-8-methylpyrazolo[1,5-c]thieno[2,3-e]pyrimidine (80.2 mg, 0.299 mmol), 2-(dicyclohexylphosphino)-2',6'-dimethoxy-1,1'-biphenyl (29 mg, 0.072 mmol) in toluene (0.2 mL) were added to a microwave vial. The vial was evacuated under high vacuum and backfilled with nitrogen. The mixture was cooled to 0° C. and the zinc reagent was added slowly via syringe. After addition, the reaction was heated to 60° C. overnight and partitioned between EtOAc and saturated NH$_4$Cl solution. The layers were separated and the aqueous extracted further with ethyl acetate (2×). The combined organics were washed with water and brine, dried over MgSO$_4$, and concentrated. The residue was dissolved in methanol and purified with preparative LCMS (XBridge C18 column, eluting with a gradient of acetonitrile/water containing 0.1% ammonium hydroxide, at flow rate of 60 mL/min) to give a colorless solid (5.3 mg, 5.7%). LCMS calculated for C$_{17}$H$_{19}$N$_4$S (M+H)$^+$: m/z=311.1; Found: 311.1. $^1$H NMR (500 MHz, CDCl$_3$) δ 8.96 (s, 1H), 7.59 (m, 1H), 7.49 (m, 1H), 2.90 (m, 1H), 2.51 (s, 3H), 2.36 (d, J=6.5 Hz, 2H), 2.06 (m, 2H), 1.97-1.88 (m, 5H), 1.37 (m, 2H). ppm.

Example 78. Methyl [((trans-4-{2-[(1R)-1-hydroxyethyl]-1H-imidazo[4,5-d]thieno[3,2-b]pyridin-1-yl}cyclohexyl)methyl]carbamate

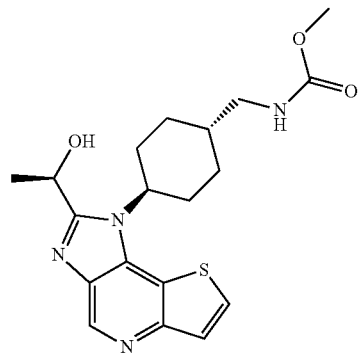 [SMILES: COC(=O)NC[C@H]1CC[C@H](n2c([C@@H](C)O)nc3cnc4ccsc4c32)CC1]

Step 1. tert-Butyl ({trans-4-[(6-nitrothieno[3,2-b]pyridin-7-yl)amino]cyclohexyl}methyl)carbamate A mixture of 7-chloro-6-nitrothieno[3,2-b]pyridine (220 mg, 1.0 mmol), tert-butyl [(trans-4-aminocyclohexyl)methyl]carbamate (250 mg, 1.1 mmol) and triethylamine (0.43 mL, 3.1 mmol) in isopropyl alcohol (8 mL) was heated at 90° C. for 2 h. The solvent was removed and the resulting residue was purified by flash chromatography (0-80% EtOAc/Hexanes) to give the desired product (0.32 g, 77%). LCMS calculated for C$_{19}$H$_{27}$N$_4$O$_4$S (M+H)$^+$: m/z=407.2; Found: 407.0.

Step 2. tert-Butyl ({trans-4-[(6-aminothieno[3,2-b]pyridin-7-yl)amino]cyclohexyl}methyl)carbamate A mixture of tert-butyl ({trans-4-[(6-nitrothieno[3,2-b]pyridin-7-yl)amino]cyclohexyl}methyl)carbamate (0.32 g, 0.79 mmol) and 10% palladium on carbon (0.01 g) in methanol (3 mL) was hydrogenated under balloon pressure of hydrogen at room temperature for 2 h. The mixture was filtered and concentrated to give the desired product (0.3 g, 100%) to be used in the next step directly. LCMS calculated for C$_{19}$H$_{29}$N$_4$O$_2$S (M+H)$^+$: m/z=377.2; Found: 377.1.

Step 3. tert-Butyl [((trans-4-{2-[(1R)-1-hydroxyethyl]-1H-imidazo[4,5-d]thieno[3,2-b]pyridin-1-yl}cyclohexyl)methyl]carbamate A mixture of (2R)-2-hydroxypropanamide (0.29 g, 3.3 mmol) and triethyloxonium tetrafluoroborate (0.61 g, 3.2 mmol) in THF (5.6 mL) was stirred at room temperature for 2 h. The solvent was removed and the residue dissolved in ethanol (2.4 mL) and added to a suspension of tert-butyl ({trans-4-[(6-aminothieno[3,2-b]pyridin-7-yl)amino]cyclohexyl}methyl)carbamate (0.30 g, 0.80 mmol) in ethanol (8.6 mL). The mixture was stirred at 85° C. for 2 h. The mixture was concentrated and purified with flash chromatography (0-10% methanol/dichloromethane) to give the desired product (0.21 g, 61%). LCMS calculated for C$_{22}$H$_{31}$N$_4$O$_3$S (M+H)$^+$: m/z=431.2; Found: 431.1.

Step 4. (1R)-1-{1-[trans-4-(Aminomethyl)cyclohexyl]-1H-imidazo[4,5-d]thieno[3,2-b]pyridin-2-yl}ethanol bis(trifluoroacetate) (Salt)

[(trans-4-{2-[(1R)-1-Hydroxyethyl]-1H-imidazo[4,5-d]thieno[3,2-b]pyridin-1-yl}cyclohexyl)methyl]carbamate (0.21 g, 0.49 mmol) was treated with trifluoroacetic acid (0.7 mL, 9 mmol) in dichloromethane (2 mL) at room temperature for 1 h. The mixture was stripped to dryness to give the desired product as TFA salt (0.35 g, 79%). LCMS calculated for $C_{17}H_{23}N_4OS$ $(M+H)^+$: m/z=331.1; Found: 331.0.

Step 5. Methyl [(trans-4-{2-[(1R)-1-hydroxyethyl]-1H-imidazo[4,5-d]thieno[3,2-b]pyridin-1-yl}cyclohexyl)methyl]carbamate To a solution of (1R)-1-{1-[trans-4-(aminomethyl)cyclohexyl]-1H-imidazo[4,5-d]thieno[3,2-b]pyridin-2-yl}ethanol bis(trifluoroacetate) (16 mg, 0.029 mmol) and triethylamine (20 µL, 0.14 mmol) in methylene chloride (1 mL) was added methyl chloroformate (2.6 µL, 0.034 mmol). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (1.4 mg, 13%). LCMS calculated for $C_{19}H_{25}N_4O_3S$ $(M+H)^+$: m/z=389.2; Found: 389.0. $^1$H NMR (DMSO-$d_6$, 500 MHz): δ 8.98 (1H, s), 8.02 (1H, d, J=5.5 Hz), 7.66 (1H, d, J=5.5 Hz), 7.24 (1H, m), 5.80 (1H, br s), 5.18 (1H, m), 4.90 (1H, br s), 3.54 (3H, s), 2.96 (2H, m), 2.38 (2H, m), 2.00-1.93 (4H, m), 1.76 (1H, m), 1.65 (3H, d, J=6.5 Hz), 1.21 (2H, m) ppm.

Example 79. N-[(trans-4-{2-[(1R)-1-Hydroxyethyl]-1H-imidazo[4,5-d]thieno[3,2-b]pyridin-1-yl}cyclohexyl)methyl]acetamide

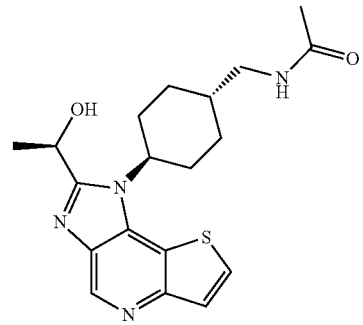 [SMILES: CC(=O)NC[C@H]1CC[C@H](n2c([C@@H](C)O)nc3cnc4ccsc4c32)CC1]

To a solution of (1R)-1-{1-[trans-4-(aminomethyl)cyclohexyl]-1H-imidazo[4,5-d]thieno[3,2-b]pyridin-2-yl}ethanol bis(trifluoroacetate) (16 mg, 0.029 mmol) and triethylamine (20. µL, 0.14 mmol) in dichloromethane (1 mL) was added acetic anhydride (4.0 µL, 0.043 mmol). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (1.4 mg, 13%). LCMS calculated for $C_{19}H_{25}N_4O_2S$ $(M+H)^+$: m/z=373.2; Found: 373.1.

Example 80. N-[(trans-4-{2-[(1R)-1-Hydroxyethyl]-1H-imidazo[4,5-d]thieno[3,2-b]pyridin-1-yl}cyclohexyl)methyl]methanesulfonamide

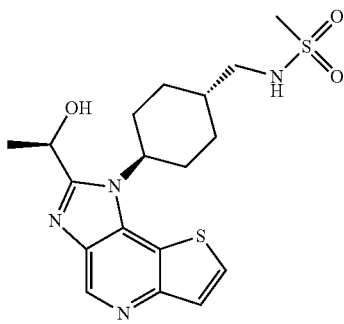 [SMILES: C[C@@H](O)c1nc2cnc3ccsc3c2n1[C@H]1CC[C@H](CNS(C)(=O)=O)CC1]

To a solution of (1R)-1-{1-[trans-4-(aminomethyl)cyclohexyl]-1H-imidazo[4,5-d]thieno[3,2-b]pyridin-2-yl}ethanol bis(trifluoroacetate) (16 mg, 0.029 mmol) and triethylamine (20. µL, 0.14 mmol in methylene chloride (1 mL) was added methanesulfonyl chloride (2.7 µL, 0.034 mmol). The mixture was stirred at room temperature for 1 h, then stripped to dryness and purified on prep-LCMS (XBridge C18 column, eluting with a gradient of acetonitrile/water containing 0.05% TFA, at flow rate of 60 mL/min) to give the desired compound as TFA salt (1.9 mg, 16%) as TFA salt. LCMS calculated for $C_{18}H_{25}N_4O_3S_2(M+H)^+$: m/z=409.1; Found: 409.1.

Example 81. N'-[(trans-4-{2-[(1R)-1-Hydroxyethyl]-1H-imidazo[4,5-d]thieno[3,2-b]pyridin-1-yl}cyclohexyl)methyl]-N,N-dimethylurea

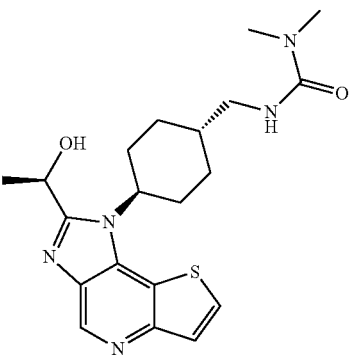 [SMILES: C[C@@H](O)c1nc2cnc3ccsc3c2n1[C@H]1CC[C@H](CNC(=O)N(C)C)CC1]

To a solution of (1R)-1-{1-[trans-4-(aminomethyl)cyclohexyl]-1H-imidazo[4,5-d]thieno[3,2-b]pyridin-2-yl}ethanol bis(trifluoroacetate) (16 mg, 0.029 mmol) and triethylamine (20 µL, 0.14 mmol) in methylene chloride (1 mL) was added N,N-dimethylcarbamoyl chloride (3.2 µL, 0.034 mmol). The mixture was stirred at room temperature for 1 h, then stripped to dryness and purified on prep-LCMS (XBridge C18 column, eluting with a gradient of acetonitrile/water containing 0.05% TFA, at flow rate of 60 mL/min) to give the desired compound as TFA salt (3.4 mg, 30%) as TFA salt. LCMS calculated for $C_{20}H_{28}N_5O_2S$ $(M+H)^+$: m/z=402.2; Found: 402.2.

Example 82. Ethyl [(trans-4-{2-[(1R)-1-hydroxyethyl]-1H-imidazo[4,5-d]thieno[3,2-b]pyridin-1-yl}cyclohexyl)methyl]carbamate

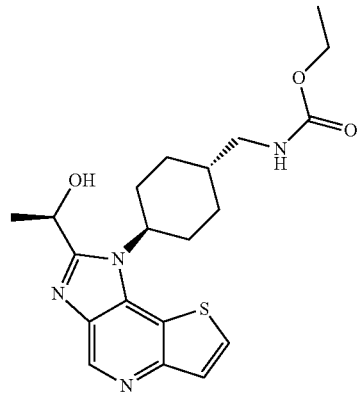 [SMILES: CCOC(=O)NC[C@H]1CC[C@H](n2c([C@@H](C)O)nc3cnc4ccsc4c32)CC1]

To a solution of (1R)-1-{1-[trans-4-(aminomethyl)cyclohexyl]-1H-imidazo[4,5-d]thieno[3,2-b]pyridin-2-yl}ethanol bis(trifluoroacetate) (18 mg, 0.032 mmol) and triethylamine (22 μL, 0.16 mmol) in methylene chloride (1 mL) was added ethyl chloroformate (3.7 μL, 0.039 mmol). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (0.9 mg, 7%). LCMS calculated for $C_{20}H_{27}N_4O_3S$ (M+H): m/z=403.2; Found: 402.9.

Example 83. Propyl [(trans-4-{2-[(1R)-1-hydroxyethyl]-1H-imidazo[4,5-d]thieno[3,2-b]pyridin-1-yl}cyclohexyl)methyl]carbamate

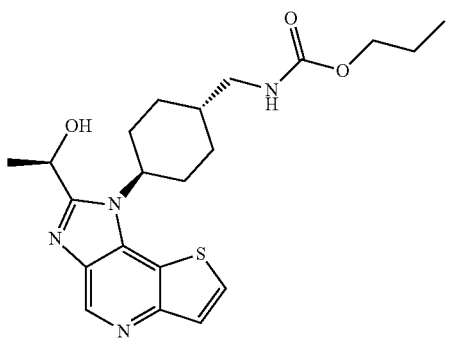 [SMILES: CCCOC(=O)NC[C@H]1CC[C@H](n2c([C@@H](C)O)nc3cnc4ccsc4c32)CC1]

To a solution of (1R)-1-{1-[trans-4-(aminomethyl)cyclohexyl]-1H-imidazo[4,5-d]thieno[3,2-b]pyridin-2-yl}ethanol bis(trifluoroacetate) (18 mg, 0.032 mmol) and triethylamine (22 μL, 0.16 mmol) in methylene chloride (1 mL) was added propyl chloroformate (4.3 μL, 0.039 mmol). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (0.9 mg, 7%). LCMS calculated for $C_{21}H_{29}N_4O_3S$ (M+H)$^+$: m/z=417.2; Found: 417.0.

Example 84. Isopropyl [(trans-4-{2-[(1R)-1-hydroxyethyl]-1H-imidazo[4,5-d]thieno[3,2-b]pyridin-1-yl}cyclohexyl)methyl]carbamate

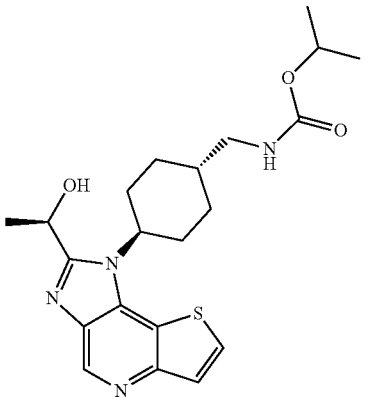 [SMILES: CC(C)OC(=O)NC[C@H]1CC[C@H](n2c([C@@H](C)O)nc3cnc4ccsc4c32)CC1]

To a solution of (1R)-1-{1-[trans-4-(aminomethyl)cyclohexyl]-1H-imidazo[4,5-d]thieno[3,2-b]pyridin-2-yl}ethanol bis(trifluoroacetate) (18 mg, 0.032 mmol) and triethylamine (22 μL, 0.16 mmol) in methylene chloride (1 mL) was added 1.0 M isopropyl chloroformate in toluene (39 μL). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (0.9 mg, 7%). LCMS calculated for $C_{21}H_{29}N_4O_3S$ (M+H)$^+$: m/z=417.2; Found: 417.1.

Example 85. Tetrahydrofuran-3-yl [(trans-4-{2-[(1R)-1-hydroxyethyl]-1H-imidazo[4,5-d]thieno[3,2-b]pyridin-1-yl}cyclohexyl)methyl]carbamate

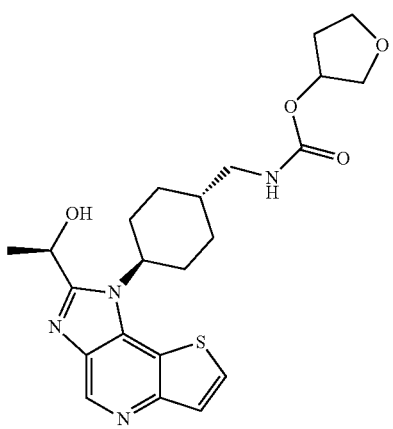 [SMILES: C[C@@H](O)c1nc2cnc3ccsc3c2n1[C@H]1CC[C@H](CNC(=O)OC2CCOC2)CC1]

To a solution of (1R)-1-{1-[trans-4-(aminomethyl)cyclohexyl]-1H-imidazo[4,5-d]thieno[3,2-b]pyridin-2-yl}ethanol bis(trifluoroacetate) (18 mg, 0.032 mmol) and triethylamine (22 μL, 0.16 mmol) in methylene chloride (1 mL) was added 4-nitrophenyl tetrahydrofuran-3-yl carbonate (9.8 mg, 0.039 mmol). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (1.8 mg, 12%). LCMS calculated for $C_{22}H_{29}N_4O_4S$ (M+H)$^+$: m/z=445.2; Found: 445.0.

Example 86. Methyl ({trans-4-[2-(cyanomethyl)-1H-imidazo[4,5-d]thieno[3,2-b]pyridin-1-yl]cyclohexyl}methyl)carbamate

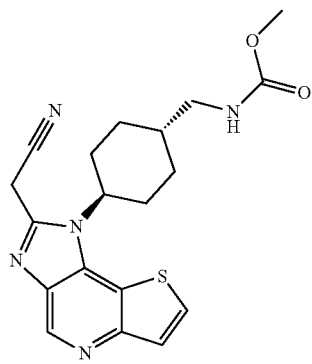 [SMILES: COC(=O)NC[C@H]1CC[C@H](n2c(CC#N)nc3cnc4ccsc4c32)CC1]

Step 1. Tert-Butyl ({trans-4-[2-(cyanomethyl)-1H-imidazo[4,5-d]thieno[3,2-b]pyridin-1-yl]cyclohexyl}methyl)carbamate A mixture of 2-cyanoacetamide (120 mg, 1.5 mmol) and triethyloxonium tetrafluoroborate (270 mg, 1.4 mmol) in THF (1.1 mL) was stirred at room temperature for 2 h. The solvent was removed and the residue dissolved in ethanol (0.5 mL) and added to a suspension of tert-butyl ({trans-4-[(6-aminothieno[3,2-b]pyridin-7-yl)amino]cyclohexyl}methyl)carbamate (150 mg, 0.40 mmol) in ethanol (1.7 mL). The mixture was stirred at 85° C. for 2 h. The solid was filtered and the filtrate was concentrated and purified on flash chromatography (0-10% methanol/dichloromethane) to give the desired product (0.12 g, 71%). LCMS calculated for $C_{22}H_{28}N_5O_2S$ (M+H)$^+$: m/z=426.2; Found: 426.0.

Step 2. {1-[trans-4-(Aminomethyl)cyclohexyl]-1H-imidazo[4,5-d]thieno[3,2-b]pyridin-2-yl}acetonitrile bis(HCl)

({trans-4-[2-(Cyanomethyl)-1H-imidazo[4,5-d]thieno[3,2-b]pyridin-1-yl]cyclohexyl}methyl)carbamate (0.12 g, 0.28 mmol)) was treated with 4.0 M hydrogen chloride in dioxane (0.5 mL) in methylene chloride (0.5 mL) at room temperature for 1 h. The solid was filtered, washed with DCM and methanol, and air-dried to give the desired product (0.10 g, 77%). LCMS calculated for $C_{17}H_{20}N_5S$ (M+H)$^+$: m/z=326.1; Found: 326.0.

Step 3. Methyl ({trans-4-[2-(cyanomethyl)-1H-imidazo[4,5-d]thieno[3,2-b]pyridin-1-yl]cyclohexyl}methyl) carbamate To a solution of {1-[trans-4-(aminomethyl)cyclohexyl]-1H-imidazo[4,5-d]thieno[3,2-b]pyridin-2-yl}acetonitrile (9.5 mg, 0.029 mmol) and triethylamine (20 μL, 0.14 mmol) in methylene chloride (1 mL) was added methyl chloroformate (2.7 μL, 0.035 mmol). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (1.4 mg, 12%). LCMS calculated for $C_{19}H_{22}N_5O_2S$ (M+H)$^+$: m/z=384.1; Found: 384.0.

Example 87. Ethyl ({trans-4-[2-(cyanomethyl)-1H-imidazo[4,5-d]thieno[3,2-b]pyridin-1-yl]cyclohexyl}methyl)carbamate

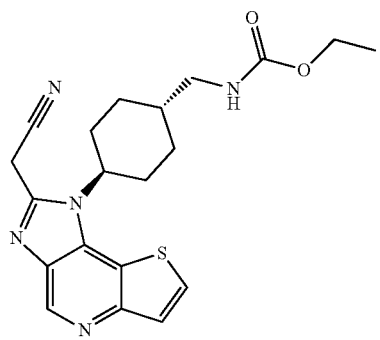 [SMILES: CCOC(=O)NC[C@H]1CC[C@H](n2c(CC#N)nc3cnc4ccsc4c32)CC1]

To a solution of {1-[trans-4-(aminomethyl)cyclohexyl]-1H-imidazo[4,5-d]thieno[3,2-b]pyridin-2-yl}acetonitrile (9.5 mg, 0.029 mmol) and triethylamine (20. μL, 0.14 mmol) in methylene chloride (1 mL) was added ethyl chloroformate (3.3 μL, 0.035 mmol). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (1.9 mg, 16%). LCMS calculated for $C_{20}H_{24}N_5O_2S$ (M+H)$^+$: m/z=398.2; Found: 397.8.

Example 88. Isopropyl ({trans-4-[2-(cyanomethyl)-1H-imidazo[4,5-d]thieno[3,2-b]pyridin-1-yl]cyclohexyl}methyl)carbamate

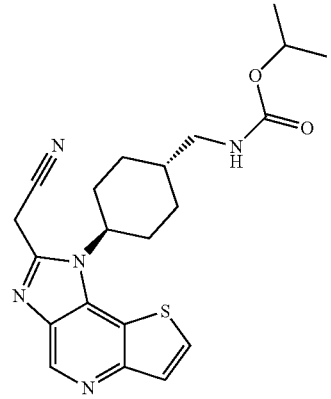 [SMILES: CC(C)OC(=O)NC[C@H]1CC[C@H](n2c(CC#N)nc3cnc4ccsc4c32)CC1]

To a solution of {1-[trans-4-(aminomethyl)cyclohexyl]-1H-imidazo[4,5-d]thieno[3,2-b]pyridin-2-yl}acetonitrile (9.5 mg, 0.029 mmol) and triethylamine (20. μL, 0.14 mmol) in methylene chloride (1 mL) was added 1.0 M isopropyl chloroformate in toluene (35 μL). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (1.5 mg, 12%). LCMS calculated for $C_{21}H_{26}N_5O_{52}S$ (M+H)$^+$: m/z=412.2; Found: 412.1.

Example 89. N-({trans-4-[2-(Cyanomethyl)-1H-imidazo[4,5-d]thieno[3,2-b]pyridin-1-yl]cyclohexyl}methyl)propanamide

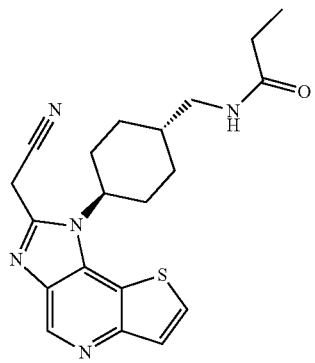 [SMILES: CCC(=O)NC[C@H]1CC[C@H](n2c(CC#N)nc3cnc4ccsc4c32)CC1]

To a solution of {1-[trans-4-(aminomethyl)cyclohexyl]-1H-imidazo[4,5-d]thieno[3,2-b]pyridin-2-yl}acetonitrile (9.5 mg, 0.029 mmol) and triethylamine (20. μL, 0.14 mmol) in methylene chloride (1 mL) was added propanoyl chloride (3.0 μL, 0.035 mmol). The mixture was stirred at room temperature for 1 h, then stripped to dryness and purified on prep-HPLC (XBridge C18 column, eluting with a gradient of acetonitrile/water containing 0.1% ammonium hydroxide, at flow rate of 60 mL/min) to give the desired product (1.1 mg, 9.9%). LCMS calculated for $C_{20}H_{24}N_5OS$ (M+H)$_+$: m/z=382.2; Found: 382.1.

Example 90. {1-[trans-4-(Cyanomethyl)cyclohexyl]-1H-imidazo[4,5-d]thieno[3,2-b]pyridin-2-yl}acetonitrile

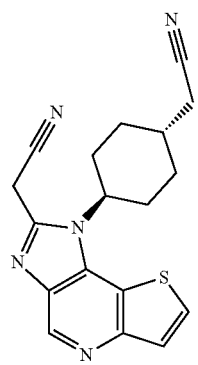 [SMILES: N#CCc1nc2cnc3ccsc3c2n1[C@H]1CC[C@H](CC#N)CC1]

A mixture of 2-cyanoacetamide (11 mg, 0.13 mmol) and triethyloxonium tetrafluoroborate (21 mg, 0.11 mmol) in THF (0.13 mL) was stirred at room temperature for 2 h. The solvent was removed and the residue dissolved in ethanol (55 μL) and added to a suspension of {trans-4-[(6-aminothieno[3,2-b]pyridin-7-yl)amino]cyclohexyl}acetonitrile (8.9 mg, 0.031 mmol) in ethanol (0.20 mL). The mixture was stirred at 85° C. for 2 h. The mixture was purified on prep-HPLC (XBridge C18 column, eluting with a gradient of acetonitrile/water containing 0.05% TFA, at flow rate of 60 mL/min) to give the desired product (2.7 mg, 26%) as TFA salt. LCMS calculated for $C_{18}H_{18}N_5S$ (M+H)$^+$: m/z=336.1; Found: 336.0.

Example 91. {(2R,5S)-5-[2-(Hydroxymethyl)-1H-imidazo[4,5-d]thieno[3,2-b]pyridin-1-yl]tetrahydro-2H-pyran-2-yl}acetonitrile

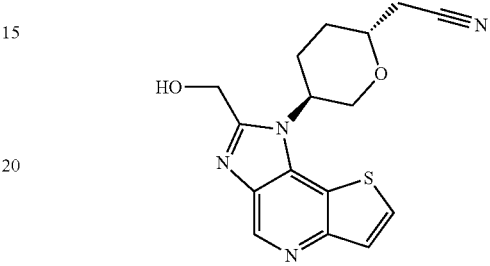

A mixture of 2-hydroxyacetamide (93.3 mg, 1.24 mmol) and triethyloxonium tetrafluoroborate (234 mg, 1.23 mmol) in THF (2 mL) was stirred at room temperature for 2 h. The solvent was removed and the residue dissolved in ethanol (0.7 mL) and added to a suspension of {(5S)-5-[(6-aminothieno[3,2-b]pyridin-7-yl)amino]tetrahydro-2H-pyran-2-yl}acetonitrile (101 mg, 0.350 mmol) in ethanol (2.6 mL). The reaction mixture was stirred at 80° C. for 1 h, and then cooled to room temperature. The solid was filtered off. The filtrate was diluted with methanol and purified with prep-LCMS (XBridge C18 column, eluting with a gradient of acetonitrile/water containing 0.1% ammonium hydroxide, at flow rate of 60 mL/min) to give the desired product (40 mg, 35%). LCMS calculated for $C_{16}H_{17}N_4O_2S$ (M+H)$^+$: m/z=329.1; Found: 329.1. $^1$H NMR (DMSO-d$_6$, 500 MHz) δ 8.98 (s, 1H), 8.04 (d, J=5.5 Hz, 1H), 7.69 (d, J=5.5 Hz, 1H), 5.89 (s, 1H), 4.92 (m, 1H), 4.87 (s, 2H), 4.28 (m, 1H), 4.18-4.11 (m, 1H), 3.98 (m, 1H), 2.95 (dd, J=17.0, 4.3 Hz, 1H), 2.83 (dd, J=17.0, 6.6 Hz, 1H), 2.64 (m, 1H), 2.49 (m, 1H), 2.22 (m, 1H), 2.06 (m, 1H) ppm.

Example A: In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). IC$_{50}$s of compounds were measured for each kinase in the 40 μL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM IC$_{50}$ measurements, ATP concentration in the reactions was 1 mM. Reactions were carried out at room temperature for 1 hour and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a PHERA star plate reader (BMG, Cary, N.C.). The Example compounds were each tested in the Example A assay (see Table 1 for data for the compounds of the examples as tested by the assay of Example A at 1 mM ATP).

TABLE 1

| Example | JAK1 IC$_{50}$ (nM) | JAK2 IC$_{50}$ (nM) | JAK2/JAK1 |
| --- | --- | --- | --- |
| 1 | ++ | +++++ | >3 |
| 2 | + | ++ | >10 |
| 3 | ++ | +++++ | >10 |
| 4 | + | +++ | >10 |
| 5 | + | +++++ | >10 |
| 6 | +++ | +++++ | >6 |
| 7 | + | +++ | >10 |
| 8 | + | ++ | >10 |
| 9 (1$^{st}$ peak) | +++++ | +++++ | |
| 9 (2$^{nd}$ peak) | ++ | +++++ | >10 |
| 10 | + | ++ | >10 |
| 11 | + | +++++ | >10 |
| 12 | + | +++ | >10 |
| 13 | + | ++++ | >10 |
| 14 | ++ | +++++ | >5 |
| 15 | +++ | +++++ | >9 |
| 16 | ++ | ++++ | >10 |
| 17 | + | ++ | >10 |
| 18 | + | ++ | >10 |
| 19 | ++ | +++++ | >10 |
| 20 | + | ++ | >10 |
| 21 | ++ | +++++ | >10 |
| 22 | ++ | +++++ | >4 |
| 23 | + | ++ | >10 |
| 24 (first peak) | + | ++++ | >10 |
| 24 (second peak) | ++ | ++++ | >10 |
| 25 | + | ++ | >6 |
| 26 | + | ++ | >10 |
| 27 | + | ++ | >10 |
| 28 | +++ | +++++ | >7 |
| 29 | ++ | +++ | >9 |
| 30 (first peak) | ++ | ++++ | >2 |
| 30 (second peak) | +++ | +++++ | >10 |
| 31 | ++ | +++++ | >10 |
| 32 | + | ++++ | >10 |
| 33 | + | ++ | >7 |
| 34 | ++ | +++ | >10 |
| 35 | + | ++++ | >10 |
| 36 (first peak) | + | ++++ | >10 |
| 36 (second peak) | + | ++ | >10 |
| 37 (first peak) | ++ | +++++ | >10 |
| 37 (second peak) | + | ++ | >10 |
| 38 | + | + | >10 |
| 39 | + | ++ | >10 |
| 40 (first peak) | + | ++ | >10 |
| 40 (second peak) | ++++ | +++++ | |
| 41 (first peak) | + | ++ | >10 |
| 41 (second peak) | ++++ | +++++ | |
| 42 | + | ++ | >10 |
| 43 | + | ++ | >10 |
| 44 | ++ | +++++ | >10 |
| 45 | + | ++++ | >10 |
| 46 | + | ++ | >3 |
| 47 | + | ++ | >10 |
| 48 | + | + | >7 |
| 49 | ++ | +++++ | >10 |
| 50 | ++ | +++++ | >10 |
| 51 | ++ | ++++ | >10 |
| 52 | ++ | +++++ | >10 |
| 53 | ++ | +++++ | >10 |
| 54 | ++ | +++++ | >10 |
| 55 | ++ | +++++ | >10 |
| 56 | ++ | +++++ | >10 |
| 57 | + | ++++ | >10 |
| 58 | + | +++++ | >10 |
| 59 | ++ | +++++ | >10 |
| 60 | ++ | +++++ | >10 |
| 61 | ++ | +++++ | >10 |
| 62 | ++ | ++++ | >10 |
| 63 | +++ | +++++ | >6 |
| 64 | + | +++++ | >10 |
| 65 | ++ | +++++ | >10 |
| 66 | ++ | +++++ | >10 |
| 67 | ++ | ++++ | >10 |
| 68 | + | +++ | >10 |
| 69 | ++ | +++++ | >10 |
| 70 | ++ | ++++ | >10 |
| 71 | + | ++ | >10 |
| 72 (second peak) | + | ++ | >5 |
| 73 | + | ++ | >10 |
| 74 | ++ | +++++ | >10 |
| 75 | + | +++ | >10 |
| 76 | + | +++ | >10 |
| 77 | + | + | >5 |
| 78 | + | ++ | >10 |
| 79 | + | +++ | >10 |
| 80 | + | +++ | >10 |
| 81 | + | ++++ | >10 |
| 82 | + | ++ | >10 |
| 83 | + | ++ | >10 |
| 84 | + | ++ | >10 |
| 85 | + | +++++ | >10 |
| 86 | + | ++ | >10 |
| 87 | + | ++ | >10 |
| 88 | + | +++++ | >10 |
| 89 | + | ++++ | >10 |
| 90 | + | ++ | >10 |
| 91 | + | ++ | >10 |

+ indicates an IC$_{50}$ of ≤100 nM
++ indicates an IC$_{50}$ of ≤1000 nM
+++ indicates an IC$_{50}$ of ≤2000 nM
++++ indicates an IC$_{50}$ of >2000 nM
+++++ indicates that the IC$_{50}$ was greater than the highest concentration tested Example B: Cellular Assays Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% CO$_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art. To assess compound effects on JAK2, primary cells or cell lines can be stimulated with JAK2-dependent growth factors such as GM-CSF or Tpo, proteins extracted from cells and analyzed by techniques familiar to those schooled in the art including Western blotting or ELISAs using antibodies that can differentiate between phosphorylated and total protein.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. Nature 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of $2\times10^6$ cells/ml at 37° C. for up to 2 days. For IL-2 stimulated cell proliferation analysis, T-cells are first treated with Phytohemagglutinin (PHA) at a final concentration of 10 µg/mL for 72 hours. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72h and the proliferation index is assessed using CellTiter-Glo Luminescent reagents following the manufactory suggested protocol (Promega; Madison, Wis.).

Example C: In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. Hematol J. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D: Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (Immunol Today. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E: In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003).

Example F: Animal Models for the Treatment of Dry Eye, Uveitis, and Conjunctivitis Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent auto-immune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccharide at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G: In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohistology and appropriate biochemical markers of bone remodeling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

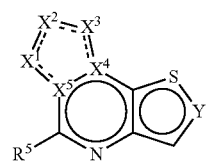

or a pharmaceutically acceptable salt thereof, wherein:
the

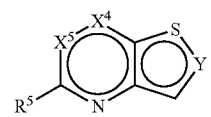

ring system is aromatic;
  each $\rlap{=}{-}$ is independently selected from a single bond and a double bond;
  Y is N or $CR^4$;
  $X^1$ is selected from $CR^1$, $CR^1R^{1a}$, $C(=O)$, N, $NR^1$, O, and S;
  $X^2$ is selected from $CR^2$, $C(=O)$, N, $NR^2$, and $C(=NR^{2a})$;
  $X^3$ is selected from $CR^3$ and $NR^3$;
  $X^4$ is selected from C and N; and $X^5$ is C; or
  $X^4$ is C; and $X^5$ is selected from C and N;

provided that:
(i) the selections for each of $X^1$, $X^2$, $X^3$, $X^4$, $X^5$ and ⸗ maintain proper valency;
(ii) when $X^1$ is O or S, then $X^2$ is not $NR^2$ and $X^2$⸗$X^3$ is not —C(=O)—$CR^3$—;
(iii) when $X^1$ is $NR^1$, then $X^2$⸗$X^3$ is not —$NR^2$—$NR^3$—;
(iv) when $X^4$ is N, then $X^1$⸗$X^2$⸗$X^3$ is not =N—$NR^2$—$NR^3$—; and
(v) when $X^5$ is N, then $X^1$⸗$X^2$ is not —$NR^1$—$NR^2$— and $X^1$⸗$X^2$⸗$X^3$ is not —$CR^1R^{1a}$—$NR^2$—$CR^3$=;

$R^1$ is selected from H, halo, CN, $NH_2$, $C_{1-3}$ alkyl, $C_{1-3}$ alkoxy, and $C_{1-3}$ haloalkyl;

$R^{1a}$ is selected from H, halo, CN, $NH_2$, $C_{1-3}$ alkyl, and $C_{1-3}$ haloalkyl;

$R^{2a}$ is selected from CN, OH, $OCH_3$, and $NO_2$;

$R^2$ is selected from H, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkyl-S—, CN, C(=O)$R^b$, C(=O)$NR^cR^d$, C(=O)$OR^a$, OC(=O) $R^b$, OC(=O)$NR^cR^d$, $NR^cR^d$, $NR^cC$(=O)$R^b$, $NR^cC$(=O)$OR^a$, $NR^cC$(=O)$NR^cR^d$, C(=$NR^e$)$R^b$, C(=$NR^e$)$NR^cR^d$, $NR^cC$(=$NR^e$)$NR^cR^d$, $NR^cS$(=O) $R^b$, $NR^cS$(=O)$_2R^b$, $NR^cS$(=O)$_2NR^cR^d$, S(=O)$R^b$, S(=O)$NR^cR^d$, S(=O)$_2R^b$, and S(=O)$_2NR^cR^d$; wherein said $C_{1-6}$ alkyl, $C_{2-6}$ alkenyl, $C_{2-6}$ alkynyl, $C_{1-6}$ alkoxy, and $C_{1-6}$ alkyl-S— are each optionally substituted with 1, 2, or 3 substituents independently selected from $Cy^2$, halo, CN, $NO_2$, $OR^a$, $SR^a$, C(=O)$R^b$, C(=O)$NR^cR^d$, C(=O)$OR^a$, OC(=O)$R^b$, OC(=O) $NR^cR^d$, C(=$NR^e$)$NR^cR^d$, $NR^cC$(=$NR^e$)$NR^cR^d$, $NR^cR^d$, $NR^cC$(=O)$R^b$, $NR^cC$(=O)$OR^a$, $NR^cC$(=O) $NR^cR^d$, $NR^cS$(=O)$R^b$, $NR^cS$(=O)$_2R^b$, $NR^cS$(=O)$_2NR^cR^d$, S(=O)$R^b$, S(=O)$NR^cR^d$, S(=O)$_2R^b$, and S(=O)$_2NR^cR^d$;

alternatively, $R^2$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $R^{21}$, $Cy^2$, CN, $NO_2$, $OR^a$, $SR^a$, C(=O)$R^b$, C(=O)$NR^cR^d$, C(=O)$OR^a$, OC(=O)$R^b$, OC(=O) $NR^cR^d$, C(=$NR^e$)$NR^cR^d$, $NR^cC$(=$NR^e$)$NR^cR^d$, $NR^cR^d$, $NR^cC$(=O)$R^b$, $NR^cC$(=O)$OR^a$, $NR^cC$(=O) $NR^cR^d$, $NR^cS$(=O)$R^b$, $NR^cS$(=O)$_2R^b$, $NR^cS$(=O)$_2NR^cR^d$, S(=O)$R^b$, S(=O)$NR^cR^d$, S(=O)$_2R^b$, and S(=O)$_2NR^cR^d$;

provided that when $X^1$⸗$X^2$⸗$X^3$ is —N=$CR^2$—$NR^3$—, $X^4$ is C, and $X^5$ is C; and $Cy^{4A}$ is unsubstituted or substituted 3-10 membered saturated heterocycloalkylene having one or more nitrogen atoms, then $R^2$ is selected from H, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkyl-S—, CN, C(=O)$R^b$, C(=O)$NR^cR^d$, C(=O)$OR^a$, OC(=O) $R^b$, OC(=O)$NR^cR^d$, $NR^cR^d$, $NR^cC$(=O)$R^b$, $NR^cC$(=O)$OR^a$, $NR^cC$(=O)$NR^cR^d$, C(=$NR^e$)$R^b$, C(=$NR^e$)$NR^cR^d$, $NR^cC$(=$NR^e$)$NR^cR^d$, $NR^cS$(=O) $R^b$, $NR^cS$(=O)$_2R^b$, $NR^cS$(=O)$_2NR^cR^d$, S(=O)$R^b$, S(=O)$NR^cR^d$, S(=O)$_2R^b$, and S(=O)$_2NR^cR^d$; wherein said $C_{1-6}$ alkyl, $C_{2-6}$ alkenyl, $C_{2-6}$ alkynyl, $C_{1-6}$ alkoxy, and $C_{1-6}$ alkyl-S— are each optionally substituted with 1, 2, or 3 substituents independently selected from $Cy^2$, halo, CN, $NO_2$, $OR^a$, $SR^a$, C(=O)$R^b$, C(=O)$NR^cR^d$, C(=O)$OR^a$, OC(=O)$R^b$, OC(=O) $NR^cR^d$, C(=$NR^e$)$NR^cR^d$, $NR^cC$(=$NR^e$)$NR^cR^d$, $NR^cR^d$, $NR^cC$(=O)$R^b$, $NR^cC$(=O)$OR^a$, $NR^cC$(=O) $NR^cR^d$, $NR^cS$(=O)$R^b$, $NR^cS$(=O)$_2R^b$, $NR^cS$(=O)$_2NR^cR^d$, S(=O)$R^b$, S(=O)$NR^cR^d$, S(=O)$_2R^b$, and S(=O)$_2NR^cR^d$;

each $R^{21}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^a$, $SR^a$, C(=O)$R^b$, C(=O)$NR^cR^d$, C(=O)$OR^a$, OC(=O) $R^b$, OC(=O)$NR^cR^d$, C(=$NR^e$)$NR^cR^d$, $NR^cC$(=$NR^e$) $NR^cR^d$, $NR^cR^d$, $NR^cC$(=O)$R^b$, $NR^cC$(=O)$OR^a$, $NR^cC$(=O)$NR^cR^d$, $NR^cS$(=O)$R^b$, $NR^cS$(=O)$_2R^b$, $NR^cS$(=O)$_2NR^cR^d$, S(=O)$R^b$, S(=O)$NR^cR^d$, S(=O)$_2$ $R^b$, and S(=O)$_2NR^cR^d$;

alternatively, when two $R^{21}$ groups are attached to the same carbon atom, the two $R^{21}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, $C_{1-3}$ alkyl, $C_{1-3}$ alkoxy, and $C_{1-3}$ haloalkyl;

each $Cy^2$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $R^{22}$, CN, $NO_2$, $OR^a$, $SR^a$, C(=O)$R^b$, C(=O)$NR^cR^d$, C(=O)$OR^a$, OC(=O)$R^b$, OC(=O) $NR^cR^d$, C(=$NR^e$)$NR^cR^d$, $NR^cC$(=$NR^e$)$NR^cR^d$, $NR^cR^d$, $NR^cC$(=O)$R^b$, $NR^cC$(=O)$OR^a$, $NR^cC$(=O) $NR^cR^d$, $NR^cS$(=O)$R^b$, $NR^cS$(=O)$_2R^b$, $NR^cS$(=O)$_2NR^cR^d$, S(=O)$R^b$, S(=O)$NR^cR^d$, S(=O)$_2R^b$, and S(=O)$_2NR^cR^d$;

each $R^a$, $R^c$, and $R^d$ are independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, C(=O)$R^{b1}$, C(=O) $NR^{c1}R^{d1}$, C(=O)$OR^{a1}$, OC(=O)$R^{b1}$, OC(=O) $NR^{c1}R^{d1}$, C(=$NR^{e1}$)$NR^{c1}R^{d1}$, $NR^{c1}C$(=$NR^{e1}$) $NR^{c1}R^{d1}$, $NR^{c1}R^{d1}$, $NR^{c1}C$(=O)$R^{b1}$, $NR^{c1}C$(=O) $OR^{a1}$, $NR^{c1}C$(=O)$NR^{c1}R^{d1}$, $NR^{c1}S$(=O)$R^{b1}$, $NR^{c1}S$(=O)$_2R^{b1}$, $NR^{c1}S$(=O)$_2NR^{c1}R^{d1}$, S(=O)$R^{b1}$, S(=O) $NR^{c1}R^{d1}$, S(=O)$_2R^{b1}$, and S(=O)$_2NR^{c1}R^{d1}$;

each $R^b$ is independently selected from $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, C(=$NR^{e1}$)$NR^{c1}R^{d1}$, $NR^{c1}C$(=$NR^{e1}$)$NR^{c1}R^{d1}$, $NR^{c1}R^{d1}$, $NR^{c1}C$(=O)$R^{b1}$, $NR^{c1}C$(=O)$OR^{a1}$, $NR^{c1}C$ (=O)NR$^{c1}$R$^{d1}$, NR$^{c1}$S(=O)R$^{b1}$, NR$^{c1}$S(=O)$_2$R$^{b1}$, NR$^{c1}$S(=O)$_2$NR$^{c1}$R$^{d1}$, S(=O)R$^{b1}$, S(=O)NR$^{c1}$R$^{d1}$, S(=O)$_2$R$^{b1}$, and S(=O)$_2$NR$^{c1}$R$^{d1}$;

each R$^e$ is independently selected from H, CN, OH, C$_{1-4}$ alkyl, C$_{1-4}$ alkoxy, NO$_2$, C(O)(C$_{1-4}$ alkyl), and S(=O)$_2$(C$_{1-4}$ alkyl);

each R$^{22}$ is independently selected from C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl are each optionally substituted with 1, 2, or 3 substituents independently selected from Cy$^3$, halo, CN, NO$_2$, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(=O)R$^{b1}$, NR$^{c1}$C(=O)OR$^{a1}$, NR$^{c1}$C(=O)NR$^{c1}$R$^{d1}$, NR$^{c1}$S(=O)R$^{b1}$, NR$^{c1}$S(=O)$_2$R$^{b1}$, NR$^{c1}$S(=O)$_2$NR$^{c1}$R$^{d1}$, S(=O)R$^{b1}$, S(=O)NR$^{c1}$R$^{d1}$, S(=O)$_2$R$^{b1}$, and S(=O)$_2$NR$^{c1}$R$^{d1}$;

each R$^{a1}$, R$^{c1}$, and R$^{d1}$ are independently selected from H, C$_{1-3}$ alkyl, C$_{2-3}$ alkenyl, C$_{2-3}$ alkynyl, and C$_{1-3}$ haloalkyl;

each R$^{b1}$ is independently selected from C$_{1-3}$ alkyl, C$_{2-3}$ alkenyl, C$_{2-3}$ alkynyl, and C$_{1-3}$ haloalkyl;

each R$^{e1}$ is independently selected from H, CN, OH, C$_{1-4}$ alkyl, and C$_{1-4}$ alkoxy;

each Cy$^3$ is independently selected from C$_{6-10}$ aryl, C$_{3-10}$ cycloalkyl, 5-10 membered heteroaryl, and 3-10 membered heterocycloalkyl, wherein said C$_{6-10}$ aryl, C$_{3-10}$ cycloalkyl, 5-10 membered heteroaryl, and 3-10 membered heterocycloalkyl are each optionally substituted with 1, 2, 3, 4, or 5 substituents independently selected from C$_{1-6}$ alkyl, C$_{2-6}$ alkenyl, C$_{2-6}$ alkynyl, C$_{1-6}$ haloalkyl, halo, CN, NO$_2$, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(=O)R$^{b1}$, NR$^{c1}$C(=O)OR$^{a1}$, NR$^{c1}$C(=O)NR$^{c1}$R$^{d1}$, NR$^{c1}$S(=O)R$^{b1}$, NR$^{c1}$S(=O)$_2$R$^{b1}$, NR$^{c1}$S(=O)$_2$NR$^{c1}$R$^{d1}$, S(=O)R$^{b1}$, S(=O)NR$^{c1}$R$^{d1}$, S(=O)$_2$R$^{b1}$, and S(=O)$_2$NR$^{c1}$R$^{d1}$;

R$^3$ is selected from -Cy$^{4A}$-Cy$^5$ or -Cy$^{4A}$-Y$^1$-Cy$^5$;

Cy$^{4A}$ is selected from C$_{6-10}$ arylene, C$_{3-10}$ cycloalkylene, 5-10 membered heteroarylene, and 3-10 membered heterocycloalkylene, wherein said C$_{6-10}$ arylene, C$_{3-10}$ cycloalkylene, 5-10 membered heteroarylene, and 3-10 membered heterocycloalkylene are optionally substituted with 1, 2, 3, or 4 independently selected R$^{31}$ groups;

Y$^1$ is C$_{1-4}$ alkylene or Y$^{11}$—C$_{1-4}$ alkylene, wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, and C$_{1-3}$ haloalkoxy, and wherein Y$^{11}$ is C(=O);

each Cy$^5$ is independently selected from C$_{6-10}$ aryl, C$_{3-10}$ cycloalkyl, 5-10 membered heteroaryl, and 3-10 membered heterocycloalkyl, wherein said C$_{6-10}$ aryl, C$_{3-10}$ cycloalkyl, 5-10 membered heteroaryl, and 3-10 membered heterocycloalkyl are optionally substituted with 1, 2, 3, or 4 independently selected R$^{32}$ groups;

Y$^2$ is Y$^{21}$, C$_{1-6}$ alkylene, C$_{2-6}$ alkenylene, C$_{2-6}$ alkynylene, C$_{1-6}$ alkylene-Y$^{21}$, C$_{2-6}$ alkenylene-Y$^{21}$, C$_{2-6}$ alkynylene-Y$^{21}$, Y$^{21}$—C$_{1-6}$ alkylene, Y$^{21}$—C$_{2-6}$ alkenylene, or Y$^{21}$—C$_{2-6}$ alkynylene, wherein said alkylene, alkenylene and alkynylene groups are each optionally substituted with 1, 2, or 3 substituents independently selected from halo, CN, OH, C$_{1-3}$ alkyl, C$_{1-3}$ alkoxy, C$_{1-3}$ haloalkyl, and C$_{1-3}$ haloalkoxy;

Y$^3$ is C$_{1-6}$ alkylene-Y$^{31}$—C$_{1-6}$ alkylene, C$_{1-6}$ alkylene-Y$^{31}$—C$_{1-6}$ alkylene-Y$^{31}$, or Y$^{31}$—C$_{1-6}$ alkylene-Y$^{31}$—C$_{1-6}$ alkylene, wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, and C$_{1-3}$ haloalkoxy;

each Cy$^7$ is independently selected from C$_{6-10}$ aryl, C$_{3-10}$ cycloalkyl, 5-10 membered heteroaryl, and 3-10 membered heterocycloalkyl, wherein said C$_{6-10}$ aryl, C$_{3-10}$ cycloalkyl, 5-10 membered heteroaryl, and 3-10 membered heterocycloalkyl are each optionally substituted with 1, 2, 3, 4, or 5 independently selected R$^{33}$ groups;

Y$^{21}$, and Y$^{31}$ are each independently selected from O, S, C(=O), C(=O)NR$^{f}$, C(=O)O, OC(=O), OC(=O)NR$^{f}$, NR$^{f}$, NR$^{f}$C(=O), NR$^{f}$C(=O)O, NR$^{f}$C(=O)NR$^{f}$, NR$^{f}$S(=O), NR$^{f}$S(=O)$_2$, NR$^{f}$S(=O)$_2$NR$^{f}$, S(=O), S(=O)NR$^{f}$, S(=O)$_2$, and S(=O)$_2$NR$^{f}$;

each R$^{31}$ is independently selected from Cy$^7$, C$_{1-6}$ alkyl, C$_{2-6}$ alkenyl, C$_{2-6}$ alkynyl, C$_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said C$_{1-6}$ alkyl, C$_{2-6}$ alkenyl, and C$_{2-6}$ alkynyl are each optionally substituted with 1, 2, or 3 substituents independently selected from halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each R$^{32}$ is independently selected from C$_{1-6}$ alkyl, C$_{2-6}$ alkenyl, C$_{2-6}$ alkynyl, C$_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said C$_{1-6}$ alkyl, C$_{2-6}$ alkenyl, and C$_{2-6}$ alkynyl are each optionally substituted with 1, 2, or 3 substituents independently selected from halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each R$^{33}$ is independently selected from halo, OH, NO$_2$, CN, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-4}$ alkoxycarbonyl, C$_{1-3}$ alkylcarbonyloxy, C$_{1-3}$ alkylcarbonylamino, C$_{1-3}$ alkylsulfonylamino, aminosulfonyl, C$_{1-3}$ alkyl(aminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino;

alternatively, when two R$^{33}$ groups are attached to the same carbon atom, the two R$^{33}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, C$_{1-3}$ alkyl, C$_{1-3}$ alkoxy, and C$_{1-3}$ haloalkyl;

each R$^{a2}$, R$^{c2}$, and R$^{d2}$ are independently selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl are each optionally substituted with 1, 2, or 3 substituents independently selected from R$^{33}$;

each R$^{b2}$ is independently selected from C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl are each optionally substituted with 1, 2, or 3 substituents independently selected from R$^{33}$;

each R$^{e2}$ is independently selected from H, CN, OH, C$_{1-4}$ alkyl, and C$_{1-4}$ alkoxy;

each R$^{f}$ is independently selected from H and C$_{1-3}$ alkyl;

R$^{4}$ is selected from H, halo, CN, NH$_2$, C$_{1-3}$ alkyl, and C$_{1-3}$ haloalkyl; and R$^{5}$ is selected from H, halo, cyano, hydroxy, amino, (C$_{1-4}$ alkyl)amino, di(C$_{1-4}$ alkyl)amino, C$_{1-4}$ alkyl, C$_{1-4}$ haloalkyl, and C$_{1-4}$ alkoxy.

2. The compound of claim 1, or a pharmaceutically acceptable salt thereof, wherein: the

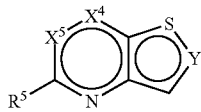

ring system is aromatic;

each ═══ is independently selected from a single bond and a double bond;

Y is N or CR$^{4}$;

X$^{1}$ is selected from CR$^{1}$, CR$^{3}$R$^{1a}$, C(═O), N, NR$^{1}$, O, and S;

X$^{2}$ is selected from CR$^{2}$, C(═O), N, NR$^{2}$, and C(═NR$^{2a}$);

X$^{3}$ is selected from CR$^{3}$ and NR$^{3}$;

X$^{4}$ is selected from C and N; and X$^{5}$ is C; or

X$^{4}$ is C; and X$^{5}$ is selected from C and N;

provided that:
(i) the selections for each of X$^{1}$, X$^{2}$, X$^{3}$, X$^{4}$, X$^{5}$ and ═══ maintain proper valency;
(ii) when X$^{1}$ is O or S, then X$^{2}$ is not NR$^{2}$ and X$^{2}$═══X$^{3}$ is not —C(═O)—CR$^{3}$—;
(iii) when X$^{1}$ is NR$^{1}$, then X$^{2}$═══X$^{3}$ is not —NR$^{2}$—NR$^{3}$—;
(iv) when X$^{4}$ is N, then X$^{1}$═══X$^{2}$═══X$^{3}$ is not ═N—NR$^{2}$—NR$^{3}$—; and
(v) when X$^{5}$ is N, then X$^{1}$═══X$^{2}$ is not —NR$^{1}$—NR$^{2}$— and X$^{1}$═══X$^{2}$═══X$^{3}$ is not —CR$^{1}$R$^{1a}$—NR$^{2}$—CR$^{3}$═;

R$^{1}$ is selected from H, halo, CN, NH$_2$, C$_{1-3}$ alkyl, C$_{1-3}$ alkoxy, and C$_{1-3}$ haloalkyl;

R$^{1a}$ is selected from H, halo, CN, NH$_2$, C$_{1-3}$ alkyl, and C$_{1-3}$ haloalkyl;

R$^{2a}$ is selected from CN, OH, OCH$_3$, and NO$_2$;

R$^{2}$ is selected from H, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ alkyl-S—, CN, OC(═O)R$^{b}$, OC(═O)NR$^{c}$R$^{d}$, NR$^{c}$R$^{d}$, NR$^{c}$C(═O)R$^{b}$, NR$^{c}$C(═O)OR$^{a}$, NR$^{c}$C(═O)NR$^{c}$R$^{d}$, C(═NR$^{e}$)R$^{b}$, C(═NR$^{e}$)NR$^{c}$R$^{d}$, NR$^{c}$C(═NR$^{e}$)NR$^{c}$R$^{d}$, NR$^{c}$S(═O)R$^{b}$, NR$^{c}$S(═O)$_2$R$^{b}$, NR$^{c}$S(═O)$_2$NR$^{c}$R$^{d}$, S(═O)R$^{b}$, S(═O)NR$^{c}$R$^{d}$, S(═O)$_2$R$^{b}$, and S(═O)$_2$NR$^{c}$R$^{d}$; wherein said C$_{1-6}$ alkyl, C$_{2-6}$ alkenyl, C$_{2-6}$ alkynyl, C$_{1-6}$ alkoxy, and C$_{1-6}$ alkyl-S— are each optionally substituted with 1, 2, or 3 substituents independently selected from Cy$^{2}$, halo, CN, NO$_2$, OR$^{a}$, SR$^{a}$, C(═O)R$^{b}$, C(═O)NR$^{c}$R$^{d}$, C(═O)OR$^{a}$, OC(═O)R$^{b}$, OC(═O)NR$^{c}$R$^{d}$, C(═NR$^{e}$)NR$^{c}$R$^{d}$, NR$^{c}$C(═NR$^{e}$)NR$^{c}$R$^{d}$, NR$^{c}$R$^{d}$, NR$^{c}$C(═O)R$^{b}$, NR$^{c}$C(═O)OR$^{a}$, NR$^{c}$C(═O)NR$^{c}$R$^{d}$, NR$^{c}$S(═O)R$^{b}$, NR$^{c}$S(═O)$_2$R$^{b}$, NR$^{c}$S(═O)$_2$NR$^{c}$R$^{d}$, S(═O)R$^{b}$, S(═O)NR$^{c}$R$^{d}$, S(═O)$_2$R$^{b}$, and S(═O)$_2$NR$^{c}$R$^{d}$;

alternatively, R$^{2}$ is selected from C$_{6-10}$ aryl, C$_{3-10}$ cycloalkyl, 5-10 membered heteroaryl, and 3-10 membered heterocycloalkyl, wherein said C$_{6-10}$ aryl, C$_{3-10}$ cycloalkyl, 5-10 membered heteroaryl, and 3-10 membered heterocycloalkyl are each optionally substituted with 1, 2, 3, 4, or 5 substituents independently selected from halo, R$^{21}$, Cy$^{2}$, CN, NO$_2$, OR$^{a}$, SR$^{a}$, C(═O)R$^{b}$, C(═O)NR$^{c}$R$^{d}$, C(═O)OR$^{a}$, OC(═O)R$^{b}$, OC(═O)NR$^{c}$R$^{d}$, C(═NR$^{e}$)NR$^{c}$R$^{d}$, NR$^{c}$C(═NR$^{e}$)NR$^{c}$R$^{d}$, NR$^{c}$R$^{d}$, NR$^{c}$C(═O)R$^{b}$, NR$^{c}$C(═O)OR$^{a}$, NR$^{c}$C(═O) NR$^{c}$R$^{d}$, NR$^{c}$S(═O)R$^{b}$, NR$^{c}$S(═O)$_2$R$^{b}$, NR$^{c}$S(═O)$_2$NR$^{c}$R$^{d}$, S(═O)R$^{b}$, S(═O)NR$^{c}$R$^{d}$, S(═O)$_2$R$^{b}$, and S(═O)$_2$NR$^{c}$R$^{d}$;

each R$^{21}$ is independently selected from C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl are each optionally substituted with 1, 2, or 3 substituents independently selected from Cy$^{2}$, halo, CN, NO$_2$, OR$^{a}$, SR$^{a}$, C(═O)R$^{b}$, C(═O)NR$^{c}$R$^{d}$, C(═O)OR$^{a}$, OC(═O)R$^{b}$, OC(═O)NR$^{c}$R$^{d}$, C(═NR$^{e}$)NR$^{c}$R$^{d}$, NR$^{c}$C(═NR$^{e}$)NR$^{c}$R$^{d}$, NR$^{c}$R$^{d}$, NR$^{c}$C(═O)R$^{b}$, NR$^{c}$C(═O)OR$^{a}$, NR$^{c}$C(═O)NR$^{c}$R$^{d}$, NR$^{c}$S(═O)R$^{b}$, NR$^{c}$S(═O)$_2$R$^{b}$, NR$^{c}$S(═O)$_2$NR$^{c}$R$^{d}$, S(═O)R$^{b}$, S(═O)NR$^{c}$R$^{d}$, S(═O)$_2$ R$^{b}$, and S(═O)$_2$NR$^{c}$R$^{d}$;

alternatively, when two R$^{21}$ groups are attached to the same carbon atom, the two R$^{21}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, C$_{1-3}$ alkyl, C$_{1-3}$ alkoxy, and C$_{1-3}$ haloalkyl;

each Cy$^{2}$ is independently selected from C$_{6-10}$ aryl, C$_{3-10}$ cycloalkyl, 5-10 membered heteroaryl, and 3-10 membered heterocycloalkyl wherein said C$_{6-10}$ aryl, C$_{3-10}$ cycloalkyl, 5-10 membered heteroaryl, and 3-10 membered heterocycloalkyl are each optionally substituted with 1, 2, 3, 4, or 5 substituents independently selected from halo, R$^{22}$, CN, NO$_2$, OR$^{a}$, SR$^{a}$, C(═O)R$^{b}$, C(═O)NR$^{c}$R$^{d}$, C(═O)OR$^{a}$, OC(═O)R$^{b}$, OC(═O) NR$^{c}$R$^{d}$, C(═NR$^{e}$)NR$^{c}$R$^{d}$, NR$^{c}$C(═NR$^{e}$)NR$^{c}$R$^{d}$, NR$^{c}$R$^{d}$, NR$^{c}$C(═O)R$^{b}$, NR$^{c}$C(═O)OR$^{a}$, NR$^{c}$C(═O)

$NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

each $R^a$, $R^c$, and $R^d$ are independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^b$ is independently selected from $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^e$ is independently selected from H, CN, OH, $C_{1-4}$ alkyl, $C_{1-4}$ alkoxy, $NO_2$, $C(O)(C_{1-4}$ alkyl), and $S(=O)_2(C_{1-4}$ alkyl);

each $R^{22}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^{a1}$, $R^{c1}$, and $R^{d1}$ are independently selected from H, $C_{1-3}$ alkyl, $C_{2-3}$ alkenyl, $C_{2-3}$ alkynyl, and $C_{1-3}$ haloalky;

each $R^{b1}$ is independently selected from $C_{1-3}$ alkyl, $C_{2-3}$ alkenyl, $C_{2-3}$ alkynyl, and $C_{1-3}$ haloalkyl;

each $R^{e1}$ is independently selected from H, CN, OH, $C_{1-4}$ alkyl, and $C_{1-4}$ alkoxy;

each $Cy^3$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $C_{1-6}$ alkyl, $C_{2-6}$ alkenyl, $C_{2-6}$ alkynyl, $C_{1-6}$ haloalkyl, halo, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

$R^3$ is $-Cy^{4A}-Cy^5$ or $-Cy^{4A}-Y^1-Cy^5$;

$Cy^{4A}$ is selected from $C_{6-10}$ arylene, $C_{3-10}$ cycloalkylene, 5-10 membered heteroarylene, and 3-10 membered heterocycloalkylene, wherein said $C_{6-10}$ arylene, $C_{3-10}$ cycloalkylene, 5-10 membered heteroarylene, and 3-10 membered heterocycloalkylene are optionally substituted with 1, 2, 3, or 4 independently selected $R^{31}$ groups, wherein said 3-10 membered heterocycloalkylene is not a saturated heterocycloalkylene group having one or more nitrogen ring members;

$Y^1$ is $C_{1-4}$ alkylene or $Y^{11}—C_{1-4}$ alkylene, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy, and wherein $Y^{11}$ is $C(=O)$;

each $Cy^5$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{32}$ groups;

$Y^2$ is $Y^{21}$, $C_{1-6}$ alkylene, $C_{2-6}$ alkenylene, $C_{2-6}$ alkynylene, $C_{1-6}$ alkylene-$Y^{21}$, $C_{2-6}$ alkenylene-$Y^{21}$, $C_{2-6}$ alkynylene-$Y^{21}$, $Y^{21}—C_{1-6}$ alkylene, $Y^{21}—C_{2-6}$ alkenylene, or $Y^{21}—C_{2-6}$ alkynylene, wherein said alkylene, alkenylene and alkynylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

$Y^3$ is $C_{1-6}$ alkylene-$Y^{31}—C_{1-6}$ alkylene, $C_{1-6}$ alkylene-$Y^{31}—C_{1-6}$ alkylene-$Y^{31}$, or $Y^{31}—C_{1-6}$ alkylene-$Y^{31}—C_{1-6}$ alkylene, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

each $Cy^7$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 independently selected $R^{33}$ groups;

$Y^{21}$, and $Y^{31}$ are each independently selected from O, S, $C(=O)$, $C(=O)NR^f$, $C(=O)O$, $OC(=O)$, $OC(=O)NR^f$, $NR^f$, $NR^fC(=O)$, $NR^fC(=O)O$, $NR^fC(=O)NR^f$, $NR^fS(=O)$, $NR^fS(=O)_2$, $NR^fS(=O)_2NR^f$, $S(=O)$, $S(=O)NR^f$, $S(=O)_2$, and $S(=O)_2NR^f$;

each $R^{31}$ is independently selected from $Cy^7$, $C_{1-6}$ alkyl, $C_{2-6}$ alkenyl, $C_{2-6}$ alkynyl, $C_{1-6}$ haloalkyl, halo, CN, $NO_2$, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)R^{b2}$, $NR^{c2}S(=O)_2R^{b2}$, $NR^{c2}S(=O)_2NR^{c2}R^{d2}$, $S(=O)R^{b2}$, $S(=O)NR^{c2}R^{d2}$, $S(=O)_2R^{b2}$, and $S(=O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{32}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)R^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each R$^{32}$ is independently selected from C$_{1-6}$ alkyl, C$_{2-6}$ alkenyl, C$_{2-6}$ alkynyl, C$_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said C$_{1-6}$ alkyl, C$_{2-6}$ alkenyl, and C$_{2-6}$ alkynyl are each optionally substituted with 1, 2, or 3 substituents independently selected from halo, CN, NO$_2$, OR$^{32}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{C2}$C(=O)OR$^{32}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each R$^{33}$ is independently selected from halo, OH, NO$_2$, CN, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-4}$ alkoxycarbonyl, C$_{1-3}$ alkylcarbonyloxy, C$_{1-3}$ alkylcarbonylamino, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino;

alternatively, when two R$^{33}$ groups are attached to the same carbon atom, the two R$^{33}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, C$_{1-3}$ alkyl, C$_{1-3}$ alkoxy, and C$_{1-3}$ haloalkyl;

each R$^{a2}$, R$^{c2}$, and R$^{d2}$ are independently selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl are each optionally substituted with 1, 2, or 3 substituents independently selected from R$^{33}$;

each R$^{b2}$ is independently selected from C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl are each optionally substituted with 1, 2, or 3 substituents independently selected from R$^{33}$;

each R$^{e2}$ is independently selected from H, CN, OH, C$_{1-4}$ alkyl, and C$_{1-4}$ alkoxy;

each R$^f$ is independently selected from H and C$_{1-3}$ alkyl;

R$^4$ is selected from H, halo, CN, NH$_2$, C$_{1-3}$ alkyl, and C$_{1-3}$ haloalkyl; and R$^5$ is selected from H, halo, cyano, hydroxy, amino, (C$_{1-4}$ alkyl)amino, di(C$_{1-4}$ alkyl)amino, C$_{1-4}$ alkyl, C$_{1-4}$ haloalkyl, and C$_{1-4}$ alkoxy.

3. The compound of claim 1, or a pharmaceutically acceptable salt thereof, wherein Y is CR$^4$.

4. The compound of claim 1, or a pharmaceutically acceptable salt thereof, wherein:
R$^2$ is H, methyl, ethyl, propyl, or isopropyl, wherein said methyl, ethyl, propyl, or isopropyl are each optionally optionally substituted with 1, 2, or 3 substituents independently selected from halo, CN, OR$^a$, NR$^c$R$^d$, NR$^c$C(=O)R$^b$, and NR$^c$S(=O)$_2$R$^b$; wherein each R$^a$, R$^c$, and R$^d$ are independently selected from H, methyl, and ethyl; and each R$^b$ is independently selected from methyl and ethyl; or alternatively, R$^2$ is cyclopropyl or an azetidine ring, each of which is optionally substituted with 1, 2, or 3 independently selected R$^{21}$ groups; and each R$^{21}$ is independently C$_{1-3}$ alkyl.

5. The compound of claim 1, or a pharmaceutically acceptable salt thereof, wherein R$^2$ is —CH$_2$—OH, —CH(CH$_3$)—OH, or —CH$_2$—NHSO$_2$CH$_3$.

6. The compound of claim 1, or a pharmaceutically acceptable salt thereof, wherein R$^4$ is H.

7. The compound of claim 1, or a pharmaceutically acceptable salt thereof, wherein R$^5$ is H.

8. The compound of claim 1, or a pharmaceutically acceptable salt thereof, wherein Cy$^{4A}$ is selected from cyclopropylene, cyclobutylene, cyclopentylene, cyclohexylene, and cycloheptylene, each of which is optionally substituted with 1, 2, 3, or 4 independently selected R$^{31}$ groups.

9. The compound of claim 1, or a pharmaceutically acceptable salt thereof, wherein Cy$^5$ is a pyridine ring, a pyrazole ring, or a triazole ring, each of which is optionally substituted with 1 or 2 independently selected R$^{32}$ groups.

10. The compound of claim 1, or a pharmaceutically acceptable salt thereof, wherein:
R$^2$ is H, methyl, ethyl, propyl, or isopropyl, wherein said methyl, ethyl, propyl, or isopropyl are each optionally optionally substituted with 1, 2, or 3 substituents independently selected from halo, CN, OR$^a$, NR$^c$R$^d$, NR$^c$C(=O)R$^b$, and NR$^c$S(=O)$_2$R$^b$; wherein each R$^a$, R$^c$, and R$^d$ are independently selected from H, methyl, and ethyl; and each R$^b$ is independently selected from methyl and ethyl; or alternatively, R$^2$ is cyclopropyl or an azetidine ring, each of which is optionally substituted with 1, 2, or 3 independently selected R$^{21}$ groups;

provided that when X$^1$═X$^2$═X$^3$ is —N=CR$^2$—NR$^3$—, X$^4$ is C, and X$^5$ is C; and Cy$^{4A}$ is unsubstituted or substituted 3-10 membered saturated heterocycloalkylene having one or more nitrogen atoms, then R$^2$ is selected from H, methyl, ethyl, propyl, or isopropyl, wherein said methyl, ethyl, propyl, or isopropyl are each optionally optionally substituted with 1, 2, or 3 substituents independently selected from halo, CN, OR$^a$, NR$^c$R$^d$, NR$^c$C(=O)R$^b$, and NR$^c$S(=O)$_2$R$^b$; wherein each R$^a$, R$^c$, and R$^d$ are independently selected from H, methyl, and ethyl; and each R$^b$ is independently selected from methyl and ethyl;

each R$^{21}$ is independently C$_{1-3}$ alkyl;

Cy$^{4A}$ is selected from C$_{3-10}$ cycloalkylene and 3-10 membered heterocycloalkylene, each of which are optionally substituted with 1, 2, 3, or 4 independently selected R$^{31}$ groups;

Cy$^5$ is C$_{6-10}$ aryl or 5-10 membered heteroaryl, which are each optionally substituted with 1 or 2 independently selected R$^{32}$ groups;

each R$^{31}$ or R$^{32}$ are each independently selected from C$_{1-6}$ alkyl, C$_{1-6}$ haloalkyl, halo, CN, OR$^{a2}$, C(=O)R$^{b2}$, C(=O)OR$^{a2}$, and NR$^{c2}$R$^{d2}$; wherein said C$_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, and $C_{1-6}$ haloalkyl, wherein said $C_{1-6}$ alkyl, and $C_{1-6}$ haloalkyl are each optionally substituted by 1, 2, or 3 CN;

each $R^{b2}$ is independently selected from $C_{1-6}$ alkyl and $C_{1-6}$ haloalkyl, which are each optionally substituted by 1, 2, or 3 CN;

$R^4$ is H; and $R^5$ is H.

11. The compound of claim 1, or a pharmaceutically acceptable salt thereof, wherein:

$R^2$ is H, methyl, ethyl, propyl, or isopropyl, wherein said methyl, ethyl, propyl, or isopropyl are each optionally optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl; or alternatively, $R^2$ is cyclopropyl or an azetidine ring, each of which is optionally substituted with 1, 2, or 3 independently selected $R^{21}$ groups;

provided that when $X^1 \text{---} X^2 \text{---} X^3$ is —N=CR$^2$—NR$^3$—, $X^4$ is C, and $X^5$ is C; and $Cy^{4A}$ is unsubstituted or substituted 3-10 membered saturated heterocycloalkylene having one or more nitrogen atoms, then $R^2$ is selected from H, methyl, ethyl, propyl, or isopropyl, wherein said methyl, ethyl, propyl, or isopropyl are each optionally optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl;

each $R^{21}$ is independently $C_{1-3}$ alkyl;

$Cy^{4A}$ is selected from $C_{3-7}$ cycloalkylene and 4-6 membered heterocycloalkylene, each of which are optionally substituted with 1, 2, 3, or 4 independently selected $R^{31}$ groups;

$Cy^5$ is phenyl, 4-6 membered heterocycloalkyl, or 5-6 membered heteroaryl, which are each optionally substituted with 1 or 2 independently selected $R^{32}$ groups;

each $R^{31}$ or $R^{32}$ are each independently selected from $C_{1-6}$ alkyl, $C_{1-6}$ haloalkyl, halo, CN, $OR^{a2}$, $C(=O)R^{b2}$, $C(=O)OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, $C_{1-6}$ haloalkyl, and wherein said $C_{1-6}$ alkyl, and $C_{1-6}$ haloalkyl are each optionally substituted by 1, 2, or 3 CN;

each $R^{b2}$ is independently selected from $C_{1-6}$ alkyl and $C_{1-6}$ haloalkyl, which are each optionally substituted by 1, 2, or 3 CN;

$R^4$ is H; and $R^5$ is H.

12. The compound of claim 1, or a pharmaceutically acceptable salt thereof, wherein:

$R^2$ is —CH$_2$—OH, —CH(CH$_3$)—OH, or —CH$_2$—NHSO$_2$CH$_3$;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

13. The compound of claim 1, or a pharmaceutically acceptable salt thereof, wherein:

$R^2$ is —CH$_2$—OH, —CH(CH$_3$)—OH, or —CH$_2$—NHSO$_2$CH$_3$;

$R^3$ is -Cy$^{4A}$-Cy$^5$;

$Cy^{4A}$ is selected from $C_{3-10}$ cycloalkylene and 3-10 membered heterocycloalkylene, each of which are optionally substituted with 1, 2, 3, or 4 independently selected $R^{31}$ groups, provided said 3-10 membered heterocycloalkylene is not a saturated heterocycloalkylene group having one or more nitrogen ring members;

$Cy^5$ is selected from 5-10 membered heteroaryl, which is optionally substituted with 1, 2, 3, or 4 independently selected $R^{32}$ groups;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl;

each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylamino sulfonyl, and $C_{1-3}$ alkylsulfonyl;

$R^4$ is H; and $R^5$ is H.

14. The compound of claim 1, or a pharmaceutically acceptable salt thereof, wherein:

$R^2$ is —CH$_2$—OH, —CH(CH$_3$)—OH, or —CH$_2$—NHSO$_2$CH$_3$;

$R^3$ is -Cy$^{4A}$-Cy$^5$;

$Cy^{4A}$ is selected from cyclohexylene and a 2H-tetrahydrofuran ring, each of which are optionally substituted with 1, 2, 3, or 4 independently selected $R^{31}$ groups;

$Cy^5$ is selected from 5-10 membered heteroaryl, which is optionally substituted with 1, 2, 3, or 4 independently selected $R^{32}$ groups;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl;

each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

15. The compound of claim 1, or a pharmaceutically acceptable salt thereof, wherein:
   $X^1 = X^2 = X^3$ is —N=CR$^2$—NR$^3$—, $X^4$ is C, $X^5$ is C, and Y is CR$^4$; or
   $X^1 = X^2 = X^3$ is —CR$^1$=CR$^2$—NR$^3$—, $X^4$ is C, $X^5$ is C, and Y is CR$^4$; or
   $X^1 = X^2 = X^3$ is —CR$^1$R$^{1a}$—C(=O)—NR$^3$—, $X^4$ is C, $X^5$ is C, and Y is CR$^4$; or
   $X^1 = X^2 = X^3$ is —O—C(=O)—NR$^3$—, $X^4$ is C, $X^5$ is C, and Y is CR$^4$; or
   $X^1 = X^2 = X^3$ is =N—CR$^2$=CR$^3$—, $X^4$ is N, $X^5$ is C, and Y is CR$^4$.

16. The compound of claim 1, having Formula IIb:

IIb or a pharmaceutically acceptable salt thereof.

17. The compound of claim 1, having Formula IIIb:

IIIb or a pharmaceutically acceptable salt thereof.

18. The compound of claim 1 is (1R)-1-{1-[cis-4-(1H-1,2,4-Triazol-1-yl)cyclohexyl]-1H-imidazo[4,5-d]thieno[3,2-b]pyridin-2-yl}ethanol, or a pharmaceutically acceptable salt thereof.

19. The compound of claim 1, selected from:
   (1R)-1-(1-{(3S)-1-[3-(1H-Pyrazol-4-yl)propanoyl]piperidin-3-yl}-1H-imidazo[4,5-d]thieno[3,2-b]pyridin-2-yl)ethanol;
   (1R)-1-{1-[(3S)-1-(3-Pyridin-3-ylpropanoyl)piperidin-3-yl]-1H-imidazo[4,5-d]thieno[3,2-b]pyridin-2-yl}ethanol;
   (1R)-1-{1-[(3S)-1-(3-Phenylbutanoyl)piperidin-3-yl]-1H-imidazo[4,5-d]thieno[3,2-b]pyridin-2-yl}ethanol; and
   (1R)-1-{1-[(3S)-1-(3-Phenylpropanoyl)piperidin-3-yl]-1H-imidazo[4,5-d]thieno[3,2-b]pyridin-2-yl}ethanol;
   or a pharmaceutically acceptable salt thereof.

20. A composition comprising a compound according to claim 1, or a pharmaceutically acceptable salt thereof, and a pharmaceutically acceptable carrier.

21. A compound of Formula I:

I or a pharmaceutically acceptable salt thereof, wherein:
   the ring system is aromatic;
   each $=$ is independently selected from a single bond and a double bond;
   Y is N or CR$^4$;
   $X^1$ is selected from CR$^1$, CR$^1$R$^{1a}$, C(=O), N, NR$^1$, O, and S;
   $X^2$ is selected from CR$^2$, C(=O), N, NR$^2$, and C(=NR$^{2a}$);
   $X^3$ is selected from CR$^3$ and NR$^3$;
   $X^4$ is selected from C and N; and $X^5$ is C; or
   $X^4$ is C; and $X^5$ is selected from C and N;
   provided that:
   (i) the selections for each of $X^1$, $X^2$, $X^3$, $X^4$, $X^5$ and $=$ maintain proper valency;
   (ii) when $X^1$ is O or S, then $X^2$ is not NR$^2$ and $X^2 = X^3$ is not —C(=O)—CR$^3$—;
   (iii) when $X^1$ is NR$^1$, then $X^2 = X^3$ is not —NR$^2$—NR$^3$—;
   (iv) when $X^4$ is N, then $X^1 = X^2 = X^3$ is not =N—NR$^2$—NR$^3$—; and
   (v) when $X^5$ is N, then $X^1 = X^2$ is not —NR$^1$—NR$^2$— and $X^1 = X^2 = X^3$ is not —CR$^1$R$^{1a}$—NR$^2$—CR$^3$=;
   R$^1$ is selected from H, halo, CN, NH$_2$, C$_{1-3}$ alkyl, C$_{1-3}$ alkoxy, and C$_{1-3}$ haloalkyl;
   R$^{1a}$ is selected from H, halo, CN, NH$_2$, C$_{1-3}$ alkyl, and C$_{1-3}$ haloalkyl;
   R$^{2a}$ is selected from CN, OH, OCH$_3$, and NO$_2$;
   R$^2$ is selected from H, halo, CN, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ alkyl-S—, CN, C(=O)R$^b$, C(=O)NR$^c$R$^d$, C(=O)OR$^a$, OC(=O)R$^b$, OC(=O)NR$^c$R$^d$, NR$^c$R$^d$, NR$^c$C(=O)R$^b$, NR$^c$C(=O)OR$^a$, NR$^c$C(=O)NR$^c$R$^d$, C(=NR$^e$)R$^b$, C(=NR$^e$)NR$^c$R$^d$, NR$^c$C(=NR$^e$)NR$^c$R$^d$, NR$^c$S(=O)R$^b$, NR$^c$S(=O)$_2$R$^b$, NR$^c$S(=O)$_2$NR$^c$R$^d$, S(=O)R$^b$, S(=O)NR$^c$R$^d$, S(=O)$_2$R$^b$, and S(=O)$_2$NR$^c$R$^d$;
   wherein said C$_{1-6}$ alkyl, C$_{2-6}$ alkenyl, C$_{2-6}$ alkynyl, C$_{1-6}$ alkoxy, and C$_{1-6}$ alkyl-S— are each optionally substituted with 1, 2, or 3 substituents independently selected from Cy$^2$, halo, CN, NO$_2$, OR$^a$, SR$^a$, C(=O)R$^b$, C(=O)NR$^c$R$^d$, C(=O)OR$^a$, OC(=O)R$^b$, OC(=O)NR$^c$R$^d$, C(=NR$^e$)NR$^c$R$^d$, NR$^c$C(=NR$^e$)NR$^c$R$^d$, NR$^c$R$^d$, NR$^c$C(=O)R$^b$, NR$^c$C(=O)OR$^a$, NR$^c$C(=O)NR$^c$R$^d$, NR$^c$S(=O)R$^b$, NR$^c$S(=O)$_2$R$^b$, NR$^c$S(=O)$_2$NR$^c$R$^d$, S(=O)R$^b$, S(=O)NR$^c$R$^d$, S(=O)$_2$R$^b$, and S(=O)$_2$NR$^c$R$^d$;
   alternatively, R$^2$ is selected from C$_{6-10}$ aryl, C$_{3-10}$ cycloalkyl, 5-10 membered heteroaryl, and 3-10 membered heterocycloalkyl, wherein said C$_{6-10}$ aryl, C$_{3-10}$ cycloalkyl, 5-10 membered heteroaryl, and 3-10 membered heterocycloalkyl are each optionally substituted with 1, 2, 3, 4, or 5 substituents independently selected from halo, $R^{21}$, $Cy^2$, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

provided that when $X^1 \text{---} X^2 \text{---} X^3$ is $-N=CR^2-NR^3-$, $X^4$ is C, and $X^5$ is C; and $Cy^4$ is unsubstituted or substituted 3-10 membered saturated heterocycloalkylene having one or more nitrogen atoms or $Cy^{4A}$ is unsubstituted or substituted 3-10 membered saturated heterocycloalkylene having one or more nitrogen atoms, then $R^2$ is selected from H, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkyl-S—, CN, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^a$, $NR^cC(=O)NR^cR^d$, $C(=NR^e)R^b$, $C(=NR^e)NR^cR^d$, $NR^cC(=NR^e)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$; wherein said $C_{1-6}$ alkyl, $C_{2-6}$ alkenyl, $C_{2-6}$ alkynyl, $C_{1-6}$ alkoxy, and $C_{1-6}$ alkyl-S— are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2 R^b$, and $S(=O)_2NR^cR^d$;

each $R^{21}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2 R^b$, and $S(=O)_2NR^cR^d$;

alternatively, when two $R^{21}$ groups are attached to the same carbon atom, the two $R^{21}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, $C_{1-3}$ alkyl, $C_{1-3}$ alkoxy, and $C_{1-3}$ haloalkyl;

each $Cy^2$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $R^{22}$, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

each $R^a$, $R^c$, and $R^d$ are independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^b$ is independently selected from $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^e$ is independently selected from H, CN, OH, $C_{1-4}$ alkyl, $C_{1-4}$ alkoxy, $NO_2$, $C(O)(C_{1-4}$ alkyl), and $S(=O)_2(C_{1-4}$ alkyl);

each $R^{22}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^{a1}$, $R^{c1}$, and $R^{d1}$ are independently selected from H, $C_{1-3}$ alkyl, $C_{2-3}$ alkenyl, $C_{2-3}$ alkynyl, and $C_{1-3}$ haloalkyl;

each $R^{b1}$ is independently selected from $C_{1-3}$ alkyl, $C_{2-3}$ alkenyl, $C_{2-3}$ alkynyl, and $C_{1-3}$ haloalkyl;

each $R^{e1}$ is independently selected from H, CN, OH, $C_{1-4}$ alkyl, and $C_{1-4}$ alkoxy;

each $Cy^3$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $C_{1-6}$ alkyl, $C_{2-6}$ alkenyl, $C_{2-6}$ alkynyl, $C_{1-6}$ haloalkyl, halo, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})$ NR$^{c1}$R$^{d1}$, NR$^{c1}$R$^{d1}$, NR$^{c1}$C(=O)R$^{b1}$, NR$^{c1}$C(=O)OR$^{a1}$, NR$^{c1}$C(=O)NR$^{c1}$R$^{d1}$, NR$^{c1}$S(=O)R$^{b1}$, NR$^{c1}$S(=O)$_2$R$^{b1}$, NR$^{c1}$S(=O)$_2$NR$^{c1}$R$^{d1}$, S(=O)R$^{b1}$, S(=O)NR$^{c1}$R$^{d1}$, S(=O)$_2$R$^{b1}$, and S(=O)$_2$NR$^{c1}$R$^{d1}$;

R$^3$ is selected from Cy$^4$, -Cy$^{4A}$-Cy$^5$, -Cy$^{4A}$-Y$^1$-Cy$^5$, -Cy$^{4A}$-Y$^1$-Cy$^{5A}$-Cy$^6$, -Cy$^{4A}$-Cy$^{5A}$-Y$^2$-Cy$^6$, -Cy$^{4A}$-Y$^1$-Cy$^{5A}$-Y$^2$-Cy$^6$, or -Cy$^{4A}$-Y$^3$-Cy$^6$;

Cy$^4$ is selected from C$_{6-10}$ aryl, C$_{3-10}$ cycloalkyl, 5-10 membered heteroaryl, and 3-10 membered heterocycloalkyl, wherein said C$_{6-10}$ aryl, C$_{3-10}$ cycloalkyl, 5-10 membered heteroaryl, and 3-10 membered heterocycloalkyl are optionally substituted with 1, 2, 3, or 4 independently selected R$^{31}$ groups;

Cy$^{4A}$ is selected from C$_{6-10}$ arylene, C$_{3-10}$ cycloalkylene, 5-10 membered heteroarylene, and 3-10 membered heterocycloalkylene, wherein said C$_{6-10}$ arylene, C$_{3-10}$ cycloalkylene, 5-10 membered heteroarylene, and 3-10 membered heterocycloalkylene are optionally substituted with 1, 2, 3, or 4 independently selected R$^{31}$ groups;

Y$^1$ is Y$^{11}$, C$_{1-6}$ alkylene, C$_{2-6}$ alkenylene, C$_{2-6}$ alkynylene, C$_{1-6}$ alkylene-Y$^{11}$, C$_{2-6}$ alkenylene-Y$^{11}$, C$_{2-6}$ alkynylene-Y$^{11}$, Y$^{11}$—C$_{1-6}$ alkylene, Y$^{11}$—C$_{2-6}$ alkenylene, or Y$^{11}$—C$_{2-6}$ alkynylene, wherein said alkylene, alkenylene and alkynylene groups are each optionally substituted with 1, 2, or 3 substituents independently selected from halo, CN, OH, C$_{1-3}$ alkyl, C$_{1-3}$ alkoxy, C$_{1-3}$ haloalkyl, and C$_{1-3}$ haloalkoxy;

Cy$^5$ is a pyridine ring, a pyrazole ring, or a triazole ring, each of which is optionally substituted with 1 or 2 independently selected R$^{32}$ groups;

Cy$^6$ is selected from C$_{6-10}$ aryl, C$_{3-10}$ cycloalkyl, 5-10 membered heteroaryl, and 3-10 membered heterocycloalkyl, wherein said C$_{6-10}$ aryl, C$_{3-10}$ cycloalkyl, 5-10 membered heteroaryl, and 3-10 membered heterocycloalkyl are optionally substituted with 1, 2, 3, or 4 independently selected R$^{32}$ groups;

Cy$^{5A}$ is selected from C$_{6-10}$ arylene, C$_{3-10}$ cycloalkylene, 5-10 membered heteroarylene, and 3-10 membered heterocycloalkylene, wherein said C$_{6-10}$ arylene, C$_{3-10}$ cycloalkylene, 5-10 membered heteroarylene, and 3-10 membered heterocycloalkylene are each optionally substituted with 1, 2, 3, or 4 independently selected R$^{32}$ groups;

Y$^2$ is Y$^{21}$, C$_{1-6}$ alkylene, C$_{2-6}$ alkenylene, C$_{2-6}$ alkynylene, C$_{1-6}$ alkylene-Y$^{21}$, C$_{2-6}$ alkenylene-Y$^{21}$, C$_{2-6}$ alkynylene-Y$^{21}$, Y$^{21}$—C$_{1-6}$ alkylene, Y$^{21}$—C$_{2-6}$ alkenylene, or Y$^{21}$—C$_{2-6}$ alkynylene, wherein said alkylene, alkenylene and alkynylene groups are each optionally substituted with 1, 2, or 3 substituents independently selected from halo, CN, OH, C$_{1-3}$ alkyl, C$_{1-3}$ alkoxy, C$_{1-3}$ haloalkyl, and C$_{1-3}$ haloalkoxy;

Y$^3$ is C$_{1-6}$ alkylene-Y$^{31}$—C$_{1-6}$ alkylene, C$_{1-6}$ alkylene-Y$^{31}$—C$_{1-6}$ alkylene-Y$^{31}$, or Y$^{31}$—C$_{1-6}$ alkylene-Y$^{31}$—C$_{1-6}$ alkylene, wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, and C$_{1-3}$ haloalkoxy;

each Cy$^7$ is independently selected from C$_{6-10}$ aryl, C$_{3-10}$ cycloalkyl, 5-10 membered heteroaryl, and 3-10 membered heterocycloalkyl, wherein said C$_{6-10}$ aryl, C$_{3-10}$ cycloalkyl, 5-10 membered heteroaryl, and 3-10 membered heterocycloalkyl are each optionally substituted with 1, 2, 3, 4, or 5 independently selected R$^{33}$ groups;

Y$^{11}$, Y$^{21}$, and Y$^{31}$ are each independently selected from O, S, C(=O), C(=O)NR$^f$, C(=O)O, OC(=O), OC(=O)NR$^f$, NR$^f$, NR$^f$C(=O), NR$^f$C(=O)O, NR$^f$C(=O)NR$^f$, NR$^f$S(=O), NR$^f$S(=O)$_2$, NR$^f$S(=O)$_2$NR$^f$, S(=O), S(=O)NR$^f$, S(=O)$_2$, and S(=O)$_2$NR$^f$;

each R$^{31}$ is independently selected from Cy$^7$, C$_{1-6}$ alkyl, C$_{2-6}$ alkenyl, C$_{2-6}$ alkynyl, C$_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said C$_{1-6}$ alkyl, C$_{2-6}$ alkenyl, and C$_{2-6}$ alkynyl are each optionally substituted with 1, 2, or 3 substituents independently selected from halo, CN, NO$_2$, OR$^{32}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each R$^{32}$ is independently selected from C$_{1-6}$ alkyl, C$_{2-6}$ alkenyl, C$_{2-6}$ alkynyl, C$_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said C$_{1-6}$ alkyl, C$_{2-6}$ alkenyl, and C$_{2-6}$ alkynyl are each optionally substituted with 1, 2, or 3 substituents independently selected from halo, CN, NO$_2$, OR$^{32}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each R$^{33}$ is independently selected from halo, OH, NO$_2$, CN, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-4}$ alkoxycarbonyl, C$_{1-3}$ alkylcarbonyloxy, C$_{1-3}$ alkylcarbonylamino, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino;

alternatively, when two R$^{33}$ groups are attached to the same carbon atom, the two R$^{33}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, C$_{1-3}$ alkyl, C$_{1-3}$ alkoxy, and C$_{1-3}$ haloalkyl;

each R$^{a2}$, R$^{c2}$, and R$^{d2}$ are independently selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, and C$_{2-6}$ alkynyl are each optionally substituted with 1, 2, or 3 substituents independently selected from $R^{33}$;

each $R^{b2}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $R^{33}$;

each $R^{e2}$ is independently selected from H, CN, OH, $C_{1-4}$ alkyl, and $C_{1-4}$ alkoxy;

each $R^f$ is independently selected from H and $C_{1-3}$ alkyl;

$R^4$ is selected from H, halo, CN, $NH_2$, $C_{1-3}$ alkyl, and $C_{1-3}$ haloalkyl; and $R^5$ is selected from H, halo, cyano, hydroxy, amino, ($C_{1-4}$ alkyl)amino, di($C_{1-4}$ alkyl)amino, $C_{1-4}$ alkyl, $C_{1-4}$ haloalkyl, and $C_{1-4}$ alkoxy; and wherein the compound is not ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile.

22. The compound of claim 21, or a pharmaceutically acceptable salt thereof, wherein:
the ring system is aromatic;

each ⸗ is independently selected from a single bond and a double bond;

Y is N or $CR^4$;

$X^1$ is selected from $CR^1$, $CR^1R^{1a}$, $C(=O)$, N, $NR^1$, O, and S;

$X^2$ is selected from $CR^2$, $C(=O)$, N, $NR^2$, and $C(=NR^{2a})$;

$X^3$ is selected from $CR^3$ and $NR^3$;

$X^4$ is selected from C and N; and $X^5$ is C; or $X^4$ is C; and $X^5$ is selected from C and N;

provided that:
(i) the selections for each of $X^1$, $X^2$, $X^3$, $X^4$, $X^5$ and ⸗ maintain proper valency;
(ii) when $X^1$ is O or S, then $X^2$ is not $NR^2$ and $X^2$ ⸗ $X^3$ is not —C(=O)—$CR^3$—;
(iii) when $X^1$ is $NR^1$, then $X^2$ ⸗ $X^3$ is not —$NR^2$—$NR^3$—;
(iv) when $X^4$ is N, then $X^1$ ⸗ $X^2$ ⸗ $X^3$ is not =N—$NR^2$—$NR^3$—; and
(v) when $X^5$ is N, then $X^1$ ⸗ $X^2$ is not —$NR^1$—$NR^2$— and $X^1$ ⸗ $X^2$ ⸗ $X^3$ is not —$CR^1R^{1a}$—$NR^2$—$CR^3$=;

$R^1$ is selected from H, halo, CN, $NH_2$, $C_{1-3}$ alkyl, $C_{1-3}$ alkoxy, and $C_{1-3}$ haloalkyl;

$R^{1a}$ is selected from H, halo, CN, $NH_2$, $C_{1-3}$ alkyl, and $C_{1-3}$ haloalkyl;

$R^{2a}$ is selected from CN, OH, $OCH_3$, and $NO_2$;

$R^2$ is selected from H, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkyl-S—, CN, $OC(=O)R^b$, $OC(=O)NR^cR^d$, $NR^cR^d$, $NR^cC(=O)R^b$, $NR^cC(=O)OR^a$, $NR^cC(=O)NR^cR^d$, $C(=NR^e)R^b$, $C(=NR^e)NR^cR^d$, $NR^cC(=NR^e)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$; wherein said $C_{1-6}$ alkyl, $C_{2-6}$ alkenyl, $C_{2-6}$ alkynyl, $C_{1-6}$ alkoxy, and $C_{1-6}$ alkyl-S— are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2 R^b$, and $S(=O)_2NR^cR^d$;

alternatively, $R^2$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $R^{21}$, $Cy^2$, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

each $R^{21}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2 R^b$, and $S(=O)_2NR^cR^d$;

alternatively, when two $R^{21}$ groups are attached to the same carbon atom, the two $R^{21}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, $C_{1-3}$ alkyl, $C_{1-3}$ alkoxy, and $C_{1-3}$ haloalkyl;

each $Cy^2$ is independently selected from $C_{6-10}$ aryl, $C_{3-10}$ cycloalkyl, 5-10 membered heteroaryl, and 3-10 membered heterocycloalkyl wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $R^{22}$, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $C(=NR^e)NR^cR^d$, $NR^cC(=NR^e)NR^cR^d$, $NR^cR^d$, $NR^cC(=O)R^b$, $NR^cC(=O)OR^a$, $NR^cC(=O)NR^cR^d$, $NR^cS(=O)R^b$, $NR^cS(=O)_2R^b$, $NR^cS(=O)_2NR^cR^d$, $S(=O)R^b$, $S(=O)NR^cR^d$, $S(=O)_2R^b$, and $S(=O)_2NR^cR^d$;

each $R^a$, $R^c$, and $R^d$ are independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)$ $OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^b$ is independently selected from $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 3-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^e$ is independently selected from H, CN, OH, $C_{1-4}$ alkyl, $C_{1-4}$ alkoxy, $NO_2$, $C(O)(C_{1-4}$ alkyl), and $S(=O)_2(C_{1-4}$ alkyl);

each $R^{22}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

each $R^{a1}$, $R^{c1}$, and $R^{d1}$ are independently selected from H, $C_{1-3}$ alkyl, $C_{2-3}$ alkenyl, $C_{2-3}$ alkynyl, and $C_{1-3}$ haloalky;

each $R^{b1}$ is independently selected from $C_{1-3}$ alkyl, $C_{2-3}$ alkenyl, $C_{2-3}$ alkynyl, and $C_{1-3}$ haloalkyl;

each $R^{e1}$ is independently selected from H, CN, OH, $C_{1-4}$ alkyl, and $C_{1-4}$ alkoxy;

each $Cy^3$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $C_{1-6}$ alkyl, $C_{2-6}$ alkenyl, $C_{2-6}$ alkynyl, $C_{1-6}$ haloalkyl, halo, CN, $NO_2$, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(=O)R^{b1}$, $NR^{c1}C(=O)OR^{a1}$, $NR^{c1}C(=O)NR^{c1}R^{d1}$, $NR^{c1}S(=O)R^{b1}$, $NR^{c1}S(=O)_2R^{b1}$, $NR^{c1}S(=O)_2NR^{c1}R^{d1}$, $S(=O)R^{b1}$, $S(=O)NR^{c1}R^{d1}$, $S(=O)_2R^{b1}$, and $S(=O)_2NR^{c1}R^{d1}$;

$R^3$ is $Cy^4$, -$Cy^{4A}$-$Cy^5$, -$Cy^{4A}$-$Y^1$-$Cy^5$, -$Cy^{4A}$-$Y^1$-$Cy^{5A}$-$Cy^6$, -$Cy^{4A}$-$Cy^{5A}$-$Y^2$-$Cy^6$, -$Cy^{4A}$-$Y^3$-$Cy^{5A}$-$Y^2$-$Cy^6$, or -$Cy^{4A}$-$Y^3$-$Cy^6$;

$Cy^4$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{31}$ groups, wherein said 3-10 membered heterocycloalkyl is not a saturated heterocycloalkyl group having one or more nitrogen ring members;

$Cy^{4A}$ is selected from $C_{6-10}$ arylene, $C_{3-10}$ cycloalkylene, 5-10 membered heteroarylene, and 3-10 membered heterocycloalkylene, wherein said $C_{6-10}$ arylene, $C_{3-10}$ cycloalkylene, 5-10 membered heteroarylene, and 3-10 membered heterocycloalkylene are optionally substituted with 1, 2, 3, or 4 independently selected $R^{31}$ groups, wherein said 3-10 membered heterocycloalkylene is not a saturated heterocycloalkylene group having one or more nitrogen ring members;

$Y^1$ is $Y^{11}$, $C_{1-6}$ alkylene, $C_{2-6}$ alkenylene, $C_{2-6}$ alkynylene, $C_{1-6}$ alkylene-$Y^{11}$, $C_{2-6}$ alkenylene-$Y^{11}$, $C_{2-6}$ alkynylene-$Y^{11}$, $Y^{11}$—$C_{1-6}$ alkylene, $Y^{11}$—$C_{2-6}$ alkenylene, or $Y^{11}$—$C_{2-6}$ alkynylene, wherein said alkylene, alkenylene and alkynylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

$Cy^5$ is a pyridine ring, a pyrazole ring, or a triazole ring, each of which is optionally substituted with 1 or 2 independently selected $R^{32}$ groups;

$Cy^6$ is selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are optionally substituted with 1, 2, 3, or 4 independently selected $R^{32}$ groups;

$Cy^{5A}$ is selected from $C_{6-10}$ arylene, $C_{3-10}$ cycloalkylene, 5-10 membered heteroarylene, and 3-10 membered heterocycloalkylene, wherein said $C_{6-10}$ arylene, $C_{3-10}$ cycloalkylene, 5-10 membered heteroarylene, and 3-10 membered heterocycloalkylene are each optionally substituted with 1, 2, 3, or 4 independently selected $R^{32}$ groups;

$Y^2$ is $Y^{21}$, $C_{1-6}$ alkylene, $C_{2-6}$ alkenylene, $C_{2-6}$ alkynylene, $C_{1-6}$ alkylene-$Y^{21}$, $C_{2-6}$ alkenylene-$Y^{21}$, $C_{2-6}$ alkynylene-$Y^{21}$, $Y^{21}$—$C_{1-6}$ alkylene, $Y^{21}$—$C_{2-6}$ alkenylene, or $Y^{21}$—$C_{2-6}$ alkynylene, wherein said alkylene, alkenylene and alkynylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

$Y^3$ is $C_{1-6}$ alkylene-$Y^{31}$—$C_{1-6}$ alkylene, $C_{1-6}$ alkylene-$Y^{31}$—$C_{1-6}$ alkylene-$Y^{31}$, or $Y^{31}$—$C_{1-6}$ alkylene-$Y^{31}$—$C_{1-6}$ alkylene, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, and $C_{1-3}$ haloalkoxy;

each $Cy^7$ is independently selected from $C_{6-10}$ aryl, $C_{3-10}$ cycloalkyl, 5-10 membered heteroaryl, and 3-10 membered heterocycloalkyl, wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 independently selected $R^{33}$ groups;

$Y^{11}$, $Y^{21}$, and $Y^{31}$ are each independently selected from O, S, $C(=O)$, $C(=O)NR^f$, $C(=O)O$, $OC(=O)$, $OC(=O)NR^f$, $NR^f$, $NR^fC(=O)$, $NR^fC(=O)O$, $NR^fC(=O)NR^f$, $NR^fS(=O)$, $NR^fS(=O)_2$, $NR^fS(=O)_2NR^f$, $S(=O)$, $S(=O)NR^f$, $S(=O)_2$, and $S(=O)_2NR^f$;

each $R^{31}$ is independently selected from $Cy^7$, $C_{1-6}$ alkyl, $C_{2-6}$ alkenyl, $C_{2-6}$ alkynyl, $C_{1-6}$ haloalkyl, halo, CN, $NO_2$, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)R^{b2}$, $NR^{c2}S(=O)_2R^{b2}$, $NR^{c2}S(=O)_2NR^{c2}R^{d2}$, $S(=O)R^{b2}$, $S(=O)NR^{c2}R^{d2}$, $S(=O)_2R^{b2}$, and $S(=O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, NO$_2$, OR$^{32}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each R$^{32}$ is independently selected from $C_{1-6}$ alkyl, $C_{2-6}$ alkenyl, $C_{2-6}$ alkynyl, $C_{1-6}$ haloalkyl, halo, CN, NO$_2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, NO$_2$, OR$^{32}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, C(=NR$^{e2}$)NR$^{c2}$R$^{d2}$, NR$^{c2}$R$^{d2}$, NR$^{c2}$C(=O)R$^{b2}$, NR$^{c2}$C(=O)OR$^{32}$, NR$^{c2}$C(=O)NR$^{c2}$R$^{d2}$, NR$^{c2}$S(=O)R$^{b2}$, NR$^{c2}$S(=O)$_2$R$^{b2}$, NR$^{c2}$S(=O)$_2$NR$^{c2}$R$^{d2}$, S(=O)R$^{b2}$, S(=O)NR$^{c2}$R$^{d2}$, S(=O)$_2$R$^{b2}$, and S(=O)$_2$NR$^{c2}$R$^{d2}$;

each R$^{33}$ is independently selected from halo, OH, NO$_2$, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonyloxy, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

alternatively, when two R$^{33}$ groups are attached to the same carbon atom, the two R$^{33}$ groups, along with the carbon atom to which they are attached, form a 3-7 membered cycloalkyl ring or a 3-7 membered heterocycloalkyl ring, wherein 1 or 2 ring members of said heterocycloalkyl ring are independently selected from N, O and S; and wherein said cycloalkyl ring and heterocycloalkyl ring are each optionally substituted with 1, 2, or 3 substituents independently selected from halo, OH, CN, $C_{1-3}$ alkyl, $C_{1-3}$ alkoxy, and $C_{1-3}$ haloalkyl;

each R$^{a2}$, R$^{c2}$, and R$^{d2}$ are independently selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from R$^{33}$;

each R$^{b2}$ is independently selected from $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl are each optionally substituted with 1, 2, or 3 substituents independently selected from R$^{33}$;

each R$^{e2}$ is independently selected from H, CN, OH, $C_{1-4}$ alkyl, and $C_{1-4}$ alkoxy;

each R$^f$ is independently selected from H and $C_{1-3}$ alkyl;

R$^4$ is selected from H, halo, CN, NH$_2$, $C_{1-3}$ alkyl, and $C_{1-3}$ haloalkyl; and R$^5$ is selected from H, halo, cyano, hydroxy, amino, ($C_{1-4}$ alkyl)amino, di($C_{1-4}$ alkyl)amino, $C_{1-4}$ alkyl, $C_{1-4}$ haloalkyl, and $C_{1-4}$ alkoxy.

23. The compound of claim 21, or a pharmaceutically acceptable salt thereof, wherein Y is CR$^4$.

24. The compound of claim 21, or a pharmaceutically acceptable salt thereof, wherein:

R$^2$ is H, methyl, ethyl, propyl, or isopropyl, wherein said methyl, ethyl, propyl, or isopropyl are each optionally optionally substituted with 1, 2, or 3 substituents independently selected from halo, CN, OR$^a$, NR$^c$R$^d$, NR$^c$C(=O)R$^b$, and NR$^c$S(=O)$_2$R$^b$; wherein each R$^a$, R$^c$, and R$^d$ are independently selected from H, methyl, and ethyl; and each R$^b$ is independently selected from methyl and ethyl; or alternatively, R$^2$ is cyclopropyl or an azetidine ring, each of which is optionally substituted with 1, 2, or 3 independently selected R$^{21}$ groups; and each R$^{21}$ is independently $C_{1-3}$ alkyl.

25. The compound of claim 21, or a pharmaceutically acceptable salt thereof, wherein R$^2$ is —CH$_2$—OH, —CH(CH$_3$)—OH, or —CH$_2$—NHSO$_2$CH$_3$.

26. The compound of claim 21, or a pharmaceutically acceptable salt thereof, wherein R$^4$ is H.

27. The compound of claim 21, or a pharmaceutically acceptable salt thereof, wherein R$^5$ is H.

28. The compound of claim 21, or a pharmaceutically acceptable salt thereof, wherein R$^3$ is Cy$^4$.

29. The compound of claim 21, or a pharmaceutically acceptable salt thereof, wherein R$^3$ is -Cy$^{44}$-Cy$^5$ or -Cy$^{44}$-Y$^1$-Cy$^5$; wherein Y$^1$ is $C_{1-4}$ alkylene or Y$^{11}$—$C_{1-4}$ alkylene; and Y$^{11}$ is C(=O).

30. The compound of claim 21, or a pharmaceutically acceptable salt thereof, wherein Cy$^4$ is selected from $C_{6-10}$ aryl, $C_{3-10}$ cycloalkyl and 3-10 membered heterocycloalkyl, each of which are optionally substituted with 1, 2, 3, or 4 independently selected R$^{31}$ groups, provided said 3-10 membered heterocycloalkyl is not a saturated heterocycloalkyl group having one or more nitrogen ring members.

31. The compound of claim 21, or a pharmaceutically acceptable salt thereof, wherein Cy$^4$ is a tetrahydro-2H-pyran ring, which is optionally substituted with 1 or 2 independently selected R$^{31}$ groups.

32. The compound of claim 21, or a pharmaceutically acceptable salt thereof, wherein Cy$^{44}$ is selected from cyclopropylene, cyclobutylene, cyclopentylene, cyclohexylene, and cycloheptylene, each of which is optionally substituted with 1, 2, 3, or 4 independently selected R$^{31}$ groups.

33. The compound of claim 21, or a pharmaceutically acceptable salt thereof, wherein:

R$^2$ is H, methyl, ethyl, propyl, or isopropyl, wherein said methyl, ethyl, propyl, or isopropyl are each optionally optionally substituted with 1, 2, or 3 substituents independently selected from halo, CN, OR$^a$, NR$^c$R$^d$, NR$^c$C(=O)R$^b$, and NR$^c$S(=O)$_2$R$^b$; wherein each R$^a$, R$^c$, and R$^d$ are independently selected from H, methyl, and ethyl; and each R$^b$ is independently selected from methyl and ethyl; or alternatively, R$^2$ is cyclopropyl or an azetidine ring, each of which is optionally substituted with 1, 2, or 3 independently selected R$^{21}$ groups;

provided that when X$^1$=X$^2$=X$^3$ is —N=CR$^2$—NR$^3$—, X$^4$ is C, and X$^5$ is C; and Cy$^4$ is unsubstituted or substituted 3-10 membered saturated heterocycloalkylene having one or more nitrogen atoms or Cy$^{44}$ is unsubstituted or substituted 3-10 membered saturated heterocycloalkylene having one or more nitrogen atoms, then $R^2$ is selected from H, methyl, ethyl, propyl, or isopropyl, wherein said methyl, ethyl, propyl, or isopropyl are each optionally optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl;

each $R^{21}$ is independently $C_{1-3}$ alkyl;

$R^3$ is $Cy^4$, $-Cy^{4A}-Cy^5$, or $-Cy^{4A}-Y^1-Cy^5$;

$Y^1$ is $C_{1-4}$ alkylene or $Y^{11}$—$C_{1-4}$ alkylene;

$Y^{11}$ is $C(=O)$;

$Cy^4$ is selected from $C_{6-10}$ aryl, $C_{3-10}$ cycloalkyl, and 3-10 membered heterocycloalkyl, each of which are optionally substituted with 1, 2, 3, or 4 independently selected $R^{31}$ group;

$Cy^{4A}$ is selected from $C_{3-10}$ cycloalkylene and 3-10 membered heterocycloalkylene, each of which are optionally substituted with 1, 2, 3, or 4 independently selected $R^{31}$ groups;

each $R^{31}$ or $R^{32}$ are each independently selected from $C_{1-6}$ alkyl, $C_{1-6}$ haloalkyl, halo, CN, $OR^{a2}$, $C(=O)R^{b2}$, $C(=O)OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, and $C_{1-6}$ haloalkyl, wherein said $C_{1-6}$ alkyl, and $C_{1-6}$ haloalkyl are each optionally substituted by 1, 2, or 3 CN;

each $R^{b2}$ is independently selected from $C_{1-6}$ alkyl and $C_{1-6}$ haloalkyl, which are each optionally substituted by 1, 2, or 3 CN;

$R^4$ is H; and $R^5$ is H.

34. The compound of claim 21, or a pharmaceutically acceptable salt thereof, wherein:

$R^2$ is H, methyl, ethyl, propyl, or isopropyl, wherein said methyl, ethyl, propyl, or isopropyl are each optionally optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl; or alternatively, $R^2$ is cyclopropyl or an azetidine ring, each of which is optionally substituted with 1, 2, or 3 independently selected $R^{21}$ groups;

provided that when $X^1 = X^2 = X^3$ is —N=$CR^2$—$NR^3$—, $X^4$ is C, and $X^5$ is C; and $Cy^4$ is unsubstituted or substituted 3-10 membered saturated heterocycloalkylene having one or more nitrogen atoms or $Cy^{4A}$ is unsubstituted or substituted 3-10 membered saturated heterocycloalkylene having one or more nitrogen atoms, then $R^2$ is selected from H, methyl, ethyl, propyl, or isopropyl, wherein said methyl, ethyl, propyl, or isopropyl are each optionally optionally substituted with 1, 2, or 3 substituents independently selected from halo, CN, $OR^a$, $NR^cR^d$, $NR^cC(=O)R^b$, and $NR^cS(=O)_2R^b$; wherein each $R^a$, $R^c$, and $R^d$ are independently selected from H, methyl, and ethyl; and each $R^b$ is independently selected from methyl and ethyl;

each $R^{21}$ is independently $C_{1-3}$ alkyl;

$R^3$ is $Cy^4$, $-Cy^{4A}-Cy^5$, or $-Cy^{4A}-Y^1-Cy^5$;

$Y^1$ is $C_{1-4}$ alkylene, $Y^{11}$—$C_{1-4}$ alkylene, or $C_{1-6}$ alkylene-$Y^{11}$;

$Y^{11}$ is $C(=O)$ or $NHC(=O)O$;

$Cy^4$ is selected from phenyl, $C_{3-7}$ cycloalkyl, and 4-6 membered heterocycloalkyl, each of which are optionally substituted with 1, 2, 3, or 4 independently selected $R^{31}$ group; $Cy^{4A}$ is selected from $C_{3-7}$ cycloalkylene and 4-6 membered heterocycloalkylene, each of which are optionally substituted with 1, 2, 3, or 4 independently selected $R^{31}$ groups;

each $R^{31}$ or $R^{32}$ are each independently selected from $C_{1-6}$ alkyl, $C_{1-6}$ haloalkyl, halo, CN, $OR^{a2}$, $C(=O)R^{b2}$, $C(=O)OR^{a2}$, and $NR^{c2}R^{d2}$; wherein said $C_{1-6}$ alkyl are each optionally substituted with 1, 2, or 3 substituents independently selected from halo, CN, $OR^{a2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{a2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$;

each $R^{a2}$, $R^{c2}$, and $R^{d2}$ are independently selected from H, $C_{1-6}$ alkyl, $C_{1-6}$ haloalkyl, and wherein said $C_{1-6}$ alkyl, and $C_{1-6}$ haloalkyl are each optionally substituted by 1, 2, or 3 CN;

each $R^{b2}$ is independently selected from $C_{1-6}$ alkyl and $C_{1-6}$ haloalkyl, which are each optionally substituted by 1, 2, or 3 CN;

$R^4$ is H; and $R^5$ is H.

35. The compound of claim 21, or a pharmaceutically acceptable salt thereof, wherein:

$R^2$ is —$CH_2$—OH, —$CH(CH_3)$—OH, or —$CH_2$—$NHSO_2CH_3$;

$R^3$ is $Cy^4$;

$Cy^4$ is selected from $C_{3-10}$ cycloalkyl and 3-10 membered heterocycloalkyl, each of which are optionally substituted with 1, 2, 3, or 4 independently selected $R^{31}$ groups, provided said 3-10 membered heterocycloalkyl is not a saturated heterocycloalkyl group having one or more nitrogen ring members;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

36. The compound of claim 21, or a pharmaceutically acceptable salt thereof, wherein:

$R^2$ is —$CH_2$—OH, —$CH(CH_3)$—OH, or —$CH_2$—$NHSO_2CH_3$;

$R^3$ is -$Cy^{4A}$-$Cy^5$;

$Cy^{4A}$ is selected from $C_{3-10}$ cycloalkylene and 3-10 membered heterocycloalkylene, each of which are optionally substituted with 1, 2, 3, or 4 independently selected $R^{31}$ groups, provided said 3-10 membered heterocycloalkylene is not a saturated heterocycloalkylene group having one or more nitrogen ring members;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl;

each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylamino sulfonyl, and $C_{1-3}$ alkylsulfonyl;

$R^4$ is H; and $R^5$ is H.

37. The compound of claim 21, or a pharmaceutically acceptable salt thereof, wherein:

$R^2$ is —$CH_2$—OH, —$CH(CH_3)$—OH, or —$CH_2$—$NHSO_2CH_3$;

$R^3$ is $Cy^4$ or -$Cy^{4A}$-$Cy^5$;

$Cy^4$ is selected from cyclohexylene and a 2H-tetrahydrofuran ring, each of which are optionally substituted with 1, 2, 3, or 4 independently selected $R^{31}$ groups;

$Cy^{4A}$ is selected from cyclohexylene and a 2H-tetrahydrofuran ring, each of which are optionally substituted with 1, 2, 3, or 4 independently selected $R^{31}$ groups;

each $R^{31}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylamino sulfonyl, and $C_{1-3}$ alkylsulfonyl;

each $R^{32}$ is independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl;

$R^4$ is H; and $R^5$ is H.

38. The compound of claim 21, or a pharmaceutically acceptable salt thereof, wherein:

$X^1 \equiv X^2 \equiv X^3$ is —N=$CR^2$—$NR^3$—, $X^4$ is C, $X^5$ is C, and Y is $CR^4$; or $X^1 \equiv X^2 \equiv X^3$ is —$CR^1$=$CR^2$—$NR^3$—, $X^4$ is C, $X^5$ is C, and Y is $CR^4$; or $X^1 \equiv X^2 \equiv X^3$ is —$CR^1R^{1a}$—C(=O)—$NR^3$—, $X^4$ is C, $X^5$ is C, and Y is $CR^4$; or $X^1 \equiv X^2 \equiv X^3$ is —O—C(=O)—$NR^3$—, $X^4$ is C, $X^5$ is C, and Y is $CR^4$; or $X^1 \equiv X^2 \equiv X^3$ is =N—$CR^2$=$CR^3$—, $X^4$ is N, $X^5$ is C, and Y is $CR^4$.

39. The compound of claim 21, having Formula IIb:

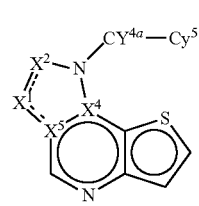

or a pharmaceutically acceptable salt thereof.

40. The compound of claim 21, having Formula IId:

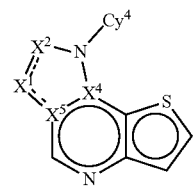

or a pharmaceutically acceptable salt thereof.

41. The compound of claim 21, having Formula IIIa:

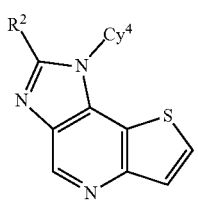

or a pharmaceutically acceptable salt thereof.

42. The compound of claim 21, having Formula IIIb:

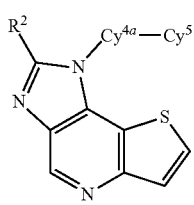

or a pharmaceutically acceptable salt thereof.

43. The compound of claim 21 is (1R)-1-{1-[cis-4-(1H-1,2,4-Triazol-1-yl)cyclohexyl]-1H-imidazo[4,5-d]thieno[3,2-b]pyridin-2-yl}ethanol, or a pharmaceutically acceptable salt thereof.

44. The compound of claim 21, selected from:
(1R)-1-(1-{(3S)-1-[3-(1H-Pyrazol-4-yl)propanoyl]piperidin-3-yl}-1H-imidazo[4,5-d]thieno[3,2-b]pyridin-2-yl)ethanol; and
(1R)-1-{1-[(3S)-1-(3-Pyridin-3-ylpropanoyl)piperidin-3-yl]-1H-imidazo[4,5-d]thieno[3,2-b]pyridin-2-yl}ethanol;

or a pharmaceutically acceptable salt thereof.

45. A composition comprising a compound according to claim 21, or a pharmaceutically acceptable salt thereof, and a pharmaceutically acceptable carrier.

46. A compound of Formula I:

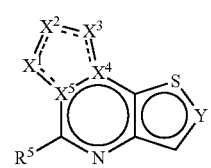

or a pharmaceutically acceptable salt thereof, wherein: the

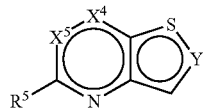

ring system is aromatic;
each ⹀ is independently selected from a single bond and a double bond;
Y is N or CR⁴;
X¹ is selected from CR¹, CR¹R¹ᵃ, C(=O), N, NR¹, O, and S;
X² is selected from CR², C(=O), N, NR², and C(=NR²ᵃ);
X³ is selected from CR³ and NR³;
X⁴ is selected from C and N; and X⁵ is C; or
X⁴ is C; and X⁵ is selected from C and N;
provided that:
(i) the selections for each of X¹, X², X³, X⁴, X⁵ and ⹀ maintain proper valency;
(ii) when X¹ is O or S, then X² is not NR² and X² ⹀ X³ is not —C(=O)—CR³—;
(iii) when X¹ is NR¹, then X² ⹀ X³ is not —NR²—NR³—;
(iv) when X⁴ is N, then X¹ ⹀ X² ⹀ X³ is not =N—NR²—NR³—; and
(v) when X⁵ is N, then X¹ ⹀ X² is not —NR¹—NR²— and X¹ ⹀ X² ⹀ X³ is not —CR¹R¹ᵃ—NR²—CR³=;
R¹ is selected from H, halo, CN, NH₂, C₁₋₃ alkyl, C₁₋₃ alkoxy, and C₁₋₃ haloalkyl;
R¹ᵃ is selected from H, halo, CN, NH₂, C₁₋₃ alkyl, and C₁₋₃ haloalkyl;
R²ᵃ is selected from CN, OH, OCH₃, and NO₂;
R² is —CH₂—OH, —CH(CH₃)—OH, or —CH₂—NHSO₂CH₃;
R³ is -Cy⁴ᴬ-Cy⁵;
Cy⁴ᴬ is selected from C₃₋₁₀ cycloalkylene and 3-10 membered heterocycloalkylene, each of which are optionally substituted with 1, 2, 3, or 4 independently selected R³¹ groups, provided said 3-10 membered heterocycloalkylene is not a saturated heterocycloalkylene group having one or more nitrogen ring members;
Cy⁵ is selected from 5-10 membered heteroaryl, which is optionally substituted with 1, 2, 3, or 4 independently selected R³² groups;
each R³¹ is independently selected from CN, OH, F, Cl, C₁₋₃ alkyl, C₁₋₃ haloalkyl, cyano-C₁₋₃ alkyl, HO—C₁₋₃ alkyl, amino, C₁₋₃ alkylamino, and di(C₁₋₃ alkyl)amino, wherein said C₁₋₃ alkyl and di(C₁₋₃ alkyl)amino is optionally substituted with 1, 2, or 3 substituents independently selected from F, Cl, C₁₋₃ alkylaminosulfonyl, and C₁₋₃ alkylsulfonyl;
each R³² is independently selected from CN, OH, F, Cl, C₁₋₃ alkyl, C₁₋₃ haloalkyl, cyano-C₁₋₃ alkyl, HO—C₁₋₃ alkyl, amino, C₁₋₃ alkylamino, and di(C₁₋₃ alkyl)amino, wherein said C₁₋₃ alkyl and di(C₁₋₃ alkyl)amino is optionally substituted with 1, 2, or 3 substituents independently selected from F, Cl, C₁₋₃ alkylamino sulfonyl, and C₁₋₃ alkylsulfonyl;
R⁴ is H; and
R⁵ is H.

47. The compound of claim 46, or a pharmaceutically acceptable salt thereof, wherein Y is CR⁴.

48. The compound of claim 46, or a pharmaceutically acceptable salt thereof, wherein Cy⁴ᴬ is selected from cyclopropylene, cyclobutylene, cyclopentylene, cyclohexylene, and cycloheptylene, each of which is optionally substituted with 1, 2, 3, or 4 independently selected R³¹ groups.

49. The compound of claim 46, or a pharmaceutically acceptable salt thereof, wherein Cy⁵ is a pyridine ring, a pyrazole ring, or a triazole ring, each of which is optionally substituted with 1 or 2 independently selected R³² groups.

50. The compound of claim 46, or a pharmaceutically acceptable salt thereof, wherein:
X¹ ⹀ X² ⹀ X³ is —N=CR²—NR³—, X⁴ is C, X⁵ is C, and Y is CR⁴; or
X¹ ⹀ X² ⹀ X³ is —CR¹=CR²—NR³—, X⁴ is C, X⁵ is C, and Y is CR⁴; or
X¹ ⹀ X² ⹀ X³ is —CR¹R¹ᵃ—C(=O)—NR³—, X⁴ is C, X⁵ is C, and Y is CR⁴; or
X¹ ⹀ X² ⹀ X³ is —O—C(=O)—NR³—, X⁴ is C, X⁵ is C, and Y is CR⁴; or
X¹ ⹀ X² ⹀ X³ is =N—CR²=CR³—, X⁴ is N, X⁵ is C, and Y is CR⁴.

51. The compound of claim 46, having Formula IIb:

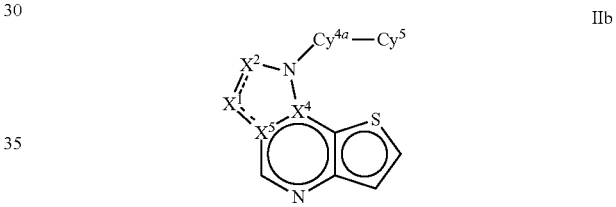

or a pharmaceutically acceptable salt thereof.

52. The compound of claim 46, having Formula IIIb:

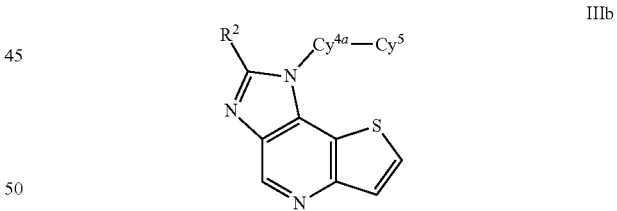

or a pharmaceutically acceptable salt thereof.

53. The compound of claim 46, selected from:
(1R)-1-{1-[cis-4-(1H-1,2,4-Triazol-1-yl)cyclohexyl]-1H-imidazo[4,5-d]thieno[3,2-b]pyridin-2-yl}ethanol;
or a pharmaceutically acceptable salt thereof.

54. A composition comprising a compound according to claim 46, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 11,161,855 B2
APPLICATION NO. : 16/454830
DATED : November 2, 2021
INVENTOR(S) : Yun-Long Li et al.

It is certified that error appears in the above-identified patent and that said Letters Patent is hereby corrected as shown below:

In the Claims

Column 176, Line 14, Claim 1, delete "S(=O)$_2$ Rb," and insert -- S(=O)$_2$Rb, --;

Column 179, Line 48, Claim 2, delete "CR$^3$R$^{1a}$," and insert -- CR$^1$R$^{1a}$, --;

Column 180, Line 21, Claim 2, delete "S(=O)$_2$ R$^b$," and insert -- S(=O)$_2$R$^b$, --;

Column 180, Line 46, Claim 2, delete "S(=O)$_2$ R$^b$," and insert -- S(=O)$_2$R$^b$, --;

Column 181, Line 53, Claim 2, delete "haloalky;" and insert -- haloalkyl; --;

Column 182, Line 63, Claim 2, delete "OR$^{32}$," and insert -- OR$^{a2}$, --;

Column 183, Line 15, Claim 2, delete "OR$^{32}$," and insert -- OR$^{a2}$, --;

Column 183, Line 19, Claim 2, delete "OR$^{32}$," and insert -- OR$^{a2}$, --;

Column 184, Lines 4-5, Claim 4, delete "optionally optionally" and insert -- optionally --;

Column 184, Lines 34-35, Claim 10, delete "optionally optionally" and insert -- optionally --;

Column 184, Line 50, Claim 10, delete "optionally optionally" and insert -- optionally --;

Column 185, Lines 19-20, Claim 11, delete "optionally optionally" and insert -- optionally --;

Column 185, Line 35, Claim 11, delete "optionally optionally" and insert -- optionally --;

Column 189, Line 35, Claim 21, delete "S(=O)$_2$ R$^b$," and insert -- S(=O)$_2$R$^b$, --;

Signed and Sealed this
First Day of March, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,161,855 B2

Column 189, Line 46, Claim 21, delete "S(=O)$_2$ R$^b$," and insert -- S(=O)$_2$R$^b$, --;

Column 192, Line 14, Claim 21, delete "OR$^{32}$," and insert -- OR$^{a2}$, --;

Column 192, Line 32, Claim 21, delete "OR$^{32}$," and insert -- OR$^{a2}$, --;

Column 194, Line 6, Claim 22, delete "S(=O)$_2$ R$^b$," and insert -- S(=O)$_2$R$^b$, --;

Column 194, Line 30, Claim 22, delete "S(=O)$_2$ R$^b$," and insert -- S(=O)$_2$R$^b$, --;

Column 195, Line 37, Claim 22, delete "haloalky;" and insert -- haloalkyl; --;

Column 195, Line 57, Claim 22, delete "-Cy$^{4A}$-Y$^3$-" and insert -- -Cy$^{4A}$-Y$^1$- --;

Column 197, Line 3, Claim 22, delete "OR$^{32}$," and insert -- OR$^{a2}$, --;

Column 197, Line 22, Claim 22, delete "OR$^{32}$," and insert -- OR$^{a2}$, --;

Column 197, Line 26, Claim 22, delete "OR$^{32}$," and insert -- OR$^{a2}$, --;

Column 198, Lines 11-12, Claim 24, delete "optionally optionally" and insert -- optionally --;

Column 198, Lines 54-55, Claim 33, delete "optionally optionally" and insert -- optionally --;

Column 199, Line 5, Claim 33, delete "optionally optionally" and insert -- optionally --;

Column 199, Lines 44-45, Claim 34, delete "optionally optionally" and insert -- optionally --;

Column 199, Line 62, Claim 34, delete "optionally optionally" and insert -- optionally --.